US007288408B2

(12) United States Patent
Dong

(10) Patent No.: US 7,288,408 B2
(45) Date of Patent: Oct. 30, 2007

(54) AMINO ACID TRANSPORTERS

(75) Inventor: Jinzhuo Dong, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 479 days.

(21) Appl. No.: 10/355,430

(22) Filed: Jan. 31, 2003

(65) Prior Publication Data

US 2003/0188332 A1 Oct. 2, 2003

Related U.S. Application Data

(60) Provisional application No. 60/353,062, filed on Feb. 1, 2002.

(51) Int. Cl.
*A01H 5/00* (2006.01)
*C12N 15/82* (2006.01)
*C12N 15/87* (2006.01)
*C12N 5/14* (2006.01)
*C07H 21/00* (2006.01)

(52) U.S. Cl. .................. 435/468; 435/320.1; 435/419; 800/287; 536/23.6

(58) Field of Classification Search ..................... None
See application file for complete search history.

(56) References Cited

U.S. PATENT DOCUMENTS 5,719,043 A 2/1998 Frommer
6,165,792 A * 12/2000 Allen et al. ................. 435/419
6,245,970 B1 * 6/2001 Frommer .................... 800/298

FOREIGN PATENT DOCUMENTS

GB 2 355 265 4/2001
WO 94/01559 1/1994

OTHER PUBLICATIONS

Guo et al. (PNAS, 101:9205-9210, 2004).*

Sasaki et al. (NCBI, GenBank, Sequence Accession No. AP003227, pp. 1-58, Published Feb. 2001).*

Hsu et al.; "Cloning a Plant Amino Acid Transporter by Functional Complementation of a Yeast Amino Acid Transport Mutant"; Proc Natl Acad Sci USA; 90:7441-7445 (Aug. 1993).

Fischer et al.; "Substrate Specificity and Expression Profile of Amino Acid Transporters (AAPs) in Arabidopsis"; J Bio Chem; 270(27):16315-16320 (1995).

Montamat et al.; "Cloning and Expression of Amino Acid Transporters from Broad Bean"; Plant Mol Biol; 41:259-268 (1999).

Bick et al.; "Amino Acid Carriers of Ricinus communis Expressed During Seedling Development: Molecular Cloning and Expression Analysis of Two Putative Amino Acid Transporters, RcAAP1 and RcAAP2"; Plant Mol Biol; 36:377-385 (1998).

Frommer et al.; "Expression Cloning in Yeast of a cDNA Encloding a Broad Specificity Amino Acid Permease from *Arabidopsis thaliana*"; Proc Natl Acad Sci USA; 90:5944-5948 (Jul. 1993).

Kwart et al.; "Differential Expression of Two Related Amino Acid Transporters with Differing Substrate Specificity in *Arabidopsis thaliana"; The Plant Journal*; 4(6):993-1002 (1993).

Li et al.; "ΔpH-Dependent Amino Acid Transport into Plasma Membrane Vesicles Isolated from Sugar Beet Leaves"; *Plant Physiol*; 94:268-277 (1990).

Rentsch et al.; "Salt Stress-Induced Proline Transporters and Salt Stress-Repressed Broad Specificity Amino Salt Permeases Identified by Suppression of a Yeast Amino Permease-Targeting Mutent"; *The Plant Cell*; 8:1437-1446 (Aug. 1996).

Lyamichev et al.; "Polymorphish Identification and Quantifative Detection of Genomic CNA by Invasive Cleavage of Oligonucleotide Probes"; *Nature Biotech*; 17:292-296 (Mar. 1999).

Lohaus et al.; "Phloem Transport of Amino Acids in Two Brassica napus L. Genotypes and one B. carinata Genotype in Relation to Their Seed Protein Content"; *Planta*; 211:833-840 (2000).

Altschul et al.; "Basic Local Alignment Search Tool"; *J Mol Biol*; 215:403-410 (1990).

Boorer et al.; "Kinetics and Specificity of a H+/Amino Acid Transporter from *Arabidopsis thaliana"; J Biol Chem*; 271(4):2213-2220 (1996).

Eksittikul et al; "Characterization of Sucrose Uptake System in Cassava (*Manihot esculenta* Crantz"; *Plant Science*; 160:733-737 (2001).

Boorer et al; "Specificity and Stoichiometry of the Arabidopsis H+/Amino Acid Transporter AAP5"; *J Biol Chem*; 272(20):13040-13046 (1997).

Kishor et al., "Overexpression of $\Delta^1$-pyrroline-5-carboxylate synthetase increases proline production and confers osmotolerance in transgenic plants," *Plant Physiol*., 108:1387-1394, 1995.

Ortiz-Lopez et al., "Amino acid transporters in plants," *Biochimica et Biophysica Acta*, 1465:275-280, 2000.

PCT Search Report for PCT/US0302978, Oct. 25, 2006.

Sasaki et al., Database EMBL, Accession No. AP003616, May 2001.

EBI Accession No. 80592 dated Oct. 31, 2006.

GenBank Accession No. AP003616 dated Sep. 15, 2004.

Miranda et al., "Amino acid permeases in developing seeds of Vicia faba L.: expression precedes storage protein synthesis and is regulated by amino acid supply," *The Plant Journal*, 28(1):61-71, 2001.

Schulze et al., "Transporters for ammonium, amino acids and peptides are expressed in pitchers of the carnivorous plant Nepenthes," *The Plant Journal*, 17(6):634-646, 1999.

supplementary Search Report for PCT/US0302978 dated Mar. 9, 2007.

Theologis et al., "Sequence and analysis of chromosome 1 of the plant Arabidopsis thaliana," *Nature*, 408:816-820, 2000.

* cited by examiner

*Primary Examiner*—Phuong T Bui
*Assistant Examiner*—Vinod Kumar
(74) *Attorney, Agent, or Firm*—Sonnenschein Nath & Rosenthal LLP

(57) ABSTRACT

The present invention includes certain nucleic acid molecules that encode amino acid transporters in a plant, and complements and fragments thereof. Also set forth herein are methods for using such nucleic acid molecules for the purpose of altering the activity of such amino acid transporters.

17 Claims, 20 Drawing Sheets

```
    M-----S-----------RLE-G-PARG---------------------------------------------------------------  Majority

1   M---VGAMRSGAMELEDRLATLPRFRGCH------------------------------------------------------------  SEQ ID NO2.PRO
1   M---------------------DKSGGEAAAAA----AAADDV-------------ERR------------------------------  SEQ ID NO4.PRO
1   M---AVSHNVGSKHGVAPLEVSVEAGNGGAAE----W-----------------------------------------------------  SEQ ID NO6.PRO
1   M---GRSGGGDGDGDGDRLLLGKPLESSSSCSSS--------------------------------------------------------  SEQ ID NO8.PRO
1   MWLWTRQKSPPVGRRPPKVSSIRPLRATQSASPTQGWIASADELYSLLTVLVTRLATRHELRALRFPNAGCWPMAQHHSSHSL  SEQ ID NO10.PRO
1   --------------------------------------------------------------------------------------  SEQ ID NO12.PRO
1   ------------GDHGAAL---------------------------------------------------PLIADQAKHA-  SEQ ID NO14.PRO
1   M---EVS-----------SVEFSHHAAAASKC------------------------------------------------------  SEQ ID NO16.PRO
1   M---EKKKSMFVEQSFPEHEISDTNKN-------------------------------------------------------------  SEG ID NO1.PRO

    ------------DDDGREKRTGTVW-TASAHIITAVIGSGVLSLAWAIAQLGWVAGPAAMLLFAFVTYYTSTLLADCYRSGDP  Majority

27  ------------DDDGKERRTGTVW-TATAHIITAVIGSGVLSLAWAMAQLGWVAGPLTLVLFAAIFFYTCGLLADCYRVGDP  SEQ ID NO2.PRO
22  --------GGDYEQDEHERR-GTVW-TATAHIVTAVIGSGVLALAWSVAQLGWVAGPLALAGFACVTYYTSTLLAGAYRAPHP  SEQ ID NO4.PRO
31  -----------LDDDGRPRRTGTFW-TASAHIVTAVIGSGVLSLAWAIAQLGWVAGPAAMLLFAFVTYYTATLLAECYRTGDP  SEQ ID NO6.PRO
32  ------------DESLVKRTGTVW-TAMAHIITAVIGSGVLSLAWSVAQLGWVGGPAAMVFFAGVTAVQSTLIADCYICHHP  SEQ ID NO8.PRO
84  EVGGVGAGGVELDDDGHAARTGNLW-TCFAHIITAVIGCGVLALSWSVAQLGWVGGPVAMLCFAFVTYLSAFLLSHCYRSPAS  SEQ ID NO10.PRO
1   -------------------------SAHIITAVIGSGVLSLGWAIAQLGWVAGPVVMLLFSLVTYYTESLLADCYRSGDP  SEQ ID NO12.PRO
18  -----AAGGI---------VRSGSMW-TAAAHVITAVIGSGVLSLAWSIAQLGWVAGPAAMLVFAAVTALQSTIFADCYRSPDP  SEQ ID NO14.PRO
15  ------------FDDDGRLKRTGTMW-TASAHIITAVIGSGVLSLAWAIAQLGWVAGPTVMLLFSFVTYYTSALLADCYRSGDA  SEQ ID NO16.PRO
25  ------------FDEDGRDKRTGT-WMTGSAHIITAVIGSGVLSLAWAIAQLGWVAGPAVLMAFSFITYFTSTMLADCYRSPDP  SEG ID NO1.PRO

    VTG----KRNYTYMDAVRSNLGGKKVWFCGPLQYANLVGTAIGYTITASISMRAIRRANCFHRHGHGA--PCSASGTP-YMII  Majority

97  VTG----KRNYTYTEAVKSNLGGWYVWFCGECQYVNMFGTGIGYTITASISAAAINKSNCFHWHGHDA--DCSQNTSA-YIIG  SEQ ID NO2.PRO
95  VTG----HRNRTYMDAVRSYLSPREVFMCGVAQYVNLWGTMVGYTITATISMAAIRQADCLRRDCAGAGARCDAPGTVL-MLA  SEQ ID NO4.PRO
102 ETG----KRNYTYMDAVRSNLGGAKVAFCGVIQYANLVGVAIGYTIAASISMKAVRRAGCFHAHGHAD -PCNSSSTF-YMIL  SEQ ID NO6.PRO
101 ERGGVVRNRS--YVDAVRIYLGDKSHLFCGEFLNLSLFGTGVVYTLTSATSMRAIRKANCYHREGHDA--PCSVGGDGYYMLL  SEQ ID NO8.PRO
166 DDGSLKRQRNYTYMDAVRTHLGEKRTWLCGLFQYLNMYGTAIAYTITTATCLRAIVRANCYHSQGHSA--PCGAGSDHLYMLL  SEQ ID NO10.PRO
56  STG----KRNYTYMDAVNANLSSIKVQICGFLQYANIVGVAIGYTIAASISMLAIRRANCFHQKGHGN--PCKISSTF-YMII  SEQ ID NO12.PRO
87  EHGP---HRNRTYAKAVDRNLGSNSSWVCMLLQHTALFGYGIAYTITASISCRAILKANCYHEHGHDA--HCDYDSNY-YMLI  SEQ ID NO14.PRO
90  CTG----KRNYTYMDAVNANLSGVKVWFCGFLQYANTVGVAIGYTIAASISMLAIQRANCFHVEGHGD--PCNISSTF-YMII  SEQ ID NO16.PRO
96  VTG----KRNYTYMEVVRSYLGGRKVQLCGLAQYGNLIGITIGYTITASISMVAVKRSNCFHKNGHNV--KCATSNTF-FMII  SEG ID NO1.PRO

    FGVVQILLSQIPDFHQIAWLSIVAAVMSFTYSSIGLGLGVAQVIANGG-VKGSLTGISVG--V-TPTQKVWRVLQALGDIAFA  Majority

173 FGVVQVIFSQLHNFHKLWWLSIIAAIMSFSYSAIAVGLSLAQIVMGPTG-KTTMTGTLVGVDV-DAAQKVWMTFQALGNVAFA  SEQ ID NO2.PRO
173 FSVVQVVLSQFPGLEHITWLSVVAAAMSFAYSFAGLGLSVGHWVSRGG---GGLGGRVASAAAASSTRKLWNVLLALGNIAFA  SEQ ID NO4.PRO
178 FGVVQILFSQIPDFDQIWWLSIVAAVMSFTYSSIGLSLGIAQTISNGG-FMGSITGISIGAGV-TSTQKIWHTLQAFGDIAFA  SEQ ID NO6.PRO
180 FGLAQVLLSQIPNFHEMAGLSIFAAVMSCFYAFVGVGLGVAKVIAN-GVIMGGIGGTPL---V-STTQKVWRVSQALGDILFA  SEQ ID NO8.PRO
247 FGAAQAVLSLIPNFHSMAWLSAVAAVMSFTYATIGLGLGLAKTIEN-GAIKGSVAGVPM---S-TAPQKVWRVAQAIGDIAFA  SEQ ID NO10.PRO
132 FGVAEIFFSQIPDFDQISWLSILAAVMSFTYSSIGLGLGVVQVIANRG-VQGSLTGITIGV-V-TPNDKVWRSLQAFGDVAFA  SEQ ID NO12.PRO
164 FGGVQLLLSFIPDFHDMAWLSVVAAAMSFSYAFIGLGLGLARTIAN-GTIKGSITGVRM---R-TPMQKVWRVSQAIGDIAFA  SEQ ID NO14.PRO
166 FGVVQIFFSQIPDFDQISWLSILAAVMSFTYSTIGLGLGIAQVVSNKG-VQGSLTGISVGL-V-TPVDKMWRSLQAFGDIAFA  SEQ ID NO16.PRO
172 FAIIQIILSQIPNFHNLSWLSILAAVMSFCYASIGVGLSIAKAAGGGEHVRTTLTGVTVGIDV-SGAEKIWRTFQAIGDIAFA  SEG ID NO1.PRO

    YSYSLILIEIQDTLKSPPPSESKTNKRATVVSVAVTTFFYMLCGCMGYAAFGDGAPGNLLTGFGFYEPFWLIDFANACIVVHL  Majority

254 YSYAIILIEIQDTLRS-PPAENKTNRRATMMGISTTTGFYMLCGCLGYAAFGNARSGNILTGFGFYEPFWLVDFANACIVVHL  SEQ ID NO2.PRO
253 YIFAEVLIEIQDTLKSPPP-ENRTNKKAAMYGIGATTIFYISVGCAGYAAFGSNAPGNILAAGGL-GPLWLVDIANMGLILHL  SEQ ID NO4.PRO
259 YSFSNILIEIQDTIKAPPPSESKVMQKATRLSVATTTIFYMLCGCMGYAAFGDKAPDNLLTGFGFFEPFWLIDIANVAIVVHL  SEQ ID NO6.PRO
258 YPFSLVLLEIEDTLRSPPP-ESETMKKATRASIAITTLFYLCCGCFGYASFGDGTPGNLLTGFGFYEPYWLIDLANLAIVLHL  SEQ ID NO8.PRO
325 YPYTIVLLEIQDTLKSPPP-ESETMQKGNVLAVLATTFFYLAVGCFGYAAFGNAAPGNLLTGFGFYEPYWLIDFANACIVLHL  SEQ ID NO10.PRO
212 YSYSLILIEIQDTIRAPPPSESTVMKRATVVSVAVTTLFYMLCGCMGYAAFGDSAPGNLLTGFGFYEPFWLLDVANAAIVVHL  SEQ ID NO12.PRO
242 YPYSLILLEIQDTLKSPPA-ENKTMKRASMISILVTTFFYLCCGCLGYAAFGSDAPGNLLTGFGLYGPYWLIDFANACIILHL  SEQ ID NO14.PRO
246 YSYSLILIEIQDTIRAPPPSESKVMHRATVVSVAVTTFFYMLCGCMGYAAFGDNAPGNLLTGFGFYEPFWLLDVANAAIAVHL  SEQ ID NO16.PRO
254 YAYSTVLIEIQDTLKAGPPSENKAMKRASLVGVSTTTFFYMLCGCVGYAAFGNDAPGNFLTGFGFYEPFWLIDFANVCIAVHL  SEG ID NO1.PRO

    VGAYQVYCQPIFAFVERWAAARWPDSAFVT-GEYTVPVPLA-A-RR-----SLNVFRLVWRTAFVAATTVVAMLLPFFNDVLG  Majority

336 VGGFQVFCQPLFAAVEGAVAARYPGST-------------------REYGAAGLNVFRLVWRTAFVAVITLLAILMPFFNSILG  SEQ ID NO2.PRO
334 IGAYQVYAQPVFASVERWAASRWPEAKFMSSA-YTVSVSIPLLQR---GSVTVAPHKLVLRTAIVGATTAVALAIPFFNAVLG  SEQ ID NO4.PRO
342 VGAYQVFCQPIFAFVERRAAAAWPDSAFVS-QELRVG-PFA-----------VSVFRLTWRSSFVCVTTVVAMLLPFFGNVVG  SEQ ID NO6.PRO
340 LGGYQVYTQPVFAFADR----KFGGGATVVEAP----LLPVPGARR----VNANVFRLCFRTAYVAATTALAVWFPYFNQIIG  SEQ ID NO8.PRO
407 LGGYQMFSQQIFTFADRSLAARFPNSAFVNK-SYAVKVPGAPASWS----YSLNLQRLCFRTAYVASTTGLALLFPYFNEVLG  SEQ ID NO10.PRO
295 VGAYQVYCQPLLAFVEKWAAQRWPDSAYII-GEVEVPLPLPASRRRCC---KVNLFRATWRTAFVVATTVVSMLLPFFNDVVG  SEQ ID NO12.PRO
324 LGGYQVYSQPIFQFAERLLAERFPDSGFVNGGSYTVRFACLRACRV----NPL---RVCLRTLYVASTTAVAVALPYFNEVLA  SEQ ID NO14.PRO
329 VGAYQVYCQPLFAFVEKWARQRWPKSRYII-GEVDVPLPLGTAGGRCY---KLSLFRLTWRTAFVVATTVVSMLLPFFNDVVG  SEQ ID NO16.PRO
337 IGAYQVFCQPIFQFVESQSAKRWPDNKFII-GEYKIHVP-------CCGDFSTNFLRLVWRTSYVVVTAVVAMIFPFFNDFLG  SEG ID NO1.PRC

    LLGALSFWPLTVYFPVEMYIVQRKVPRWSTRWVALQALSVVCLVVSAAAAAGSVAGVVSSLK-Y--PFKTLS-        Majority

401 ILGSIAFWPLTVFFPVEMYIRQRQVRRFSTKWIALQSLSFVCFLVTAASCAASVQGVVDSLKTYV-PFKTRS.        SEQ ID NO2.PRO
413 LLGAFSFWPLTVYFPISMHIAQGKIARGTKWWCLLQALSMVCLVISVAVGVGSVTDIVDSLKASSSPFKIVG.        SEQ ID NO4.PRO
412 FLGAVSFWPLTVYFPVEMYIKQRRVPRGSTKWICLQTLSVSCLLVSVAAAD.                            SEQ ID NO6.PRO
411 LLGSFTFWPLAVYFPVEMYLTRNKVAPWTNQWLAIHAFSLVCLLISAFASVGSAVGVFG---------SETS.        SEQ ID NO8.PRO
485 VLGAVVFWPLAIYLPVEMYCVQRGVLPWTRTWVALQAFSVVCFVVGTFAFVGSVEGVIR---------KRLG.        SEQ ID NO10.PRO
374 FLGALGFWPLTVYFPVEMYVVQKKVPRWSSRWVCLQMLSLGCLVISIAAAAGSIAGIASDLKVYR-PF--KSY        SEQ ID NO12.PRO
400 LLGALSFWPLAIYFPVEMYFIQRNVRRWSARWVVLQTFSVVCLLVSAFALVGSIEGLIS---------KKL-G        SEQ ID NO14.PRO
408 LLGALGFWPLTVYFPVEMYIVQKKVPRWSTRWVCLQLLSVACLVITVASAAGSVAGIVSDLKVYK-PFVTTS.        SEQ ID NO16.PRO
412 LIGAASFWPLTVYFPIEMHIAQKKIPKFSFTWTWLKILSWTCFIVSLVAAAGSVQGLIQSLKDFK-PFQA-P.        SEG ID NO1.PRO
```

Fig. 15

```
    MA-G----VKK----VEAG-----PLGXADAPDLDDDGRXKRTGTLWTASAHIITAVIGSGVLSLAWAIAQLGWVAGPAV Majority

1   MAKDVEMAVRNGDGGGGGGYYATHPHGGAGGEDVDDDGKQRRTGNVWTASAHIITAVIGSGVLSLAWATAQLGWVVGPVT SEQ ID NO24.PRO
1   M--GMERPQEKVATTTTAAF-NLAESGYADRPDLDDDGREKRTGTIVTASAHIITAVIGSGVLSLAWAIAQLGWVIGPAV SEQ ID NO26.PRO
1   MASG-QKVVKPMEVSVEAG-------NAGEAAWLDDDGRARRTGTFWTASAHIITAVIGSGVLSLAWAIAQLGWVAGPAV SEQ ID NO28.PRO
1   MAPQL-------------------PIEVASAPKLDDDGHPQRTGNLWTCVAHIITAVIGCGVLALSWSVAQLGWVAGPIA SEQ ID NO30.PRO
1   ------------------------PL-ISDRPK---HAAIVRSGTHWTAAAHVITAVIGSGVLSLAWSVAQLGWLAGPGM SEQ ID NO32.PRO
1   M-------EKKKSMFVEQSF-PEHEIGDTNK-NEDEDGRDKRTGTWMTGSAHIITAVIGSGVLSLAWAIAQLGWVAGPAV SEG ID NO1.PRO

    LVAFAFVTYFTSTLLADCYRSPDPVTG-KRNYTYMDAVRANLGGAKVWLCGVAQYVNLVGVGIGYTITASISMRAIKRAN Majority

81  IMLFALITYYTSGLLADCYRTGDPVSG-KRNYTYMDAVAAYLGGWCVWSCGVFQYVNLVGTAIGYTITASISAAAVHKAN SEQ ID NO24.PRO
78  LVAFSVITWFCSSLLADCYRSPDPVIG-KRNYTYGQAVRANLGVAKYRLCSVAQYVNLVGVTIGYTITTAISMGAIKRSN SEQ ID NO26.PRO
73  MLLFAFVIYYTSTLLAECYRTGDPATG-KRNYTYMDAVRANLGGAKVTFCGVIQYANLVGVAIGYTIASSISMRAIRRAG SEQ ID NO28.PRO
62  MVCFAFVTYISAFLLSHCYRSEGSEK-MQRNYSYMDAVRVHLGRKHTWLCGLLQYLNLYGIGIAYTITTATCMRAIKRAN SEQ ID NO30.PRO
53  MLVFAAVTALQSALFADCYRSPDPEVGPHRNRTYANAVERNLGSSSAWVCLLLQQTALFGYGIAYTITASISCRAILRSN SEQ ID NO32.PRO
72  IMAFSFITYFTSTMLADCYRSPDPVTG-KRNYTYMEVVRSYLGGRKVQLCGLAQYGNLIGITIGYTITASISMVAVKRSN SEG ID NO1.PRO

    CFHKNGHDAPCXSSGTT-YMILFGAAQILLSQIPNFHDLAWLSIVAAVMSFAYSTIGLGLGLAKTIGGGT-VKGTLTGVT Majority

160 CYHKNGHDADCGVYDTT-YMIVFGVVQIFFSMLPNFSDISWLSILAAVMSFSYSTIAVGLSLARTISGAT-GKTTLTGVE SEQ ID NO24.PRO
157 WFHRNGHDAACLASDTT-NMILIFAGIQILLSQLPNFHKIWWLSIVAAVMSLAYSTIGLGLSIAKIAGGA-HPEATLTGVT SEQ ID NO26.PRO
152 CFHHNGHGDPCRSSSNP-YMILFGAVQIVFSQIPDFDQIWWLSIVAAVMSFTYSGIGLSLGIVQTISNGG-IQGSLTGIS SEQ ID NO28.PRO
141 CYHSEGRDAPCDSNGEHFYMLLFGAAQLLLSFIPNFHKMAWLSVVAAIMSFAYSTIGLGLGLAKTIGDGT-VKGNIAGVA SEQ ID NO30.PRO
133 CYHTHGHDAPCK-YGGSYYMLMFGAAQLFLSFIPDFHDMAWLSVLAAVMSFSYSFIGLGLGLANTIANGT-IKGSITGAP SEQ ID NO32.PRO
151 CFHKNGHNVKCATSNTP-FMILFAIIQIILSQIPNFHNLSWLSILAAVMSFCYASIGVGLSIAKAAGGGEHVRTTLTGVT SEG ID NO1.PRO

    VGVDVSSAQKVWRVFQAIGDIAFAYSYSNVLIEIQDTLKAPPA-ENKTMKKASLIGVSTTTFFYMLCGCLGYAAFGNAAP Majority

238 VGVDVTSAQKIWLAFQALGDIAFAYSYSMILIEIQDTVKSPPA-ENKTMKKATLLGVSTTTAFYMLCGCLGYAAFGNAAP SEQ ID NO24.PRO
235 VGVDVSASEKIWRTFQSLGDIAFAYSYSNVLIEIQDTLRSSPA-ENEVMKKASFIGVSTTTTFYMLCGVLGYAAFGNRAP SEQ ID NO26.PRO
230 IGVGVSSTQKVWRSLQAFGDIAFAYSFSNILIEIQDTIKAPPSEAKVMKSATRLSVATTTVFYMLCGCMGYAAFGDAAP SEQ ID NO28.PRO
220 M---ATPMQKVWRVAQAIGDIAFAYPYTIVLLEIQDTLRSPPP-ESETMQKGNVIAVLATTFFYLCVGCFGYSAFGNAAP SEQ ID NO30.PRO
211 T---RTPVQKVWHVSQAIGDIAFAYPYSLILLEIQDTLKAPPA-ENKTMKKASIISIVVTTFFYLCCGCFGYAAFGSDAP SEQ ID NO32.PRO
230 VGIDVSGAEKIWRTFQAIGDIAFAYAYSTVLIEIQDTLKAGPPSENKAMKRASLVGVSTTTFFYMLCGCVGYAAFGNDAP SEG ID NO1.PRO

    GNLLTGFGFYEPFWLIDFANVCIVVHLVGAYQVFCQPIFQFAERFAARRWPDSAFVNGERXVKLPL-----------GAGD Majority

317 GNMLTGFGFYEPYWLIDFANVCIVVHLVGAYQVFCQPIFAAVETFAARRWPGSEFITRERPV---V----------AGRS SEQ ID NO24.PRO
314 GNFLTGFGFYEPFWLVDVGNVCIVVHLVGAYQVFCQPIYQFAEAWARSRWPDSAFVNGERVLRLPL----------GAGD SEQ ID NO26.PRO
310 DNLLTGFGFYEPFWLLDVANVAIVVHLVGAYQVFVQPIFAFVERWASRRWPDSAFIAKELRV---G-------------P SEQ ID NO28.PRO
296 GNLLTGFGFYEPYWLIDFANACIVLHLLGGYQMFSQQIFTFADRCFAASFPNSAFVNRSYSVKI--LPWRRGGGGGGAGR SEQ ID NO30.PRO
287 GNLLTGFGFYEPYWLIDFANACIILHLLGGYQVYSQPIYQFADRFFAERYPASRFVNDFHTVKLPLLP-----------P SEQ ID NO32.PRO
310 GNFLTGFGFYEPFWLIDFANVCIAVHLIGAYQVFCQPIFQFVESQSAKRWPDNKFITGEYKIHVP-----------CCGD SEG ID NO1.PRO

    FSVNLLRLVWRTAYVVVTTVVAMAFPFFNDVLGLLGAVSFWPLTVYFPVEMYIAQRKVPRWSPRWVALQTLSVLCFLVSX Majority

384 FSVNMFRLTWRTAFVVVSTVLAIVMPFFNDILGFLGAVGFWPLTVYYPVEMYIRQRRIQRYTSRWVALQTLSLLCFLVSL SEQ ID NO24.PRO
384 FPVSALRLVWRTAYVVLTAVAAMAFPFFNDFLGLIGAVSFWPLTVYFPVQMYMSQAKVPA---------------ILADV SEQ ID NO26.PRO
374 FALSLFRLTWRSAFVCLTTVVAMLIPFFGNVVGLLGAVSFWPLTVYFPVEMYIAQRGVPRGSARWVSLKTLSACCLVVSI SEQ ID NO28.PRO
374 YEVNLQRVCFRTVYVASTTGLALVFPYFNEVLGVLGALVFWPLAIYLPVEMYCVQRRISPWTPRWVALQAFSVVCFVVGT SEQ ID NO30.PRO
356 CRVNLLRVCFRTVYVASTTAVALAFPYFNEVLALLGALNFWPLAIYFPVEMYFIQRHVPRWSPRWVVLQSFSVLCLLVSA SEQ ID NO32.PRO
379 FSINFLRLVWRTSYVVVTAVVAMIFPFFNDFLGLIGAASFWPLTVYFPIEMHIAQKKIPK--------------E---- SEG ID NO1.PRO

    AAAVGSI-GVI-----------------D-L-------------------------------IQ-L---K--QLX-     Majority

464 ASAVASTRASASRSSTTSPSRPSRDPDHDGLFFLLLHPDEKRFQKHMHNKCRKLAKSLVTSSVRWSVRRRRVQLV.     SEQ ID NO24.PRO
449 DVD-----------ERAQPRLPRRLPPRRRRLHPGPHQIRRTLQ-----------------AIQRLLMIKLIIIC.     SEQ ID NO26.PRO
454 AAAAGSIADVI-----------------DAL---------------------KVYRPFSG.                    SEQ ID NO28.PRO
454 FAFVGSVEGVIRKR---------------------------------------------------------IG.     SEQ ID NO30.PRO
436 FALVGSIQGLISQK---------------------------------------------------------I-G     SEQ ID NO32.PRO
440 --------------SFTWIWL--KILSWTCFIVSLVAAAGSVQG-----------------LIQSLKDFKPFCAP.     SEG ID NO1.PRO
```

Fig. 16

```
    MVEKASG-VG-----QTIGVS-D-------------------------SKCFDDDGRLKRTGTVW-TASAHIITAVIGSGVLSLA Majority

1   MG---SMHIETP---EPFADG---------------------------SKNFDDDGKAKRTGT-WITASAHIITAVIGSGVLSLA SEQ ID NO34.PRO
1   M-GEEEIDDS-----PLIQGFPSGDV---------------------------PPRRTGNVE-RAVAHIITGVIGAGVLSLA SEQ ID NO36.PRO
1   MVEKD-G-VGSKYLQQTLNVSIDMH------------------QHGISKCFDDDGRPKRTGTVW-TSSAHIITAVIGSGVLSLA SEQ ID NO38.PRO
1   MDGKKSLQIT-----RSGTGAYDDDG-------------------------HAKRTGNLQ-SAVAHIITAVIGSGVLSLA SEQ ID NO40.PRO
1   MDGKNSLQIT-----RSGIGAYDDDG-------------------------HAKRTGNLQ-SAVAHIITAVIGSGVLSLA SEQ ID NO42.PRO
1   MVEKD-G-VGSKYLQQTLNVSIDMH------------------QHGISKCFDDDGRPKRTGTVW-TSSAHIITAVIGSGVLSLA SEQ ID NO44.PRO
1   MLPRSRT-LPSRIHQGIIEERHDVRPYVQVEVRPNNIQTETQAMNIQSNYSKCFDDDGRLKRTGTFW-TATAHIITAVIGSGVLSLA SEQ ID NO46.PRO
1   MGVAAESESN-----DNIPLLLTQSAY-------------------------PSKHDDDGRLKRRGT-WLTATSHIVTAVIGSGVLSLP SEQ ID NO48.PRO
1   MVEYASR-TNLSY----------------CRDYGIEEDSIDDMPLKSDPECYDDDGHLKRTGTTW-TSSHIITAVVGSGVLSLA SEQ ID NO50.PRO
1   MMENC-G--------KQTPEVSNDTL------------------QRVGSKSFDDDGRLKRTGTIW-TASAHIITAVIGSGVLSLA SEQ ID NO52.PRO
1   PRVRES---------QANGVH---------------------------ESKHDDDGRDKRRGT-WLTATSHIVTAVIGSGVLSLA SEQ ID NO54.PRO
1   MGKGKSMFVEQSFPEHEIGDT---------------------------NKNFDEDGRDKRTGT-WMTGSAHIITAVIGSGVLSLA SEQ ID NO1.PRO

    WAIAQLGWIAGPAVLLLFSIVTYYTSTLLADCYRTPDPVTGKRNYT-YMDAVKSYLGGKG--VKLCGLVQYANLFGVAIGYTITAST Majority

52  WAIAQMGWVAGPAVLFVFSLIIYFTSTLLADCYRSPDPVHGKRNYT-YSEVVKANLGGRKFQ--LCGLAQYINLVGVTIGYTITASL SEQ ID NO34.PRO
49  WSVAQLGWIAGPFIIVGAGTFLSANLLSDCYRFPIPLYGNIRCPSYIDAVKVYLGDSR--QKVCGVLVHASLYGATTAYVITSAT SEQ ID NO36.PRO
64  WAIAQLGWIAGPIVMVIFSAIFYYTSTLLADCYRTGDPVTGKRNYT-YMDAIQSNFGGNGFKVKLCGLVQYVNLFGVAIGYTIAAST SEQ ID NO38.PRO
50  WSTSQLGWIGGPVALLCCAIVTYISSFLLSDCYRTPDPVTGKRNY-SYMDAVRVYLGYKR--TCVAGFLQFLTLYGTSIAYVLTTAT SEQ ID NO40.PRO
50  WSTSQLGWIGGPFSLLCCAIVTYISSFLLSDCYRTPDPVTGKRNY-SYMDAVRVYLGYKR--TCVAGFLQFLTLYGTSIAYVLTTAT SEQ ID NO42.PRO
64  WAIAQLGWIAGPIVMVIFSAIFYYTSTLLADCYRTGDPVTGKRNYT-YMDAIQSNFGGNGFKVKLCGLVQYVNLFGVAIGYTIAAST SEQ ID NO44.PRO
86  WAVAQLGWVAGPVVMFLFAVVNLYTSNLLTQCYRTGDSVNGHRNYT-YMEAVKSILGGK--KVKLCGLIQYINLFGVAIGYTIAASV SEQ ID NO46.PRO
51  WSTAQLGWLAGPFSILLLASTFLFSSFLLCNTYRHPHPEYGPNRSASYLDVVHLHLGISN--GRLSGLLVSISLYGFAIAFVITTAI SEQ ID NO48.PRO
68  WAIAQMGWIAGPAVMILFSIVTLYTSSFLADCYRTGDPMFGKRNYT-FMDAVSTILG--SYSVTFCGIVQYLNLFGSAIGYTIAASL SEQ ID NO50.PRO
58  WAIAQLGWIAGPVVMILFSIVTYYTSTLLAFCYRSGDQLSGKRNYT-YTQAVRSYLGG-FSVKFCGWVQYANLFGVAIGYTIAASI SEQ ID NO52.PRO
49  WAVAQLGWIAGPAILTIFSVITVFTSSLLSDCYRYPDSVHGTRNHN-YREMVKNILGGKKYL--FCGLAQFANLIGTGIGYTVTASI SEQ ID NO54.PRO
58  WAIAQLGWVAGPAVLMAFSFITYFTSTMLADCYRSPDPVTGKRNYT-YMEVVRSYLGGRKVQ--LCGLAQYGNLIGITIGYTITASI SEQ ID NO1.PRO

    SMMAIKRSNCY-HKSGHEAPCKISSNPYMILFGIVQILFSQIPDFHNLWWLSIVAAVMSFTYSSIGLGLGIAKVIENG--VKGSLTG Majority

136 SMGAVKKSNCL-HKHGHQDECKVKDNAFMIAFACIQILLSQIPNFHKLSWLSIVAAVMSFAYSSIGLGLSIAKIIGGG-HVRTTLTG SEQ ID NO34.PRO
134 SIRAILKSNCY-HKEGHQAPCKYGDAVYMMLFGLVQIIMSFIPDLHNMAWVSIVAAIMSFTYSSIGLGLGITTVIENG-RIMGSLTG SEQ ID NO36.PRO
150 SMMAIERSNCF-HKSGGKDPCHINSNMYMISFGIVEILFSQIPGFDQLWWLSIVAAVMSFTYSTIGLGLGIGKVIENGG-VGGSLTG SEQ ID NO38.PRO
134 SLSAILRSNCY-HKKGHEAPCKYGGNLYMALFGLVQIVMSFIPDLHNMAWVSVVAALMSFTYSFIGLGLGIATVIKNG-RIMGSLTG SEQ ID NO40.PRO
134 SLSAILRSNCY-HKKGHEAPCKYGGNLYMALFGLVQIVMSFIPDLHNMAWVSVVAALMSFTYSFIGLGLGIATVIKNG-RIMGSLTG SEQ ID NO42.PRO
150 SMMAIERSNCF-HKSGGKDPCHINSNMYMISFGIVEILFSQIPGFDQLWWLSIVAAVMSFTYSTIGLGLGIGKVIENGG-VGGSLTG SEQ ID NO44.PRO
170 SMMAIKRSNCF-HSSHGKDPCHMSSNGYMITFGIAEVIFSQIPDFDQVWWLSIVAAIMSFTYSSVGLSLGVAKVAENKT-FKGSLMG SEQ ID NO46.PRO
136 SLRTIQNSFCY-HNKGPEAACESVDAYYMLLFGAIQIVLSQIPNFHNIKWLSVVAAIMSFTYSFIGMGLSLAQIIEKG-HAEGSIGG SEQ ID NO48.PRO
152 SMMAIQRSHCIIQSSDGPNQCNISSIPYTICFGAVQIFFSQIPDFHNMWWLSIVASVMSFTYSIIGLVLGITKIAETGT-FKGSLTG SEQ ID NO50.PRO
142 SMMAIKRSNCY-HSSGGKNPCKMNSNWYMISYGVSEIIFSQIPDFHELWWLSIVAAVMSFTYSFIGLGLGIGKVIGNGR-IKGSLTG SEQ ID NO52.PRO
133 SMVAVIRSNCF-HRYGHEAKCHTSNYPYMTIFAVIQILLSQIPDFQELSGLSIIAAVMSFGYSSIGIGLSIAKIAGGND-AKTSLTG SEQ ID NO54.PRO
142 SMVAVKRSNCF-HKNGHNVKCATSNTPFMIIFAIIQIILSQIPNFHNLSWLSILAAVMSFCYASIGVGLSIAKAAGGGEHVRTTLTG SEQ ID NO1.PRO

    ITIGTVTD--------KVWRVFQALGDIAFAYSYSIILIEIQDTLKS-PPSENKTMKKASLISIAVTTFFYMLCGCFGYAAFGDDAP Majority

221 V---------EVSGTEKVWKMFQAIGDIAFAYAFSNVLIEIQDTLKSSPP-ENKVMKRASLIGIMTTTLFYVLCGCLGYAAFGNDAP SEQ ID NO34.PRO
219 VPASNIAD--------KLWLVFQGIGDIAFAYPYTVILLEIQDTLESPPPENKTMKKASMIAILITTFFYLCCGCFGYAAFGNQTP SEQ ID NO36.PRO
235 ITIGTVTQ------TDKVWRTMQALGDIAFAYSYSLILIEIQDTVKS-PPSESKTMKKASFISVAVTSIFYMLCGCFGYAAFGDASP SEQ ID NO38.PRO
219 IPTDKIAD--------KFWLVFQALGDIAFAYPYSILLLEIQDTLES-PPPENQTMKKASMVAIFITTFFYLCCGCFGYAAFGNDTP SEQ ID NO40.PRO
219 IPTDKIAD--------KFWLVFQALGDIAFAYPYSILLLEIQDTLES-PPPENQTMKKASMVAIFITTFFYLCCGCFGYAAFGNDTP SEQ ID NO42.PRO
235 ITIGTVTQ------TDKVWRTMQALGDIAFAYSYSLILIEIQDTVKS-PPSESKTMKKASFISVAVTSIFYMLCGCFGYAAFGDASP SEQ ID NO44.PRO
255 ISIGTVTQAGTVTSTQKIWRSLQALGAMAFAYSFSIILIEIQDTIKS-PPAEHKTMRKATTLSIAVTTVFYLLCGCMGYAAFGDNAP SEQ ID NO46.PRO
221 ISTSNGAE--------KLWLVSQALGDISFSYPFSTILMEIQDTLKS-PPPENQTMKKASVIAVSVTTFLYLSCGGAGYAAFGDNTP SEQ ID NO48.PRO
238 ISIGTVTEG------PKVWGVFQALGNIAFAYSYSFVLLEIQDTIKS-PPSEVKTMKKAAKLSIAVTTTFYMLCGCVGYAAFGDSAP SEQ ID NO50.PRO
227 VTIGTVTE-----SQKIWRTFQALGNIAFAYSYSMILIEIQDTIKS-PPAESEТMSKATLISVLVTTVFYMLCGCFGYASFGDASP SEQ ID NO52.PRO
218 LIVGE-----DVTSQEKLWNTFQAIGNIAFAYAFSQVLVEIQDTLKSSPP-ENQAMKKATFAGCSTTSLFYMLCGLLGYAAFGNKAP SEQ ID NO54.PRO
228 VTVGI-----DVSGAEKIWRTFQAIGDIAFAYAYSTVLIEIQDTLKAGPPSENKAMKRASLVGVSTTTFFYMLCGCVGYAAFGNDAP SEQ ID NO1.PRO

    GNLLTGFGFYEPYWLIDIANACIVIHLVGAYQVYSQPLFAFVEKWAAKRFPDSGFVNKEYEIKIPGLGPFQLNLFRLVWRTAYVILT Majority

298 SNFLTGFGFYEPFWLIDFANVCIAVHLVGAYQVFVQPIFGFVEKWSKENWTESQFINGEHTLNIPLCGSYNVNFFRVVWRTAYVIIT SEQ ID NO34.PRO
297 GNLLTGFGFYEPYWLIDFANACIVLHLVGGYQIYSQPIYGAVDRWCSKRYPNSGFVNNFYQLKLPRLPAFQLNMFRICFRTAYVVST SEQ ID NO36.PRO
315 GNLLTGFGFYNPYWLLDIANAAIVIHLVGSYQVYCQPLFAFVEKHAAQMFPDSDFLNKEIEIPIPGFHPYRLNLFRLVWRTIYVMLS SEQ ID NO38.PRO
297 GNLLTGFGFFEPFWLIDLANACIILHLVGGYQIYSQPIYSTVDRWASRKFPNSGFVNNFYKVKLPLLPGFQLNLFRFCFRTTYVIST SEQ ID NO40.PRO
297 GNLLTGFGFFEPFWLIDLANACIILHLVGGYQIYSQPIYSTVDRWASRKFPNSGFVNNFYRVKLPLLPGFQLNLFRFCFRTTYVISS SEQ ID NO42.PRO
315 GNLLTGFGFYNPYWLLDIANAAIVIHLVGSYQVYCQPLFAFVEKHAAQMFPDSDFLNKEIEIPIPGFHPYRLNLFRLVWRTIYVMLS SEQ ID NO44.PRO
341 GNLLTGFGFYNPYWLLDIANLAIVIHLVGAYQVFSQPLFAFVEKWSVRKWPKSNFVTAEYDIPIPCFGVYQLNFFRLVWRTIFVLLT SEQ ID NO46.PRO
299 GNLLTGFVSSKSYWLVNFANACIVVHLVGSYQVYSQPLFGTVENWFRFRFPDSEFVNHTYILKLPLLPAFELNLFSLSFRTAYVASA SEQ ID NO48.PRO
318 GNLLAGFGFHKLYWLVDIANAAIVIHLVGAYQVYAQPLFAFVEKETAKRWPK---IDKEFQISIPGLQSYNQNIFSLVCRTVFVIIT SEQ ID NO50.PRO
307 GNLLTGFGFYNPYWLIDIANAGIVIHLVGAYQVFCQPLFSFVESNAAERFPNSDFMSREFEVPIPGCKPYKLNLFRLVWRTLFVILS SEQ ID NO52.PRO
299 GNFLTGFGFYEPYWLVDIGNVFVFVHLVGAYQVFTQPVFQLVETWVAKRWPESNFMGKEYRV-----GKFRFNGFRMIWRTVYVIFT SEQ ID NO54.PRO
310 GNFLTGFGFYEPFWLIDFANVCIAVHLIGAYQVFCQPIFQFVESQSAKRWPDNKFITGEYKIHVPCCGDFSINFLRLVWRTSYVVVT SEQ ID NO1.PRO

    TVIAMLLPFFNDILGLLGAIGFWPLTVYFPVEMYIVQKKIPKWSSKWIGLQILSFACLLVLTLLAAAGSIAGIVSDLKTYKPF----- Majority

385 AVVAMLLPFFNDFLALIGALSFWPLTVVFPIEMYIKKSNMQRFSFTWTWLKILSWVCLIISIISLVGSIQGLSVSIKKYKPFQAEQ. SEQ ID NO34.PRO
384 TGLAILFPYFNQVIGVLGALGFWPLAIYFPVEMYFVQRKVEANSRKWIVLRTFSFICFLVSLLGLIGSLEGIISEKLS. SEQ ID NO36.PRO
402 TVISMLLPFFNDIGGLLGAFGFWPLTVYFPVEMYIIQKRIPKWSTKWICLQILSMTCLLMTIGAAAGSIAGIAIDLRTYKPFKTNY. SEQ ID NO38.PRO
384 TGLAIFFPYFNQILGVLGAINFWPLAIYFPVEMYFVQKKIAAWSRKWIVLRTFSFACFLVTGMGLVGSLEGIVSAKLK. SEQ ID NO40.PRO
384 IGLAIFFPYFNQILGVLGAINFWPLAIYFPVEMYFVQQKIAAWSSKWIVLRTFSFACFLVTVMGLVGSLEGIVSAKLK. SEQ ID NO42.PRO
402 TVISMLLPFFNDIGGLLGAFGFWPLTVYFPVEMYIIQKRIPKWSTKWICLQILSMTCLLMTIGAAAGSIAGIAIDLRTYKPFKTNY. SEQ ID NO44.PRO
428 TLIAMLMPFFNDVVGILGAFGFWPLTVYFPIDMYISQKKIGRWTSRWIGLQLLSVSCLIISLLAAVGSMAGVVLDLKTYKPFKTSY. SEQ ID NO46.PRO
386 TVIAMIFPYFNQILGVLGSIIFWPLTIYFPVEIYLSQSSTVSWTTKWVLLRTFSFFGFLFGLFTLIGCIKGIVTEKIS. SEQ ID NO48.PRO
402 TVISTLLPFFNDILGVIGALGFWPLTVYFPVENYILQKRIPKWSMRWISLELMSVVCLLVTIAAGLGSVVGVYLDLQ. SEQ ID NO50.PRO
394 TVIAMLLPFFNDIVGLIGAIGFWPLTVYLPVEMYILQTKIPKWGIKWIGLQMLSVACFVITILAAAGSIAGVIDDLKVYKPFVTSY. SEQ ID NO52.PRO
381 AVVAMILPFFNSIVGLLGAISFFPLTVYFPTENYLVQAKVPKFSLVWIGVKILSGFSLIVTIVAAAGSIQGIIADLRIYEPF----K SEQ ID NO54.PRO
397 AVVAMIFPFFNDFLGLIGAASFWPLTVYFPIEMHIAQKKIPKFSFTWTWLKILSWTCFIVSLVAAAGSVQGLIQSLKDFKPFQA-P. SEQ ID NO1.PRO
```

Fig. 17

SEQUENCE LISTING

```
<160> NUMBER OF SEQ ID NOS: 73

<210> SEQ ID NO 1
<211> LENGTH: 481
<212> TYPE: PRT
<213> ORGANISM: Arabidopsis thaliana

<400> SEQUENCE: 1

Met Glu Lys Lys Lys Ser Met Phe Val Glu Gln Ser Phe Pro Glu His
1               5                   10                  15

Glu Ile Gly Asp Thr Asn Lys Asn Phe Asp Glu Asp Gly Arg Asp Lys
            20                  25                  30

Arg Thr Gly Thr Trp Met Thr Gly Ser Ala His Ile Ile Thr Ala Val
        35                  40                  45

Ile Gly Ser Gly Val Leu Ser Leu Ala Trp Ala Ile Ala Gln Leu Gly
    50                  55                  60

Trp Val Ala Gly Pro Ala Val Leu Met Ala Phe Ser Phe Ile Thr Tyr
65                  70                  75                  80

Phe Thr Ser Thr Met Leu Ala Asp Cys Tyr Arg Ser Pro Asp Pro Val
                85                  90                  95

Thr Gly Lys Arg Asn Tyr Thr Tyr Met Glu Val Val Arg Ser Tyr Leu
            100                 105                 110

Gly Gly Arg Lys Val Gln Leu Cys Gly Leu Ala Gln Tyr Gly Asn Leu
        115                 120                 125

Ile Gly Ile Thr Ile Gly Tyr Thr Ile Thr Ala Ser Ile Ser Met Val
    130                 135                 140

Ala Val Lys Arg Ser Asn Cys Phe His Lys Asn Gly His Asn Val Lys
145                 150                 155                 160

Cys Ala Thr Ser Asn Thr Pro Phe Met Ile Ile Phe Ala Ile Ile Gln
                165                 170                 175

Ile Ile Leu Ser Gln Ile Pro Asn Phe His Asn Leu Ser Trp Leu Ser
            180                 185                 190

Ile Leu Ala Ala Val Met Ser Phe Cys Tyr Ala Ser Ile Gly Val Gly
        195                 200                 205

Leu Ser Ile Ala Lys Ala Ala Gly Gly Gly Glu His Val Arg Thr Thr
    210                 215                 220

Leu Thr Gly Val Thr Val Gly Ile Asp Val Ser Gly Ala Glu Lys Ile
225                 230                 235                 240

Trp Arg Thr Phe Gln Ala Ile Gly Asp Ile Ala Phe Ala Tyr Ala Tyr
                245                 250                 255

Ser Thr Val Leu Ile Glu Ile Gln Asp Thr Leu Lys Ala Gly Pro Pro
            260                 265                 270

Ser Glu Asn Lys Ala Met Lys Arg Ala Ser Leu Val Gly Val Ser Thr
        275                 280                 285

Thr Thr Phe Phe Tyr Met Leu Cys Gly Cys Val Gly Tyr Ala Ala Phe
    290                 295                 300
```

-continued

```
Gly Asn Asp Ala Pro Gly Asn Phe Leu Thr Gly Phe Gly Phe Tyr Glu
305                 310                 315                 320

Pro Phe Trp Leu Ile Asp Phe Ala Asn Val Cys Ile Ala Val His Leu
                325                 330                 335

Ile Gly Ala Tyr Gln Val Phe Cys Gln Pro Ile Phe Gln Phe Val Glu
            340                 345                 350

Ser Gln Ser Ala Lys Arg Trp Pro Asp Asn Lys Phe Ile Thr Gly Glu
        355                 360                 365

Tyr Lys Ile His Val Pro Cys Cys Gly Asp Phe Ser Ile Asn Phe Leu
    370                 375                 380

Arg Leu Val Trp Arg Thr Ser Tyr Val Val Val Thr Ala Val Val Ala
385                 390                 395                 400

Met Ile Phe Pro Phe Phe Asn Asp Phe Leu Gly Leu Ile Gly Ala Ala
                405                 410                 415

Ser Phe Trp Pro Leu Thr Val Tyr Phe Pro Ile Glu Met His Ile Ala
            420                 425                 430

Gln Lys Lys Ile Pro Lys Phe Ser Phe Thr Trp Thr Trp Leu Lys Ile
        435                 440                 445

Leu Ser Trp Thr Cys Phe Ile Val Ser Leu Val Ala Ala Ala Gly Ser
    450                 455                 460

Val Gln Gly Leu Ile Gln Ser Leu Lys Asp Phe Lys Pro Phe Gln Ala
465                 470                 475                 480

Pro


<210> SEQ ID NO 2
<211> LENGTH: 471
<212> TYPE: PRT
<213> ORGANISM: Zea mays

<400> SEQUENCE: 2

Met Val Gly Ala Met Arg Gly Gly Ala Met Glu Leu Glu Asp Arg Leu
1               5                   10                  15

Ala Thr Leu Pro Arg Phe Arg Gly Asp His Asp Asp Asp Gly Lys Glu
            20                  25                  30

Arg Arg Thr Gly Thr Val Trp Thr Ala Thr Ala His Ile Ile Thr Ala
        35                  40                  45

Val Ile Gly Ser Gly Val Leu Ser Leu Ala Trp Ala Met Ala Gln Leu
    50                  55                  60

Gly Trp Val Ala Gly Pro Leu Thr Leu Val Leu Phe Ala Ala Ile Thr
65                  70                  75                  80

Phe Tyr Thr Cys Gly Leu Leu Ala Asp Cys Tyr Arg Val Gly Asp Pro
                85                  90                  95

Val Thr Gly Lys Arg Asn Tyr Thr Tyr Thr Glu Ala Val Lys Ser Asn
            100                 105                 110

Leu Gly Gly Trp Tyr Val Trp Phe Cys Gly Phe Cys Gln Tyr Val Asn
        115                 120                 125

Met Phe Gly Thr Gly Ile Gly Tyr Thr Ile Thr Ala Ser Ile Ser Ala
    130                 135                 140

Ala Ala Ile Asn Lys Ser Asn Cys Phe His Trp His Gly His Asp Ala
145                 150                 155                 160

Asp Cys Ser Gln Asn Thr Ser Ala Tyr Ile Ile Gly Phe Gly Val Val
                165                 170                 175

Gln Val Ile Phe Ser Gln Leu His Asn Phe His Lys Leu Trp Trp Leu
            180                 185                 190
```

```
Ser Ile Ile Ala Ala Ile Met Ser Phe Ser Tyr Ser Ala Ile Ala Val
        195                 200                 205

Gly Leu Ser Leu Ala Gln Ile Val Met Gly Pro Thr Gly Lys Thr Thr
    210                 215                 220

Met Thr Gly Thr Leu Val Gly Val Asp Val Asp Ala Ala Gln Lys Val
225                 230                 235                 240

Trp Met Thr Phe Gln Ala Leu Gly Asn Val Ala Phe Ala Tyr Ser Tyr
                245                 250                 255

Ala Ile Ile Leu Ile Glu Ile Gln Asp Thr Leu Arg Ser Pro Pro Ala
            260                 265                 270

Glu Asn Lys Thr Met Arg Arg Ala Thr Met Met Gly Ile Ser Thr Thr
        275                 280                 285

Thr Gly Phe Tyr Met Leu Cys Gly Cys Leu Gly Tyr Ala Ala Phe Gly
    290                 295                 300

Asn Ala Ala Ser Gly Asn Ile Leu Thr Gly Phe Gly Phe Tyr Glu Pro
305                 310                 315                 320

Phe Trp Leu Val Asp Phe Ala Asn Ala Cys Ile Val Val His Leu Val
                325                 330                 335

Gly Gly Phe Gln Val Phe Cys Gln Pro Leu Phe Ala Ala Val Glu Gly
            340                 345                 350

Ala Val Ala Ala Arg Tyr Pro Gly Ser Thr Arg Glu Tyr Gly Ala Ala
        355                 360                 365

Gly Leu Asn Val Phe Arg Leu Val Trp Arg Thr Ala Phe Val Ala Val
    370                 375                 380

Ile Thr Leu Leu Ala Ile Leu Met Pro Phe Phe Asn Ser Ile Leu Gly
385                 390                 395                 400

Ile Leu Gly Ser Ile Ala Phe Trp Pro Leu Thr Val Phe Phe Pro Val
                405                 410                 415

Glu Met Tyr Ile Arg Gln Arg Gln Val Arg Arg Phe Ser Thr Lys Trp
            420                 425                 430

Ile Ala Leu Gln Ser Leu Ser Phe Val Cys Phe Leu Val Thr Ala Ala
        435                 440                 445

Ser Cys Ala Ala Ser Val Gln Gly Val Val Asp Ser Leu Lys Thr Tyr
    450                 455                 460

Val Pro Phe Lys Thr Arg Ser
465                 470


<210> SEQ ID NO 3
<211> LENGTH: 1821
<212> TYPE: DNA
<213> ORGANISM: Zea mays

<400> SEQUENCE: 3

cggacgcgtg ggcggacgcg tgggcggacg cgtgggcgca ccccgcgctc ggcggactct     60

tttgctgctg cacctgccat cgtcacgcac cggtgtgtgg agcgaagcca gcgagcgaga    120

agtagccaca gagcggcctc agagagacgt gcagatcgag agagagacga acagagagag    180

cgattcatgg taggtgcgat gcgcggcgga gccatggagt tggaggaccg cctggccacc    240

cttcctcgct tccgcggcga tcacgatgac gacggcaagg aaaggaggac agggacggta    300

tggacggcaa cggcgcacat catcacggcg gtgatcggct ccggcgtgct gtcgctggcg    360

tgggcgatgg cgcagctggg gtgggtggcc gggccgttga ccctggtgct cttcgcggcg    420

atcaccttct acacctgcgg cctcctcgca gactgctacc gcgttggcga ccccgtgacg    480
```

-continued

```
ggcaagcgca actacaccta caccgaggcc gtcaagagca acctgggcgg ctggtacgtc    540

tggttctgcg gcttctgcca gtacgtcaac atgttcggca caggcatcgg ctacaccatc    600

acagcctcca tcagtgcagc ggccatcaac aagtccaact gcttccactg gcacggccac    660

gatgccgact gcagccagaa caccagcgcc tacatcatcg gcttcggcgt ggtgcaggtc    720

atcttcagcc agctccacaa cttccacaag ctgtggtggc tttccatcat cgccgccatc    780

atgtccttct cctactccgc catcgccgtg ggcctctccc tggcgcagat cgtcatgggc    840

cccacgggga agaccaccat gaccggcacc ctggtcgggg tggacgtgga cgctgcgcag    900

aaggtgtgga tgacgttcca ggcgctgggc aacgtggcct tcgcgtactc gtacgccatc    960

atcctcatcg agatccagga cacgctgcgc tccccgcccg ccgagaacaa gaccatgcgc   1020

cgcgccacca tgatgggcat ctccaccacc accggcttct acatgttgtg cggctgcctc   1080

ggctacgccg cgttcggcaa cgccgcgtcg gggaacatcc tcaccggctt cggcttctac   1140

gagcccttct ggctcgtcga cttcgccaac gcctgcatcg tcgtgcacct cgtcggcggc   1200

ttccaggtct tctgccagcc gctgttcgcg gccgtcgagg gcgccgtggc ggcgcggtac   1260

cccgggtcga cgcgcgagta cggcgccgcg ggcctcaacg tcttccgcct cgtgtggcgc   1320

acggcgttcg tggctgtcat cacgctgctg gccatcctca tgcccttctt caacagcatc   1380

ctgggcatcc tcggcagcat cgccttctgg ccgctcaccg tcttcttccc cgtcgagatg   1440

tacatccggc agcggcaggt gcgaaggttc agcaccaagt ggatagcgct gcagagcctc   1500

agcttcgtct gtttcctcgt caccgccgcc tcctgcgcgg cctccgtgca gggcgtggtc   1560

gactcgctca agacctacgt gccgttcaag acgaggtcgt gagctcctgc tgcttagtta   1620

ttatacatgt agcatacata ctactcgtgc ctcctttgta gtggcaccga aacaaactga   1680

gcaaactcag ccaaattagt tatgcgggag tttaattttg aactactagt atgttgctgt   1740

cgaatgcaac aaaactaata acgtttacag tttttctatt tggcaaaaaa aaaaaaaaaa   1800

aaaaaaaaaa aaaaaaaaaa a                                              1821
```

<210> SEQ ID NO 4
<211> LENGTH: 484
<212> TYPE: PRT
<213> ORGANISM: Zea mays

<400> SEQUENCE: 4

```
Met Asp Lys Ser Gly Gly Glu Ala Ala Ala Ala Ala Ala Ala Ala Asp
1               5                   10                  15

Asp Val Glu Arg Arg Gly Gly Asp Tyr Glu Gln Asp Glu His Glu Arg
            20                  25                  30

Arg Gly Thr Val Trp Thr Ala Thr Ala His Ile Val Thr Ala Val Ile
        35                  40                  45

Gly Ser Gly Val Leu Ala Leu Ala Trp Ser Val Ala Gln Leu Gly Trp
    50                  55                  60

Val Ala Gly Pro Leu Ala Leu Ala Gly Phe Ala Cys Val Thr Tyr Tyr
65                  70                  75                  80

Thr Ser Thr Leu Leu Ala Gly Ala Tyr Arg Ala Pro His Pro Val Thr
                85                  90                  95

Gly His Arg Asn Arg Thr Tyr Met Asp Ala Val Arg Ser Tyr Leu Ser
            100                 105                 110

Pro Arg Glu Val Phe Met Cys Gly Val Ala Gln Tyr Val Asn Leu Trp
        115                 120                 125

Gly Thr Met Val Gly Tyr Thr Ile Thr Ala Thr Ile Ser Met Ala Ala
```

-continued

```
    130                 135                 140

Ile Arg Gln Ala Asp Cys Leu Arg Arg Asp Gly Ala Gly Ala Gly Ala
145                 150                 155                 160

Arg Cys Asp Ala Pro Gly Thr Val Leu Met Leu Ala Phe Ser Val Val
                165                 170                 175

Gln Val Val Leu Ser Gln Phe Pro Gly Leu Glu His Ile Thr Trp Leu
            180                 185                 190

Ser Val Val Ala Ala Ala Met Ser Phe Ala Tyr Ser Phe Ala Gly Leu
        195                 200                 205

Gly Leu Ser Val Gly His Trp Val Ser Arg Gly Gly Gly Gly Leu Gly
    210                 215                 220

Gly Arg Val Ala Gly Ala Ala Ala Ala Ser Ser Thr Arg Lys Leu Trp
225                 230                 235                 240

Asn Val Leu Leu Ala Leu Gly Asn Ile Ala Phe Ala Tyr Thr Phe Ala
                245                 250                 255

Glu Val Leu Ile Glu Ile Gln Asp Thr Leu Lys Ser Pro Pro Pro Glu
            260                 265                 270

Asn Arg Thr Met Lys Lys Ala Ala Met Tyr Gly Ile Gly Ala Thr Thr
        275                 280                 285

Ile Phe Tyr Ile Ser Val Gly Cys Ala Gly Tyr Ala Ala Phe Gly Ser
    290                 295                 300

Asn Ala Pro Gly Asn Ile Leu Ala Ala Gly Gly Leu Gly Pro Leu Trp
305                 310                 315                 320

Leu Val Asp Ile Ala Asn Met Cys Leu Ile Leu His Leu Ile Gly Ala
                325                 330                 335

Tyr Gln Val Tyr Ala Gln Pro Val Phe Ala Ser Val Glu Arg Trp Ala
            340                 345                 350

Ala Ser Arg Trp Pro Glu Ala Lys Phe Met Ser Ser Ala Tyr Thr Val
        355                 360                 365

Ser Val Ser Ile Pro Leu Leu Gln Arg Gly Ser Val Thr Val Ala Pro
    370                 375                 380

His Lys Leu Val Leu Arg Thr Ala Ile Val Gly Ala Thr Thr Ala Val
385                 390                 395                 400

Ala Leu Ala Ile Pro Phe Phe Asn Ala Val Leu Gly Leu Leu Gly Ala
                405                 410                 415

Phe Ser Phe Trp Pro Leu Thr Val Tyr Phe Pro Ile Ser Met His Ile
            420                 425                 430

Ala Gln Gly Lys Ile Ala Arg Gly Thr Lys Trp Trp Cys Leu Leu Gln
        435                 440                 445

Ala Leu Ser Met Val Cys Leu Val Ile Ser Val Ala Val Gly Val Gly
    450                 455                 460

Ser Val Thr Asp Ile Val Asp Ser Leu Lys Ala Ser Ser Ser Pro Phe
465                 470                 475                 480

Lys Ile Val Gly


<210> SEQ ID NO 5
<211> LENGTH: 1640
<212> TYPE: DNA
<213> ORGANISM: Zea mays

<400> SEQUENCE: 5

cccacgcgtc cgcccacgcg tccgcccacg cgtccgccca cgcgtccgct cctctctttc      60

cccggcacct gtcacgggag gaggatggac aagagcggcg gcgaggcggc ggcggcggca     120
```

-continued

```
gcagcagcag acgacgtcga gcggcggggg ggcgactacg agcaagacga gcacgagcgg    180

agagggacgg tgtggacggc gacggcgcac attgtgacgg cggtgatcgg ctccggcgtg    240

ctggcgctgg cctggagcgt ggcgcagctg ggctgggtcg cggggcccct cgcgctcgcc    300

ggcttcgcgt gcgtcaccta ctacacctcc acgctgctcg ccggcgccta ccgcgcgccg    360

caccccgtca ccggccacag gaaccgcacc tacatggacg ccgtcagatc gtacctcagt    420

cccagggagg tgttcatgtg cggggtcgcg cagtacgtga acctgtgggg caccatggtc    480

gggtacacca tcacggcgac cataagcatg gccgcgatca ggcaggccga ctgcctccgc    540

cgggacggcg ccggcgccgg cgcgcgctgc gacgcgccag ggaccgtgct gatgctggcg    600

ttcagcgtgg tccaggtggt gctgtcccag ttcccgggcc tggagcacat cacctggctg    660

tccgtcgtcg cggcggccat gtcgttcgcc tactccttcg ccggcctcgg cctctccgta    720

gggcactggg tgtctcgtgg cggcggcggc ctcgggggca gggttgcagg tgccgccgcg    780

gcatcctcca ccaggaagct ctggaacgtg cttctcgccc tggggaacat tgccttcgcc    840

tacactttcg ctgaagtatt gatcgagatc caggatacac tcaagtcacc accaccggag    900

aacaggacga tgaagaaggc agcaatgtac gggatcggag ccaccaccat cttctacatc    960

tccgtcggct gcgctgggta cgccgcgttc ggttcgaatg ctccgggcaa catcttggcg   1020

gcaggcgggc tgggtccctt gtggctcgtc gacattgcca acatgtgcct catcctccac   1080

ctgatcggtg cataccaggt atacgctcag cctgtcttcg cttcggttga gaggtgggcc   1140

gcctcacggt ggccagaagc caagttcatg agcagcgcat acaccgtgtc cgtcagcatc   1200

cccctcttgc agagaggatc ggtcaccgtc gcgccgcaca agctcgtcct gaggaccgcc   1260

atagtcggcg cgacgactgc ggtggcgctg gcgataccct tcttcaacgc cgtgctgggg   1320

ctcctcggcg cgttcagctt ctggccgctc acggtctact tccccatcag catgcacatc   1380

gcccagggca agatcgccag gggggaccaag tggtggtgcc ttctgcaggc tctgagcatg  1440

gtttgcttgg tgatctcggt ggccgtgggt gtaggctctg tcactgacat tgtcgatagc   1500

ctcaaggcct cttctagccc tttcaaaatt gtaggctaac aggttactgt agtcatgtac   1560

aatgctctga gccgatcgtg cgttgaggtt taaaagaact gtggtgcgcg aaaaaaaaaa   1620

aaaaaaaaaa aaaaaaaaaa                                               1640
```

<210> SEQ ID NO 6
<211> LENGTH: 462
<212> TYPE: PRT
<213> ORGANISM: Zea mays

<400> SEQUENCE: 6

```
Met Ala Val Ser His Asn Val Gly Ser Lys His Gly Val Ala Pro Leu
1               5                   10                  15

Glu Val Ser Val Glu Ala Gly Asn Gly Gly Ala Ala Glu Trp Leu Asp
            20                  25                  30

Asp Asp Gly Arg Pro Arg Arg Thr Gly Thr Phe Trp Thr Ala Ser Ala
        35                  40                  45

His Ile Val Thr Ala Val Ile Gly Ser Gly Val Leu Ser Leu Ala Trp
    50                  55                  60

Ala Ile Ala Gln Leu Gly Trp Val Ala Gly Pro Ala Ala Met Leu Leu
65                  70                  75                  80

Phe Ala Phe Val Thr Tyr Tyr Thr Ala Thr Leu Leu Ala Glu Cys Tyr
                85                  90                  95

Arg Thr Gly Asp Pro Glu Thr Gly Lys Arg Asn Tyr Thr Tyr Met Asp
```

-continued

```
            100                 105                 110

Ala Val Arg Ser Asn Leu Gly Gly Ala Lys Val Ala Phe Cys Gly Val
        115                 120                 125

Ile Gln Tyr Ala Asn Leu Val Gly Val Ala Ile Gly Tyr Thr Ile Ala
    130                 135                 140

Ala Ser Ile Ser Met Lys Ala Val Arg Arg Ala Gly Cys Phe His Ala
145                 150                 155                 160

His Gly His Ala Asp Pro Cys Asn Ser Ser Ser Thr Pro Tyr Met Ile
                165                 170                 175

Leu Phe Gly Val Val Gln Ile Leu Phe Ser Gln Ile Pro Asp Phe Asp
            180                 185                 190

Gln Ile Trp Trp Leu Ser Ile Val Ala Ala Val Met Ser Phe Thr Tyr
        195                 200                 205

Ser Ser Ile Gly Leu Ser Leu Gly Ile Ala Gln Thr Ile Ser Asn Gly
    210                 215                 220

Gly Phe Met Gly Ser Leu Thr Gly Ile Ser Ile Gly Ala Gly Val Thr
225                 230                 235                 240

Ser Thr Gln Lys Ile Trp His Thr Leu Gln Ala Phe Gly Asp Ile Ala
                245                 250                 255

Phe Ala Tyr Ser Phe Ser Asn Ile Leu Ile Glu Ile Gln Asp Thr Ile
            260                 265                 270

Lys Ala Pro Pro Pro Ser Glu Ser Lys Val Met Gln Lys Ala Thr Arg
        275                 280                 285
Leu Ser Val Ala Thr Thr Thr Ile Phe Tyr Met Leu Cys Gly Cys Met
    290                 295                 300

Gly Tyr Ala Ala Phe Gly Asp Lys Ala Pro Asp Asn Leu Leu Thr Gly
305                 310                 315                 320

Phe Gly Phe Phe Glu Pro Phe Trp Leu Ile Asp Ile Ala Asn Val Ala
                325                 330                 335

Ile Val Val His Leu Val Gly Ala Tyr Gln Val Phe Cys Gln Pro Ile
            340                 345                 350

Phe Ala Phe Val Glu Arg Arg Ala Ala Ala Ala Trp Pro Asp Ser Ala
        355                 360                 365

Phe Val Ser Gln Glu Leu Arg Val Gly Pro Phe Ala Val Ser Val Phe
    370                 375                 380

Arg Leu Thr Trp Arg Ser Ser Phe Val Cys Val Thr Thr Val Val Ala
385                 390                 395                 400

Met Leu Leu Pro Phe Phe Gly Asn Val Val Gly Phe Leu Gly Ala Val
                405                 410                 415

Ser Phe Trp Pro Leu Thr Val Tyr Phe Pro Val Glu Met Tyr Ile Lys
            420                 425                 430

Gln Arg Arg Val Pro Arg Gly Ser Thr Lys Trp Ile Cys Leu Gln Thr
        435                 440                 445

Leu Ser Val Ser Cys Leu Leu Val Ser Val Ala Ala Ala Asp
    450                 455                 460


<210> SEQ ID NO 7
<211> LENGTH: 1535
<212> TYPE: DNA
<213> ORGANISM: Zea mays

<400> SEQUENCE: 7

gaattcggct cgagttcact cactaacggc cgtgcttgca ctcgcagcgc atcacttgct     60

actttggtag tggagagcag aaagaacaga gctagattat tcccaacaag ctacagcaaa    120
```

-continued

```
ttagttgctc ttcatggccg tgtcacacaa cgttgggagc aagcacggtg tcgcgccgct    180

ggaggtgtcg gtggaggccg ggaacggcgg agccgccgag tggctggacg acgatggccg    240

gcctcgccgc acgggcacgt tctggacggc cagcgcgcac atcgtcaccg ccgtcatcgg    300

ctccggggtg ctctcgctcg cctgggcgat cgcgcagctg ggctgggtcg ccggccccgc    360

cgccatgctc ctcttcgcct tcgtcacata ctacaccgcc acgctgctcg ccgagtgcta    420

ccgcacgggc gacccggaga cgggcaagcg caactacacc tacatggacg ccgtgcgctc    480

caacctcggc ggcgccaagg tcgcgttctg cggcgtcata cagtacgcca acctcgtcgg    540

cgtcgccatc ggctacacca tcgcggcgtc catcagcatg aaggccgtca ggagagctgg    600

gtgcttccac gcccacgggc acgctgatcc ctgcaacagc tccagcaccc cgtacatgat    660

cctcttcggc gtcgtgcaga tcctcttctc gcagataccc gacttcgacc agatttggtg    720

gctctccatt gtcgccgccg tcatgtcctt cacttactct tccatcgggc tctccctcgg    780

catcgcacag accatctcca atggtgggtt catgggcagt ctcactggca tcagcatcgg    840

cgccggtgtc acctccacgc agaagatctg gcatacgctt caggcattcg gagacatcgc    900

cttcgcctac tccttctcca acatcctcat cgagatccaa gacacgatca aggcaccgcc    960

accgtcggag tccaaggtga tgcagaaggc gacgcgcctc agcgtggcga cgaccaccat   1020

cttctacatg ctgtgcgggt gcatggggta cgcggcgttc ggcgacaagg cgccggacaa   1080

cctcctcacc ggcttcggct tcttcgagcc gttctggctc atcgacatcg ccaacgtcgc   1140

catcgtcgtg cacctggtcg gcgcgtacca ggtgttctgc cagcccatct tcgccttcgt   1200

cgagcgccgc gccgccgcgg cctggcccga cagcgccttc gtctcccagg agctccgcgt   1260

gggccccttc gcggtcagcg tgttccgcct gacatggcgg tcgtccttcg tgtgcgtcac   1320

caccgtcgtt gccatgctgc tgccgttctt cggcaacgtg gtggggttcc tcggcgccgt   1380

ctccttctgg ccgctcaccg tctacttccc cgtcgagatg tacatcaagc agcgccgcgt   1440

gccgcgcggc agcaccaagt ggatctgtct ccagacgctc agcgtcagct gcctcctcgt   1500

ctccgtggcg gccgccgact agtgagctcg tcgac                              1535
```

<210> SEQ ID NO 8
<211> LENGTH: 473
<212> TYPE: PRT
<213> ORGANISM: Zea mays

<400> SEQUENCE: 8

```
Met Gly Arg Ser Gly Gly Gly Asp Gly Asp Gly Asp Gly Asp Arg Leu
1               5                   10                  15

Leu Leu Gly Lys Pro Leu Glu Ser Ser Ser Ser Cys Ser Ser Ser Asp
            20                  25                  30

Glu Ser Leu Val Lys Arg Thr Gly Thr Val Trp Thr Ala Met Ala His
        35                  40                  45

Ile Ile Thr Ala Val Ile Gly Ser Gly Val Leu Ser Leu Ala Trp Ser
    50                  55                  60

Val Ala Gln Leu Gly Trp Val Gly Gly Pro Ala Ala Met Val Phe Phe
65                  70                  75                  80

Ala Gly Val Thr Ala Val Gln Ser Thr Leu Ile Ala Asp Cys Tyr Ile
                85                  90                  95

Cys His His Pro Glu Arg Gly Gly Val Val Arg Asn Arg Ser Tyr Val
            100                 105                 110

Asp Ala Val Arg Ile Tyr Leu Gly Asp Lys Ser His Leu Phe Cys Gly
        115                 120                 125
```

```
Phe Phe Leu Asn Leu Ser Leu Phe Gly Thr Gly Val Val Tyr Thr Leu
    130                 135                 140

Thr Ser Ala Thr Ser Met Arg Ala Ile Arg Lys Ala Asn Cys Tyr His
145                 150                 155                 160

Arg Glu Gly His Asp Ala Pro Cys Ser Val Gly Gly Asp Gly Tyr Tyr
                165                 170                 175

Met Leu Leu Phe Gly Leu Ala Gln Val Leu Leu Ser Gln Ile Pro Asn
            180                 185                 190

Phe His Glu Met Ala Gly Leu Ser Ile Phe Ala Ala Val Met Ser Cys
        195                 200                 205

Phe Tyr Ala Phe Val Gly Val Gly Leu Gly Val Ala Lys Val Ile Ala
    210                 215                 220

Asn Gly Val Ile Met Gly Gly Ile Gly Gly Ile Pro Leu Val Ser Thr
225                 230                 235                 240

Thr Gln Lys Val Trp Arg Val Ser Gln Ala Leu Gly Asp Ile Leu Phe
                245                 250                 255

Ala Tyr Pro Phe Ser Leu Val Leu Leu Glu Ile Glu Asp Thr Leu Arg
            260                 265                 270

Ser Pro Pro Pro Glu Ser Glu Thr Met Lys Lys Ala Thr Arg Ala Ser
        275                 280                 285

Ile Ala Ile Thr Thr Leu Phe Tyr Leu Cys Cys Gly Cys Phe Gly Tyr
    290                 295                 300

Ala Ser Phe Gly Asp Gly Thr Pro Gly Asn Leu Leu Thr Gly Phe Gly
305                 310                 315                 320

Phe Tyr Glu Pro Tyr Trp Leu Ile Asp Leu Ala Asn Leu Ala Ile Val
                325                 330                 335

Leu His Leu Leu Gly Gly Tyr Gln Val Tyr Thr Gln Pro Val Phe Ala
            340                 345                 350

Phe Ala Asp Arg Lys Phe Gly Gly Gly Ala Thr Val Val Glu Ala Pro
        355                 360                 365

Leu Leu Pro Val Pro Gly Ala Arg Arg Val Asn Ala Asn Val Phe Arg
    370                 375                 380

Leu Cys Phe Arg Thr Ala Tyr Val Ala Ala Thr Thr Ala Leu Ala Val
385                 390                 395                 400

Trp Phe Pro Tyr Phe Asn Gln Ile Ile Gly Leu Leu Gly Ser Phe Thr
                405                 410                 415

Phe Trp Pro Leu Ala Val Tyr Phe Pro Val Glu Met Tyr Leu Thr Arg
            420                 425                 430

Asn Lys Val Ala Pro Trp Thr Asn Gln Trp Leu Ala Ile His Ala Phe
        435                 440                 445

Ser Leu Val Cys Leu Leu Ile Ser Ala Phe Ala Ser Val Gly Ser Ala
    450                 455                 460

Val Gly Val Phe Gly Ser Glu Thr Ser
465                 470

<210> SEQ ID NO 9
<211> LENGTH: 1700
<212> TYPE: DNA
<213> ORGANISM: Zea mays

<400> SEQUENCE: 9

gaaggagaag ggggagctgt aatcctacct aagaagcggc gatggggcgg tcaggaggcg     60

gcgacgggga cggcgacggc gaccggctcc tcctcggcaa gcccttggag tcgtcgtcgt    120
```

-continued

```
cgtgcagctc gtccgacgag agcctggtca agagaaccgg cacggtatgg acggcgatgg    180

cgcacatcat cacggcggtg atcgggtccg gcgtgctgtc cctggcgtgg agcgtggcgc    240

agctggggtg ggtgggcggg cctgcggcga tggtgttctt cgccggcgtc accgcggtgc    300

agtccaccct catcgccgac tgctacatct gccaccaccc ggagcgagga ggcgtcgtca    360

ggaaccgctc ctacgtcgac gccgtgcgca tctacctggg cgacaagagc catttgtttt    420

gcggcttctt cctcaacctg agcttgtttg gcaccggtgt ggtgtacacg ctcacttccg    480

ccactagcat gagggcgatc cggaaggcca attgctacca cagggaaggc cacgacgcgc    540

cgtgctcggt gggaggagac ggctactaca tgctgctctt cggcctcgcg caggtgctgc    600

tgtcgcagat acccaacttc cacgagatgg cggggctctc catcttcgcc gccgtcatgt    660

cctgcttcta cgccttcgtc ggcgtcggcc tcggcgtcgc caaagtcatc gcaaacgggg    720

tgatcatggg cggcatcgga ggcatcccgc tggtgtccac gacgcagaag gtgtggcgag    780

tctcgcaggc cctcggggac atcttgttcg cctacccttt ctcgttggtg ctgctggaaa    840

tagaggacac gctgaggtcg ccgccgccgg agagcgagac gatgaaaaag gcgacgagag    900

cgagcatcgc tatcaccacc ctcttctacc tctgctgcgg gtgctttggc tacgcgtcgt    960

tcggcgacgg caccccgggc aacctcctca ccggcttcgg cttctacgag ccctactggc   1020

tcatcgacct cgccaacctc gccatcgttc tccacctcct cggcggctac caggtgtaca   1080

cgcagccggt gttcgcgttc gcggaccgca agttcggcgg cggggccacg gtcgtcgagg   1140

cgccgctgct gccggtgccg ggcgcgcgcc gcgtgaacgc gaacgtgttc aggctgtgct   1200

tccgcacggc gtacgtggcg gcgaccacgg cgctggccgt ctggttcccc tacttcaacc   1260

agatcatcgg gctgctcggc tccttcacct tctggccgct cgccgtctac ttccccgtcg   1320

agatgtacct cacgaggaac aaggtggcgc cgtggaccaa ccagtggctc gccatccatg   1380

cgttcagcct cgtctgcctg ctcatcagcg cgttcgcctc cgtcggctct gcggttggcg   1440

tgttcgggtc ggagacgagc tgattcaaac tctgcaaatg caattgccgg ccacttttcg   1500

gacatgcatg ttctgtgcat atactgcgct tgtacattta gcgttatacc tagtactgga   1560

acggtcaggc cgggccccga gcctcgtgct taggctcaaa cgggtctggg cccagaaggt   1620

ccaaattttt ttggatcata ccgtgtcagc ctaaagagta gaaatagtgg tttagccagg   1680

ctctaaaaaa aaaaaaaaaa                                               1700
```

```
<210> SEQ ID NO 10
<211> LENGTH: 547
<212> TYPE: PRT
<213> ORGANISM: Zea mays

<400> SEQUENCE: 10

Met Trp Leu Trp Thr Arg Gln Lys Ser Pro Pro Val Gly Arg Arg Pro
1               5                   10                  15

Pro Lys Val Ser Ser Ile Arg Pro Leu Arg Ala Thr Gln Ser Ala Ser
            20                  25                  30

Pro Thr Gln Gly Trp Ile Ala Ser Ala Asp Glu Leu Tyr Ser Leu Leu
        35                  40                  45

Thr Val Leu Val Thr Arg Leu Ala Thr Arg His Glu Leu Arg Ala Leu
    50                  55                  60

Arg Phe Pro Asn Ala Gly Cys Trp Pro Met Ala Gln His His Gly Ser
65                  70                  75                  80

His Ser Leu Glu Val Gly Gly Val Gly Ala Gly Gly Val Glu Leu Asp
                85                  90                  95
```

-continued

```
Asp Asp Gly His Ala Ala Arg Thr Gly Asn Leu Trp Thr Cys Phe Ala
            100                 105                 110

His Ile Ile Thr Ala Val Ile Gly Cys Gly Val Leu Ala Leu Ser Trp
        115                 120                 125

Ser Val Ala Gln Leu Gly Trp Val Gly Gly Pro Val Ala Met Leu Cys
    130                 135                 140

Phe Ala Phe Val Thr Tyr Leu Ser Ala Phe Leu Leu Ser His Cys Tyr
145                 150                 155                 160

Arg Ser Pro Ala Ser Asp Asp Gly Ser Leu Lys Arg Gln Arg Asn Tyr
                165                 170                 175

Thr Tyr Met Asp Ala Val Arg Thr His Leu Gly Glu Lys Arg Thr Trp
            180                 185                 190

Leu Cys Gly Leu Phe Gln Tyr Leu Asn Met Tyr Gly Thr Ala Ile Ala
        195                 200                 205

Tyr Thr Ile Thr Thr Ala Thr Cys Leu Arg Ala Ile Val Arg Ala Asn
    210                 215                 220

Cys Tyr His Ser Gln Gly His Ser Ala Pro Cys Gly Ala Gly Gly Asp
225                 230                 235                 240

His Leu Tyr Met Leu Leu Phe Gly Ala Ala Gln Ala Val Leu Ser Leu
                245                 250                 255

Ile Pro Asn Phe His Ser Met Ala Trp Leu Ser Ala Val Ala Ala Val
            260                 265                 270

Met Ser Phe Thr Tyr Ala Thr Ile Gly Leu Gly Leu Gly Leu Ala Lys
        275                 280                 285

Thr Ile Glu Asn Gly Ala Ile Lys Gly Ser Val Ala Gly Val Pro Met
    290                 295                 300

Ser Thr Ala Pro Gln Lys Val Trp Arg Val Ala Gln Ala Ile Gly Asp
305                 310                 315                 320

Ile Ala Phe Ala Tyr Pro Tyr Thr Ile Val Leu Leu Glu Ile Gln Asp
                325                 330                 335

Thr Leu Lys Ser Pro Pro Pro Glu Ser Glu Thr Met Gln Lys Gly Asn
            340                 345                 350

Val Leu Ala Val Leu Ala Thr Thr Phe Phe Tyr Leu Ala Val Gly Cys
        355                 360                 365

Phe Gly Tyr Ala Ala Phe Gly Asn Ala Ala Pro Gly Asn Leu Leu Thr
    370                 375                 380

Gly Phe Gly Phe Tyr Glu Pro Tyr Trp Leu Ile Asp Phe Ala Asn Ala
385                 390                 395                 400

Cys Ile Val Leu His Leu Leu Gly Gly Tyr Gln Met Phe Ser Gln Gln
                405                 410                 415

Ile Phe Thr Phe Ala Asp Arg Ser Leu Ala Ala Arg Phe Pro Asn Ser
            420                 425                 430

Ala Phe Val Asn Lys Ser Tyr Ala Val Lys Val Pro Gly Ala Pro Ala
        435                 440                 445

Ser Trp Ser Tyr Ser Leu Asn Leu Gln Arg Leu Cys Phe Arg Thr Ala
    450                 455                 460

Tyr Val Ala Ser Thr Thr Gly Leu Ala Leu Leu Phe Pro Tyr Phe Asn
465                 470                 475                 480

Glu Val Leu Gly Val Leu Gly Ala Val Val Phe Trp Pro Leu Ala Ile
                485                 490                 495

Tyr Leu Pro Val Glu Met Tyr Cys Val Gln Arg Gly Val Leu Pro Trp
            500                 505                 510
```

-continued

```
Thr Arg Thr Trp Val Ala Leu Gln Ala Phe Ser Val Val Cys Phe Val
        515                 520                 525

Val Gly Thr Phe Ala Phe Val Gly Ser Val Glu Gly Val Ile Arg Lys
    530                 535                 540

Arg Leu Gly
545
```

```
<210> SEQ ID NO 11
<211> LENGTH: 1906
<212> TYPE: DNA
<213> ORGANISM: Zea mays

<400> SEQUENCE: 11

gctcgtcctg cttcgtacta ccagtagtag cacgtaaacc agggcgccac gccagccgga      60

tcggatcgtc ttggatgtgg gcatgtggct gtggacgaga caaaagtctc cgcccgtcgg     120

ccgtcgcccg ccaaaggtct cttcgatccg gcctctccgg gccacccagt cggccagtcc     180

cacacaagga tggatcgcta gcgccgatga gctatactct ttgctcactg tactagtcac     240

acgattggct acacgacacg agctcagagc tctcaggttt cccaacgccg gctgctggcc     300

aatggcgcag caccacggca gccactccct ggaggtcggc ggcgtcggcg ccggcggcgt     360

cgagctcgac gacgacggcc acgccgcgcg caccggcaac ctatggacct gcttcgcgca     420

catcatcacc gccgtgatcg gctgcggcgt gctggcgctc tcgtggagcg tcgcgcagct     480

gggctgggtg ggcggccctg tcgccatgct ctgcttcgcc ttcgtcacct acctctccgc     540

cttcctcctg tcccactgct acaggtcccc tgcctccgat gatggctccc tgaaacgcca     600

gaggaactac acctacatgg acgccgtcag gacgcacctg gggggagaagc gcacctggct     660

ctgcggcctg ttccagtacc tcaacatgta cgggaccgca atcgcctaca ccatcaccac     720

ggcgacctgt ctcagggcga tcgtgagggc caactgctac cacagccagg gccacagcgc     780

tccctgcggc gccggcggcg accacctcta catgctgctc ttcggggcgg cccaggcggt     840

gctgtccctc atacccaact tccacagcat ggcctggctc tccgccgtcg ccgccgtcat     900

gtccttcacc tacgccacca tcggcctcgg cctcggcctc gccaagacca tagaaaatgg     960

ggcgatcaaa ggaagcgtcg ccggagttcc gatgagcacc gcgccgcaga aagtctggcg    1020

agtcgcgcag gccatcggcg acatcgcgtt cgcctacccg tacaccattg tcctactgga    1080

gatacaggac acgctcaaat cgccgccacc agagagcgag acgatgcaga aggggaacgt    1140

gctcgcggtc ctggccacca cgttcttcta cctcgccgtg ggtgcttcg ggtacgccgc    1200

cttcggcaac gctgcgccgg gcaacctgct caccggcttc ggcttctacg agccgtactg    1260

gctcatcgac ttcgccaacg cctgcatcgt gctccacctg cttggtggct accagatgtt    1320

cagccagcag atcttcacct tcgcggaccg gtccttggcg gccaggttcc cgaacagcgc    1380

gttcgtgaac aaatcctacg ccgtgaaggt gcccggcgcg ccggcgtcgt ggagctacag    1440

cctcaacctg cagcggctgt gtttccggac ggcgtacgtg gcgagcacca cggggctggc    1500

cctcctcttc ccctacttca acgaggtgct gggcgtgctg ggcgccgtcg tcttctggcc    1560

cctcgccatc tacctccccg tcgagatgta ctgcgtccag cgcggggtcc tgccgtggac    1620

gcggacgtgg gtcgcgcttc aggcattcag cgtcgtctgc ttcgtcgtcg gcaccttcgc    1680

cttcgtcggc tccgtcgagg gagtcatccg caagaggctc ggctagttgt ggtattagcg    1740

ccttttctgt cgtcaaccat gtcatgaatg gtggaagtgt gtaaagagag tgtactgtat    1800

ctaagttttt tttatttccc tgtgttcgct tagccatgag cccatgacca tgatgattga    1860
```

-continued

```
tgaatatatc tacccgtgcg tgtttagatc caaaaaaaaa aaaaaa                 1906


<210> SEQ ID NO 12
<211> LENGTH: 447
<212> TYPE: PRT
<213> ORGANISM: Zea mays

<400> SEQUENCE: 12

Pro Arg Val Arg Ser Ala His Ile Ile Thr Ala Val Ile Gly Ser Gly
1               5                   10                  15

Val Leu Ser Leu Gly Trp Ala Ile Ala Gln Leu Gly Trp Val Ala Gly
            20                  25                  30

Pro Val Val Met Leu Leu Phe Ser Leu Val Thr Tyr Tyr Thr Ser Ser
        35                  40                  45

Leu Leu Ala Asp Cys Tyr Arg Ser Gly Asp Pro Ser Thr Gly Lys Arg
    50                  55                  60

Asn Tyr Thr Tyr Met Asp Ala Val Asn Ala Asn Leu Ser Gly Ile Lys
65                  70                  75                  80

Val Gln Ile Cys Gly Phe Leu Gln Tyr Ala Asn Ile Val Gly Val Ala
                85                  90                  95

Ile Gly Tyr Thr Ile Ala Ala Ser Ile Ser Met Leu Ala Ile Arg Arg
            100                 105                 110

Ala Asn Cys Phe His Gln Lys Gly His Gly Asn Pro Cys Lys Ile Ser
        115                 120                 125

Ser Thr Pro Tyr Met Ile Ile Phe Gly Val Ala Glu Ile Phe Phe Ser
    130                 135                 140

Gln Ile Pro Asp Phe Asp Gln Ile Ser Trp Leu Ser Ile Leu Ala Ala
145                 150                 155                 160

Val Met Ser Phe Thr Tyr Ser Ser Ile Gly Leu Gly Leu Gly Val Val
                165                 170                 175

Gln Val Ile Ala Asn Arg Gly Val Gln Gly Ser Leu Thr Gly Ile Thr
            180                 185                 190

Ile Gly Val Val Thr Pro Met Asp Lys Val Trp Arg Ser Leu Gln Ala
        195                 200                 205

Phe Gly Asp Val Ala Phe Ala Tyr Ser Tyr Ser Leu Ile Leu Ile Glu
    210                 215                 220

Ile Gln Asp Thr Ile Arg Ala Pro Pro Pro Ser Glu Ser Thr Val Met
225                 230                 235                 240

Lys Arg Ala Thr Val Val Ser Val Ala Val Thr Thr Leu Phe Tyr Met
                245                 250                 255

Leu Cys Gly Cys Met Gly Tyr Ala Ala Phe Gly Asp Gly Ala Pro Gly
            260                 265                 270

Asn Leu Leu Thr Gly Phe Gly Phe Tyr Glu Pro Phe Trp Leu Leu Asp
        275                 280                 285

Val Ala Asn Ala Ala Ile Val Val His Leu Val Gly Ala Tyr Gln Val
    290                 295                 300

Tyr Cys Gln Pro Leu Leu Ala Phe Val Glu Lys Trp Ala Ala Gln Arg
305                 310                 315                 320

Trp Pro Asp Ser Ala Tyr Ile Thr Gly Glu Val Glu Val Pro Leu Pro
                325                 330                 335

Leu Pro Ala Ser Arg Arg Arg Cys Cys Lys Val Asn Leu Phe Arg Ala
            340                 345                 350

Thr Trp Arg Thr Ala Phe Val Val Ala Thr Thr Val Val Ser Met Leu
        355                 360                 365
```

-continued

```
Leu Pro Phe Phe Asn Asp Val Val Gly Phe Leu Gly Ala Leu Gly Phe
    370                 375                 380

Trp Pro Leu Thr Val Tyr Phe Pro Val Glu Met Tyr Val Val Gln Lys
385                 390                 395                 400

Lys Val Pro Arg Trp Ser Ser Arg Trp Val Cys Leu Gln Met Leu Ser
                405                 410                 415

Leu Gly Cys Leu Val Ile Ser Ile Ala Ala Ala Ala Gly Ser Ile Ala
            420                 425                 430

Gly Ile Ala Ser Asp Leu Lys Val Tyr Arg Pro Phe Lys Ser Tyr
        435                 440                 445
```

<210> SEQ ID NO 13
<211> LENGTH: 1558
<212> TYPE: DNA
<213> ORGANISM: Zea mays

<400> SEQUENCE: 13

```
ccacgcgtcc ggagcgcgca catcatcacg gcggtgatcg gctccggggt gctctcgctg     60
gggtgggcca tcgcgcagct cggctgggtg gccggacccg tcgtcatgct gctcttctcg    120
ctcgtcacct actacacctc gtcgctgctc gcagactgct accgctccgg cgaccccagc    180
accggcaagc ggaactacac ctacatggac gccgtcaacg cgaacctcag tggcatcaag    240
gtccagatct gcgggttcct gcagtacgcc aacatcgtgg gcgtggccat cggctacacc    300
atcgctgcct ccattagcat gctcgcgatc aggagggcca actgcttcca ccagaaggga    360
cacggcaacc cctgcaagat ctccagcacg ccctacatga tcatcttcgg cgtggcggag    420
atcttcttct cgcagatccc ggacttcgac cagatctcct ggctctccat cctcgccgcc    480
gtcatgtcct tcacctactc ctccattggg ctcggcctgg gcgtcgtcca agtcatcgcg    540
aacagaggcg tgcagggcag cctgaccggc atcaccatcg gcgtggtgac cccgatggac    600
aaggtgtggc gcagcctcca ggcgttcggc gacgtcgcct tcgcctactc ctactccctc    660
atcctgatcg agatccagga caccatccgg gcgccgccgc cgtcggagtc gacggtgatg    720
aagcgcgcca cggtggtgag cgtggcggtc accacgctct tctacatgct gtgcggctgc    780
atggggtacg cggcgttcgg cgacggcgcg cccgggaacc tcctcacggg cttcggcttc    840
tacgagccct tctggctcct ggacgtggcc aacgccgcca tcgtggtcca cctggtcggc    900
gcctaccagg tctactgcca gccgctgctc gccttcgtgg agaagtgggc cgcgcagcgg    960
tggccggact cggcgtacat caccggggag gtcgaggtcc cgctcccgct cccggcgagc   1020
cggcggcggt gctgcaaggt gaacctgttc cgggcgacgt ggcggacggc gttcgtcgtg   1080
gccacgacgg tcgtgtccat gctgctgccc ttcttcaacg acgtggtggg cttcctgggc   1140
gcgctcggct tctggccgct caccgtctac ttccccgtcg agatgtacgt ggtgcagaag   1200
aaggtgccgc ggtggagctc ccggtgggtg tgcctgcaga tgctcagcct cggctgcctc   1260
gtcatctcca tcgccgccgc agccgggtcc atcgccggca tcgcgtccga cctcaaagtc   1320
taccgcccgt tcaagtccta ctgatcagat tcacggccta cgggagacgc agcagcatgt   1380
ggtatatagg catatactag caaccatgtt cgtgagttgc aactcataag tacttaaatc   1440
agactctgca tcattgctaa acgcgagttt ttttaacttg tatacgcatg attcatgagt   1500
cccaattaca tatgaaaagg atgcaaaaaa aaaaaaaaaa aaaaaaaaaa aaaaaaa      1558
```

<210> SEQ ID NO 14
<211> LENGTH: 462
<212> TYPE: PRT

<213> ORGANISM: Zea mays

<400> SEQUENCE: 14

```
Gly Asp His Gly Ala Ala Leu Pro Leu Ile Ala Asp Gln Ala Lys His
1               5                   10                  15

Ala Ala Ala Gly Gly Ile Val Arg Ser Gly Ser Met Trp Thr Ala Ala
            20                  25                  30

Ala His Val Ile Thr Ala Val Ile Gly Ser Gly Val Leu Ser Leu Ala
        35                  40                  45

Trp Ser Ile Ala Gln Leu Gly Trp Val Ala Gly Pro Ala Ala Met Leu
    50                  55                  60

Val Phe Ala Ala Val Thr Ala Leu Gln Ser Thr Leu Phe Ala Asp Cys
65                  70                  75                  80

Tyr Arg Ser Pro Asp Pro Glu His Gly Pro His Arg Asn Arg Thr Tyr
                85                  90                  95

Ala Lys Ala Val Asp Arg Asn Leu Gly Ser Asn Ser Ser Trp Val Cys
            100                 105                 110

Met Leu Leu Gln His Thr Ala Leu Phe Gly Tyr Gly Ile Ala Tyr Thr
        115                 120                 125

Ile Thr Ala Ser Ile Ser Cys Arg Ala Ile Leu Lys Ala Asn Cys Tyr
    130                 135                 140

His Glu His Gly His Asp Ala His Cys Asp Tyr Asp Gly Asn Tyr Tyr
145                 150                 155                 160

Met Leu Ile Phe Gly Gly Val Gln Leu Leu Leu Ser Phe Ile Pro Asp
                165                 170                 175

Phe His Asp Met Ala Trp Leu Ser Val Val Ala Ala Ala Met Ser Phe
            180                 185                 190

Ser Tyr Ala Phe Ile Gly Leu Gly Leu Gly Leu Ala Arg Thr Ile Ala
        195                 200                 205

Asn Gly Thr Ile Lys Gly Ser Ile Thr Gly Val Arg Met Arg Thr Pro
    210                 215                 220

Met Gln Lys Val Trp Arg Val Ser Gln Ala Ile Gly Asp Ile Ala Phe
225                 230                 235                 240

Ala Tyr Pro Tyr Ser Leu Ile Leu Leu Glu Ile Gln Asp Thr Leu Lys
                245                 250                 255

Ser Pro Pro Ala Glu Asn Lys Thr Met Lys Arg Ala Ser Met Ile Ser
            260                 265                 270

Ile Leu Val Thr Thr Phe Phe Tyr Leu Cys Cys Gly Cys Leu Gly Tyr
        275                 280                 285

Ala Ala Phe Gly Ser Asp Ala Pro Gly Asn Leu Leu Thr Gly Phe Gly
    290                 295                 300

Leu Tyr Gly Pro Tyr Trp Leu Ile Asp Phe Ala Asn Ala Cys Ile Ile
305                 310                 315                 320

Leu His Leu Leu Gly Gly Tyr Gln Val Tyr Ser Gln Pro Ile Phe Gln
                325                 330                 335

Phe Ala Glu Arg Leu Leu Ala Glu Arg Phe Pro Asp Ser Gly Phe Val
            340                 345                 350

Asn Gly Gly Ser Tyr Thr Val Arg Phe Ala Cys Leu Arg Ala Cys Arg
        355                 360                 365

Val Asn Pro Leu Arg Val Cys Leu Arg Thr Leu Tyr Val Ala Ser Thr
    370                 375                 380

Thr Ala Val Ala Val Ala Leu Pro Tyr Phe Asn Glu Val Leu Ala Leu
385                 390                 395                 400
```

-continued

```
Leu Gly Ala Leu Ser Phe Trp Pro Leu Ala Ile Tyr Phe Pro Val Glu
                405                 410                 415

Met Tyr Phe Ile Gln Arg Asn Val Arg Arg Trp Ser Ala Arg Trp Val
            420                 425                 430

Val Leu Gln Thr Phe Ser Val Val Cys Leu Leu Val Ser Ala Phe Ala
        435                 440                 445

Leu Val Gly Ser Ile Glu Gly Leu Ile Ser Lys Lys Leu Gly
    450                 455                 460
```

<210> SEQ ID NO 15
<211> LENGTH: 1617
<212> TYPE: DNA
<213> ORGANISM: Zea mays

<400> SEQUENCE: 15

```
gcggggatca cggcgccgcc ctgcccctca tcgcggacca ggcgaaacat gccgccgccg      60

gtggcatcgt ccgaagcggg agcatgtgga cggcagcggc acacgtgatc acggcggtga     120

tcgggtccgg cgtgctgtcg ctggcgtgga gcatcgcgca gctggggtgg gtggccgggc     180

cggccgccat gctcgtcttc gcggccgtga cggcgctcca gtccacgctc ttcgccgact     240

gctaccggtc gccggacccc gagcacggcc ctcaccgcaa ccgcacctac gccaaagccg     300

tggaccgcaa cctaggtagc aacagctcgt gggtgtgcat gcttctgcag cacacggccc     360

tgttcggcta tggcatcgcc tacaccatca cggcctccat cagctgcagg gcgatcctga     420

aggcgaactg ctaccacgag catgggcatg acgcgcactg cgactacgat ggcaactact     480

acatgctcat cttcggcggc gtccagctcc tcctctcctt catacctgac ttccacgaca     540

tggcgtggct ctccgtcgtc gccgcggcca tgtcgttctc gtacgccttc atcggcctcg     600

gcctcggcct cgcaagaacc attgctaacg ggacgatcaa aggaagcata acaggtgttc     660

ggatgaggac gcctatgcag aaggtttggc gcgtctcgca ggccatcggc gacattgcct     720

tcgcgtaccc ctactccttg atcctcctgg aaatacagga caccctgaag tcaccgccgg     780

ccgagaacaa gacgatgaag agggcgtcga tgatctcgat cctcgtcacg acattcttct     840

acctctgctg cggctgcttg ggctacgccg ccttcggcag cgacgcgccg ggcaacctcc     900

ttaccggctt cggcttgtac ggtccgtact ggctcatcga cttcgccaac gcgtgcatca     960

tcctccacct gctgggcggg taccaggtgt acagccagcc gatattccag ttcgcggagc    1020

ggctcttggc ggagcggttc ccggacagcg ggttcgtgaa cggcggctcc tacaccgtcc    1080

ggttcgcgtg cctgcgggcg tgccgggtga acccgctgcg cgtgtgcctc cggacgctgt    1140

acgtggcctc cacgacggcg gtggccgtgg cgttacccta cttcaacgag gtgctggcgc    1200

tgctgggcgc gctcagcttc tggccgctgg ccatctactt ccccgtggag atgtacttca    1260

tccagcggaa cgtgcgccgg tggtccgccc gctgggtcgt cctgcagacc ttcagcgtcg    1320

tctgcctgct cgtcagcgcc ttcgcgctcg tcggctccat cgaggggcta atcagcaaga    1380

agctaggcta ggctaggcta gtccgatcca gtggaacacc ctatctgcag gtctgtcaga    1440

gagtggcagc gggctcggtt attttcacag tgttgccttc ctcctgcatc gggttgtaag    1500

ttgtaacata tatgtcgtat tgatactggc gagttcagat gttcagaaga agtagaacgc    1560

gtgtgacgat tctgtgttaa aaaaaaaaaa aaaaaaaaaa aaaaaaaaaa aaaaaaa       1617
```

<210> SEQ ID NO 16
<211> LENGTH: 478
<212> TYPE: PRT
<213> ORGANISM: Zea mays

```
<400> SEQUENCE: 16

Met Glu Val Ser Ser Val Glu Phe Gly His His Ala Ala Ala Ala Ser
1               5                   10                  15

Lys Cys Phe Asp Asp Asp Gly Arg Leu Lys Arg Thr Gly Thr Met Trp
            20                  25                  30

Thr Ala Ser Ala His Ile Ile Thr Ala Val Ile Gly Ser Gly Val Leu
        35                  40                  45

Ser Leu Ala Trp Ala Ile Ala Gln Leu Gly Trp Val Ala Gly Pro Thr
    50                  55                  60

Val Met Leu Leu Phe Ser Phe Val Thr Tyr Tyr Thr Ser Ala Leu Leu
65                  70                  75                  80

Ala Asp Cys Tyr Arg Ser Gly Asp Ala Cys Thr Gly Lys Arg Asn Tyr
                85                  90                  95

Thr Tyr Met Asp Ala Val Asn Ala Asn Leu Ser Gly Val Lys Val Trp
            100                 105                 110

Phe Cys Gly Phe Leu Gln Tyr Ala Asn Ile Val Gly Val Ala Ile Gly
        115                 120                 125

Tyr Thr Ile Ala Ala Ser Ile Ser Met Leu Ala Ile Gln Arg Ala Asn
    130                 135                 140

Cys Phe His Val Glu Gly His Gly Asp Pro Cys Asn Ile Ser Ser Thr
145                 150                 155                 160

Pro Tyr Met Ile Ile Phe Gly Val Val Gln Ile Phe Phe Ser Gln Ile
                165                 170                 175

Pro Asp Phe Asp Gln Ile Ser Trp Leu Ser Ile Leu Ala Ala Val Met
            180                 185                 190

Ser Phe Thr Tyr Ser Thr Ile Gly Leu Gly Leu Gly Ile Ala Gln Val
        195                 200                 205

Val Ser Asn Lys Gly Val Gln Gly Ser Leu Thr Gly Ile Ser Val Gly
    210                 215                 220

Leu Val Thr Pro Val Asp Lys Met Trp Arg Ser Leu Gln Ala Phe Gly
225                 230                 235                 240

Asp Ile Ala Phe Ala Tyr Ser Tyr Ser Leu Ile Leu Ile Glu Ile Gln
                245                 250                 255

Asp Thr Ile Arg Ala Pro Pro Pro Ser Glu Ser Lys Val Met Arg Arg
            260                 265                 270

Ala Thr Val Val Ser Val Ala Val Thr Thr Phe Phe Tyr Met Leu Cys
        275                 280                 285

Gly Cys Met Gly Tyr Ala Ala Phe Gly Asp Asn Ala Pro Gly Asn Leu
    290                 295                 300

Leu Thr Gly Phe Gly Phe Tyr Glu Pro Phe Trp Leu Leu Asp Val Ala
305                 310                 315                 320

Asn Ala Ala Ile Ala Val His Leu Val Gly Ala Tyr Gln Val Tyr Cys
                325                 330                 335

Gln Pro Leu Phe Ala Phe Val Glu Lys Trp Ala Arg Gln Arg Trp Pro
            340                 345                 350

Lys Ser Arg Tyr Ile Thr Gly Glu Val Asp Val Pro Leu Pro Leu Gly
        355                 360                 365

Thr Ala Gly Gly Arg Cys Tyr Lys Leu Ser Leu Phe Arg Leu Thr Trp
    370                 375                 380

Arg Thr Ala Phe Val Val Ala Thr Thr Val Val Ser Met Leu Leu Pro
385                 390                 395                 400

Phe Phe Asn Asp Val Val Gly Leu Leu Gly Ala Leu Gly Phe Trp Pro
```

-continued

```
            405                 410                 415

Leu Thr Val Tyr Phe Pro Val Glu Met Tyr Ile Val Gln Lys Lys Val
        420                 425                 430

Pro Arg Trp Ser Thr Arg Trp Val Cys Leu Gln Leu Leu Ser Val Ala
    435                 440                 445

Cys Leu Val Ile Thr Val Ala Ser Ala Ala Gly Ser Val Ala Gly Ile
450                 455                 460

Val Ser Asp Leu Lys Val Tyr Lys Pro Phe Val Thr Thr Ser
465                 470                 475


<210> SEQ ID NO 17
<211> LENGTH: 1977
<212> TYPE: DNA
<213> ORGANISM: Zea mays

<400> SEQUENCE: 17

ccacgcgtcc gctacaatat atatccggct ctctctgtgt gcgtgctcta actgcagcgg     60

agcctcacag ttgttcgtgt gctgtgtatt tgtcactggt ggtgctgtgc agaccaagct    120

actgcgggag ggagaagggt gtgtgccggc ccgccgccaa gcactgctac ccggccggcg    180

gccatggagg tgagctccgt ggagttcggt catcacgcgg cggccgcctc aaagtgcttt    240

gacgacgacg gtcgcctcaa gcgcacaggg acgatgtgga cggcgagcgc gcacattatc    300

acggccgtga tagggtccgg ggtgctgtcg ctcgcgtggg ccatcgcgca gctcggctgg    360

gtggcaggcc ccaccgtcat gctgctcttc tccttcgtca cctactacac atcggcccta    420

ctcgccgact gctaccgctc cggcgacgcc tgcaccggca agcgcaacta cacgtacatg    480

gacgcggtta acgccaatct cagtggcgtc aaggtctggt tctgcgggtt cctgcagtac    540

gccaacatcg tcggagtcgc cataggctac accattgccg cctctattag catgctggcg    600

atccagaggg cgaactgctt ccacgtggag gggcacgggg acccctgcaa catctccagc    660

acgccctaca tgatcatctt cggcgtcgtg cagattttct tctcgcagat cccggacttc    720

gaccagatat cgtggctctc catcctcgcc gccgtcatgt cgttcaccta ctccaccatc    780

ggcctgggcc tgggcatcgc gcaggtggtg tccaacaagg gcgtgcaggg cagcctgacg    840

gggatcagcg tcggcttggt caccccggtc gacaagatgt ggcgcagcct gcaggcgttc    900

ggcgacatcg ccttcgccta ctcctactcg ctcatcctca tcgagatcca ggacaccatc    960

cgcgcgccgc cgccgtccga gtccaaggtc atgcggcgcg ccaccgtcgt cagcgtggcc   1020

gtcaccacgt tcttctacat gctgtgcggg tgcatggggt acgccgcgtt cggggacaac   1080

gcccccggga acctcctcac gggcttcggc ttctacgagc ccttctggct cctcgacgtc   1140

gccaacgccg ccatcgccgt gcacctcgtc ggcgcctacc aggtctactg ccagcccctg   1200

ttcgccttcg tcgagaagtg ggcgcgccag aggtggccca agtcccgcta catcacgggc   1260

gaggtcgacg tcccgctccc gctcgggacc gccggcggcc ggtgctacaa gctcagcctg   1320

ttccggctga cgtggcggac ggcgttcgtg gtggccacga cggtggtgtc catgctgctg   1380

cccttcttca acgacgtggt cgggctcctg ggcgcgctgg ggttctggcc gctcaccgtc   1440

tacttccccg tggagatgta catcgtgcag aagaaggtgc ccaggtggag cacgcggtgg   1500

gtgtgcctgc agctgctcag cgtcgcctgc ctcgtcatca ccgtcgcctc cgccgcaggc   1560

tccgttgccg ggatcgtctc tgacctcaaa gtgtacaaac cgttcgtcac cacctcctga   1620

tcgaccgtac gtcctagctt ccgtgcagtt caaaacacat acgcacgaac agatcattaa   1680

ttggcgccta gtatatatgt gcagtcttta attaaattaa ctaggcatta atcgatcgat   1740
```

```
taccactacg tcgttctagt gatgcgcgta gcttgcatca tcgctcgctg atttaatttc   1800

cattgttttt ctttgatgat ctggttagcc gaaatggcta gtgaattaag agaaaacaaa   1860

tagtagcagt actgtgtgag taatcccaag tcaaatacgt tattgaagtt gtcggcggta   1920

caaaacgctt gtaaaatgtt tgtgtttcaa ttaatcaaga agaattgtac gtgtttc      1977
```

```
<210> SEQ ID NO 18
<211> LENGTH: 884
<212> TYPE: DNA
<213> ORGANISM: Zea mays

<400> SEQUENCE: 18

cccgttcctc tctatctcac acacaggcac accgagtaga aggcggcagt tgccagccag     60

cacaagcaga gcgcaacccg tgggcggcag cggcacgcaa tggtgtcgga gaggcagcag    120

gcggcgggga aggtggccgc cttcaacctc acggaggccg ggttcggcga cgggtcggac    180

ctgctggacg acgacgggcg cgagaggcgc acggggaccc tggtgacggc gagcgcgcac    240

atcatcacgg cggtgatcgg gtcgggcgtg ctgtcgctgg cgtgggcgat cgcgcagctg    300

gggtgggtga tcggccccgt ggtgctgctg gccttctccg ccatcacctg gttctgctcc    360

agcctactcg ccgactgcta ccgcgcgccg ccgggccccg gccagggcaa gcggaactac    420

acctacggac aggccgtcag gtcatacctg ggggagtcca agtaccggct gtgctcgctg    480

gcgcagtacg tcaacctggt gggcgtcacc atcggctaca ccatcaccac ggccatcagc    540

atgggggcga tcaagcgttc caactgcttc cacagcaggg gccacggcgc cgactgcgag    600

gcgtccaaca ccaccaacat gatcatcttc gcgggcatcc agatcctgct gtcgcagctc    660

cccaacttcc acaagctctg gtggctctcc atcgtcgccg ccgtcatgtc cctcgcctac    720

tcctccatcg gactcggcct ctccatcgca aagatcgcag gcaagctcat gcatggcagc    780

tactgtacgt acgttctatc tctcattctg agtcgagact ttggggtgca cgttaagacg    840

tcgctgactg gtgccgccgt gggggtggac gtcaccgcgg ccga                     884
```

```
<210> SEQ ID NO 19
<211> LENGTH: 693
<212> TYPE: DNA
<213> ORGANISM: Zea mays

<400> SEQUENCE: 19

ggctcgagag ctcatcaacg ccacctacta cgtgcgcgtg ccgccatgcc tcctcctcct     60

ccgcacgtcg tcgtcctcgt cgccgccgcc caccctcgcc gtcgcgccgc tcaagctcgt    120

cctgcgcacc atcgtcatca tgttcacaac gctcgtcgcc atgctggtgc ccttcttcaa    180

cgccgtgctg ggcctcatcg gcgcgctcgg cttctggccg ctctccgtct acttccccgt    240

cagcatgcac atggcaaggc tcaacatccg acgcggagag atccgctggt ggatgctgca    300

ggccatgagc ttcgtctgcc tcctcatctc cgtcgcagcc agcatcggat ccgtgcacga    360

catcgtgcac aacctcaagg ccgccgcgcc attcaacact gcaaactgat taataaacat    420

gcatttacta gtatatatac ggatcggatc ggaggagtga tgggttaatt agtttcttaa    480

ttagctttgg ctactatatc tatcagtatc agagtcagag gagcagaggg ccggccacat    540

gcatggcctt tttgtgtttc ttgattatat atctggcaaa tttgatctgt cgagcagatt    600

ttcatgcatg catgcatgct gctaattcgg acgtacgttg aactagtaat aatattatta    660

tttgtaatgt aaaaaaaaaa aaaaaaaaaa aaa                                693
```

<210> SEQ ID NO 20
<211> LENGTH: 726
<212> TYPE: DNA
<213> ORGANISM: Zea mays

<400> SEQUENCE: 20

```
ccacgcgtcc gcacgtccag gctagtgctg ggggtcacca cgacgctggt gatcgtcaac      60
tgcctcacca cgttccagat ctacgccatg ccggtgtacg acaacatgga ggccgggtac     120
gtgcacaaga agaaccgccc gtgcccgtgg tggatgcgct cgggcttccg cgccttcttc     180
ggcgcggtca acttcctcat cgccgtcgcg ctgccgttcc tgtcgcagct cgccggcctc     240
ctcggaggga tctcgctgcc ggtcaccctg gcctacccgt gcttcatgtg ggtggccatc     300
aagaagccgc ggaagggcac cgccacgtgg aacgtcaact gggcgctggg aatcctcggc     360
atgagcataa gccttgtcct catagtcgga aacctgtggg gccttgtgga gaaaggcttg     420
cgggtcaagt tctttaagcc tgccgattcc cagtgaaaaa aaggatgcag atttgtcaat     480
cggttagatt tgtaatgcca tgcttttata tatgttgatt tcttcgccaa gaacgtataa     540
tgtcctcctg caccttgaca atttgcaaga aagcaaagtc cagttaaggt actcgtggtc     600
gttcctcgtg ccattgtgcc ttttgctcat tttttttct ttatttatgc gctttatata      660
aaaaaaaaaa aaaaaaaaaa aaaaaaaaaa aaaaaaaaaa aaaaaaaaaa aaaaaaaaaa     720
aaaaaa                                                                726
```

<210> SEQ ID NO 21
<211> LENGTH: 1155
<212> TYPE: DNA
<213> ORGANISM: Zea mays

<400> SEQUENCE: 21

```
ccacgcgtcc gatgtccttc acctactccg ccatcggctt gtccctcggc atcgcgcaga      60
ctgttgcaaa cggtgggttc aagggaagcc tcaccggcat cagcatcggc gccgacgtca     120
cctccacgca gaaagtgtgg cacagcctgc aggccttcgg cgacatcgcg ttcgcctact     180
ccttctccaa catcctcatc gagatccaag acacgatcaa ggcaccgccg ccgtcggagt     240
cgaaggtgat gcagaaggcg acgcggctga gcgtggcgac gacgaccatc ttctacatgc     300
tgtgcgggtg catggggtac gcggcgttcg gcgacaaggc gccggacaac ctgctgacgg     360
ggttcggctt cttcgagcca ttctggctga tcgacgtggc caacgtggcc atcgtggtgc     420
acctggtggg cgcgtaccag gtgttctgcc agcccatctt cgccttcgtg gagcggcgcg     480
ccgccgcggc ctggcccgac agcgccttcg tcgcgcggga gctccgcgtg gggcccctcg     540
ccctcagcgt gttccgcctc acgtggcggt cggcgttcgt gtgcgtcacc accgtcgtgg     600
ccatgctgct ccccttcttc ggcaacgtgg tggggttcct cggcgccgtc tccttctggc     660
ccctcaccgt ctacttcccc gtcgagatgt acatcaagca gcgccgcgtg ccccgcggca     720
gcaccaagtg ggtctgcctc cagacgctca gcgtcgcgtg cctggtcgtc tccatcgccg     780
ccgccgccgg ctccatcgcc gacgtcatcg aggcgctcaa ggtttaccac ccgttcagca     840
gttaattctt gctgctgtgg ctgtgctggg gcctggactg gcctgggttt ggacgtatgt     900
gcatgcagca ttcattgcgg tgcgttcaac tgtggtcaac aagggaggga gacggatgca     960
gatgtttgca tggaggcccc tatagaacaa gtgaaaggtt taggcgccct tgtgcacatg    1020
ctggtcgcat tccttgcaag aataccaggg gtggggccag aatggcatga gctgggtgtt    1080
tgttgtgatg acgagtctac tgtaggtgta tgaagcagca acaaaaaaca tgttcctttc    1140
```

```
aaaaaaaaaa aaaaa                                                    1155

<210> SEQ ID NO 22
<211> LENGTH: 1013
<212> TYPE: DNA
<213> ORGANISM: Zea mays

<400> SEQUENCE: 22

ccacgcgtcc gacgttgcct tcgcgtacac ctactccatg cttctcatag aaatccagga     60

cactgtgaag gcaccgccat cagagaacgt gacgatgaag agggccagct tctacggcat    120

cagcgtgacg accatcttct acgtctcgct cgggtgcatc ggctacgcgg ccttcggcaa    180

cgccgcgccg gggaacgtgc ttaccggctt cgacgagccg ttctggctcg tcgacgtcgc    240

caacatcgcc gtggtcgtcc acttggttgg ggcatatcag gtgtacgcgc agccgatctt    300

cgcgtgctac gagaagtggc tggggtcccg gtggccggac tcggccttct tccaccacga    360

gtacgcggtg cgcctgcccg gctgcgcggt gcggttcacg atgtgcaagc tggtgctgcg    420

cacggcgttc gtggccgcca cgacggtggt gtcgctgatg ctgcccttct tcaacgccgt    480

gctcgggctg ctgggcgcca tcgccttctg gccgctgacg gtgtacttcc cggtgaccat    540

gtacatcgcg caggccaagg tggcgcccgg cagccgcaag tgggtggcgc tgcaggcgct    600

caatgtgggc gcgctcctgg tttcgctgct cgccgccgtg ggctccgtgg ccgacatggt    660

gcagcgcctg ggccatgtca ccatctttca gacgcagctc tgaaacaagt attcagatct    720

tatgcatggg aacgcgcttg cagaggcata catcatacac atgcttgtgc cgtatattca    780

cctgtgatct tagtacattg gttttggaag aacaactaaa aatggagcat gtaagtcatt    840

ccacctagat ttcgtgcatt gcaagagtgc tttttggggt gaaatagcag acagtgcaca    900

ctccatgaca catttgaagc ccagctaagc gttgggctga attaatgatt atgtttcttc    960

aaaaaaaaaa aaaaaaaaaa aaaaaaaaaa aaaaaaaaaa aaaaaaaaaa aaa          1013

<210> SEQ ID NO 23
<211> LENGTH: 999
<212> TYPE: DNA
<213> ORGANISM: Zea mays

<400> SEQUENCE: 23

ccacgcgtcc gctcctacgc ctacatcctc atcgagatac aggacacgat caaggcgccg     60

ccgccatcgg aagtgacggt gatgaagaag gccacgatgg tgagcgtggc gacgacgacg    120

gtgttctaca tgctgtgcgg ctgcatgggc tacgcggcgt tcggcgacga cgccccggac    180

aacctcctga ccgggttcgg cttctacgag cccttctggc tcctggacgt cgccaacgcc    240

gccatcgtcg tgcacctcgt tggcgcgtac caggtcttct gccagccgct cttcgccttc    300

gtggagaagc gggcggcagc caggtggccc gacagccggt tcatgacccg ggagctgagg    360

ctggggccct tcgtgctcgg cgtgttccgt ctcacctggc ggacggcctt cgtctgcctc    420

accaccgtcg tcgccatgat gctccctttc ttcggcgacg tcgtggggct gctcggcgcc    480

gtctccttct ggccgctcag cgtctacttc cccgtcgaga tgtacaaagc gcagcgtcgc    540

gtgcgcaggt ggagcacgcg ctggctctgc ctccagacgc tcagcgccgt gtgcctcctc    600

gtttccatcg ccggcgccgt tggctccacg gccggcgtca taaacgcagt caatttgcac    660

cgaccattca gtggctaaga gcgtgtgctc tactgctccg tgcatcctcg tcttctctcg    720

ctccgtcgca gtcactatct atagcggacc aaattaacca agcactccat tagcgtggct    780
```

```
gtttatcaag cctgctcctg ttctgtttat gcaggcggag cctgcagctt gtttgcacgc    840

ccggggcata aagttggtgt ccatcttcta catgtcacgg ttatattgta ttttttttaag    900

atgagcacgc ctgatcacac cctaagattc ctgtaaggta cactccaatg agaggtagat    960

tgaaggcaaa aaaaaaaaaa aaaaaaaaaa aaaaaaaaa                           999
```

<210> SEQ ID NO 24
<211> LENGTH: 538
<212> TYPE: PRT
<213> ORGANISM: Oryza sativa

<400> SEQUENCE: 24

```
Met Ala Lys Asp Val Glu Met Ala Val Arg Asn Gly Asp Gly Gly Gly
1               5                   10                  15

Gly Gly Gly Tyr Tyr Ala Thr His Pro His Gly Gly Ala Gly Gly Glu
            20                  25                  30

Asp Val Asp Asp Asp Gly Lys Gln Arg Arg Thr Gly Asn Val Trp Thr
        35                  40                  45

Ala Ser Ala His Ile Ile Thr Ala Val Ile Gly Ser Gly Val Leu Ser
    50                  55                  60

Leu Ala Trp Ala Thr Ala Gln Leu Gly Trp Val Val Gly Pro Val Thr
65                  70                  75                  80

Leu Met Leu Phe Ala Leu Ile Thr Tyr Tyr Thr Ser Gly Leu Leu Ala
                85                  90                  95

Asp Cys Tyr Arg Thr Gly Asp Pro Val Ser Gly Lys Arg Asn Tyr Thr
            100                 105                 110

Tyr Met Asp Ala Val Ala Ala Tyr Leu Gly Gly Trp Gln Val Trp Ser
        115                 120                 125

Cys Gly Val Phe Gln Tyr Val Asn Leu Val Gly Thr Ala Ile Gly Tyr
    130                 135                 140

Thr Ile Thr Ala Ser Ile Ser Ala Ala Ala Val His Lys Ala Asn Cys
145                 150                 155                 160

Tyr His Lys Asn Gly His Asp Ala Asp Cys Gly Val Tyr Asp Thr Thr
                165                 170                 175

Tyr Met Ile Val Phe Gly Val Val Gln Ile Phe Phe Ser Met Leu Pro
            180                 185                 190

Asn Phe Ser Asp Leu Ser Trp Leu Ser Ile Leu Ala Ala Val Met Ser
        195                 200                 205

Phe Ser Tyr Ser Thr Ile Ala Val Gly Leu Ser Leu Ala Arg Thr Ile
    210                 215                 220

Ser Gly Ala Thr Gly Lys Thr Thr Leu Thr Gly Val Glu Val Gly Val
225                 230                 235                 240

Asp Val Thr Ser Ala Gln Lys Ile Trp Leu Ala Phe Gln Ala Leu Gly
                245                 250                 255

Asp Ile Ala Phe Ala Tyr Ser Tyr Ser Met Ile Leu Ile Glu Ile Gln
            260                 265                 270

Asp Thr Val Lys Ser Pro Pro Ala Glu Asn Lys Thr Met Lys Lys Ala
        275                 280                 285

Thr Leu Leu Gly Val Ser Thr Thr Thr Ala Phe Tyr Met Leu Cys Gly
    290                 295                 300

Cys Leu Gly Tyr Ala Ala Phe Gly Asn Ala Ala Pro Gly Asn Met Leu
305                 310                 315                 320

Thr Gly Phe Gly Phe Tyr Glu Pro Tyr Trp Leu Ile Asp Phe Ala Asn
                325                 330                 335
```

-continued

```
Val Cys Ile Val Val His Leu Val Gly Ala Tyr Gln Val Phe Cys Gln
            340                 345                 350

Pro Ile Phe Ala Ala Val Glu Thr Phe Ala Ala Arg Arg Trp Pro Gly
        355                 360                 365

Ser Glu Phe Ile Thr Arg Glu Arg Pro Val Val Ala Gly Arg Ser Phe
    370                 375                 380

Ser Val Asn Met Phe Arg Leu Thr Trp Arg Thr Ala Phe Val Val Val
385                 390                 395                 400

Ser Thr Val Leu Ala Ile Val Met Pro Phe Phe Asn Asp Ile Leu Gly
                405                 410                 415

Phe Leu Gly Ala Val Gly Phe Trp Pro Leu Thr Val Tyr Tyr Pro Val
            420                 425                 430

Glu Met Tyr Ile Arg Gln Arg Arg Ile Gln Arg Tyr Thr Ser Arg Trp
        435                 440                 445

Val Ala Leu Gln Thr Leu Ser Leu Leu Cys Phe Leu Val Ser Leu Ala
    450                 455                 460

Ser Ala Val Ala Ser Thr Arg Ala Ser Ala Ser Arg Ser Ser Thr Thr
465                 470                 475                 480

Ser Pro Ser Arg Pro Ser Arg Asp Pro Asp His Asp Gly Leu Phe Phe
                485                 490                 495

Leu Leu Leu His Pro Asp Glu Lys Arg Phe Gln Lys His Met His Asn
            500                 505                 510

Lys Cys Arg Lys Leu Ala Lys Ser Leu Val Thr Ser Ser Val Arg Trp
        515                 520                 525

Ser Val Arg Arg Arg Arg Val Gln Leu Val
    530                 535
```

<210> SEQ ID NO 25
<211> LENGTH: 1829
<212> TYPE: DNA
<213> ORGANISM: Oryza sativa

<400> SEQUENCE: 25

```
gtcgacccac gcgtccgacc cggcctagcg agcgagagag agggaagggt tgcgacttgc      60

gactcgcgag cggcgagatg gcgaaggacg tggagatggc ggtgcggaac ggagacggcg     120

gcggcggcgg cggctactac gccacccacc cgcacggcgg cgccggcggc gaggacgtcg     180

acgacgacgg caagcagcgg cgaaccggta acgtatggac ggcgagcgcg cacatcatca     240

cggcggtgat cggctccggc gtgctctctc tcgcatgggc aacggcgcag ctcggctggg     300

tggtcgggcc ggtgactctg atgctcttcg ccctcatcac gtactacacc tctgggctcc     360

tcgccgactg ctaccgcact ggcgatccgg tcagcggcaa gcgcaactac acctacatgg     420

atgccgttgc ggcctactta ggtggctggc aagtctggtc ctgtggtgtt ttccaatatg     480

tcaacctggt tgggacagca attgggtaca caatcacagc atccatcagc gcagcggctg     540

tgcacaaggc caactgctac cacaagaacg gccacgatgc cgattgcggt gtctacgaca     600

ccacgtacat gatcgtcttt ggagtcgtcc agatcttctt ctccatgctg cccaacttca     660

gtgacctctc atggctttcc atcctcgccg cggtcatgtc attctcatac tcgaccattg     720

ccgttggcct ctcgcttgcg cgaacaatat caggtgctac tggtaagact actctgactg     780

gcgttgaggt tggagttgac gtcacttcag cccagaagat ctggctcgcg ttccaagcgc     840

tcggtgacat cgcgttcgcc tactcctact ccatgatcct tatagaaatt caggacacgg     900

tgaagtctcc accggcggag aacaagacga tgaagaaggc aacgctgctg gggtgtcga      960
```

-continued

```
ccacgacggc gttctacatg ctgtgcgggt gcctggggta cgcggcgttc gggaacgcgg   1020

cgccggggaa catgctcacc gggttcggct tctacgagcc ctactggctg atcgacttcg   1080

ccaacgtctg catcgtggtc cacctggtcg gcgcctacca ggtgttctgc cagcccatct   1140

tcgccgccgt cgagacgttc gccgccaggc ggtggccggg ctcggagttc atcacccggg   1200

agcgccccgt cgtggccggc aggtcgttca gcgtcaacat gttcaggctg acgtggcgga   1260

cggcgttcgt ggtcgtcagc acggtgctcg ccatcgtgat gcccttcttc aacgacatcc   1320

tgggcttcct cggcgccgtc gggttctggc cgctgacggt gtactacccg gtggagatgt   1380

acatccggca gcggcggata cagcggtaca cgtccaggtg ggtggcgctg cagacgctca   1440

gcctcctctg cttcctcgtc tcgctcgcct ccgccgtcgc ctccacgagg gcgtcagcga   1500

gtcgctcaag cactacgtcc ccttcaagac caagtcgtga tcccgatcac gacggccttt   1560

ttttttgct tttgcatcct gatgaaaaaa gatttcagaa acatatgcac aacaaatgcc   1620

ggaagttagc caagagtttg gtcaccagct cggtgcgttg gtcggtcagg aggaggaggg   1680

ttcaacttgt gtaggttaag aaatgctaga gagtatggag accatcttcg attgctgctc   1740

atgtatagaa aaaagaggaa gcttcgtatt catgtaatga atcggaatgt ttaacaaaca   1800

aggcttgttc tgaaaaaaaa aaaaaaaaa                                     1829
```

<210> SEQ ID NO 26
<211> LENGTH: 495
<212> TYPE: PRT
<213> ORGANISM: Oryza sativa

<400> SEQUENCE: 26

```
Met Gly Met Glu Arg Pro Gln Glu Lys Val Ala Thr Thr Thr Thr Ala
1               5                   10                  15

Ala Phe Asn Leu Ala Glu Ser Gly Tyr Ala Asp Arg Pro Asp Leu Asp
            20                  25                  30

Asp Asp Gly Arg Glu Lys Arg Thr Gly Thr Leu Val Thr Ala Ser Ala
        35                  40                  45

His Ile Ile Thr Ala Val Ile Gly Ser Gly Val Leu Ser Leu Ala Trp
    50                  55                  60

Ala Ile Ala Gln Leu Gly Trp Val Ile Gly Pro Ala Val Leu Val Ala
65                  70                  75                  80

Phe Ser Val Ile Thr Trp Phe Cys Ser Ser Leu Leu Ala Asp Cys Tyr
                85                  90                  95

Arg Ser Pro Asp Pro Val His Gly Lys Arg Asn Tyr Thr Tyr Gly Gln
            100                 105                 110

Ala Val Arg Ala Asn Leu Gly Val Ala Lys Tyr Arg Leu Cys Ser Val
        115                 120                 125

Ala Gln Tyr Val Asn Leu Val Gly Val Thr Ile Gly Tyr Thr Ile Thr
    130                 135                 140

Thr Ala Ile Ser Met Gly Ala Ile Lys Arg Ser Asn Trp Phe His Arg
145                 150                 155                 160

Asn Gly His Asp Ala Ala Cys Leu Ala Ser Asp Thr Thr Asn Met Ile
                165                 170                 175

Ile Phe Ala Gly Ile Gln Ile Leu Leu Ser Gln Leu Pro Asn Phe His
            180                 185                 190

Lys Ile Trp Trp Leu Ser Ile Val Ala Ala Val Met Ser Leu Ala Tyr
        195                 200                 205

Ser Thr Ile Gly Leu Gly Leu Ser Ile Ala Lys Ile Ala Gly Gly Ala
    210                 215                 220
```

-continued

His Pro Glu Ala Thr Leu Thr Gly Val Thr Val Gly Val Asp Val Ser
225 230 235 240

Ala Ser Glu Lys Ile Trp Arg Thr Phe Gln Ser Leu Gly Asp Ile Ala
245 250 255

Phe Ala Tyr Ser Tyr Ser Asn Val Leu Ile Glu Ile Gln Asp Thr Leu
260 265 270

Arg Ser Ser Pro Ala Glu Asn Glu Val Met Lys Lys Ala Ser Phe Ile
275 280 285

Gly Val Ser Thr Thr Thr Thr Phe Tyr Met Leu Cys Gly Val Leu Gly
290 295 300

Tyr Ala Ala Phe Gly Asn Arg Ala Pro Gly Asn Phe Leu Thr Gly Phe
305 310 315 320

Gly Phe Tyr Glu Pro Phe Trp Leu Val Asp Val Gly Asn Val Cys Ile
325 330 335

Val Val His Leu Val Gly Ala Tyr Gln Val Phe Cys Gln Pro Ile Tyr
340 345 350

Gln Phe Ala Glu Ala Trp Ala Arg Ser Arg Trp Pro Asp Ser Ala Phe
355 360 365

Val Asn Gly Glu Arg Val Leu Arg Leu Pro Leu Gly Ala Gly Asp Phe
370 375 380

Pro Val Ser Ala Leu Arg Leu Val Trp Arg Thr Ala Tyr Val Val Leu
385 390 395 400

Thr Ala Val Ala Ala Met Ala Phe Pro Phe Phe Asn Asp Phe Leu Gly
405 410 415

Leu Ile Gly Ala Val Ser Phe Trp Pro Leu Thr Val Tyr Phe Pro Val
420 425 430

Gln Met Tyr Met Ser Gln Ala Lys Val Pro Ala Ile Leu Ala Asp Val
435 440 445

Asp Val Asp Glu Arg Ala Gln Pro Arg Leu Pro Arg Arg Leu Pro Pro
450 455 460

Arg Arg Arg Arg Leu His Pro Gly Pro His Gln Ile Arg Arg Thr Leu
465 470 475 480

Gln Ala Ile Gln Arg Leu Leu Met Ile Lys Leu Ile Ile Ile Cys
485 490 495

<210> SEQ ID NO 27
<211> LENGTH: 1993
<212> TYPE: DNA
<213> ORGANISM: Oryza sativa

<400> SEQUENCE: 27
tcccggggta cgacccatcg ccgtccgccc attaccacct ccacctcgcg cactcagtct 60
gtactacctg tacgtacgtg gccgccgcta gctaagctag gaattgaaat ggggatggag 120
aggccgcaag agaaggtggc caccaccacc accgccgcct tcaacctcgc cgagtccggc 180
tacgccgacc gccccgacct cgacgacgac ggccgcgaga agcgcacagg gacgctggtg 240
acggcgagcg cgcacataat aacggcggtg atcggctccg gcgtgctgtc gctggcgtgg 300
gcgatagcgc agctggggtg ggtgatcggg ccggccgtgc tggtggcgtt ctcggtcata 360
acctggttct gctccagcct cctcgccgac tgctaccgat ctcccgaccc cgtccatggc 420
aagcgcaact acacctacgg ccaagccgtc agggccaacc taggtgtggc caagtacagg 480
ctctgctcgg tggcacagta cgtcaatctc gtcggcgtca ccattggcta caccatcact 540
acggccatca gcatgggtgc gatcaaacgg tccaactggt tccatcgcaa cggccacgac 600

```
gcagcctgct tggcatctga cacgaccaac atgatcatat ttgctggcat ccaaatcctc    660

ctctcgcagc tgccgaattt tcacaaaatt tggtggctct ccattgtcgc tgctgtcatg    720

tcactggcct actcaaccat tggccttggc ctctccattg caaaaattgc aggtggggcc    780

caccccgagg caaccctcac aggggtgact gttggagtgg atgtgtctgc aagtgagaaa    840

atctggagaa cttttcagtc acttggtgac attgcctttg catactccta ctccaatgtc    900

ctcatagaaa ttcaggacac gctgcggtcg agcccggcgg agaacgaggt gatgaagaag    960

gcgtcgttca tcggagtctc gacgacgacg acgttctaca tgctgtgcgg cgtgctcggc   1020

tacgcggcgt tcggcaaccg cgcgccgggg aacttcctca ccggcttcgg cttctacgag   1080

cccttctggc tcgtcgacgt cggcaacgtc tgcatcgtcg tccacctcgt cggcgcctac   1140

caggtcttct gccagcccat ctaccagttc gccgaggcct gggcgcgctc gcggtggccg   1200

gacagcgcct tcgtcaacgg cgagcgcgtg ctccggctgc cgctcggcgc cggcgacttc   1260

cccgtcagcg cgctccgcct cgtctggcgc acggcctacg tcgtgctcac cgccgtcgcc   1320

gccatggcgt tccccttctt caacgacttc ctcggcctca tcggcgccgt ctccttctgg   1380

ccgctcaccg tctacttccc cgtccagatg tacatgtctc aggccaaggt cccggcgatt   1440

ctcgccgacg tggacgtgga tgaacgtgct cagcctcgcc tgcctcgtcg tctccctcct   1500

cgccgccgcc ggctccatcc agggcctcat caaatccgtc gcacattaca agccattcag   1560

cgtctcctca tgatcaaatt aataattatt tgttaatact gatgatgatg atgatatgat   1620

ccatcgatcg atgaagaaca aatatatata tatagcgaga tcgatcgatc gatcaagatc   1680

gtgaatgata tatataatac atagttaatc aatcagatgt taattaagtc gtgttcgtgc   1740

gtgtctttca gagttcagat cgacaggttg atttgagatg agtgctcaag tgtttcgtca   1800

gatgtaatta actatgtaag tggtaaattt agcctgatga tgatgatgat cagtctgaat   1860

ggatgtcatg taagtggtaa atttgacatg aatgtaacaa agtagtagct tagttgcaga   1920

atttcagtag cctaaatgga tgatatatca gtctgaactt caataacaag ttaacagcta   1980

gatttccgtt gac                                                      1993
```

```
<210> SEQ ID NO 28
<211> LENGTH: 475
<212> TYPE: PRT
<213> ORGANISM: Oryza sativa

<400> SEQUENCE: 28

Met Ala Ser Gly Gln Lys Val Val Lys Pro Met Glu Val Ser Val Glu
1               5                   10                  15

Ala Gly Asn Ala Gly Glu Ala Ala Trp Leu Asp Asp Asp Gly Arg Ala
            20                  25                  30

Arg Arg Thr Gly Thr Phe Trp Thr Ala Ser Ala His Ile Ile Thr Ala
        35                  40                  45

Val Ile Gly Ser Gly Val Leu Ser Leu Ala Trp Ala Ile Ala Gln Leu
    50                  55                  60

Gly Trp Val Ala Gly Pro Ala Val Met Leu Leu Phe Ala Phe Val Ile
65                  70                  75                  80

Tyr Tyr Thr Ser Thr Leu Leu Ala Glu Cys Tyr Arg Thr Gly Asp Pro
                85                  90                  95

Ala Thr Gly Lys Arg Asn Tyr Thr Tyr Met Asp Ala Val Arg Ala Asn
            100                 105                 110

Leu Gly Gly Ala Lys Val Thr Phe Cys Gly Val Ile Gln Tyr Ala Asn
```

-continued

```
        115                 120                 125

Leu Val Gly Val Ala Ile Gly Tyr Thr Ile Ala Ser Ser Ile Ser Met
    130                 135                 140

Arg Ala Ile Arg Arg Ala Gly Cys Phe His His Asn Gly His Gly Asp
145                 150                 155                 160

Pro Cys Arg Ser Ser Ser Asn Pro Tyr Met Ile Leu Phe Gly Ala Val
                165                 170                 175

Gln Ile Val Phe Ser Gln Ile Pro Asp Phe Asp Gln Ile Trp Trp Leu
            180                 185                 190

Ser Ile Val Ala Ala Val Met Ser Phe Thr Tyr Ser Gly Ile Gly Leu
        195                 200                 205

Ser Leu Gly Ile Val Gln Thr Ile Ser Asn Gly Gly Ile Gln Gly Ser
    210                 215                 220

Leu Thr Gly Ile Ser Ile Gly Val Gly Val Ser Ser Thr Gln Lys Val
225                 230                 235                 240

Trp Arg Ser Leu Gln Ala Phe Gly Asp Ile Ala Phe Ala Tyr Ser Phe
                245                 250                 255

Ser Asn Ile Leu Ile Glu Ile Gln Asp Thr Ile Lys Ala Pro Pro Pro
            260                 265                 270

Ser Glu Ala Lys Val Met Lys Ser Ala Thr Arg Leu Ser Val Ala Thr
        275                 280                 285

Thr Thr Val Phe Tyr Met Leu Cys Gly Cys Met Gly Tyr Ala Ala Phe
    290                 295                 300

Gly Asp Ala Ala Pro Asp Asn Leu Leu Thr Gly Phe Gly Phe Tyr Glu
305                 310                 315                 320

Pro Phe Trp Leu Leu Asp Val Ala Asn Val Ala Ile Val Val His Leu
                325                 330                 335

Val Gly Ala Tyr Gln Val Phe Val Gln Pro Ile Phe Ala Phe Val Glu
            340                 345                 350

Arg Trp Ala Ser Arg Arg Trp Pro Asp Ser Ala Phe Ile Ala Lys Glu
        355                 360                 365

Leu Arg Val Gly Pro Phe Ala Leu Ser Leu Phe Arg Leu Thr Trp Arg
    370                 375                 380

Ser Ala Phe Val Cys Leu Thr Thr Val Val Ala Met Leu Leu Pro Phe
385                 390                 395                 400

Phe Gly Asn Val Val Gly Leu Leu Gly Ala Val Ser Phe Trp Pro Leu
                405                 410                 415

Thr Val Tyr Phe Pro Val Glu Met Tyr Ile Ala Gln Arg Gly Val Pro
            420                 425                 430

Arg Gly Ser Ala Arg Trp Val Ser Leu Lys Thr Leu Ser Ala Cys Cys
        435                 440                 445

Leu Val Val Ser Ile Ala Ala Ala Ala Gly Ser Ile Ala Asp Val Ile
    450                 455                 460

Asp Ala Leu Lys Val Tyr Arg Pro Phe Ser Gly
465                 470                 475


<210> SEQ ID NO 29
<211> LENGTH: 1609
<212> TYPE: DNA
<213> ORGANISM: Oryza sativa

<400> SEQUENCE: 29

cacacttcct caaatcctcc aacacctcga tccattcgca gtagctgcga ggtgtctgac      60

atggcgtcgg ggcagaaggt ggtgaagccg atggaggtgt cggtggaggc cgggaacgcc     120
```

```
ggggaggcgg cgtggctgga cgacgacggg cgggcgcggc ggacgggcac gttctggacg    180
gcgagcgcgc acatcatcac cgccgtcatc ggctccggcg tgctgtcgct ggcgtgggcg    240
atcgcgcagc tgggctgggt ggccggcccc gccgtgatgc tcctcttcgc cttcgtcatc    300
tactacacct ccaccctcct cgccgagtgc taccgcaccg gcgaccctgc caccggcaag    360
cgcaactaca cctacatgga cgccgtgcgc gccaacctcg gcggcgccaa ggtcaccttc    420
tgcggcgtca tccagtacgc caacctcgtc ggcgtcgcca tcggctacac catcgcgtcg    480
tccatcagca tgcgcgccat caggagggcc ggctgcttcc accacaacgg ccatggtgac    540
ccgtgccgca gctccagcaa cccttacatg atcctcttcg gcgccgtgca gatcgtcttc    600
tcgcagatcc ctgacttcga ccagatttgg tggctgtcca tcgtcgccgc cgtcatgtcc    660
ttcacctact ccggcatcgg cctctccctc ggcatcgtcc agactatctc caatggcggg    720
atccagggca gcctcaccgg catcagcatc ggagtcggcg tcagctcgac gcagaaggtg    780
tggcgcagct tgcaggcatt cggcgacatc gccttcgcat actccttctc caacatcctc    840
atcgagatcc aagacacgat caaggcgccg ccgccgtcgg aggcgaaggt gatgaagagc    900
gcaacgaggc tgagcgtggc gacgaccacg gtgttctaca tgctgtgcgg gtgcatgggc    960
tacgcggcgt tcggcgacgc ggcgcccgac aacctcctca ccggcttcgg gttctacgag   1020
cccttctggc tgctcgacgt cgccaacgtc gccatcgtcg tgcacctcgt cggcgcctac   1080
caggtgttcg tccagccaat cttcgccttc gtcgagcgct gggcctcccg ccggtggccg   1140
gacagcgcgt tcatcgccaa ggagctccgc gtggggccct tcgcgctcag cctcttccgc   1200
ctgacgtggc gctcggcgtt cgtctgcctc accaccgtcg tcgccatgct cctccccttc   1260
ttcggcaacg tggtgggtct cctcggcgcc gtctccttct ggccgctcac cgtctacttc   1320
cccgtcgaga tgtacatcgc gcagcgcggc gtgccacgtg gcagcgcgag gtgggtctca   1380
ctcaagacgc tcagcgcgtg ctgcctcgtc gtctccatcg ccgccgccgc gggctccatt   1440
gctgacgtca tcgacgcgct caaggtgtac aggccgttca gcggatgatt cttctgattc   1500
tctcttgctg ctttgagcag agcatccact ggtaaaaagt ggacagtaat ttcttttttt   1560
tacagtctat ggacgtagta cagtaaaaaa gtgtgtacaa ctgtaaaaa               1609
```

<210> SEQ ID NO 30
<211> LENGTH: 469
<212> TYPE: PRT
<213> ORGANISM: Oryza sativa

<400> SEQUENCE: 30

```
Met Ala Pro Gln Leu Pro Leu Glu Val Ala Ser Ala Pro Lys Leu Asp
1               5                   10                  15

Asp Asp Gly His Pro Gln Arg Thr Gly Asn Leu Trp Thr Cys Val Ala
            20                  25                  30

His Ile Ile Thr Ala Val Ile Gly Cys Gly Val Leu Ala Leu Ser Trp
        35                  40                  45

Ser Val Ala Gln Leu Gly Trp Val Ala Gly Pro Ile Ala Met Val Cys
    50                  55                  60

Phe Ala Phe Val Thr Tyr Ile Ser Ala Phe Leu Leu Ser His Cys Tyr
65                  70                  75                  80

Arg Ser Pro Gly Ser Glu Lys Met Gln Arg Asn Tyr Ser Tyr Met Asp
                85                  90                  95

Ala Val Arg Val His Leu Gly Arg Lys His Thr Trp Leu Cys Gly Leu
            100                 105                 110
```

-continued

```
Leu Gln Tyr Leu Asn Leu Tyr Gly Ile Gly Ile Ala Tyr Thr Ile Thr
        115                 120                 125

Thr Ala Thr Cys Met Arg Ala Ile Lys Arg Ala Asn Cys Tyr His Ser
    130                 135                 140

Glu Gly Arg Asp Ala Pro Cys Asp Ser Asn Gly Glu His Phe Tyr Met
145                 150                 155                 160

Leu Leu Phe Gly Ala Ala Gln Leu Leu Leu Ser Phe Ile Pro Asn Phe
                165                 170                 175

His Lys Met Ala Trp Leu Ser Val Val Ala Ala Ile Met Ser Phe Ala
            180                 185                 190

Tyr Ser Thr Ile Gly Leu Gly Leu Gly Leu Ala Lys Thr Ile Gly Asp
        195                 200                 205

Gly Thr Val Lys Gly Asn Ile Ala Gly Val Ala Met Ala Thr Pro Met
    210                 215                 220

Gln Lys Val Trp Arg Val Ala Gln Ala Ile Gly Asp Ile Ala Phe Ala
225                 230                 235                 240

Tyr Pro Tyr Thr Ile Val Leu Leu Glu Ile Gln Asp Thr Leu Arg Ser
                245                 250                 255

Pro Pro Pro Glu Ser Glu Thr Met Gln Lys Gly Asn Val Ile Ala Val
            260                 265                 270

Leu Ala Thr Thr Phe Phe Tyr Leu Cys Val Gly Cys Phe Gly Tyr Ser
        275                 280                 285

Ala Phe Gly Asn Ala Ala Pro Gly Asn Leu Leu Thr Gly Phe Gly Phe
    290                 295                 300

Tyr Glu Pro Tyr Trp Leu Ile Asp Phe Ala Asn Ala Cys Ile Val Leu
305                 310                 315                 320

His Leu Leu Gly Gly Tyr Gln Met Phe Ser Gln Gln Ile Phe Thr Phe
                325                 330                 335

Ala Asp Arg Cys Phe Ala Ala Ser Phe Pro Asn Ser Ala Phe Val Asn
            340                 345                 350

Arg Ser Tyr Ser Val Lys Ile Leu Pro Trp Arg Arg Gly Gly Gly Gly
        355                 360                 365

Gly Gly Ala Gly Arg Tyr Glu Val Asn Leu Gln Arg Val Cys Phe Arg
    370                 375                 380

Thr Val Tyr Val Ala Ser Thr Thr Gly Leu Ala Leu Val Phe Pro Tyr
385                 390                 395                 400

Phe Asn Glu Val Leu Gly Val Leu Gly Ala Leu Val Phe Trp Pro Leu
                405                 410                 415

Ala Ile Tyr Leu Pro Val Glu Met Tyr Cys Val Gln Arg Arg Ile Ser
            420                 425                 430

Pro Trp Thr Pro Arg Trp Ala Ala Leu Gln Ala Phe Ser Val Val Cys
        435                 440                 445

Phe Val Val Gly Thr Phe Ala Phe Val Gly Ser Val Glu Gly Val Ile
    450                 455                 460

Arg Lys Arg Leu Gly
465
```

<210> SEQ ID NO 31
<211> LENGTH: 1632
<212> TYPE: DNA
<213> ORGANISM: Oryza sativa

<400> SEQUENCE: 31

```
gtcgacccac gcgtccgcaa cgagtcaaat ttgaaggctt cactgagcct ttgacaatgg     60
```

```
cgccgcagct gccgctcgag gtggcctctg ctcccaagct cgacgacgac ggccacccac    120
aacgcaccgg gaatctatgg acgtgcgtag cgcacattat caccgcggtg atcgggtgcg    180
gcgtgctggc gctgtcgtgg agcgtcgcgc agctcggctg ggtggccggc cccatcgcca    240
tggtgtgctt cgccttcgtc acctacatct cggccttcct gctgtcgcac tgctacaggt    300
ctcctggctc ggagaagatg cagaggaact actcctacat ggacgccgtc agagttcact    360
tagggaggaa gcacacttgg ttatgtgggt tgctgcagta cctgaacttg tacgggatag    420
gaattgctta cacaatcact acggcaactt gtatgagggc aattaagagg gcgaactgct    480
accacagcga aggccgtgac gctccctgcg actcgaacgg tgaacacttc tacatgctgc    540
tcttcggagc agcccagctg ctgctgtcct tcatacccaa tttccacaag atggcgtggc    600
tgtccgtcgt cgcggcgatc atgtccttcg cctactccac catcggcctc ggcctcggcc    660
tcgccaagac cattggtgat ggaactgtca aagggaacat tgccggtgtt gcgatggcca    720
ccccaatgca gaaagtttgg cgagtggctc aagcaattgg cgacatcgca ttcgcctacc    780
cgtacaccat cgttctcctg gagatacagg acacgctgag atcgccaccg ccggagagcg    840
agacgatgca gaagggcaac gtgatcgcgg tcctcgccac caccttcttc tacctctgcg    900
tcggctgctt cggctactcc gccttcggca acgccgcgcc gggcaacctc ctcaccggct    960
tcggcttcta cgagccctac tggctcatag acttcgccaa tgcctgcatc gtgctccacc   1020
tcctcggcgg ctaccagatg tttagccagc agatattcac gttcgccgac cggtgcttcg   1080
cggcgagctt cccgaacagc gcgttcgtga acaggtcgta ctccgtcaag atcctcccgt   1140
ggcggcgcgg cggcggcggc ggcggcgcgg ggaggtacga ggtgaacctg cagcgggtgt   1200
gcttcaggac ggtgtacgtg gcgagcacga cggggctggc gctggtgttc ccctacttca   1260
acgaggtgct gggcgtgctc ggcgcgctcg tgttctggcc gctcgccatc tacctccccg   1320
tcgagatgta ctgcgtgcag cggcggatct cgccgtggac gccgcggtgg gccgcgctgc   1380
aggcgttcag cgtcgtctgc ttcgtcgtcg gcacgttcgc gttcgtcggc tcggtggaag   1440
gcgtcatcag aaagaggctt ggctagctag ctagctagta gcgagtaatt tagcctggtc   1500
atcgagaacg aaatgtaaag ctagctcagt gtgccatttc atctgaagta aaaaggcgcg   1560
gtgaactgta caatacatat gcagaaaaaa tgataaacat aagatgttgg ttattaaaaa   1620
aaaaaaaaaa aa                                                        1632
```

<210> SEQ ID NO 32
<211> LENGTH: 451
<212> TYPE: PRT
<213> ORGANISM: Oryza sativa

<400> SEQUENCE: 32

```
Pro Leu Ile Ser Asp Arg Pro Lys His Ala Ala Ile Val Arg Ser Gly
1               5                   10                  15

Thr Glu Trp Thr Ala Ala Ala His Val Ile Thr Ala Val Ile Gly Ser
            20                  25                  30

Gly Val Leu Ser Leu Ala Trp Ser Val Ala Gln Leu Gly Trp Leu Ala
        35                  40                  45

Gly Pro Gly Met Met Leu Val Phe Ala Ala Val Thr Ala Leu Gln Ser
    50                  55                  60

Ala Leu Phe Ala Asp Cys Tyr Arg Ser Pro Asp Pro Glu Val Gly Pro
65                  70                  75                  80

His Arg Asn Arg Thr Tyr Ala Asn Ala Val Glu Arg Asn Leu Gly Ser
```

-continued

```
                85                  90                  95

Ser Ser Ala Trp Val Cys Leu Leu Leu Gln Gln Thr Ala Leu Phe Gly
            100                 105                 110

Tyr Gly Ile Ala Tyr Thr Ile Thr Ala Ser Ile Ser Cys Arg Ala Ile
        115                 120                 125

Leu Arg Ser Asn Cys Tyr His Thr His Gly His Asp Ala Pro Cys Lys
    130                 135                 140

Tyr Gly Gly Ser Tyr Tyr Met Leu Met Phe Gly Ala Ala Gln Leu Phe
145                 150                 155                 160

Leu Ser Phe Ile Pro Asp Phe His Asp Met Ala Trp Leu Ser Val Leu
                165                 170                 175

Ala Ala Val Met Ser Phe Ser Tyr Ser Phe Ile Gly Leu Gly Leu Gly
            180                 185                 190

Leu Ala Asn Thr Ile Ala Asn Gly Thr Ile Lys Gly Ser Ile Thr Gly
        195                 200                 205

Ala Pro Thr Arg Thr Pro Val Gln Lys Val Trp His Val Ser Gln Ala
    210                 215                 220

Ile Gly Asp Ile Ala Phe Ala Tyr Pro Tyr Ser Leu Ile Leu Leu Glu
225                 230                 235                 240

Ile Gln Asp Thr Leu Lys Ala Pro Pro Ala Glu Asn Lys Thr Met Lys
                245                 250                 255

Lys Ala Ser Ile Ile Ser Ile Val Val Thr Thr Phe Phe Tyr Leu Cys
            260                 265                 270

Cys Gly Cys Phe Gly Tyr Ala Ala Phe Gly Ser Asp Ala Pro Gly Asn
        275                 280                 285

Leu Leu Thr Gly Phe Gly Phe Tyr Glu Pro Tyr Trp Leu Ile Asp Phe
    290                 295                 300

Ala Asn Ala Cys Ile Ile Leu His Leu Leu Gly Gly Tyr Gln Val Tyr
305                 310                 315                 320

Ser Gln Pro Ile Tyr Gln Phe Ala Asp Arg Phe Phe Ala Glu Arg Tyr
                325                 330                 335

Pro Ala Ser Arg Phe Val Asn Asp Phe His Thr Val Lys Leu Pro Leu
            340                 345                 350

Leu Pro Pro Cys Arg Val Asn Leu Leu Arg Val Cys Phe Arg Thr Val
        355                 360                 365

Tyr Val Ala Ser Thr Thr Ala Val Ala Leu Ala Phe Pro Tyr Phe Asn
    370                 375                 380

Glu Val Leu Ala Leu Leu Gly Ala Leu Asn Phe Trp Pro Leu Ala Ile
385                 390                 395                 400

Tyr Phe Pro Val Glu Met Tyr Phe Ile Gln Arg His Val Pro Arg Trp
                405                 410                 415

Ser Pro Arg Trp Val Val Leu Gln Ser Phe Ser Val Leu Cys Leu Leu
            420                 425                 430

Val Ser Ala Phe Ala Leu Val Gly Ser Ile Gln Gly Leu Ile Ser Gln
        435                 440                 445

Lys Leu Gly
450
```

<210> SEQ ID NO 33
<211> LENGTH: 1692
<212> TYPE: DNA
<213> ORGANISM: Oryza sativa

<400> SEQUENCE: 33

-continued

```
gcggccgccg ccgccgttcc tctcatctcg gatcgcccca agcatgccgc catcgtcaga     60

agcgggacgg agtggacggc ggcggcgcac gtgatcacgg cggtgatcgg gtccggggtg    120

ctgtcgctgg cgtggagcgt ggcgcagctg ggtggctgg cggggccggg gatgatgctc    180

gtgttcgcgg ccgtgacggc gctgcagtcg gcgctgttcg ccgactgcta ccgctcgccg    240

gacccggagg tcggcccgca ccgcaaccgc acctacgcca acgccgtcga gcgcaaccta    300

ggtagctcga gcgcgtgggt ctgcttgttg ctgcagcaaa cggccttgtt cggctacggc    360

atcgcctaca ccatcaccgc ctccatcagt tgcagggcga tcctgaggtc caactgctac    420

cacacgcacg gccacgacgc gccctgcaaa tacgggggta gctactacat gctcatgttc    480

ggcgcggcgc agctgttcct ctccttcata ccggacttcc acgacatggc gtggctgtcg    540

gtcctcgccg cggtcatgtc gttctcctac tcgttcatcg gcctcggcct cggcctcgcc    600

aacacaattg ctaatggaac gatcaaagga agcataacag gtgctccaac gagaacccct    660

gtgcagaagg tctggcacgt ctcgcaggcc atcggcgaca tcgcattcgc gtacccgtac    720

tcattaatcc tcttggaaat tcaggacaca ctgaaggctc caccggccga gaacaagacg    780

atgaagaagg cgtccatcat ctcgatcgtc gtcaccacct tcttctacct ctgctgcggc    840

tgcttcggct acgccgcctt cgggagcgac gcccctggca acctcctcac cggcttcggc    900

ttctacgagc cctactggct catcgacttc gccaacgcct gcatcatcct ccacctgctc    960

ggcggctacc aggtgtacag ccagccgata taccagttcg cggacaggtt cttcgcggag   1020

aggtacccgg cgagccggtt cgtgaacgac ttccacacgg tgaagctgcc gctgctgccg   1080

ccgtgtcggg tgaacctcct gcgggtgtgc ttccggacgg tgtacgtggc gagcaccacg   1140

gcggtggcgc tcgccttccc ctacttcaac gaggtgctcg cgctgctcgg cgccctcaac   1200

ttctggccgc tcgccatcta cttccccgtg gagatgtact tcatccagcg ccatgtcccg   1260

cggtggtcgc cccggtgggt cgtgctgcag tcgttcagcg tcctctgcct cctcgtcagc   1320

gccttcgcgc tcgtcggctc catccagggc ctcatcagcc agaagctagg ctaaagattt   1380

agcctagcat cctgaatttc ggatttgctt tttctttgtg taaccgtaat gggatgagaa   1440

tgcatttggt ggtcgtgtgt tgtttgtaac aactggggag cggagctttg tccctggtga   1500

atggcgcgat gaactcatga acaatagcat agtggtggtg gtacattgtg tctgcagggg   1560

tcagagggtg gtggcactct gtttttcagt gcctttcctc ctgtgctgca gagaaactgc   1620

tcctatatat gtacagaatg tcgtcatatt attgccatga tacttggaaa aaaaaaaaaa   1680

aaaaaaaaaa aa                                                       1692
```

<210> SEQ ID NO 34
<211> LENGTH: 470
<212> TYPE: PRT
<213> ORGANISM: Glycine max

<400> SEQUENCE: 34

```
Met Gly Ser Met His Ile Glu Thr Pro Glu Thr Phe Ala Asp Gly Ser
1               5                   10                  15

Lys Asn Phe Asp Asp Asp Gly Arg Ala Lys Arg Thr Gly Thr Trp Ile
            20                  25                  30

Thr Ala Ser Ala His Ile Ile Thr Ala Val Ile Gly Ser Gly Val Leu
        35                  40                  45

Ser Leu Ala Trp Ala Ile Ala Gln Met Gly Trp Val Ala Gly Pro Ala
    50                  55                  60

Val Leu Phe Val Phe Ser Leu Ile Thr Tyr Phe Thr Ser Thr Leu Leu
```

-continued

```
65                  70                  75                  80

Ala Asp Cys Tyr Arg Ser Pro Asp Pro Val His Gly Lys Arg Asn Tyr
                85                  90                  95

Thr Tyr Ser Glu Val Val Lys Ala Asn Leu Gly Gly Arg Lys Phe Gln
            100                 105                 110

Leu Cys Gly Leu Ala Gln Tyr Ile Asn Leu Val Gly Val Thr Ile Gly
        115                 120                 125

Tyr Thr Ile Thr Ala Ser Leu Ser Met Gly Ala Val Lys Lys Ser Asn
    130                 135                 140

Cys Leu His Lys His Gly His Gln Asp Glu Cys Lys Val Lys Asp Asn
145                 150                 155                 160

Ala Phe Met Ile Ala Phe Ala Cys Ile Gln Ile Leu Leu Ser Gln Ile
                165                 170                 175

Pro Asn Phe His Lys Leu Ser Trp Leu Ser Ile Val Ala Ala Val Met
            180                 185                 190

Ser Phe Ala Tyr Ser Ser Ile Gly Leu Gly Leu Ser Ile Ala Lys Ile
        195                 200                 205

Ile Gly Gly Gly His Val Arg Thr Thr Leu Thr Gly Val Glu Val Ser
    210                 215                 220

Gly Thr Glu Lys Val Trp Lys Met Phe Gln Ala Ile Gly Asp Ile Ala
225                 230                 235                 240

Phe Ala Tyr Ala Phe Ser Asn Val Leu Ile Glu Ile Gln Asp Thr Leu
                245                 250                 255

Lys Ser Ser Pro Pro Glu Asn Lys Val Met Lys Arg Ala Ser Leu Ile
            260                 265                 270

Gly Ile Met Thr Thr Thr Leu Phe Tyr Val Leu Cys Gly Cys Leu Gly
        275                 280                 285

Tyr Ala Ala Phe Gly Asn Asp Ala Pro Ser Asn Phe Leu Thr Gly Phe
    290                 295                 300

Gly Phe Tyr Glu Pro Phe Trp Leu Ile Asp Phe Ala Asn Val Cys Ile
305                 310                 315                 320

Ala Val His Leu Val Gly Ala Tyr Gln Val Phe Val Gln Pro Ile Phe
                325                 330                 335

Gly Phe Val Glu Lys Trp Ser Lys Glu Asn Trp Thr Glu Ser Gln Phe
            340                 345                 350

Ile Asn Gly Glu His Thr Leu Asn Ile Pro Leu Cys Gly Ser Tyr Asn
        355                 360                 365

Val Asn Phe Phe Arg Val Val Trp Arg Thr Ala Tyr Val Ile Ile Thr
    370                 375                 380

Ala Val Val Ala Met Leu Leu Pro Phe Phe Asn Asp Phe Leu Ala Leu
385                 390                 395                 400

Ile Gly Ala Leu Ser Phe Trp Pro Leu Thr Val Tyr Phe Pro Ile Glu
                405                 410                 415

Met Tyr Ile Lys Lys Ser Asn Met Gln Arg Phe Ser Phe Thr Trp Thr
            420                 425                 430

Trp Leu Lys Ile Leu Ser Trp Val Cys Leu Ile Ile Ser Ile Ile Ser
        435                 440                 445

Leu Val Gly Ser Ile Gln Gly Leu Ser Val Ser Ile Lys Lys Tyr Lys
    450                 455                 460

Pro Phe Gln Ala Glu Gln
465                 470
```

<210> SEQ ID NO 35

<211> LENGTH: 1905
<212> TYPE: DNA
<213> ORGANISM: Glycine max

<400> SEQUENCE: 35

```
ttgtgatctc tccgtaggga caataccatg cctcttggtc ctttctctaa tccaaatatc     60

tctccgttaa tgctctcacc acaaacttca atagactagc caaaagctaa caccaactat    120

aggccaaatc accaataaat attatttccc gttcttttgg cgtgttggcc acccactgaa    180

cacatttgca ctcacacata gaagcagaga gaggccattg gttggtttca gagatgggaa    240

gcatgcacat agaaacccca gaaacttttg ctgatggtag caaaaacttc gatgatgatg    300

gacgagctaa aagaactggg acttggatta ctgcaagtgc tcatatcata acggctgtga    360

ttggttctgg agtgctatct cttgcatggg caattgcaca gatgggttgg gtagctggtc    420

ctgcagtgct ctttgtcttc tctttgataa catacttcac ctccactctt ctcgctgact    480

gttaccgttc acctgaccct gtacatggca agcgaaacta cacatattct gaggttgtca    540

aagccaacct aggaggaaga aaatttcagc tgtgtggatt ggctcagtat ataaatcttg    600

ttggtgtaac aatcggctac actataactg catcacttag tatgggggcg gtgaagaagt    660

cgaactgttt acacaaacat ggccatcaag acgagtgcaa agttaaggac aacgctttta    720

tgattgcttt tgcctgcatc caaattcttc taagccaaat accaaacttc cataagctct    780

cttggctctc tatcgtagca gctgttatgt cttttgctta ttcttccatt gggcttggcc    840

tttccatagc caaaatcata ggtgggggac acgtgcgaac aaccttaaca ggggtggaag    900

tttcgggaac ggaaaaggtt tggaaaatgt ttcaagctat cggtgacatt gcctttgctt    960

atgctttttc taatgtccta attgagatcc aggacacact gaaatcaagc ccacctgaga   1020

acaaagtcat gaagagagca agtttgattg gcattatgac tacaacattg ttttatgtac   1080

tatgtgggtg cttaggctat gctgcatttg gaaatgatgc accatctaat ttcctcacag   1140

gattcggctt ctatgagccc ttttggctaa tagactttgc caatgtctgc atagcagtgc   1200

acttagttgg ggcataccag gtctttgtcc aacctatatt tgggtttgtg gaaaagtgga   1260

gcaaagaaaa ttggacagaa agccaattta taaatggcga gcatactttg aacattcctc   1320

tatgtggaag ctacaatgtg aacttcttta gggtagtgtg gaggactgca tatgtgatta   1380

tcactgccgt tgtagctatg ttactcccat tcttcaatga ctttttggcc cttattggtg   1440

cactctcttt ctggccattg acggtttact tccctataga gatgtacatt aagaagtcaa   1500

atatgcaaag attttccttc acctggactt ggctcaagat attgagttgg gtttgcttga   1560

tcatttctat tatctcactt gtgggttcca tccaaggcct ttcggttagt atcaagaaat   1620

acaagccctt ccaagcagaa caatagaact ttcatactta gtattccaac ttgagccaag   1680

agtttctatt gagggcgaca aaatttgtat tactatgttt tgaaatagtt gttatatttt   1740

caattctcga aatcgagaca acttgttata ctaaagtaat ataataaaat gtttagtttg   1800

ctatgttaaa aaaaaaaaaa aaagggcggc cgcccttttt tttttttttt taattaataa   1860

aaaaattaat cttattataa aaaaaaaaaa aaaaaaaaaa aaaaa                   1905
```

<210> SEQ ID NO 36
<211> LENGTH: 461
<212> TYPE: PRT
<213> ORGANISM: Glycine max

<400> SEQUENCE: 36

```
Met Gly Glu Glu Glu Ile Asp Asp Ser Pro Leu Ile Gln Gly Phe Pro
```

-continued

```
1               5                   10                  15

Ser Gly Asp Val Pro Phe Arg Arg Thr Gly Asn Val Glu Arg Ala Val
            20                  25                  30

Ala His Ile Ile Thr Gly Val Ile Gly Ala Gly Val Leu Ser Leu Ala
        35                  40                  45

Trp Ser Val Ala Gln Leu Gly Trp Ile Ala Gly Pro Phe Ile Ile Ile
    50                  55                  60

Val Phe Ala Gly Thr Thr Phe Leu Ser Ala Asn Leu Leu Ser Asp Cys
65                  70                  75                  80

Tyr Arg Phe Pro His Pro Leu Tyr Gly Asn Ile Arg Cys Pro Ser Tyr
                85                  90                  95

Ile Asp Ala Val Lys Val Tyr Leu Gly Asp Ser Arg Gln Lys Val Cys
            100                 105                 110

Gly Val Leu Val His Ala Ser Leu Tyr Gly Ala Thr Thr Ala Tyr Val
        115                 120                 125

Ile Thr Ser Ala Thr Ser Ile Arg Ala Ile Leu Lys Ser Asn Cys Tyr
    130                 135                 140

His Lys Glu Gly His Gln Ala Pro Cys Lys Tyr Gly Asp Ala Val Tyr
145                 150                 155                 160

Met Met Leu Phe Gly Leu Val Gln Ile Ile Met Ser Phe Ile Pro Asp
                165                 170                 175

Leu His Asn Met Ala Trp Val Ser Ile Val Ala Ala Ile Met Ser Phe
            180                 185                 190

Thr Tyr Ser Ser Ile Gly Leu Gly Leu Gly Ile Thr Thr Val Ile Glu
        195                 200                 205

Asn Gly Arg Ile Met Gly Ser Leu Thr Gly Val Pro Ala Ser Asn Ile
    210                 215                 220

Ala Asp Lys Leu Trp Leu Val Phe Gln Gly Ile Gly Asp Ile Ala Phe
225                 230                 235                 240

Ala Tyr Pro Tyr Thr Val Ile Leu Leu Glu Ile Gln Asp Thr Leu Glu
                245                 250                 255

Ser Pro Pro Pro Glu Asn Lys Thr Met Lys Lys Ala Ser Met Ile Ala
            260                 265                 270

Ile Leu Ile Thr Thr Phe Phe Tyr Leu Cys Cys Gly Cys Phe Gly Tyr
        275                 280                 285

Ala Ala Phe Gly Asn Gln Thr Pro Gly Asn Leu Leu Thr Gly Phe Gly
    290                 295                 300

Phe Tyr Glu Pro Tyr Trp Leu Ile Asp Phe Ala Asn Ala Cys Ile Val
305                 310                 315                 320

Leu His Leu Val Gly Gly Tyr Gln Ile Tyr Ser Gln Pro Ile Tyr Gly
                325                 330                 335

Ala Val Asp Arg Trp Cys Ser Lys Arg Tyr Pro Asn Ser Gly Phe Val
            340                 345                 350

Asn Asn Phe Tyr Gln Leu Lys Leu Pro Arg Leu Pro Ala Phe Gln Leu
        355                 360                 365

Asn Met Phe Arg Ile Cys Phe Arg Thr Ala Tyr Val Val Ser Thr Thr
    370                 375                 380

Gly Leu Ala Ile Leu Phe Pro Tyr Phe Asn Gln Val Ile Gly Val Leu
385                 390                 395                 400

Gly Ala Leu Gly Phe Trp Pro Leu Ala Ile Tyr Phe Pro Val Glu Met
                405                 410                 415

Tyr Phe Val Gln Arg Lys Val Glu Ala Trp Ser Arg Lys Trp Ile Val
            420                 425                 430
```

```
Leu Arg Thr Phe Ser Phe Ile Cys Phe Leu Val Ser Leu Leu Gly Leu
        435                 440                 445

Ile Gly Ser Leu Glu Gly Ile Ile Ser Glu Lys Leu Ser
    450                 455                 460


<210> SEQ ID NO 37
<211> LENGTH: 1614
<212> TYPE: DNA
<213> ORGANISM: Glycine max

<400> SEQUENCE: 37

gttgtaaaaa agattcatgt tcagttagta tcttgtgaag gcgatcgaat actagaaaga     60

aacaaatcga tcaagcttga aagataggaa gaatttaaga aatgggtgag gaggaaatag    120

atgattctcc cttgattcaa ggttttcctt ccggcgacgt gccatttagg agaactggta    180

atgtagagag ggcagtagca catataataa ctggtgtgat aggggcaggg gtgctgtctc    240

tagcatggtc tgtggcacag ttagggtgga ttgctggtcc ttttatcatc atagtctttg    300

caggaacaac ctttctttca gcaaaccttc tttctgactg ctacagattc cctcatcctc    360

tctatggcaa cattaggtgc ccctcctaca ttgatgctgt caaggtttac ctaggagact    420

caaggcaaaa ggtgtgtgga gtgctggtgc atgcgagctt atatggtgcc accacggcct    480

atgtcattac atctgccacc agcatcagag caatactgaa atcaaattgt tatcacaagg    540

aagggcatca ggctccttgt aaatatgggg atgcagtata tatgatgctg tttggactag    600

ttcagatcat aatgtcattc ataccagatc tccacaacat ggcatgggtt tcaattgttg    660

cggccataat gtcctttaca tactcatcta ttggacttgg acttggcatc acaacagtaa    720

tagaaaatgg aagaattatg ggtagtttaa caggagtacc ggcttcaaat attgctgaca    780

agttatggtt agtcttccaa ggaattggtg atattgcctt tgcctatcca tacacagtca    840

tcctccttga gatacaggac actctagagt ctcctccacc agaaaacaag accatgaaaa    900

aggcctccat gattgctatc ctcattacaa cattcttcta cctctgctgt ggatgctttg    960

gatatgcggc ttttggaaat caaacaccag gaaacctctt gacagggttt ggattttacg   1020

agccttactg gctcattgac tttgccaatg cttgcattgt tcttcacttg gtaggaggat   1080

atcagattta cagtcagccg atatatggtg ctgttgacag atggtgttca aaaagatacc   1140

ccaacagtgg atttgtgaat aatttctacc aattgaaact gcctcggttg ccagcttttc   1200

agctaaacat gttcaggata tgttttagaa cagcttatgt ggtttccacg actggacttg   1260

cgatcctatt tccttacttc aatcaagtta taggagtgtt aggagcctta ggcttttggc   1320

cattggctat atatttcccg gtagagatgt actttgtgca gaggaaagtt gaagcttggt   1380

ctagaaaatg gattgtcctc aggaccttca gctttatttg ctttctggtg tcattactgg   1440

gtctcattgg atcacttgaa ggaatcataa gcgagaaact aagctaatga agggtgcttc   1500

atttgtttga gtttaatgtc ttgttgctca tatcttccat gtaattcagt ttcatgctaa   1560

ttctattact attgagagtt aataaagggg ataccaatta aaaaaaaaaa aaaa         1614


<210> SEQ ID NO 38
<211> LENGTH: 487
<212> TYPE: PRT
<213> ORGANISM: Glycine max

<400> SEQUENCE: 38

Met Val Glu Lys Asp Gly Val Gly Ser Lys Tyr Leu Gln Gln Thr Leu
1               5                   10                  15
```

-continued

```
Asn Val Ser Ile Asp Met His Gln His Gly Ile Ser Lys Cys Phe Asp
            20                  25                  30

Asp Asp Gly Arg Pro Lys Arg Thr Gly Thr Val Trp Thr Ser Ser Ala
        35                  40                  45

His Ile Ile Thr Ala Val Ile Gly Ser Gly Val Leu Ser Leu Ala Trp
    50                  55                  60

Ala Ile Ala Gln Leu Gly Trp Ile Ala Gly Pro Ile Val Met Val Ile
65                  70                  75                  80

Phe Ser Ala Ile Thr Tyr Tyr Thr Ser Thr Leu Leu Ala Asp Cys Tyr
                85                  90                  95

Arg Thr Gly Asp Pro Val Thr Gly Lys Arg Asn Tyr Thr Tyr Met Asp
            100                 105                 110

Ala Ile Gln Ser Asn Phe Gly Gly Asn Gly Phe Lys Val Lys Leu Cys
        115                 120                 125

Gly Leu Val Gln Tyr Val Asn Leu Phe Gly Val Ala Ile Gly Tyr Thr
    130                 135                 140

Ile Ala Ala Ser Thr Ser Met Met Ala Ile Glu Arg Ser Asn Cys Phe
145                 150                 155                 160

His Lys Ser Gly Gly Lys Asp Pro Cys His Ile Asn Ser Asn Met Tyr
                165                 170                 175

Met Ile Ser Phe Gly Ile Val Glu Ile Leu Phe Ser Gln Ile Pro Gly
            180                 185                 190

Phe Asp Gln Leu Trp Trp Leu Ser Ile Val Ala Ala Val Met Ser Phe
        195                 200                 205

Thr Tyr Ser Thr Ile Gly Leu Gly Leu Gly Ile Gly Lys Val Ile Glu
    210                 215                 220

Asn Gly Gly Val Gly Gly Ser Leu Thr Gly Ile Thr Ile Gly Thr Val
225                 230                 235                 240

Thr Gln Thr Asp Lys Val Trp Arg Thr Met Gln Ala Leu Gly Asp Ile
                245                 250                 255

Ala Phe Ala Tyr Ser Tyr Ser Leu Ile Leu Ile Glu Ile Gln Asp Thr
            260                 265                 270

Val Lys Ser Pro Pro Ser Glu Ser Lys Thr Met Lys Lys Ala Ser Phe
        275                 280                 285

Ile Ser Val Ala Val Thr Ser Ile Phe Tyr Met Leu Cys Gly Cys Phe
    290                 295                 300

Gly Tyr Ala Ala Phe Gly Asp Ala Ser Pro Gly Asn Leu Leu Thr Gly
305                 310                 315                 320

Phe Gly Phe Tyr Asn Pro Tyr Trp Leu Leu Asp Ile Ala Asn Ala Ala
                325                 330                 335

Ile Val Ile His Leu Val Gly Ser Tyr Gln Val Tyr Cys Gln Pro Leu
            340                 345                 350

Phe Ala Phe Val Glu Lys His Ala Ala Gln Met Phe Pro Asp Ser Asp
        355                 360                 365

Phe Leu Asn Lys Glu Ile Glu Ile Pro Ile Pro Gly Phe His Pro Tyr
    370                 375                 380

Arg Leu Asn Leu Phe Arg Leu Val Trp Arg Thr Ile Tyr Val Met Leu
385                 390                 395                 400

Ser Thr Val Ile Ser Met Leu Leu Pro Phe Phe Asn Asp Ile Gly Gly
                405                 410                 415

Leu Leu Gly Ala Phe Gly Phe Trp Pro Leu Thr Val Tyr Phe Pro Val
            420                 425                 430
```

-continued

```
Glu Met Tyr Ile Ile Gln Lys Arg Ile Pro Lys Trp Ser Thr Lys Trp
        435                 440                 445

Ile Cys Leu Gln Ile Leu Ser Met Thr Cys Leu Leu Met Thr Ile Gly
    450                 455                 460

Ala Ala Ala Gly Ser Ile Ala Gly Ile Ala Ile Asp Leu Arg Thr Tyr
465                 470                 475                 480

Lys Pro Phe Lys Thr Asn Tyr
                485


<210> SEQ ID NO 39
<211> LENGTH: 1825
<212> TYPE: DNA
<213> ORGANISM: Glycine max

<400> SEQUENCE: 39

ccacgcgtcc gtacggctgc gagaagacga cagaaggggg aggcacaaca gctactccag     60

ctcttttgca ttgcttgtag cagaagctgc tgctgcagct tattaaagaa agaaagcctc    120

caagacaaga tggttgagaa ggatggcgtt ggcagcaagt atcttcaaca aacacttaac    180

gtctccatcg acatgcatca acacggaatc tctaagtgtt tcgacgacga tggtcgcccg    240

aaaagaaccg ggacggtgtg gacttcaagt gcacacataa taactgcagt gattgggtct    300

ggggtgctat ctctggcttg ggctatagct cagcttggat ggattgctgg tcctattgtc    360

atggttatct tttctgccat cacttactac acttccactc ttctcgctga ttgttaccgc    420

accggtgatc ctgtaactgg caagagaaac tacacttaca tggacgctat tcagtctaac    480

tttggtggaa atggctttaa ggtcaagctg tgcgggctag ttcagtatgt taacctttttc    540

ggagtggcca ttggttacac tatagcggct tccactagca tgatggcaat tgaaagatct    600

aattgtttcc acaagagtgg agggaaagat ccgtgccaca ttaacagcaa catgtacatg    660

atttcatttg gtatagtgga aattcttttc tcacaaattc cgggcttcga tcaactgtgg    720

tggctctcca ttgtagctgc tgtcatgtcc ttcacatact ccactattgg gctaggcctt    780

ggtattggga aagttattga aaatggagga gttggaggaa gcctaaccgg gataacaatt    840

ggtaccgtga cccaaactga taaagtttgg agaaccatgc aagctcttgg tgacatagcc    900

tttgcttatt catactccct catccttata gaaattcagg acacagtgaa atcccctcca    960

tcagagtcaa aaacaatgaa gaaggctagt ttcatcagtg ttgcagtaac tagcattttc   1020

tacatgcttt gtggttgctt tggttatgct gcttttggag atgcaagccc tggaaacctt   1080

ctcactggtt ttggcttcta caacccatac tggctccttg acatagctaa tgctgccata   1140

gtgatccacc ttgttggttc ataccaagtt tactgccagc ccctcttcgc cttcgtcgag   1200

aaacacgcgg cgcaaatgtt cccagatagt gattttctga acaaagaaat tgaaattcca   1260

atccctggtt tccatcccta caggctcaac ctcttcaggt tggtttggag gacaatatat   1320

gtaatgttga gcactgtaat atcaatgctc ctcccattct tcaatgacat aggtggactt   1380

cttggagcat ttggattttg gccccttaca gtgtatttcc cagtggagat gtacattatt   1440

caaaagagaa taccaaagtg gagcacaaag tggatctgcc tccaaatact tagcatgact   1500

tgccttttga tgactatagg agctgcagct ggctctattg ctgggattgc cattgatctt   1560

cgaacttaca agccattcaa gaccaactat tgattaaact atgattgcca ttgatagaga   1620

tttcagaaac caaatttcat ttcttggtca tattcttatg aagccaagga tatatggtga   1680

tcttgtttgt ttatggccta gcagtcctgt gtgttccact tctttctact gtgtatctgt   1740

tactctctag ctcgttctgc aacctaattc aaaatggaag aaatgaagta aaaacaaaaa   1800
```

```
aaaaaaaaaa aaaaaaaaaa aaaaa                                         1825

<210> SEQ ID NO 40
<211> LENGTH: 461
<212> TYPE: PRT
<213> ORGANISM: Glycine max

<400> SEQUENCE: 40

Met Asp Gly Lys Lys Ser Leu Gln Ile Thr Arg Ser Gly Thr Gly Ala
1               5                   10                  15

Tyr Asp Asp Asp Gly His Ala Lys Arg Thr Gly Asn Leu Gln Ser Ala
            20                  25                  30

Val Ala His Ile Ile Thr Ala Val Ile Gly Ser Gly Val Leu Ser Leu
        35                  40                  45

Ala Trp Ser Thr Ser Gln Leu Gly Trp Ile Gly Gly Pro Val Ala Leu
    50                  55                  60

Leu Cys Cys Ala Ile Val Thr Tyr Ile Ser Ser Phe Leu Leu Ser Asp
65                  70                  75                  80

Cys Tyr Arg Thr Pro Asp Pro Val Thr Gly Lys Arg Asn Tyr Ser Tyr
                85                  90                  95

Met Asp Ala Val Arg Val Tyr Leu Gly Tyr Lys Arg Thr Cys Val Ala
            100                 105                 110

Gly Phe Leu Gln Phe Leu Thr Leu Tyr Gly Thr Ser Ile Ala Tyr Val
        115                 120                 125

Leu Thr Thr Ala Thr Ser Leu Ser Ala Ile Leu Arg Ser Asn Cys Tyr
    130                 135                 140

His Lys Lys Gly His Glu Ala Pro Cys Lys Tyr Gly Gly Asn Leu Tyr
145                 150                 155                 160

Met Ala Leu Phe Gly Leu Val Gln Ile Val Met Ser Phe Ile Pro Asp
                165                 170                 175

Leu His Asn Met Ala Trp Val Ser Val Val Ala Ala Leu Met Ser Phe
            180                 185                 190

Thr Tyr Ser Phe Ile Gly Leu Gly Leu Gly Ile Ala Thr Val Ile Lys
        195                 200                 205

Asn Gly Arg Ile Met Gly Ser Leu Thr Gly Ile Pro Thr Asp Lys Ile
    210                 215                 220

Ala Asp Lys Phe Trp Leu Val Phe Gln Ala Leu Gly Asp Ile Ala Phe
225                 230                 235                 240

Ala Tyr Pro Tyr Ser Ile Leu Leu Leu Glu Ile Gln Asp Thr Leu Glu
                245                 250                 255

Ser Pro Pro Pro Glu Asn Gln Thr Met Lys Lys Ala Ser Met Val Ala
            260                 265                 270

Ile Phe Ile Thr Thr Phe Phe Tyr Leu Cys Cys Gly Cys Phe Gly Tyr
        275                 280                 285

Ala Ala Phe Gly Asn Asp Thr Pro Gly Asn Leu Leu Thr Gly Phe Gly
    290                 295                 300

Phe Phe Glu Pro Phe Trp Leu Ile Asp Leu Ala Asn Ala Cys Ile Ile
305                 310                 315                 320

Leu His Leu Val Gly Gly Tyr Gln Ile Tyr Ser Gln Pro Ile Tyr Ser
                325                 330                 335

Thr Val Asp Arg Trp Ala Ser Arg Lys Phe Pro Asn Ser Gly Phe Val
            340                 345                 350

Asn Asn Phe Tyr Lys Val Lys Leu Pro Leu Leu Pro Gly Phe Gln Leu
        355                 360                 365
```

-continued

```
Asn Leu Phe Arg Phe Cys Phe Arg Thr Thr Tyr Val Ile Ser Thr Thr
    370                 375                 380

Gly Leu Ala Ile Phe Phe Pro Tyr Phe Asn Gln Ile Leu Gly Val Leu
385                 390                 395                 400

Gly Ala Ile Asn Phe Trp Pro Leu Ala Ile Tyr Phe Pro Val Glu Met
                405                 410                 415

Tyr Phe Val Gln Asn Lys Ile Ala Ala Trp Ser Ser Lys Trp Ile Val
            420                 425                 430

Leu Arg Thr Phe Ser Phe Ala Cys Phe Leu Val Thr Gly Met Gly Leu
        435                 440                 445

Val Gly Ser Leu Glu Gly Ile Val Ser Ala Lys Leu Lys
    450                 455                 460


<210> SEQ ID NO 41
<211> LENGTH: 1924
<212> TYPE: DNA
<213> ORGANISM: Glycine max

<400> SEQUENCE: 41

gacatggtcc taaagtctgg cctgagatga atataaaatg gactaatctt cttctggctt     60

gttttcttca gaatcatggg ggttacacag agttacaaat tgctgcaaat ggaataactt    120

gttttcttca gtggcttctc tctacctctc acctgaaatc aacttgtaat cttcatgagc    180

ttgcattgaa ttgatacttt gataaagatg gatgggaaaa aatctctaca aataactaga    240

agtggtactg gtgcttatga tgatgatgga catgccaaaa ggactgggaa tttgcagagt    300

gctgtagctc atatcattac tgctgttatt ggttctggtg ttctctctct tgcatggagc    360

acttctcagt taggatggat tggagggcca gttgcattgc tttgttgtgc aattgttacc    420

tatatttctt cattcctcct gtctgattgc tacagaactc ctgatcctgt cactgggaaa    480

agaaactact cttacatgga tgctgttaga gtttatcttg gttataaaag gacatgtgta    540

gctggcttcc ttcaattttt gactttgtat ggtactagta ttgcttatgt actaaccaca    600

gcaactagtc tgagtgcaat tctgagatca aattgttatc acaagaaagg gcatgaagct    660

ccttgtaaat atggtggcaa tctgtatatg gcactgtttg gacttgttca gattgtaatg    720

tcattcatac cggatctcca taacatggca tgggtttcag ttgttgcagc acttatgtcc    780

tttacatact cattcattgg actaggactt ggcatagcaa cggtcataaa aaatggaaga    840

attatgggaa gcttgacagg aataccaact gataaaattg ctgacaaatt ttggttagtc    900

ttccaagcac ttggtgacat tgcctttgcc tatccatact ccattctcct tcttgagatc    960

caggacactc tagagtctcc tccaccagaa aatcaaacca tgaaaaaggc ctccatggtt   1020

gcaatcttca ttacaacatt cttctacctg tgctgtggat gctttggata tgcagctttt   1080

ggaaatgata caccaggaaa cctcttgaca gggtttggct tttttgagcc tttctggctc   1140

attgaccttg ctaatgcttg catcattctt cacttggtgg gaggatatca gatttacagt   1200

caaccaatat acagtactgt tgatagatgg gcttcaagaa aattccccaa cagtggcttt   1260

gtgaataatt tctacaaagt gaaactgcct ttgcttccag gttttcagct aaatcttttc   1320

aggttctgtt ttagaacaac ctatgtgatc tcaaccactg gtcttgcaat ctttttttcct  1380

tacttcaacc aaatcctagg agtgttagga gccataaact tctggccatt ggctatatac   1440

ttcccagtag agatgtactt tgtacagaac aaaattgcag cttggagtag caaatggatt   1500

gttcttagaa cattcagctt tgcttgcttt cttgtcactg gaatgggctt ggttggctca   1560
```

-continued

```
cttgaaggaa tagtaagtgc caaattaaag tagctgaaag atttatgcca ctccccttag   1620

taatgcttac tatatttgag tttgtagcta gattgatggt tgtataatgt ttcatgtaaa   1680

aaagtttaaa gttgatgcta agattgttga gagttagata gggagtaagc aattgtgggg   1740

gatttctgaa agtgaataaa gtggtactgt agtctttgga ataatacaag ttttgtttta   1800

tgcagaactc acctcaaagg agagagttca aacgaatttg tagtttgata ttgatgttat   1860

tgtgctgtat caaaaaaaaa aaaaaaaaaa aaaaaaaaaa aaaaaaaaaa aaaaaaaaaa   1920

aaaa                                                                1924
```

```
<210> SEQ ID NO 42
<211> LENGTH: 461
<212> TYPE: PRT
<213> ORGANISM: Glycine max

<400> SEQUENCE: 42

Met Asp Gly Lys Asn Ser Leu Gln Ile Thr Arg Ser Gly Ile Gly Ala
1               5                   10                  15

Tyr Asp Asp Asp Gly His Ala Lys Arg Thr Gly Asn Leu Gln Ser Ala
            20                  25                  30

Val Ala His Ile Ile Thr Ala Val Ile Gly Ser Gly Val Leu Ser Leu
        35                  40                  45

Ala Trp Ser Thr Ser Gln Leu Gly Trp Ile Gly Gly Pro Phe Ser Leu
    50                  55                  60

Leu Cys Cys Ala Ile Val Thr Tyr Ile Ser Ser Phe Leu Leu Ser Asp
65                  70                  75                  80

Cys Tyr Arg Thr Pro Asp Pro Val Thr Gly Lys Arg Asn Tyr Ser Tyr
                85                  90                  95

Met Asp Ala Val Arg Val Tyr Leu Gly Tyr Lys Arg Thr Cys Val Ala
            100                 105                 110

Gly Phe Leu Gln Phe Leu Thr Leu Tyr Gly Thr Ser Ile Ala Tyr Val
        115                 120                 125

Leu Thr Thr Ala Thr Ser Leu Ser Ala Ile Leu Arg Ser Asn Cys Tyr
    130                 135                 140

His Lys Lys Gly His Glu Ala Pro Cys Lys Tyr Gly Gly Asn Leu Tyr
145                 150                 155                 160

Met Ala Leu Phe Gly Leu Val Gln Ile Val Met Ser Phe Ile Pro Asp
                165                 170                 175

Leu His Asn Met Ala Trp Val Ser Val Val Ala Ala Leu Met Ser Phe
            180                 185                 190

Thr Tyr Ser Phe Ile Gly Leu Gly Leu Gly Ile Ala Thr Val Ile Lys
        195                 200                 205

Asn Gly Arg Ile Met Gly Ser Leu Thr Gly Ile Pro Thr Asp Lys Ile
    210                 215                 220

Ala Asp Lys Phe Trp Leu Val Phe Gln Ala Leu Gly Asp Ile Ala Phe
225                 230                 235                 240

Ala Tyr Pro Tyr Ser Ile Leu Leu Leu Glu Ile Gln Asp Thr Leu Glu
                245                 250                 255

Ser Pro Pro Pro Glu Asn Gln Thr Met Lys Lys Ala Ser Met Val Ala
            260                 265                 270

Ile Phe Ile Thr Thr Phe Phe Tyr Leu Cys Cys Gly Cys Phe Gly Tyr
        275                 280                 285

Ala Ala Phe Gly Asn Asp Thr Pro Gly Asn Leu Leu Thr Gly Phe Gly
    290                 295                 300
```

```
Phe Phe Glu Pro Phe Trp Leu Ile Asp Leu Ala Asn Ala Cys Ile Ile
305                 310                 315                 320

Leu His Leu Val Gly Gly Tyr Gln Ile Tyr Ser Gln Pro Ile Tyr Ser
                325                 330                 335

Thr Val Asp Arg Trp Ala Ser Arg Lys Phe Pro Asn Ser Gly Phe Val
            340                 345                 350

Asn Asn Phe Tyr Arg Val Lys Leu Pro Leu Leu Pro Gly Phe Gln Leu
        355                 360                 365

Asn Leu Phe Arg Phe Cys Phe Arg Thr Thr Tyr Val Ile Ser Thr Ile
    370                 375                 380

Gly Leu Ala Ile Phe Phe Pro Tyr Phe Asn Gln Ile Leu Gly Val Leu
385                 390                 395                 400

Gly Ala Ile Asn Phe Trp Pro Leu Ala Ile Tyr Phe Pro Val Glu Met
                405                 410                 415

Tyr Phe Val Gln Gln Lys Ile Ala Ala Trp Ser Ser Lys Trp Ile Val
            420                 425                 430

Leu Arg Thr Phe Ser Phe Ala Cys Phe Leu Val Thr Val Met Gly Leu
        435                 440                 445

Val Gly Ser Leu Glu Gly Ile Val Ser Ala Lys Leu Lys
    450                 455                 460
```

<210> SEQ ID NO 43
<211> LENGTH: 1893
<212> TYPE: DNA
<213> ORGANISM: Glycine max

<400> SEQUENCE: 43

```
acgtaagcta gctttggcat ctttttcccc tttttcctcc aagcctataa ctatattcaa     60

cccaatctgc actggaccaa gtgtaaaaag acattttcct gatcttctgc tgtgccaaga    120

aagcagtaat ctccatgagc ttctattgaa ttgatacttt gatcaagatg gatgggaaaa    180

actctcttca aataactaga agtggtattg gtgcttatga tgatgatgga catgccaaaa    240

ggactgggaa tttgcagagt gctgtagctc atatcattac tgctgttatt ggttctggtg    300

ttctttctct tgcatggagc acttcccaat taggatggat tggagggcca ttttccttgc    360

tttgttgtgc aattgtcacc tatatttctt cattcctcct gtctgattgc tacagaactc    420

ctgatcctgt cactgggaaa agaaactact cttacatgga tgctgttaga gtttatcttg    480

gttataaaag gacatgtgta gctggcttcc ttcaattttt gactttgtat gggactagta    540

ttgcttatgt actaaccaca gcaaccagtc tgagtgcaat tctgagatca aattgctatc    600

acaagaaagg gcatgaggct ccttgcaaat atgggggcaa tctgtatatg gcactgtttg    660

gacttgttca gattgtaatg tcattcatac cggatctcca taacatggca tgggtttcag    720

ttgttgccgc acttatgtcc tttacatact cattcattgg actaggactt ggcatagcaa    780

cagtcataaa aaatggaaga attatgggga gcttgacagg aataccaact gataaaattg    840

ctgacaaatt ttggttggtc ttccaagcac ttggtgacat tgcctttgcc tatccatact    900

ccattctcct tcttgagatc caggacactc tagagtctcc tccaccagaa aatcaaacaa    960

tgaaaaaggc ttccatggtt gcaatcttca ttacaacatt cttctacctg tgctgtggat   1020

gctttggata tgcagctttt ggaaatgata caccaggaaa cctcttgaca gggtttggat   1080

tttttgagcc tttctggctc attgaccttg ctaatgcttg catcattctt cacttggtgg   1140

gaggatatca gatttacagt caaccaatat acagtactgt tgacagatgg gcttcaagaa   1200

aattccccaa cagtggcttt gtgaataatt tctacagagt gaaacttcct ttgcttcctg   1260
```

gttttcagct aaatcttttc aggttctgct ttagaacaac ctatgtgatc tcaaccattg 1320
gtcttgcaat ctttttccct tacttcaacc aaatcctagg agtgttagga gccataaact 1380
tctggccatt ggctatatat ttcccagtag agatgtactt tgtacagcag aaaattgcag 1440
cttggagtag caaatggatt gttcttagaa cattcagctt tgcttgcttt ctggtcactg 1500
taatgggctt ggttggctca cttgaaggaa tagtaagtgc caaattaaaa tagctgaaag 1560
cctgaaaggt tgtttatgcc actcccctta gtaatgctta ctctatttga gtttgtagat 1620
tgatggttat ataatgtttc atataaaaaa gtttaaagct gaatgctagt gttattgaga 1680
gtaagataga gtacaagcaa ttgtgggga tttcagaaag tgaataaagt ggtactgcca 1740
gtgccattgg aataatacaa gtttgtttg atgaagaact cacctcaaag gagagaattc 1800
taacaaattt gtagtttgat attaatgtaa ttgtactgta tcatcaaata gattatatca 1860
aattttaaat taatgattaa aaaaaaaaaa aaa 1893

<210> SEQ ID NO 44
<211> LENGTH: 513
<212> TYPE: PRT
<213> ORGANISM: Glycine max

<400> SEQUENCE: 44

Met Leu Pro Arg Ser Arg Thr Leu Pro Ser Arg Ile His Gln Gly Ile
1 5 10 15

Ile Glu Glu Arg His Asp Val Arg Pro Tyr Val Gln Val Glu Val Arg
20 25 30

Pro Asn Asn Ile Gln Thr Glu Thr Gln Ala Met Asn Ile Gln Ser Asn
35 40 45

Tyr Ser Lys Cys Phe Asp Asp Asp Gly Arg Leu Lys Arg Thr Gly Thr
50 55 60

Phe Trp Thr Ala Thr Ala His Ile Ile Thr Ala Val Ile Gly Ser Gly
65 70 75 80

Val Leu Ser Leu Ala Trp Ala Val Ala Gln Leu Gly Trp Val Ala Gly
85 90 95

Pro Val Val Met Phe Leu Phe Ala Val Val Asn Leu Tyr Thr Ser Asn
100 105 110

Leu Leu Thr Gln Cys Tyr Arg Thr Gly Asp Ser Val Asn Gly His Arg
115 120 125

Asn Tyr Thr Tyr Met Glu Ala Val Lys Ser Ile Leu Gly Gly Lys Lys
130 135 140

Val Lys Leu Cys Gly Leu Ile Gln Tyr Ile Asn Leu Phe Gly Val Ala
145 150 155 160

Ile Gly Tyr Thr Ile Ala Ala Ser Val Ser Met Met Ala Ile Lys Arg
165 170 175

Ser Asn Cys Tyr His Ser Ser His Gly Lys Asp Pro Cys His Met Ser
180 185 190

Ser Asn Gly Tyr Met Ile Thr Phe Gly Ile Ala Glu Val Ile Phe Ser
195 200 205

Gln Ile Pro Asp Phe Asp Gln Val Trp Trp Leu Ser Ile Val Ala Ala
210 215 220

Ile Met Ser Phe Thr Tyr Ser Ser Val Gly Leu Ser Leu Gly Val Ala
225 230 235 240

Lys Val Ala Glu Asn Lys Thr Phe Lys Gly Ser Leu Met Gly Ile Ser
245 250 255

-continued

```
Ile Gly Thr Val Thr Gln Ala Gly Thr Val Thr Ser Thr Gln Lys Ile
            260                 265                 270

Trp Arg Ser Leu Gln Ala Leu Gly Ala Met Ala Phe Ala Tyr Ser Phe
        275                 280                 285

Ser Ile Ile Leu Ile Glu Ile Gln Asp Thr Ile Lys Phe Pro Pro Ala
    290                 295                 300

Glu His Lys Thr Met Arg Lys Ala Thr Thr Leu Ser Ile Ala Val Thr
305                 310                 315                 320

Thr Val Phe Tyr Leu Leu Cys Gly Cys Met Gly Tyr Ala Ala Phe Gly
                325                 330                 335

Asp Asn Ala Pro Gly Asn Leu Leu Thr Gly Phe Gly Phe Tyr Asn Pro
            340                 345                 350

Tyr Trp Leu Leu Asp Ile Ala Asn Leu Ala Ile Val Ile His Leu Val
        355                 360                 365

Gly Ala Tyr Gln Val Phe Ser Gln Pro Leu Phe Ala Phe Val Glu Lys
    370                 375                 380

Trp Ser Val Arg Lys Trp Pro Lys Ser Asn Phe Val Thr Ala Glu Tyr
385                 390                 395                 400

Asp Ile Pro Ile Pro Cys Phe Gly Val Tyr Gln Leu Asn Phe Phe Arg
                405                 410                 415

Leu Val Trp Arg Thr Ile Phe Val Leu Leu Thr Thr Leu Ile Ala Met
            420                 425                 430

Leu Met Pro Phe Phe Asn Asp Val Val Gly Ile Leu Gly Ala Phe Gly
        435                 440                 445

Phe Trp Pro Leu Thr Val Tyr Phe Pro Ile Asp Met Tyr Ile Ser Gln
    450                 455                 460
Lys Lys Ile Gly Arg Trp Thr Ser Arg Trp Ile Gly Leu Gln Leu Leu
465                 470                 475                 480

Ser Val Ser Cys Leu Ile Ile Ser Leu Leu Ala Ala Val Gly Ser Met
                485                 490                 495

Ala Gly Val Val Leu Asp Leu Lys Thr Tyr Lys Pro Phe Lys Thr Ser
            500                 505                 510

Tyr


<210> SEQ ID NO 45
<211> LENGTH: 1743
<212> TYPE: DNA
<213> ORGANISM: Glycine max

<400> SEQUENCE: 45

gaattcggct cgagcagctt tcttcttagt atcgagcttc atatttcaca gccatgttgc     60

caagaagtag aacccttcct agcagaatcc accaaggaat tatagaagag aggcacgatg    120

tcaggcccta cgtacaagta gaagtgcgac ccaataatat ccaaacggag acccaagcga    180

tgaatatcca gtctaactat tccaagtgct tcgatgatga tggtcgcttg aagagaacag    240

gaacattttg gacggcaact gctcatatca tcactgctgt gatagggtcg ggagtccttt    300

cactagcatg ggcggttgct cagcttggtt gggttgctgg acctgttgtc atgtttctct    360

ttgccgtcgt caatctctac acttccaacc tattaacaca gtgttacagg accggtgact    420

ccgttaatgg acacagaaat tacacctaca tggaggctgt caagtccatc ttgggaggaa    480

aaaaggtcaa gttatgtggc ctcatccaat atatcaatct gtttggagtt gcaatcgggt    540

acaccattgc tgcctctgtc agtatgatgg ccataaaaag gtcgaattgc tatcacagca    600

gtcatggaaa agatccctgc cacatgtcaa gcaatgggta tatgataaca tttggaatag    660
```

-continued

```
cagaagtgat attttcccaa atcccagact ttgatcaggt gtggtggcta tccatagttg    720
cagctatcat gtccttcact tattcttcag ttggattgag tcttggagtg gccaaagtag    780
cagaaaataa aactttcaaa ggaagcctga tgggaattag cattggcaca gtaacacaag    840
ccggaacagt caccagcaca cagaaaatat ggaggagttt acaagctctt ggggcaatgg    900
cctttgcata ctccttttcc attatcctca tcgaaattca ggacaccata aaatttcctc    960
ctgcagagca caagaccatg agaaaggcca caacattgag catcgcggtt accacagtgt   1020
tctatttact ctgtggatgc atgggttatg cagccttcgg agataatgca cctggaaatc   1080
tcttgactgg ttttgggttc tataaccctt attggcttct ggacattgcc aaccttgcaa   1140
ttgttatcca cctagttggg gcatatcagg tttttccca gcccttattt gcatttgtgg    1200
aaaaatggag tgtacgcaaa tggccaaaga gcaattttgt cacggcagaa tatgatatac   1260
cgattccctg ctttggtgtg taccaactca acttcttccg cttagtatgg agaaccattt   1320
ttgtgctgtt gacgaccctc atagccatgc tcatgccttt tttcaacgat gtggttggaa   1380
tacttggcgc ttttgggttc tggcccttaa cagtttattt ccctatcgac atgtatattt   1440
cgcaaaagaa gattggacga tggactagtc ggtggattgg acttcaatta cttagtgtca   1500
gttgcctcat catttcattg ttagctgcag ttggttccat ggcaggggtt gttttggacc   1560
tcaagactta taagccattt aaaactagtt attaagtgag atttaaagaa ggtcgtagaa   1620
atagaagtgt ttaagcttga tgatattata gaaaactaat gataagttgg tttgtgaaat   1680
ttaagtatat acgctccatg ccgctgctgt tagagcaatt gatttgagaa aaaaaaaaaa   1740
aaa                                                                 1743
```

```
<210> SEQ ID NO 46
<211> LENGTH: 513
<212> TYPE: PRT
<213> ORGANISM: Glycine max

<400> SEQUENCE: 46

Met Leu Pro Arg Ser Arg Thr Leu Pro Ser Arg Ile His Gln Gly Ile
1               5                   10                  15

Ile Glu Glu Arg His Asp Val Arg Pro Tyr Val Gln Val Glu Val Arg
            20                  25                  30

Pro Asn Asn Ile Gln Thr Glu Thr Gln Ala Met Asn Ile Gln Ser Asn
        35                  40                  45

Tyr Ser Lys Cys Phe Asp Asp Asp Gly Arg Leu Lys Arg Thr Gly Thr
    50                  55                  60

Phe Trp Thr Ala Thr Ala His Ile Ile Thr Ala Val Ile Gly Ser Gly
65                  70                  75                  80

Val Leu Ser Leu Ala Trp Ala Val Ala Gln Leu Gly Trp Val Ala Gly
                85                  90                  95

Pro Val Val Met Phe Leu Phe Ala Val Val Asn Leu Tyr Thr Ser Asn
            100                 105                 110

Leu Leu Thr Gln Cys Tyr Arg Thr Gly Asp Ser Val Asn Gly His Arg
        115                 120                 125

Asn Tyr Thr Tyr Met Glu Ala Val Lys Ser Ile Leu Gly Gly Lys Lys
    130                 135                 140

Val Lys Leu Cys Gly Leu Ile Gln Tyr Ile Asn Leu Phe Gly Val Ala
145                 150                 155                 160

Ile Gly Tyr Thr Ile Ala Ala Ser Val Ser Met Met Ala Ile Lys Arg
                165                 170                 175
```

-continued

```
Ser Asn Cys Tyr His Ser Ser His Gly Lys Asp Pro Cys His Met Ser
            180                 185                 190

Ser Asn Gly Tyr Met Ile Thr Phe Gly Ile Ala Glu Val Ile Phe Ser
        195                 200                 205

Gln Ile Pro Asp Phe Asp Gln Val Trp Trp Leu Ser Ile Val Ala Ala
    210                 215                 220

Ile Met Ser Phe Thr Tyr Ser Ser Val Gly Leu Ser Leu Gly Val Ala
225                 230                 235                 240

Lys Val Ala Glu Asn Lys Thr Phe Lys Gly Ser Leu Met Gly Ile Ser
                245                 250                 255

Ile Gly Thr Val Thr Gln Ala Gly Thr Val Thr Ser Thr Gln Lys Ile
            260                 265                 270

Trp Arg Ser Leu Gln Ala Leu Gly Ala Met Ala Phe Ala Tyr Ser Phe
        275                 280                 285
Ser Ile Ile Leu Ile Glu Ile Gln Asp Thr Ile Lys Ser Pro Pro Ala
    290                 295                 300

Glu His Lys Thr Met Arg Lys Ala Thr Thr Leu Ser Ile Ala Val Thr
305                 310                 315                 320

Thr Val Phe Tyr Leu Leu Cys Gly Cys Met Gly Tyr Ala Ala Phe Gly
                325                 330                 335

Asp Asn Ala Pro Gly Asn Leu Leu Thr Gly Phe Gly Phe Tyr Asn Pro
            340                 345                 350

Tyr Trp Leu Leu Asp Ile Ala Asn Leu Ala Ile Val Ile His Leu Val
        355                 360                 365

Gly Ala Tyr Gln Val Phe Ser Gln Pro Leu Phe Ala Phe Val Glu Lys
    370                 375                 380

Trp Ser Val Arg Lys Trp Pro Lys Ser Asn Phe Val Thr Ala Glu Tyr
385                 390                 395                 400

Asp Ile Pro Ile Pro Cys Phe Gly Val Tyr Gln Leu Asn Phe Phe Arg
                405                 410                 415

Leu Val Trp Arg Thr Ile Phe Val Leu Leu Thr Thr Leu Ile Ala Met
            420                 425                 430

Leu Met Pro Phe Phe Asn Asp Val Val Gly Ile Leu Gly Ala Phe Gly
        435                 440                 445

Phe Trp Pro Leu Thr Val Tyr Phe Pro Ile Asp Met Tyr Ile Ser Gln
    450                 455                 460

Lys Lys Ile Gly Arg Trp Thr Ser Arg Trp Ile Gly Leu Gln Leu Leu
465                 470                 475                 480

Ser Val Ser Cys Leu Ile Ile Ser Leu Leu Ala Ala Val Gly Ser Met
                485                 490                 495

Ala Gly Val Val Leu Asp Leu Lys Thr Tyr Lys Pro Phe Lys Thr Ser
            500                 505                 510

Tyr

<210> SEQ ID NO 47
<211> LENGTH: 1862
<212> TYPE: DNA
<213> ORGANISM: Glycine max

<400> SEQUENCE: 47

ccacgcgtcc ggtatcgagc tacatatttc acagccatgt tgccaagaag tagaaccctt     60

cctagcagaa tccaccaagg aattatagaa gagaggcacg atgtcaggcc ctacgtacaa    120

gtagaagtgc gacccaataa tatccaaacg gagacccaag cgatgaatat ccagtctaac    180

tattccaagt gcttcgatga tgatggtcgc ttgaagagaa caggaacatt ttggacggca    240
```

```
actgctcata tcatcactgc tgtgataggg tcgggagtcc tttcactagc atgggcggtt     300

gctcagcttg gttgggttgc tggacctgtt gtcatgtttc tctttgccgt cgtcaatctc     360

tacacttcca acctattaac acagtgttac aggaccggtg actccgttaa tggacacaga     420

aattacacct acatggaggc tgtcaagtcc atcttgggag gaaaaaaggt caagttatgt     480

ggcctcatcc aatatatcaa tctgtttgga gttgcaatcg ggtacaccat tgctgcctct     540

gtcagtatga tggccataaa aaggtcgaat tgctatcaca gcagtcatgg aaaagatccc     600

tgccacatgt caagcaatgg gtatatgata acatttggaa tagcagaagt gatattttcc     660

caaatcccag actttgatca ggtgtggtgg ctatccatag ttgcagctat catgtccttc     720

acttattctt cagttggatt gagtcttgga gtggccaaag tagcagaaaa taaaactttc     780

aaaggaagcc tgatgggaat tagcattggc acagtaacac aagccggaac agtcaccagc     840

acacagaaaa tatggaggag tttacaagct cttggggcaa tggcctttgc atactccttt     900

tccattatcc tcatcgaaat tcaggacacc ataaaatctc ctcctgcaga gcacaagacc     960

atgagaaagg ccacaacatt gagcatcgcg gttaccacag tgttctattt actctgtgga    1020

tgcatgggtt atgcagcctt cggagataat gcacctggaa atctcttgac tggttttggg    1080

ttctataacc cttattggct tctggacatt gccaaccttg caattgttat ccacctagtt    1140

ggggcatatc aggttttttc ccagccctta tttgcatttg tggaaaaatg gagtgtacgc    1200

aaatggccaa agagcaattt tgtcacggca gaatatgata taccgattcc ctgctttggt    1260

gtgtaccaac tcaacttctt ccgcttagta tggagaacca tttttgtgct gttgacgacc    1320

ctcatagcca tgctcatgcc tttttttcaac gatgtggttg gaatacttgg cgcttttggg    1380

ttctggccct taacagttta tttccctatc gacatgtata tttcgcaaaa gaagattgga    1440

cgatggacta gtcggtggat tggacttcaa ttacttagtg tcagttgcct catcatttca    1500

ttgttagctg cagttggttc catggcaggg gttgttttgg acctcaagac ttataagcca    1560

tttaaaacta gttattaagt gagatttaaa gaaggtcgta gaaatagaag tgtttaagct    1620

tgatgatatt atagaaaact aatgataagt tggtttgtga aatttaagta tatacgctcc    1680

atgccgctgc tgttagagca attgatttga gaagaagaaa aaaatgataa ttggacataa    1740

catacctcag aatttggacg tatacgtgtc tgtgtaactg ctatattgaa gtcaattgta    1800

aggaataaaa gtctttgaac gtgttatttc tttaaaaaaa aaaaaaaaaa aaaaaaaaaa    1860

aa                                                                    1862
```

<210> SEQ ID NO 48
<211> LENGTH: 463
<212> TYPE: PRT
<213> ORGANISM: Glycine max

<400> SEQUENCE: 48

```
Met Gly Val Ala Ala Glu Ser Glu Ser Asn Asp Asn Ile Pro Leu Leu
1               5                   10                  15

Leu Thr Gln Ser Ala Tyr Pro Leu Lys Arg Thr Gly Thr Val Trp Thr
            20                  25                  30

Ala Val Ala His Ile Val Thr Gly Val Ile Gly Ser Gly Val Leu Ser
        35                  40                  45

Leu Pro Trp Ser Thr Ala Gln Leu Gly Trp Leu Ala Gly Pro Phe Ser
    50                  55                  60

Ile Leu Leu Ile Ala Ser Thr Thr Leu Phe Ser Ser Phe Leu Leu Cys
65                  70                  75                  80
```

-continued

```
Asn Thr Tyr Arg His Pro His Pro Glu Tyr Gly Pro Asn Arg Ser Ala
                85                  90                  95

Ser Tyr Leu Asp Val Val His Leu His Leu Gly Ile Ser Asn Gly Arg
            100                 105                 110

Leu Ser Gly Leu Leu Val Ser Ile Ser Leu Tyr Gly Phe Ala Ile Ala
        115                 120                 125

Phe Val Ile Thr Thr Ala Ile Ser Leu Arg Thr Ile Gln Asn Ser Phe
    130                 135                 140

Cys Tyr His Asn Lys Gly Pro Glu Ala Ala Cys Glu Ser Val Asp Ala
145                 150                 155                 160

Tyr Tyr Met Leu Leu Phe Gly Ala Ile Gln Ile Val Leu Ser Gln Ile
                165                 170                 175

Pro Asn Phe His Asn Ile Lys Trp Leu Ser Val Val Ala Ala Ile Met
            180                 185                 190

Ser Phe Thr Tyr Ser Phe Ile Gly Met Gly Leu Ser Ile Ala Gln Ile
        195                 200                 205

Ile Glu Lys Gly His Ala Glu Gly Ser Ile Gly Gly Ile Ser Thr Ser
    210                 215                 220

Asn Gly Ala Glu Lys Leu Trp Leu Val Ser Gln Ala Leu Gly Asp Ile
225                 230                 235                 240

Ser Phe Ser Tyr Pro Phe Ser Thr Ile Leu Met Glu Ile Gln Asp Thr
                245                 250                 255

Leu Lys Ser Pro Pro Pro Glu Asn Gln Thr Met Lys Lys Ala Ser Val
            260                 265                 270

Ile Ala Val Ser Val Thr Thr Phe Leu Tyr Leu Ser Cys Gly Gly Ala
        275                 280                 285

Gly Tyr Ala Ala Phe Gly Asp Asn Thr Pro Gly Asn Leu Leu Thr Gly
    290                 295                 300

Phe Val Ser Ser Lys Ser Tyr Trp Leu Val Asn Phe Ala Asn Ala Cys
305                 310                 315                 320

Ile Val Val His Leu Val Gly Ser Tyr Gln Val Tyr Ser Gln Pro Leu
                325                 330                 335

Phe Gly Thr Val Glu Asn Trp Phe Arg Phe Arg Phe Pro Asp Ser Glu
            340                 345                 350

Phe Val Asn His Thr Tyr Ile Leu Lys Leu Pro Leu Leu Pro Ala Phe
        355                 360                 365

Glu Leu Asn Phe Leu Ser Leu Ser Phe Arg Thr Ala Tyr Val Ala Ser
    370                 375                 380

Thr Thr Val Ile Ala Met Ile Phe Pro Tyr Phe Asn Gln Ile Leu Gly
385                 390                 395                 400

Val Leu Gly Ser Ile Ile Phe Trp Pro Leu Thr Ile Tyr Phe Pro Val
                405                 410                 415

Glu Ile Tyr Leu Ser Gln Ser Ser Thr Val Ser Trp Thr Thr Lys Trp
            420                 425                 430

Val Leu Leu Arg Thr Phe Ser Phe Phe Gly Phe Leu Phe Gly Leu Phe
        435                 440                 445

Thr Leu Ile Gly Cys Ile Lys Gly Ile Val Thr Glu Lys Ile Ser
    450                 455                 460
```

<210> SEQ ID NO 49
<211> LENGTH: 2191
<212> TYPE: DNA
<213> ORGANISM: Glycine max -continued

<400> SEQUENCE: 49

```
ggctcgagct cgagccgggc acatagcatc ggatctgata ttggtctgaa gatgggtgtg      60
gctgctgagt ctgagtcaaa tgacaacatc ccgctgttac tcacccaatc tgcttaccct     120
ctcaaaagga cagggacggt gtggacagca gtggcacaca tagtgacagg ggtgatagga     180
tccggagtgc tgtctctgcc atggagcact gcacagcttg ggtggcttgc aggccccttc     240
tccatccttc tcattgcttc caccactctc ttctcttctt ttcttctatg caacacttat     300
cgccatcccc atcccgaata cggtcccaac agaagtgcct cctaccttga tgttgttcat     360
tgcatttagg aataagtaat ggacggctca gtggccttct tgtcagtatt agtttgtatg     420
gttttgcaat tgccttcgtc attacaacag ctatcagctt aagaacaatc caaaattcat     480
tttgttacca caacaaaggg cctgaagcag catgtgagtc tgtagatgca tattatatgc     540
tactttttgg ggctatccaa attgttctct cacagatacc caacttccat aacatcaaat     600
ggctgtcggt tgttgctgca attatgtcct ttacttattc tttcatagga atggggcttt     660
ccattgctca aatcatagaa aaaggacatg ctgagggtag cattggagga atcagtacct     720
ctaatggagc tgaaaagtta tggctggttt ctcaagcact tggtgacata tcattctcat     780
atccattctc gacaattctt atggaaatac aggatacttt gaaatcgcct ccaccagaaa     840
accaaaccat gaagaaggcc tcagtaatag cggtcagtgt cacaacattc ttgtacctca     900
gttgtggagg tgctggatat gctgcctttg gtgataatac accaggaaac cttttaacag     960
gtttcgtatc ctccaagtct tattggctag tgaactttgc taacgcttgt atagtggttc    1020
acctagttgg ttcatatcag gtgtatagcc agccactttt tggcactgtg gagaattggt    1080
tccgttttag attcccagat agtgaatttg tgaatcacac atatatcttg aaactcccgt    1140
tgcttccagc ctttgaactt aattttctca gcctgtcttt ccgaactgct tatgttgcat    1200
ccacaactgt gatcgcaatg atatttccct acttcaatca gattttgggg gttctgggta    1260
gcatcatttt ttggccgttg accatatatt ttccagtgga aatatacttg agtcagtcca    1320
gtactgtatc atggacgact aagtgggtac tgcttcggac tttcagcttt tttggctttt    1380
tgtttggatt gttcactctc attggatgta ttaaaggaat agtaactgaa aaaataagct    1440
gagaagcttt gagacctctc caaggaatta gactcagata gccttctttt ttttctccac    1500
ttttctcctt tcaagaccca caaataatga ggatcatctg caatgtcttt tccacatatt    1560
cactcaatta ctaacttgga accattacat aaagatcgga catctatctc agtaaattag    1620
acataaaaca cgtatttgag atccgaactg tccgatcttt attcaatggt tacaaatgca    1680
ctaactgtgt gagggcaagg aataggagac tgcaccgaat ccagttggac aataaacatg    1740
cagattctct catattttca ataggaatag tgattctgta tttgttcacc tgctgaaggt    1800
atccactgct gaaatgaatg agctcaacac tcctacttcc tcggttcttc cactgttata    1860
caaacaaatt gaaagtggac attattattt tccgtgggaa aattttcagt tctatttgat    1920
tattgtttga agtcttatcg atactattta gattaagcca actttggtat aaatataagt    1980
tcctcacaag tgacctctca atgttgttga ccttttactt cagtaacttt gctgcaaccc    2040
gatcttcgct ttggatagga ttccctattg taaaaaaata cagtatttaa tgtagtaaat    2100
ctatttacat ccatgtctct gcatttccat tcagggcata acaaaattgg agaatttaaa    2160
gaaacatgaa gcattcgtgt tttgattacc c                                   2191
```

<210> SEQ ID NO 50
<211> LENGTH: 478

<212> TYPE: PRT
<213> ORGANISM: Glycine max

<400> SEQUENCE: 50

```
Met Val Glu Tyr Ala Ser Arg Thr Asn Leu Ser Tyr Cys Arg Asp Tyr
1               5                   10                  15

Gly Ile Glu Glu Asp Ser Ile Asp Asp Met Pro Leu Lys Ser Asp Pro
            20                  25                  30

Glu Cys Tyr Asp Asp Asp Gly His Leu Lys Arg Thr Gly Thr Ile Trp
        35                  40                  45

Thr Thr Ser Ser His Ile Ile Thr Ala Val Val Gly Ser Gly Val Leu
    50                  55                  60

Ser Leu Ala Trp Ala Ile Ala Gln Met Gly Trp Ile Ala Gly Pro Ala
65                  70                  75                  80

Val Met Ile Leu Phe Ser Ile Val Thr Leu Tyr Thr Ser Ser Phe Leu
                85                  90                  95

Ala Asp Cys Tyr Arg Thr Gly Asp Pro Met Phe Gly Lys Arg Asn Tyr
            100                 105                 110

Thr Phe Met Asp Ala Val Ser Thr Ile Leu Gly Gly Tyr Ser Val Thr
        115                 120                 125

Phe Cys Gly Ile Val Gln Tyr Leu Asn Leu Phe Gly Ser Ala Ile Gly
    130                 135                 140

Tyr Thr Ile Ala Ala Ser Leu Ser Met Met Ala Ile Gln Arg Ser His
145                 150                 155                 160

Cys Ile Ile Gln Ser Ser Asp Gly Glu Asn Gln Cys Asn Ile Ser Ser
                165                 170                 175

Ile Pro Tyr Thr Ile Cys Phe Gly Ala Val Gln Ile Phe Phe Ser Gln
            180                 185                 190

Ile Pro Asp Phe His Asn Met Trp Trp Leu Ser Ile Val Ala Ser Val
        195                 200                 205

Met Ser Phe Thr Tyr Ser Ile Ile Gly Leu Val Leu Gly Ile Thr Lys
    210                 215                 220

Ile Ala Glu Thr Gly Thr Phe Lys Gly Ser Leu Thr Gly Ile Ser Ile
225                 230                 235                 240

Gly Thr Val Thr Glu Gly Pro Lys Val Trp Gly Val Phe Gln Ala Leu
                245                 250                 255

Gly Asn Ile Ala Phe Ala Tyr Ser Tyr Ser Phe Val Leu Leu Glu Ile
            260                 265                 270

Gln Asp Thr Ile Lys Ser Pro Pro Ser Glu Val Lys Thr Met Lys Lys
        275                 280                 285

Ala Ala Lys Leu Ser Ile Ala Val Thr Thr Thr Phe Tyr Met Leu Cys
    290                 295                 300

Gly Cys Val Gly Tyr Ala Ala Phe Gly Asp Ser Ala Pro Gly Asn Leu
305                 310                 315                 320

Leu Ala Gly Phe Gly Phe His Lys Leu Tyr Trp Leu Val Asp Ile Ala
                325                 330                 335

Asn Ala Ala Ile Val Ile His Leu Val Gly Ala Tyr Gln Val Tyr Ala
            340                 345                 350

Gln Pro Leu Phe Ala Phe Val Glu Lys Glu Thr Ala Lys Arg Trp Pro
        355                 360                 365

Lys Ile Asp Lys Glu Phe Gln Ile Ser Ile Pro Gly Leu Gln Ser Tyr
    370                 375                 380

Asn Gln Asn Ile Phe Ser Leu Val Cys Arg Thr Val Phe Val Ile Ile
385                 390                 395                 400
```

```
Thr Thr Val Ile Ser Thr Leu Leu Pro Phe Phe Asn Asp Ile Leu Gly
            405                 410                 415

Val Ile Gly Ala Leu Gly Phe Trp Pro Leu Thr Val Tyr Phe Pro Val
        420                 425                 430

Glu Met Tyr Ile Leu Gln Lys Arg Ile Pro Lys Trp Ser Met Arg Trp
    435                 440                 445

Ile Ser Leu Glu Leu Met Ser Val Val Cys Leu Leu Val Thr Ile Ala
450                 455                 460

Ala Gly Leu Gly Ser Val Val Gly Val Tyr Leu Asp Leu Gln
465                 470                 475
```

<210> SEQ ID NO 51
<211> LENGTH: 1988
<212> TYPE: DNA
<213> ORGANISM: Glycine max

<400> SEQUENCE: 51

```
gacaactgag aaaggcaaga agcagccgtg tgggtcacct cattggactg acttcaccgc     60

agaaagggga gggaactgca aatccgcaat tctctctctc ccgataacgc cacagcacag    120

tttctttgta tttcacagta caatcaaatc tcttgtccat ctaaagatgg tagaatatgc    180

ttcgagaacc aaccttagct actgtcgaga ttatggcatt gaggaggact ccatagatga    240

catgccttta aaaagtgacc ccgaatgcta tgacgatgat ggccatctta aacgaacagg    300

gaccatttgg actacaagct cccacataat aacagctgtg gtaggatctg ggtgctctc     360

cttagcctgg gcaatagctc agatgggttg gattgctggt cctgcagtga tgatcttatt    420

cagcatagtc actttgtata cttcatcatt tctagctgat tgttatcgta ctggtgaccc    480

catgtttggg aagagaaact atactttcat ggatgcagtt agcaccattc tgggcgggta    540

cagtgttacg ttttgtggga tagttcagta cttgaatctt ttcggaagtg caataggata    600

cacaattgcg gcttccctta gcatgatggc aatccaaagg tctcactgta tcatccaatc    660

ctctgatgga gaaaaccaat gcaatatttc aagtatccca tacacgatct gttttggtgc    720

agtgcaaatt ttcttttcac aaattccaga ttttcataac atgtggtggc tctcaatagt    780

tgcttcagtc atgtctttca cctattccat aattggcctc gttcttggaa ttaccaaaat    840

tgcagaaacg ggaactttca agggtagcct cactggaata agcattggaa ctgtgacgga    900

aggcccaaaa gtttggggtg ttttccaagc tcttggtaac atagccttcg cctattcata    960

ttctttcgtt ctcctagaaa ttcaggatac catcaaatct ccaccatctg aagtaaaaac   1020

aatgaagaag gctgcaaagt taagtattgc agtgaccaca acattttata tgctttgtgg   1080

ctgcgtaggc tatgctgctt ttggagattc agcacctggg aacctgcttg ctggatttgg   1140

tttccataaa ctatattggc ttgtggatat tgctaatgct gctattgtaa ttcaccttgt   1200

gggggcatac caagtgtatg ctcaacccct ctttgccttt gtagagaagg agacagcaaa   1260

aagatggccc aaaattgaca aggaattcca aatttctatt cccggtttgc aatcctacaa   1320

tcagaacata tttagcctag tttgtaggac agtgtttgtg atcataacca ctgttatatc   1380

aacgttgctt ccattcttca atgatatttt gggagtgatt ggagcattgg ggttttggcc   1440

tttaactgtc tactttcctg tggagatgta tatattgcaa aagaggattc caaaatggag   1500

tatgagatgg atttctctgg aattgatgag tgtggtgtgc ctcttagtaa caattgcggc   1560

tggtcttggc tcagtggttg gtgtctatct tgacctccag taatacaatc cattcagttc   1620

agatcattaa actccacata acatctattg cctccttggg aatgtaagaa actctgaggg   1680
```

```
tggtgatggt tgtgatctct attgtatcat catcttacaa gtggtgctaa ctcaaaatta   1740

tccctatgat aatttaagaa gagtcggcac ttgaaataat tgctgcccaa tgtattttag   1800

atacttctag tctgcatttt ttcattattt tgtaccaata gaagtggtac gtcaaaatga   1860

ttaaataagt tgtagtaatt tactatgtta tattgcttat gcaatttgtt tgtattttta   1920

tgagatttgt aatttaatgt aaatattatt ttttccgtat tggatatatg ttaattgtat   1980

tgtcttag                                                            1988
```

<210> SEQ ID NO 52
<211> LENGTH: 479
<212> TYPE: PRT
<213> ORGANISM: Glycine max

<400> SEQUENCE: 52

```
Met Met Glu Asn Gly Gly Lys Gln Thr Phe Glu Val Ser Asn Asp Thr
1               5                   10                  15

Leu Gln Arg Val Gly Ser Lys Ser Phe Asp Asp Asp Gly Arg Leu Lys
            20                  25                  30

Arg Thr Gly Thr Ile Trp Thr Ala Ser Ala His Ile Ile Thr Ala Val
        35                  40                  45

Ile Gly Ser Gly Val Leu Ser Leu Ala Trp Ala Ile Ala Gln Leu Gly
    50                  55                  60

Trp Ile Ala Gly Pro Val Val Met Ile Leu Phe Ser Ile Val Thr Tyr
65                  70                  75                  80

Tyr Thr Ser Thr Leu Leu Ala Thr Cys Tyr Arg Ser Gly Asp Gln Leu
                85                  90                  95

Ser Gly Lys Arg Asn Tyr Thr Tyr Thr Gln Ala Val Arg Ser Tyr Leu
            100                 105                 110

Gly Gly Phe Ser Val Lys Phe Cys Gly Trp Val Gln Tyr Ala Asn Leu
        115                 120                 125

Phe Gly Val Ala Ile Gly Tyr Thr Ile Ala Ala Ser Ile Ser Met Met
    130                 135                 140

Ala Ile Lys Arg Ser Asn Cys Tyr His Ser Ser Gly Gly Lys Asn Pro
145                 150                 155                 160

Cys Lys Met Asn Ser Asn Trp Tyr Met Ile Ser Tyr Gly Val Ser Glu
                165                 170                 175

Ile Ile Phe Ser Gln Ile Pro Asp Phe His Glu Leu Trp Trp Leu Ser
            180                 185                 190

Ile Val Ala Ala Val Met Ser Phe Thr Tyr Ser Phe Ile Gly Leu Gly
        195                 200                 205

Leu Gly Ile Gly Lys Val Ile Gly Asn Gly Arg Ile Lys Gly Ser Leu
    210                 215                 220

Thr Gly Val Thr Ile Gly Thr Val Thr Glu Ser Gln Lys Ile Trp Arg
225                 230                 235                 240

Thr Phe Gln Ala Leu Gly Asn Ile Ala Phe Ala Tyr Ser Tyr Ser Met
                245                 250                 255

Ile Leu Ile Glu Ile Gln Asp Thr Ile Lys Ser Pro Pro Ala Glu Ser
            260                 265                 270

Glu Thr Met Ser Lys Ala Thr Leu Ile Ser Val Leu Val Thr Thr Val
        275                 280                 285

Phe Tyr Met Leu Cys Gly Cys Phe Gly Tyr Ala Ser Phe Gly Asp Ala
    290                 295                 300

Ser Pro Gly Asn Leu Leu Thr Gly Phe Gly Phe Tyr Asn Pro Phe Trp
```

-continued

```
305                 310                 315                 320

Leu Ile Asp Ile Ala Asn Ala Gly Ile Val Ile His Leu Val Gly Ala
                325                 330                 335

Tyr Gln Val Tyr Cys Gln Pro Leu Phe Ser Phe Val Glu Ser Asn Ala
            340                 345                 350

Ala Glu Arg Phe Pro Asn Ser Asp Phe Met Ser Arg Glu Phe Glu Val
        355                 360                 365

Pro Ile Pro Gly Cys Lys Pro Tyr Lys Leu Asn Leu Phe Arg Leu Val
    370                 375                 380

Trp Arg Thr Leu Phe Val Ile Leu Ser Thr Val Ile Ala Met Leu Leu
385                 390                 395                 400

Pro Phe Phe Asn Asp Ile Val Gly Leu Ile Gly Ala Ile Gly Phe Trp
                405                 410                 415

Pro Leu Thr Val Tyr Leu Pro Val Glu Met Tyr Ile Thr Gln Thr Lys
            420                 425                 430

Ile Pro Lys Trp Gly Ile Lys Trp Ile Gly Leu Gln Met Leu Ser Val
        435                 440                 445

Ala Cys Phe Val Ile Thr Ile Leu Ala Ala Ala Gly Ser Ile Ala Gly
    450                 455                 460

Val Ile Asp Asp Leu Lys Val Tyr Lys Pro Phe Val Thr Ser Tyr
465                 470                 475


<210> SEQ ID NO 53
<211> LENGTH: 1873
<212> TYPE: DNA
<213> ORGANISM: Glycine max

<400> SEQUENCE: 53

atataaaaat agagggatct ccttctctta tccagagaag catatataga gaaagaaaga      60

aggccctgcc ctatatagct gaaggcagtg tgcacaaact ctgagactgc atattagagt     120

ttgagtcttc actctgaagc ctaacttggg tttgtgtctc tcatagcaag atgatggaaa     180

acggtggcaa acagacattt gaagtctcca atgacacgct tcaacgagta ggttccaaga     240

gctttgatga tgatggccgt ctcaaaagaa ctggaactat ttggactgca agtgcccaca     300

taataacagc tgttattggt tctggggtgc tatctttggc ttgggctatt gctcagctag     360

gttggattgc tggtcctgtg gtgatgattc tattctctat tgtgacttat tatacctcaa     420

ctcttctagc tacttgttac cgttctggtg accaactcag tggcaagaga aactacactt     480

acacacaagc tgttagatcc taccttggcg gtttttcggt caagttttgt gggtgggttc     540

agtatgcgaa cctttttgga gtggcaattg ggtacaccat agcagcttcc ataagcatga     600

tggcaatcaa aggtctaaat tgttatcata gtagcggggg gaaaaatcca tgcaaaatga     660

acagcaattg gtacatgatt tcatatggtg tttcggaaat tatcttctcc caaattccag     720

atttccatga gttgtggtgg ctctctattg tagctgctgt catgtccttc acatactcat     780

tcattggact tggccttggt attggtaaag ttataggaaa cggaagaatt aaaggaagcc     840

taactggtgt aactattggg actgtgacag aatcccaaaa aatttggaga actttccaag     900

cgcttggaaa catagccttt gcttactcct actcaatgat ccttattgaa attcaggaca     960

caatcaaatc ccctccagca gagtcagaga caatgtccaa ggctacttta ataagtgttt    1020

tggtcacaac cgttttctat atgctatgtg gttgctttgg ctatgcttct tttggagatg    1080

caagtccggg aaaccttctc actggctttg gcttctataa cccattttgg ctcattgaca    1140

tagccaatgc tggcattgtt atccaccttg ttggtgcata ccaagtttac tgccaacccc    1200
```

```
tcttctcatt cgtcgaatca aatgcggcag aaaggttccc taatagtgat tttatgagca   1260

gagagtttga agtaccaatc cctggttgca aaccctacaa gctcaacctc ttcaggttgg   1320

tttggaggac actttttgtg attttgtcaa ctgtgatagc catgctccta ccattcttca   1380

atgacattgt agggcttatt ggagccattg gattttggcc cctcactgtg tatttaccag   1440

tggagatgta tataactcaa actaagatac caaagtgggg cataaaatgg ataggcctac   1500

aaatgcttag tgttgcatgc tttgtaatta ctatattagc tgcagcaggt tccattgctg   1560

gggttattga tgatcttaaa gtttacaagc catttgttac cagctactaa ttcaatagga   1620

taattactta gtgatcatga tcaccattgt cagagatttc attagcaaca agaaaaaaaa   1680

aagaaggtaa attgttgcaa attgaaatca acaggaaggt ggtcttactt gtttattgct   1740

tagtaacctt gtatcttctg tatctttgtt ttttttgtt tgtgtgtgtg tgttctctta   1800

ctttgtaact tgctctgtat ccctaatttg caatgagaaa tggaggaaat gaagcagagg   1860

ctttcaaatt atc                                                      1873
```

<210> SEQ ID NO 54
<211> LENGTH: 463
<212> TYPE: PRT
<213> ORGANISM: Glycine max

<400> SEQUENCE: 54

```
Pro Arg Val Arg Glu Ser Gln Ala Asn Gly Val His Ser Ser Lys His
1               5                   10                  15

Asp Asp Asp Gly Arg Leu Lys Arg Arg Gly Thr Trp Leu Thr Ala Thr
            20                  25                  30

Ser His Ile Val Thr Ala Val Ile Gly Ser Gly Val Leu Ser Leu Ala
        35                  40                  45

Trp Ala Val Ala Gln Leu Gly Trp Ile Ala Gly Pro Ala Ile Leu Thr
    50                  55                  60

Ile Phe Ser Val Ile Thr Val Phe Thr Ser Ser Leu Leu Ser Asp Cys
65                  70                  75                  80

Tyr Arg Tyr Pro Asp Ser Val His Gly Thr Arg Asn His Asn Tyr Arg
                85                  90                  95

Glu Met Val Lys Asn Ile Leu Gly Gly Arg Lys Tyr Leu Phe Cys Gly
            100                 105                 110

Leu Ala Gln Phe Ala Asn Leu Ile Gly Thr Gly Ile Gly Tyr Thr Val
        115                 120                 125

Thr Ala Ser Ile Ser Met Val Ala Val Ile Arg Ser Asn Cys Phe His
    130                 135                 140

Lys Tyr Gly His Glu Ala Lys Cys His Thr Ser Asn Tyr Pro Tyr Met
145                 150                 155                 160

Thr Ile Phe Ala Val Ile Gln Ile Leu Leu Ser Gln Ile Pro Asp Phe
                165                 170                 175

Gln Glu Leu Ser Gly Leu Ser Ile Ile Ala Ala Val Met Ser Phe Gly
            180                 185                 190

Tyr Ser Ser Ile Gly Ile Gly Leu Ser Ile Ala Lys Ile Ala Gly Gly
        195                 200                 205

Asn Asp Ala Lys Thr Ser Leu Thr Gly Leu Ile Val Gly Glu Asp Val
    210                 215                 220

Thr Ser Gln Glu Lys Leu Trp Asn Thr Phe Gln Ala Ile Gly Asn Ile
225                 230                 235                 240

Ala Phe Ala Tyr Ala Phe Ser Gln Val Leu Val Glu Ile Gln Asp Thr
```

-continued

```
                245                 250                 255

Leu Lys Ser Ser Pro Pro Glu Asn Gln Ala Met Lys Lys Ala Thr Leu
            260                 265                 270

Ala Gly Cys Ser Ile Thr Ser Leu Phe Tyr Met Leu Cys Gly Leu Leu
        275                 280                 285

Gly Tyr Ala Ala Phe Gly Asn Lys Ala Pro Gly Asn Phe Leu Thr Gly
    290                 295                 300

Phe Gly Phe Tyr Glu Pro Tyr Trp Leu Val Asp Ile Gly Asn Val Phe
305                 310                 315                 320

Val Phe Val His Leu Val Gly Ala Tyr Gln Val Phe Thr Gln Pro Val
                325                 330                 335

Phe Gln Leu Val Glu Thr Trp Val Ala Lys Arg Trp Pro Glu Ser Asn
            340                 345                 350

Phe Met Gly Lys Glu Tyr Arg Val Gly Lys Phe Arg Phe Asn Gly Phe
        355                 360                 365

Arg Met Ile Trp Arg Thr Val Tyr Val Ile Phe Thr Ala Val Val Ala
    370                 375                 380

Met Ile Leu Pro Phe Phe Asn Ser Ile Val Gly Leu Leu Gly Ala Ile
385                 390                 395                 400

Ser Phe Phe Pro Leu Thr Val Tyr Phe Pro Thr Glu Met Tyr Leu Val
                405                 410                 415

Gln Ala Lys Val Pro Lys Phe Ser Leu Val Trp Ile Gly Val Lys Ile
            420                 425                 430

Leu Ser Gly Phe Cys Leu Ile Val Thr Leu Val Ala Ala Ala Gly Ser
        435                 440                 445

Ile Gln Gly Ile Ile Ala Asp Leu Arg Ile Tyr Glu Pro Phe Lys
    450                 455                 460


<210> SEQ ID NO 55
<211> LENGTH: 1572
<212> TYPE: DNA
<213> ORGANISM: Glycine max

<400> SEQUENCE: 55

ccacgcgtcc gggaatcgca agcaaatggt gtacacagct ctaaacatga tgatgatggt     60

cgcttaaaac gaagaggaac atggttaact gcgacttcac acatagtgac ggctgttatt    120

gggtctgggg tcctatcact ggcatgggcc gttgctcagt tgggctggat tgctgggcct    180

gccattctga caatcttttc tgtcatcact gtcttcactt cttctctgct cagcgattgt    240

tataggtacc ctgactctgt tcatggaacc agaaaccata actacaggga gatggtaaaa    300

aatattctag gaggacgtaa atacctgttt tgtggattgg cccagttcgc aaatctgatt    360

ggaacaggca ttggatacac cgttactgca tccattagca tggtggctgt cataagatcg    420

aattgctttc acaagtatgg gcacgaagcg aagtgtcata catcaaatta cccatatatg    480

accatctttg cggtcataca gattttatta agccaaatcc ctgatttcca ggaactctca    540

ggcctctcta ttattgctgc cgtcatgtct tttggttatt cttccatagg cattggtctc    600

tccatagcca aaattgcagg aggaaacgat gccaagacaa gtctaacggg gctcatcgtt    660

ggagaagacg tgacaagcca ggagaaacta tggaacactt tccaagcaat tggaaacatt    720

gcttttgcat acgccttcag tcaagtactt gttgagatac aggacacgtt aaaatcaagc    780

ccaccagaaa atcaagccat gaaaaaggca acccttgctg gatgctcgat cacctcactg    840

ttttatatgt tatgtggcct attaggctat gcagcattcg ggaacaaggc acccggaaac    900
```

-continued

```
ttcttaacag gatttgggtt ttatgaacca tattggcttg ttgacattgg taatgtcttc    960

gtatttgttc atttagtggg cgcctaccag gtattcacac aaccagtttt ccagcttgtg   1020

gaaacttggg ttgcgaagcg ttggcctgaa agcaacttca tgggaaaaga atatcgtgtt   1080

ggcaagttca gattcaatgg attcaggatg atatggagga cagtgtacgt gattttcaca   1140

gcagtggttg ctatgatact tcccttcttc aacagcattg tgggtttgct tggagctatt   1200

tccttctttc ctttgacagt gtattttcca acagagatgt atctggtgca ggctaaagtt   1260

cccaagtttt ctctggtctg gattggggtc aaaattctaa gtggcttctg cttgattgtc   1320

actcttgttg ctgcagctgg atcaatccaa ggaatcatcg cagaccttag aatctatgag   1380

cccttcaagt aaatatcctt tgtgtagttt agctctttgg atgaacaatg gtttgtggct   1440

aagtttgtgg tcattattga tcagttgttt ggataaactt tctttcaagt gttttcataa   1500

tatatacttt tataatggat cgataagaat gcttttagat cctagaaaaa ttttaaattg   1560

ctttttgtcc tc                                                       1572
```

<210> SEQ ID NO 56
<211> LENGTH: 1564
<212> TYPE: DNA
<213> ORGANISM: Glycine max

<400> SEQUENCE: 56

```
ccacgcgtcc gcccacgcgt ccgaaatggc tgtcggttgt tgctgcaatt atgtccttta     60

cttattcttt cataggaatg ggctttccca ttgctcaaat catagaaaaa ggacatgctg    120

agggtagcat tggaggaatc agtacctcca gtggagctga aaagctatgg ctggtttctc    180

aagcacttgg tgacatatca ttctcatatc cgttctccac aattcttatg gaaatacagg    240

atactttgaa atcacctcca ccagaaaacc aaaccatgaa gaaggcctca ggaatagcgg    300

tcaccgtcac tacattcgtg tacctcagtt gtggaggtgc tggatatgct gcctttggtg    360

ataatacacc aggaaacctt ttaacaggtt ttggatcctc caagttttat tggcttgtga    420

actttgctaa tgcttgttta gtggttcacc tagttggttc atatcaggtg tatagccagc    480

ctctttttgc cactgttgag aattggttcc gttttagatt cccagatagt gaatttgtga    540

atcacacata tatgttgaaa ctcccgttgc ttccaacctt tgaacttaat tttctcagcc    600

tgtctttccg aactgcttat gttgcatcaa caactgtgat tgcaatgata tttccctact    660

tcaatcagat tttgggggtt ctgggtagca tcatttttg gccattgacc atatattttc     720

cggtggaaat atacttgact cagtccagta ctgtatcatg gacgactaag tgggtactgc    780

ttcgaacttt cagcattttc ggctttttat ttggattgtt cactcttatt ggatgtatta    840

aaggtatagt aactgaaaaa ataagctgag aagctttgag acctctccaa ggaattagac    900

tcaggcagcc tacatttttt tcttccactt ttctcgttgc aatggccttt ccacacatta    960

actcagttag taacttggaa ccattagatg aagacacgat ctttattgaa ctgttgcaaa   1020

tgcaaggaat aggagattgc actgaatcca gttggacatt aaacgtgcag attctctcat   1080

attttcaata ggactagtgg ttctgtattt ggtcacatgc ggaaggtatc cactactgaa   1140

tgaatgaact caaactcaac atttctactt cctcggttct tcttccacta tgttatacaa   1200

acaaattgaa agtggacttt tttttctatt tcgtggggaa attttcagct ctaattgatt   1260

ttttgtttca agtcttatcg ataatattta gattaagcca agcttgctat aattataagc   1320

tcctcacaag tgacccttca atgttgttga ccttttactt cagtaacttt ggtggaaccc   1380

gatcttagct ttggatagga ttccctttgg taaaaaatac agtatttgat gtactaaaca   1440
```

```
atctattccc tttgtttaaa tttattgtta aactgcaaaa cgtgcatgtt ctctgcattt   1500

ccattcagag catgacaaaa ttggagtatt tcaagaaaaa aaaaaaaaaa aaaaaaaaaa   1560

aaaa                                                                 1564


<210> SEQ ID NO 57
<211> LENGTH: 823
<212> TYPE: DNA
<213> ORGANISM: Glycine max

<400> SEQUENCE: 57

aaatgttccc agatagtgat tttctgaaca aagaaattga aattccaatc cctggtttcc     60

atccctacag gctcaacctc ttcaggttgg tttggaggac aatatatgta atgttgagca    120

ctgtaatatc aatgctcctc ccattcttca atgacatagg tggacttctt ggagcatttg    180

gattttggcc ccttacagtg tatttcccag tggagatgta cattattcaa aagagaatac    240

caaagtggag cacaaagtgg atctgcctcc aaatacttag catgacttgc cttttgatga    300

ctataggagc tgcagctggc tctattgctg ggattgccat tgatcttcga acttacaagc    360

cattcaagac caactattga ttaaactatg attgccattg atagagattt cagaaaccaa    420

atttcatttc ttggtcatat tcttatgaag ccaaggatat atggtgatct tgtttgttta    480

tggcctagca gccctgtgtg ttccacttct ttctactgtg tatctgttac tctctagctc    540

gttctgcaac ctaattcaaa atggaagaaa tgaagtaaaa gcatataaat ctagtgtaat    600

tataatcata ttttcatttt ttcccttctg ttttactttt atttaagaat aaaatatgtt    660

tttttatac caatataggt ctagttggta aggaacaaat tcatgttcca aaattatgag     720

tttggttccc actatccatg taggaatctt attaggagtc atttgtgttc tttgaatgaa    780

atctgtcctg aggtagtaca ttctcgaaaa aaaaaaaaaa aaa                      823


<210> SEQ ID NO 58
<211> LENGTH: 861
<212> TYPE: DNA
<213> ORGANISM: Glycine max

<400> SEQUENCE: 58

aaagcaattt gcatccacaa aacttgcaag aagctgcatc tcctgttttg tggatgcagc     60

ttcttgcaag tttttgaata atcccttcat gatcggtttt gggatcttgc aacttttctt    120

gtcccaaatt ccaaacttcc atgagcttac atggctctca actgctgcct gtatcacctc    180

ttttggttat gtattcattg gcagtgggct gtgtctcttg gtcgtcctct caggaaaagg    240

agcagcaacc agcataaccg gaaccaaact acctgcagag gataaacttc tgagggtttt    300

cactggattg ggaaacatag ctcttgcatg cacttacgct actgttattt atgatataat    360

ggacacatta aagtcccatc catcagaaaa taaacaaatg aaaagggcta acgtgctagg    420

ggtcacagca atggcaatat tgttcttgct atgcagtggc cttggctatg ctgcttttgg    480

tgataacaca cctgggaaca tcttgactgg atttaccgaa cccttctggt tggttgcact    540

ggggaacgga ttcatcgtaa tccacatgat tggagcatat caggttcgat cattctttca    600

ctgaaacata attaagttac tcatttttaa ttttgttctt gtaaaatatt tttgtattta    660

atttgtaatt tactgaaata tacgctttta atccgtatca ttatatttct gttcttgaat    720

aatgacttga tataacgaga ccgtgttact tgtcaataat ctgtttatca tgtcactgcg    780

taacggatat ttttttgaa gggtgcttac tattcaatgg taaagactga atatataatt     840
```

caaaataaaa aaaaaaaaaa a 861

<210> SEQ ID NO 59
<211> LENGTH: 630
<212> TYPE: DNA
<213> ORGANISM: Glycine max

<400> SEQUENCE: 59
gagcaatttt gtcaccgcag aatatgatat acccattccc tgctttggtg tgtaccaact 60
caacttcttc cgcttagtat ggaggaccat ttttgtgctg ttgacgaccc tcatagccat 120
gctcatgcct tttttcaacg atgtggttgg aatacttggc gcttttgggt tctggccctt 180
gacagtttat ttccctattg acatgtatat ttcgcaaaag aagattggac gatggaccag 240
tcgctggctt ggacttcagt tacttagtgc cagttgcctc atcatttcat tgttagctgc 300
agttggttcc atggcagggg tggttttgga cctcaagact tacaagccat ttaaaactag 360
ttattaaatc aaggccgtaa gaaatagcta gaagtgtttg aacatatgat atttttatac 420
aaaactaatg ataagttagt ttgtgaaatt aaagtatata cgttccatgc ctgctgctgt 480
tagagcaact tgatttgagg aaaaaagtga taattggaca taatatacct cagatttgga 540
cgtatacagt ctgtgtatgt gtgttatttt acaaggaata aaagtctttg aacgtgttat 600
ttctttagtc ataaaaaaaa aaaaaaaaaa 630

<210> SEQ ID NO 60
<211> LENGTH: 468
<212> TYPE: DNA
<213> ORGANISM: Glycine max

<400> SEQUENCE: 60
ccacgcgtcc ggaaataggt gctaacatcg cctggccaaa ttcagatttc attaacaagg 60
aatatccatt cattgtgggc ggtttaatgg tccgtttcaa cttgtttaga ttagtttgga 120
ggacgatttt tgtaatattg gccacaattc ttgcgatggt aatgccgttt tttagtgagg 180
ttctttccct tcttggagca attgggtttg ggcctctagt tgtctttatt cccatacaaa 240
tgcacattgc tcagaaaagc attaggaaac tatcattgag gtggtgtgga ctccaatttt 300
taagttgcct gagctttatt gtttcactgg gcgctgtggt aggttcagtt catggaatta 360
ttcaggattt ccacaaaagc gaccttttca tgtacaaaca atagtccctt tggaaaccaa 420
aatctgaaat aaataccttt ctatattaat ataaaaaaaa aaaaaaaa 468

<210> SEQ ID NO 61
<211> LENGTH: 1175
<212> TYPE: DNA
<213> ORGANISM: Glycine max

<400> SEQUENCE: 61
gaagaattaa aggaagccta actggtgtaa ctattgggac tgtgacagaa tcccaaaaaa 60
tttggagaac tttccaagcg cttggaaaca tagcctttgc ttactcctac tcaatgatcc 120
ttattgaaat tcagaaaaca acacaaacaa caaattgaag tctaaattaa aatggtggtt 180
gttatggaac aggacacaat caaatcccct ccagcagagt cagagacaat gtccaaggct 240
actttaataa gtgttttggt cacaaccgtt ttctatatgc tatgtggttg ctttggctat 300
gcttcttttg gagatgcaag tccgggaaac cttctcactg gctttggctt ctataaccca 360
ttttggctca ttgacatagc caatgctggc attgttatcc accttgttgg tgcataccaa 420
gtttactgcc aacccctctt ctcattcgtc gaatcaaatg cggcagaaag gttccctaat 480
agtgatttta tgagcagaga gtttgaagta ccaatccctg gttgcaaacc ctacaagctc 540
aacctcttca ggttggtttg gaggacactt tttgtgattt tgtcaactgt gatagccatg 600
ctcctaccat tcttcaatga cattgtaggg cttattggag ccattggatt ttggcccctc 660
actgtgtatt taccagtgga gatgtatata actcaaacta agataccaaa gtggggcata 720
aaatggatag gcctacaaat gcttagtgtt gcatgctttg taattactat attagctgca 780
gcaggttcca ttgctggggt tattgatgat cttaaagttt acaagccatt tgttaccagc 840
tactaattca ataggataat tacttagtga tcatgatcac cattgtcaga gatttcatta 900
gcaacaagaa aaaaaaaaga aggtaaattg ttgcaaattg aaatcaacag gaaggtggtc 960
ttacttgttt attgcttagt aaccttgtat cttctgtatc tttgtttttt tttgtttgtg 1020
tgtgtgtgtt ctcttacttt gtaacttgct ctgtatccct aatttgcaat gagaaatgga 1080
ggaaatgaag cagaggcttt caaattatca aagcttttct ctctgagtca agccacttgc 1140
ataaaaaaaa aaaaaaaaaa aaaaaaaaaa aaaaa 1175

<210> SEQ ID NO 62
<211> LENGTH: 17
<212> TYPE: DNA
<213> ORGANISM: synthetic

<400> SEQUENCE: 62
atttaggtga cactata 17

<210> SEQ ID NO 63
<211> LENGTH: 20
<212> TYPE: DNA
<213> ORGANISM: synthetic

<400> SEQUENCE: 63
taatacgact cactataggg 20

<210> SEQ ID NO 64
<211> LENGTH: 481
<212> TYPE: PRT
<213> ORGANISM: Arabidopsis thaliana

<400> SEQUENCE: 64

Met Glu Lys Lys Lys Ser Met Phe Val Glu Gln Ser Phe Pro Glu His
1 5 10 15

Glu Ile Gly Asp Thr Asn Lys Asn Phe Asp Glu Asp Gly Arg Asp Lys
20 25 30

Arg Thr Gly Thr Trp Met Thr Gly Ser Ala His Ile Ile Thr Ala Val
35 40 45

Ile Gly Ser Gly Val Leu Ser Leu Ala Trp Ala Ile Ala Gln Leu Gly
50 55 60

Trp Val Ala Gly Pro Ala Val Leu Met Ala Phe Ser Phe Ile Thr Tyr
65 70 75 80

Phe Thr Ser Thr Met Leu Ala Asp Cys Tyr Arg Ser Pro Asp Pro Val
85 90 95

Thr Gly Lys Arg Asn Tyr Thr Tyr Met Glu Val Val Arg Ser Tyr Leu
100 105 110

Gly Gly Arg Lys Val Gln Leu Cys Gly Leu Ala Gln Tyr Gly Asn Leu
115 120 125

Ile Gly Ile Thr Ile Gly Tyr Thr Ile Thr Ala Ser Ile Ser Met Val
130 135 140

```
Ala Val Lys Arg Ser Asn Cys Phe His Lys Asn Gly His Asn Val Lys
145                 150                 155                 160

Cys Ala Thr Ser Asn Thr Pro Phe Met Ile Ile Phe Ala Ile Ile Gln
                165                 170                 175

Ile Ile Leu Ser Gln Ile Pro Asn Phe His Asn Leu Ser Trp Leu Ser
            180                 185                 190

Ile Leu Ala Ala Val Met Ser Phe Cys Tyr Ala Ser Ile Gly Val Gly
        195                 200                 205

Leu Ser Ile Ala Lys Ala Ala Gly Gly Gly Glu His Val Arg Thr Thr
    210                 215                 220

Leu Thr Gly Val Thr Val Gly Ile Asp Val Ser Gly Ala Glu Lys Ile
225                 230                 235                 240

Trp Arg Thr Phe Gln Ala Ile Gly Asp Ile Ala Phe Ala Tyr Ala Tyr
                245                 250                 255

Ser Thr Val Leu Ile Glu Ile Gln Asp Thr Leu Lys Ala Gly Pro Pro
            260                 265                 270

Ser Glu Asn Lys Ala Met Lys Arg Ala Ser Leu Val Gly Val Ser Thr
        275                 280                 285

Thr Thr Phe Phe Tyr Met Leu Cys Gly Cys Val Gly Tyr Ala Ala Phe
    290                 295                 300

Gly Asn Asp Ala Pro Gly Asn Phe Leu Thr Gly Phe Gly Phe Tyr Glu
305                 310                 315                 320

Pro Phe Trp Leu Ile Asp Phe Ala Asn Val Cys Ile Ala Val His Leu
                325                 330                 335

Ile Gly Ala Tyr Gln Val Phe Cys Gln Pro Ile Phe Gln Phe Val Glu
            340                 345                 350

Ser Gln Ser Ala Lys Arg Trp Pro Asp Asn Lys Phe Ile Thr Gly Glu
        355                 360                 365

Tyr Lys Ile His Val Pro Cys Cys Gly Asp Phe Ser Ile Asn Phe Leu
    370                 375                 380

Arg Leu Val Trp Arg Thr Ser Tyr Val Val Val Thr Ala Val Val Ala
385                 390                 395                 400

Met Ile Phe Pro Phe Phe Asn Asp Phe Leu Gly Leu Ile Gly Ala Ala
                405                 410                 415

Ser Phe Trp Pro Leu Thr Val Tyr Phe Pro Ile Glu Met His Ile Ala
            420                 425                 430

Gln Lys Lys Ile Pro Lys Phe Ser Phe Thr Trp Thr Trp Leu Lys Ile
        435                 440                 445

Leu Ser Trp Thr Cys Phe Ile Val Ser Leu Val Ala Ala Ala Gly Ser
    450                 455                 460

Val Gln Gly Leu Ile Gln Ser Leu Lys Asp Phe Lys Pro Phe Gln Ala
465                 470                 475                 480

Pro
```

<210> SEQ ID NO 65
<211> LENGTH: 1682
<212> TYPE: DNA
<213> ORGANISM: Arabidopsis thaliana

<400> SEQUENCE: 65

```
ggtaccggtc cggaattccc gggtcgaccc acgcgtccgc ggacgcgtgg tagatggaga     60

agaagaagag catgttcgtt gaacagagct tcccggagca tgaaattggc gatactaaca    120

aaaactttga cgaggatggc cgcgacaaaa gaactgggac atggatgacc gggagtgcac    180
```

```
acataataac ggccgtgata gggtcgggag tgttgtcttt ggcgtgggca atcgcacaac    240
ttggatgggt ggcaggaccc gccgtactaa tggctttttc tttcataaca tattttacat    300
caaccatgct tgccgattgt taccgttccc ctgaccctgt taccggcaaa cgcaactaca    360
cctacatgga agttgtccga tcctatctag gaggaagaaa agtgcaatta tgtggattgg    420
ctcaatacgg gaatctgatt ggaataacaa tcggctacac aatcacagct tcaattagca    480
tggtggcagt gaagaggtcg aattgtttcc acaaaaatgg gcataatgtt aaatgtgcca    540
cttcaaacac tcccttcatg atcatatttg caatcatcca aattattctt agccaaatcc    600
caaatttcca taacctctct tggctctcca ttcttgcggc cgtaatgtcc ttttgttatg    660
cctccatcgg tgttggtctc tccatcgcca aagcggcggg tggcggtgag cacgtaagaa    720
caacactgac aggagttacg gtcgggattg atgtatcggg tgccgagaaa atatggagaa    780
cgttccaagc gattggggac attgcatttg cctacgcata ctcaactgtt ctcattgaaa    840
tacaggacac cttgaaagca ggtcctccat cggagaacaa agccatgaaa agagcaagcc    900
ttgtgggtgt ctccacaaca accttcttct acatgttatg cggttgtgtt ggttacgctg    960
cctttggaaa tgatgctcct ggaaatttcc taactggttt tggtttctat gagccattct   1020
ggctaatcga ctttgccaat gtctgcatcg ccgtgcacct tatcggcgcc taccaagtct   1080
tttgtcaacc aatttttcag ttcgtagaga gccagagcgc gaaacgttgg cctgataaca   1140
agtttattac aggagaatac aaaatccatg tcccttgctg tggtgatttt agtatcaact   1200
tcctcagatt ggtatggagg acttcatatg ttgtggtcac cgcggttgta gccatgatct   1260
tccctttctt caacgatttc ttgggtctta ttggagcagc ttccttctgg cctttgactg   1320
tttactttcc cattgagatg catattgctc agaagaagat accgaaattc tctttcactt   1380
ggacttggtt aaaaatcttg agttggactt gtttcattgt gtccctcgtt gctgcagccg   1440
gatcagtgca aggactcata caaagtctca aggatttcaa gcctttccag gctccttagt   1500
gaaatatgtg ttctcgccaa cgtctccaag aacacaagtt ccatgcactc tcttccctcc   1560
aataaaagtt tctatttctt tgtagtttat tggtgtgaga caatctcata ccaaatattg   1620
tacctctact tgcttgtctt aaacaaatct atcatcagtt tatcccaaaa aaaaaaaaaa   1680
aa                                                                  1682
```

<210> SEQ ID NO 66
<211> LENGTH: 1658
<212> TYPE: DNA
<213> ORGANISM: Arabidopsis thaliana

<400> SEQUENCE: 66

```
tcttcttctt attttatcat agctaagctc aaaaacaatc gatagatgga gaagaagaag     60
agcatgttcg ttgaacagag cttcccggag catgaaattg gcgatactaa caaaaacttt    120
gacgaggatg gccgcgacaa aagaactggg acatggatga ccgggagtgc acacataata    180
acggccgtga tagggtcggg agtgttgtct ttggcgtggg caatcgcaca acttggatgg    240
gtggcaggac ccgccgtact aatggctttt tctttcataa catattttac atcaaccatg    300
cttgccgatt gttaccgttc ccctgaccct gttaccggca aacgcaacta cacctacatg    360
gaagttgtcc gatcctatct aggaggaaga aaagtgcaat tatgtggatt ggctcaatac    420
gggaatctga ttggaataac aatcggctac acaatcacag cttcaattag catggtggca    480
gtgaagaggt cgaattgttt ccacaaaaat gggcataatg ttaaatgtgc cacttcaaac    540
```

```
actcccttca tgatcatatt tgcaatcatc caaattattc ttagccaaat cccaaatttc    600

cataacctct cttggctctc cattcttgcg gccgtaatgt ccttttgtta tgcctccatc    660

ggtgttggtc tctccatcgc caaagcggcg ggtggcggtg agcacgtaag aacaacactg    720

acaggagtta cggtcgggat tgatgtatcg ggtgccgaga aaatatggag aacgttccaa    780

gcgattgggg acattgcatt tgcctacgca tactcaactg ttctcattga aatacaggac    840

accttgaaag caggtcctcc atcggagaac aaagccatga aaagagcaag ccttgtgggt    900

gtctccacaa caaccttctt ctacatgtta tgcggttgtg ttggttacgc tgcctttgga    960

aatgatgctc ctggaaattt cctaactggt tttggtttct atgagccatt ctggctaatc   1020

gactttgcca atgtctgcat cgccgtgcac cttatcggcg cctaccaagt cttttgtcaa   1080

ccaatttttc agttcgtaga gagccagagc gcgaaacgtt ggcctgataa caagtttatt   1140

acaggagaat acaaaatcca tgtcccttgc tgtggtgatt ttagtatcaa cttcctcaga   1200

ttggtatgga ggacttcata tgttgtggtc accgcggttg tagccatgat cttccctttc   1260

ttcaacgatt tcttgggtct tattggagca gcttccttct ggcctttgac tgtttacttt   1320

cccattgaga tgcatattgc tcagaagaag ataccgaaat tctctttcac ttggacttgg   1380

ttaaaaatct tgagttggac ttgtttcatt gtgtccctcg ttgctgcagc cggatcagtg   1440

caaggactca tacaaagtct caaggatttc aagcctttcc aggctcctta gtgaaatatg   1500

tgttctcgcc aacgtctcca agaacacaag ttccatgcac tctcttccct ccaataaaag   1560

tttctatttc tttgtagttt attggtgtga gacaatctca taccaaatat tgtacctcta   1620

cttgcttgtc ttaaacaaat ctatcatcag tttatccc                            1658
```

<210> SEQ ID NO 67
<211> LENGTH: 17
<212> TYPE: PRT
<213> ORGANISM: synthetic
<220> FEATURE:
<221> NAME/KEY: MISC_FEATURE
<222> LOCATION: (3)..(3)
<223> OTHER INFORMATION: Xaa is either I or V
<220> FEATURE:
<221> NAME/KEY: MISC_FEATURE
<222> LOCATION: (4)..(4)
<223> OTHER INFORMATION: Xaa is either I or V
<220> FEATURE:
<221> NAME/KEY: MISC_FEATURE
<222> LOCATION: (6)..(6)
<223> OTHER INFORMATION: Xaa is either A or G
<220> FEATURE:
<221> NAME/KEY: MISC_FEATURE
<222> LOCATION: (10)..(10)
<223> OTHER INFORMATION: Xaa is either A, S, or C
<220> FEATURE:
<221> NAME/KEY: MISC_FEATURE
<222> LOCATION: (14)..(14)
<223> OTHER INFORMATION: Xaa is either S or A
<220> FEATURE:
<221> NAME/KEY: MISC_FEATURE
<222> LOCATION: (16)..(16)
<223> OTHER INFORMATION: Xaa is either S, A, or G.

<400> SEQUENCE: 67

```
Ala His Xaa Xaa Thr Xaa Val Ile Gly Xaa Gly Val Leu Xaa Leu Xaa
1               5                   10                  15

Trp
```

<210> SEQ ID NO 68
<211> LENGTH: 1069
<212> TYPE: DNA

<213> ORGANISM: Brassica napus

<400> SEQUENCE: 68

```
atggacgttg ttcgatctta cctcggtggt aggaaagtgc agctttgtgg agtggcacag     60
tatgggaatc tgataggaat cactgttggg tacaccatca ctgcttctat tagtttggta    120
gcgatcggga aagcgaactg ttaccacaat aaagggcacc atgcagattg tacaatatcg    180
aactatccat atatggcggc cttcgggatc attcagatcc ttcttagcca gatccccaac    240
tttcacaagc tctcttttct ctcccttatg gctgcggtta tgtctttcgc ttacgcaagt    300
attgggattg gccttgccat cgcgacggtc gcaggtggga aagtgggtaa gacgaatatg    360
acgggaacgg tggtaggagt tgatgtaact gcggctcaga agatatggag atcgtttcaa    420
gcggttggag acatagcgtt tgcatatgct tacgccacgg ttctcattga gattcaggac    480
acattgagat ctagccccgc agagaacaaa gctatgaaaa gagcaagttt tgtgggagta    540
tcaaccacca ctttcttcta catcttatgt ggttgtcttg gatatgctgc atttggaaac    600
aaagcccctg gtgatttcct cacagatttc ggattctacg agccattttg gctcattgac    660
tttgcaaacg cttgcattgc tttccatctc attggtgcct atcaggtgtt cgcgcagccc    720
atattccagt ttgttgagaa gaaatgcaat agaaactggc ctgacaacaa gttcatcaca    780
tctgaatatt cagtaaacat accattcctt ggaaaattca acatcaacct cttcagacta    840
gtgtggagga cagcttatgt ggttataaca actttagtag ctatgatatt ccctttcttc    900
aacgccatct tgggtcttat cggagcagct tccttctggc ctttaactgt ttatttcccc    960
gtggagatgc acatagcaca aactaaggtt aagaaatact ctcctagatg gattgggctg   1020
aaaatgttgt gctgggtttg cttgatcgtc tccctgttag ctgctgctg              1069
```

<210> SEQ ID NO 69
<211> LENGTH: 402
<212> TYPE: DNA
<213> ORGANISM: Brassica napus

<400> SEQUENCE: 69

```
gcgtccgatc atcaatacgt agactggaag ggcttgtaga ccttaagatc aagcattact     60
ccagcgattg atccaactcc ggcgaccacc gagatcacta gacaagcaac actaagcatc    120
tgtaaacaaa cccacctcgt gctccacttc tccaccttcc tctgctttat atacatctcc    180
accgggaaat aaaccgtcaa gggccagaac cctaaggctc ctaagatccc aaccacgtcg    240
ttgaagaacg gcattagcat tgatatcacg gtggttagaa cgacgaaaca gcaccggaaa    300
actaccctga aaacgtttgt tttgtatgga gacctaaacc ctgggatttt gatttggagt    360
tccttggtga gcaagtcact gcctggaaac ctctctgaga ct                      402
```

<210> SEQ ID NO 70
<211> LENGTH: 422
<212> TYPE: DNA
<213> ORGANISM: Brassica napus

<400> SEQUENCE: 70

```
gcgacttcat tgctaaagat atcaagatcc ctattccagg gttcaagcct ttccgtttga     60
acttcttcag gttgatatgg aggacagtgt ttgtgatcat aacaacactt atctcaatgc    120
ttcttccttt cttcaacgac gttgtggggt tgctaggggc acttggcttt tggccattga    180
cggtttactt tccggtggag atgtacattg agcagaagaa gatacctaga tggagcaccc    240
aatgggtttg tcttcaagtc ttcagctcag cttgtttggt agttagcatt gctgcggctg    300
```

-continued

```
cagggtcgat agctggagtt gttcttgatc tcaagtcata caagccattt caaagcaact    360

actaatactc tttttgaacc aagaacagtc aaaaagaatc aaagacgtgg agtacttatg    420

ag                                                                    422
```

<210> SEQ ID NO 71
<211> LENGTH: 1665
<212> TYPE: DNA
<213> ORGANISM: Arabidopsis thaliana

<400> SEQUENCE: 71

```
cttaaaacat ttattttatc ttcttcttgt tctctctttc tctttctctc atcactatga     60

agagtttcaa cacagaagga cacaaccact ccacggcgga atccggcgat gcctacaccg    120

tgtcggaccc gacaaagaac gtcgatgaag atggtcgaga gaagcgtacc gggacgtggc    180

ttacggcgag tgcgcatatt atcacggcgg tgataggctc cggagtgttg tctttagcat    240

gggctatagc tcagcttggt tggatcgcag ggacatcgat cttactcatt ttctcgttca    300

ttacttactt cacctccacc atgcttgccg attgctaccg tgcgccggat cccgtcaccg    360

gaaaacggaa ttacacttac atggacgttg ttcgatctta cctcggtggt aggaaagtgc    420

agctctgtgg agtggcacaa tatgggaatc tgattggggt cactgttggt tacaccatca    480

ctgcttctat tagtttggta gcggtaggga aatcgaactg cttccacgat aaagggcaca    540

ctgcggattg tactatatcg aattatccgt atatggcggt ttttggcatt attcaggtta    600

ttcttagcca gatcccaaat ttccacaagc tctcttttct ttccattatg gccgcggtca    660

tgtcctttac ttatgcaact attggaatcg gtctagccat cgcaaccgtc gcaggtggga    720

aagtgggtaa gacgagtatg acgggcacag cggttggagt agatgtaacc gcagctcaaa    780

agatatggag atcgtttcaa gcggttgggg acatagcgtt cgcctatgct tatgccacgg    840

ttctcatcga gattcaggat acactaagat ctagcccagc tgagaacaaa gccatgaaaa    900

gagcaagtct tgtgggagta tcaaccacca ctttttteta catcttatgt ggatgcatcg    960

gctatgctgc atttggaaac aatgcccctg gagatttcct cacagatttc gggtttttcg   1020

agcccttttg gctcattgac tttgcaaacg cttgcatcgc tgtccacctt attggtgcct   1080

atcaggtgtt cgcgcagccg atattccagt ttgttgagaa aaaatgcaac agaaactatc   1140

cagacaacaa gttcatcact tctgaatatt cagtaaacgt acctttcctt ggaaaattca   1200

acattagcct cttcagattg gtgtggagga cagcttatgt ggttataacc actgttgtag   1260

ctatgatatt ccctttcttc aacgcgatct taggtcttat cggagcagct tccttctggc   1320

ctttaacggt ttatttccct gtggagatgc acattgcaca aaccaagatt aagaagtact   1380

ctgctagatg gattgcgctg aaaacgatgt gctatgtttg cttgatcgtc tcgctcttag   1440

ctgcagccgg atccatcgca ggacttataa gtagtgtcaa aacctacaag cccttccgga   1500

ctatgcatga gtgagtttga gatcctcaag agagtcaaaa atatatgtag tagtttggtc   1560

tttctgttaa actatctggt gtctaaatcc aatgagaatg ctttattgct aaaacttcat   1620

gaatctctct gtatctacat ctttcaatct aagctacgtc agggc                   1665
```

<210> SEQ ID NO 72
<211> LENGTH: 1740
<212> TYPE: DNA
<213> ORGANISM: Arabidopsis thaliana

<400> SEQUENCE: 72

-continued

```
ctattttata attcctcttc tttttgttca tagctttgta attatagtct tatttctctt     60

taaggctcaa taagaggaga tgggtgaaac cgctgccgcc aataaccacc gtcaccacca    120

ccatcacggc caccaggtct ttgacgtggc cagccacgat ttcgtccctc cacaaccggc    180

ttttaaatgc ttcgatgatg atggccgcct caaaagaact gggactgttt ggaccgcgag    240

cgctcatata ataactgcgg ttatcggatc cggcgttttg tcattggcgt gggcgattgc    300

acagctcgga tggatcgctg gccctgctgt gatgctattg ttctctcttg ttactcttta    360

ctcctccaca cttcttagcg actgctacag aaccggcgat gcagtgtctg gcaagagaaa    420

ctacacttac atggatgccg ttcgatcaat tctcggtggg ttcaagttca agatttgtgg    480

gttgattcaa tacttgaatc tctttggtat cgcaattgga tacacgatag cagcttccat    540

aagcatgatg gcgatcaaga gatccaactg cttccacaag agtggaggaa aagacccatg    600

tcacatgtcc agtaatcctt acatgatcgt atttggtgtg gcagagatct tgctctctca    660

ggttcctgat ttcgatcaga tttggtggat ctccattgtt gcagctgtta tgtccttcac    720

ttactctgcc attggtctag ctcttggaat cgttcaagtt gcagcgaatg gagttttcaa    780

aggaagtctc actggaataa gcatcggaac agtgactcaa acacagaaga tatggagaac    840

cttccaagca cttggagaca ttgcctttgc gtactcatac tctgttgtcc taatcgagat    900

tcaggatact gtaagatccc caccggcgga atcgaaaacg atgaagaaag caacaaaaat    960

cagtattgcc gtcacaacta tcttctacat gctatgtggc tcaatgggtt atgccgcttt   1020

tggagatgca gcaccgggaa acctcctcac cggttttgga ttctacaacc cgttttggct   1080

ccttgacata gctaacgccg ccattgttgt ccacctcgtt ggagcttacc aagtctttgc   1140

tcagcccatc tttgccttta ttgaaaaatc agtcgcagag agatatccag acaatgactt   1200

cctcagcaag gaatttgaaa tcagaatccc cggatttaag tctccttaca aagtaaacgt   1260

tttcaggatg gtttacagga gtggctttgt cgttacaacc accgtgatat cgatgctgat   1320

gccgtttttt aacgacgtgg tcgggatctt aggggcgtta gggttttggc ccttgacggt   1380

ttattttccg gtggagatgt atattaagca gaggaaggtt gagaaatgga gcacgagatg   1440

ggtgtgttta cagatgctta gtgttgcttg tcttgtgatc tcggtggtcg ccggggttgg   1500

atcaatcgcc ggagtgatgc ttgatcttaa ggtctataag ccattcaagt ctacatattg   1560

atgattatgg accatgaaca acagagagag ttggtgtgta aagtttacca tttcaaagaa   1620

aactccaaaa atgtgtatat tgtatgttgt tctcatttcg tatggtctca tctttgtaat   1680

aaaatttaaa acttatgtta taaattataa aaaaaaaaaa aaaaaaaaaa aaaaaaaaaa   1740
```

<210> SEQ ID NO 73
<211> LENGTH: 1867
<212> TYPE: DNA
<213> ORGANISM: Arabidopsis thaliana

<400> SEQUENCE: 73

```
aaagatcaac tctttcaaac acttactctg catgtaactt catagattga acgaagaacc     60

aaaaaaacag agcaaaacaa acaaaagatg gttcaaaacc accaaacagt tctcgccgtc    120

gatatgccac aaaccggcgg ctccaagtac ttggacgacg acgggaaaaa caaaagaact    180

gggagtgttt ggacggcgag tgcacacata ataacggcag tgataggttc gggagttttg    240

tcactagcgt gggctacggc gcagctaggt tggctcgccg gaccggtggt gatgttgctc    300

ttctctgccg tcacttattt cacttcttct cttcttgctg cttgttaccg ctccggcgac    360

cctatctccg gcaagaggaa ctacacttat atggatgctg tccgatcaaa tctcggtggc    420
```

-continued

```
gtgaaggtga cgctatgtgg gattgttcag tatcttaata tctttggtgt tgctattggc    480
tacacaattg cttcagctat aagcatgatg gcaataaaga gatcaaactg tttccacaag    540
agtggaggga aagatccatg tcacatgaac agtaatcctt acatgatagc ttttggatta    600
gtccagattc tattctctca gattccagat tttgatcaac tttggtggct ctcaatcctc    660
gccgccgtta tgtccttcac ttattcctca gccggtctcg ccctcggcat agcccaagtt    720
gtcgttaatg ggaaggtgaa gggaagtctc actgggatta gcataggagc agtaacagag    780
acacagaaga tatggaggac ctttcaagct cttggagaca ttgcttttgc ttactcttac    840
tccattatcc tcatcgagat tcaggacaca gtgaagtcac caccatcaga agagaagacg    900
atgaagaagg caacacttgt gagcgtcagt gtaacgacta tgttctatat gttgtgtgga    960
tgtatgggat atgcagcctt tggagacttg tctccgggaa atctcttaac cggtttcggg   1020
ttttataatc cttattggct tcttgacatt gcaaatgcag ccattgtgat tcaccttatt   1080
ggtgcatacc aagtctattg ccaacctctg tttgctttca tcgagaagca agcttccatt   1140
caattccctg atagtgagtt cattgcaaaa gatatcaaaa ttccaattcc tggtttcaag   1200
cctctccgct tgaatgtctt caggttgata tggaggacag tgtttgtgat cataacgaca   1260
gttatctcaa tgcttcttcc gtttttcaac gacgttgtgg gtctgctcgg ggcactaggg   1320
ttttggccat tgacggtgta ttttccagtg gaaatgtaca tcgcgcagaa gaagatacct   1380
agatggagca ccagatgggt ttgccttcaa gtcttcagct tagggtgtct agtagttagc   1440
attgctgcag ctgcagggtc catagctgga gtacttcttg atctaaagtc ctacaagcca   1500
tttcgaagcg aatactgatc aacttgaata gtagccaatt caaagcgatg actaagtcag   1560
ttttaaacac aatggatata tcaagaacag tcaagagaac caagaaccat gaatttggga   1620
attttgatca gctttttttt atatagatag aagcaataat gctgttagtt cttctctata   1680
atcttctctg taccctgaag gcaagaattg tagtcctaat gagtaaatct tcgattaatg   1740
acagagtcat gtgctacaac agaatcatga actagcacca taatagtata ttaccattgt   1800
ggtaaaattt caataacaag ttcttgtact taaaaaaaaa aaaaaaaaaa aaaaaaaaaa   1860
aaaaaaa                                                             1867
```

AMINO ACID TRANSPORTERS

This application claims priority to U.S. Provisional Application No. 60/353,062 filed Feb. 1, 2002.

Transport processes play an important role in nitrogen allocation in higher plants. *Arabidopsis*, as well as other plants, possess multiple forms of amino acid transporters characterized according to their specificity for or affinity to individual amino acids. For example, there are generic amino acid transporters that are able to transfer a broad spectrum of amino acids. There are also more specific amino acid transporters that are able to transport primarily proline or cationic amino acids. See Li et al., *Plant Physiol*. 94:268-277 (1990).

A native plant system for amino acid transport would be preferably augmented to provide a plant capable of producing grain having increased protein content. Accordingly, it would be useful to identify nucleic acid molecules that when introduced into a plant result in increased amino acid transport activity, resulting in the accumulation of increased levels of protein. Conversely, using down regulation strategies with such identified nucleic acid molecules can provide plants with reduced levels of protein, thereby allowing a greater carbon flow to other processes such as oil production. Such plants, or parts thereof, would be useful in providing new and improved foods and feeds for human and animal nutrition needs.

SUMMARY OF THE INVENTION

The present invention includes and provides a method for producing a plant having tissue with an increased amino acid content comprising: (A) transforming the plant with a nucleic acid molecule encoding a plant amino acid transporter; and, (B) growing the plant.

The present invention includes and provides a method of accumulating amino acids in a tissue of a plant comprising: (A) transforming the plant with a nucleic acid molecule encoding a plant amino acid transporter; and, (B) growing the plant.

The present invention includes and provides a method for obtaining a plant having tissue with an increased amino acid content, comprising: (A) providing seed comprising an introduced nucleic acid molecule encoding a plant amino acid transporter; and, (B) planting the seed.

The present invention includes and provides a transformed plant comprising an introduced nucleic acid molecule encoding an amino acid transporter, wherein a tissue of the plant has an increased amount of protein relative to an untransformed plant with a similar genetic background.

The present invention includes and provides a transformed plant comprising an introduced nucleic acid molecule encoding an amino acid transporter.

The present invention includes and provides a transformed plant comprising a nucleic acid molecule comprising a promoter region which functions in plant cells to cause the production of an mRNA molecule, wherein the promoter region is linked to a transcribed nucleic acid molecule having a transcribed strand and a non-transcribed strand, wherein the transcribed strand is complementary to a nucleic acid molecule comprising a nucleic acid sequence selected from the group consisting of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 65, 68, 69, and 70, and wherein the transcribed nucleic acid molecule is linked to a 3' non-translated sequence that functions in the plant cells to cause termination of transcription and addition of polyadenylated ribonucleotides to a 3' end of the mRNA sequence.

The present invention includes and provides a substantially purified nucleic acid molecule, comprising a sequence that has at least 75% identity with a sequence selected from the group consisting of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof.

The present invention includes and provides a nucleic acid molecule comprising a contiguous sequence of at least 15 nucleotides from a sequence selected from the group consisting of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof.

The present invention includes and provides a substantially purified nucleic acid molecule that encodes a protein having an amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

The present invention includes and provides a substantially purified polypeptide having an amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

The present invention includes and provides a substantially purified polypeptide comprising an amino acid sequence of at least 30 contiguous amino acids of a sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

BRIEF DESCRIPTION OF THE SEQUENCE LISTING

SEQ ID NO: 1 is an amino acid sequence for the *Arabidopsis* AAP6 protein NCBI database, Accession Number X95736.

SEQ ID NO: 2 is the predicted amino acid sequence of clone ID LIB3332-019-P1-K1-A6, a maize amino acid transporter.

SEQ ID NO: 3 is the nucleic acid sequence of clone ID LIB3332-019-P1-K1-A6, a maize amino acid transporter gene.

SEQ ID NO: 4 is the predicted amino acid sequence of clone UC-ZMF1B73151A04B1, a maize amino acid transporter.

SEQ ID NO: 5 is the nucleic acid sequence of clone UC-ZMF1B73151A04B1, a maize amino acid transporter gene.

SEQ ID NO: 6 is the predicted amino acid sequence of clone 700202115H1, a maize amino acid transporter.

SEQ ID NO: 7 is the nucleic acid sequence of clone 700202115H1, a maize amino acid transporter gene.

SEQ ID NO: 8 is the predicted amino acid sequence of clone LIB3689-227-Q1-K6-A12, a maize amino acid transporter.

SEQ ID NO: 9 is the nucleic acid sequence of clone LIB3689-227-Q1-K6-A12, a maize amino acid transporter gene.

SEQ ID NO: 10 is the predicted amino acid sequence of clone LB3632-059-Q6-K6-D5, a maize amino acid transporter.

SEQ ID NO: 11 is the nucleic acid sequence of clone LB3632-059-Q6-K6-D5, a maize amino acid transporter gene.

SEQ ID NO: 12 is the predicted amino acid sequence of clone UC-ZMFLB73290D08B1, a maize amino acid transporter.

SEQ ID NO: 13 is the nucleic acid sequence of clone UC-ZMFLB73290D08B1, a maize amino acid transporter gene.

SEQ ID NO: 14 is the predicted amino acid sequence of clone LIB3079-043-Q1-K2-B1, a maize amino acid transporter.

SEQ ID NO: 15 is the nucleic acid sequence of clone LIB3079-043-Q1-K2-B1, a maize amino acid transporter gene.

SEQ ID NO: 16 is the predicted amino acid sequence of clone UC-ZMROB73055H08, a maize amino acid transporter.

SEQ ID NO: 17 is the nucleic acid sequence of clone UC-ZMROB73055H08, a maize amino acid transporter gene.

SEQ ID NO: 18 is the nucleic acid sequence of clone LIB3137-003-B10, a partial maize amino acid transporter gene.

SEQ ID NO: 19 is the nucleic acid sequence of clone 700050676H1, a partial maize amino acid transporter gene.

SEQ ID NO: 20 is the nucleic acid sequence of clone 700076634H1, a partial maize amino acid transporter gene.

SEQ ID NO: 21 is the nucleic acid sequence of clone 700102233H1, a partial maize amino acid transporter gene.

SEQ ID NO: 22 is the nucleic acid sequence of clone LIB3059-048-Q1-K1-H6, a partial maize amino acid transporter gene.

SEQ ID NO: 23 is the nucleic acid sequence of clone LIB3355-054-P1-K1-A6, a partial maize amino acid transporter gene.

SEQ ID NO: 24 is the predicted amino acid sequence of clone UC-osflm202054e03b1, a rice amino acid transporter.

SEQ ID NO: 25 is the nucleic acid sequence of clone UC-osflm202054e03b1, a rice amino acid transporter gene.

SEQ ID NO: 26 is the predicted amino acid sequence of clone ORYSA-14MAR01-CLUSTER4446_1, a rice amino acid transporter.

SEQ ID NO: 27 is the nucleic acid sequence of clone ORYSA-14MAR01-CLUSTER4446_1, a rice amino acid transporter gene.

SEQ ID NO: 28 is the predicted amino acid sequence of clone fC-osflM202028F09, a rice amino acid transporter.

SEQ ID NO: 29 is the nucleic acid sequence of clone fC-osflM202028F09, a rice amino acid transporter gene.

SEQ ID NO: 30 is the predicted amino acid sequence of clone LIB3475-006-A4_FLI, a rice amino acid transporter.

SEQ ID NO: 31 is the nucleic acid sequence of clone LIB3475-006-A4_FLI, a rice amino acid transporter gene.

SEQ ID NO: 32 is the predicted amino acid sequence of clone UC-OSFLM202073D08, a rice amino acid transporter.

SEQ ID NO: 33 is the nucleic acid sequence of clone UC-OSFLM202073D08, a rice amino acid transporter gene.

SEQ ID NO: 34 is the predicted amino acid sequence of clone 701045628H1, a soybean amino acid transporter.

SEQ ID NO: 35 is the nucleic acid sequence of clone 701045628H1, a soybean amino acid transporter gene.

SEQ ID NO: 36 is the predicted amino acid sequence of clone 701208649H1, a soybean amino acid transporter.

SEQ ID NO: 37 is the nucleic acid sequence of clone701208649H1, a soybean amino acid transporter gene.

SEQ ID NO: 38 is the predicted amino acid sequence of clone LIB3107-061-Q1-K1-F5, a soybean amino acid transporter.

SEQ ID NO: 39 is the nucleic acid sequence of clone LIB3107-061-Q1-K1-F5, a soybean amino acid transporter gene.

SEQ ID NO: 40 is the predicted amino acid sequence of clone JC-GMFL02220088D03A1, a soybean amino acid transporter.

SEQ ID NO: 41 is the nucleic acid sequence of clone JC-GMFL02220088D03A1, a soybean amino acid transporter gene.

SEQ ID NO: 42 is the predicted amino acid sequence of clone JC-GMFL02220106H05A1, a soybean amino acid transporter.

SEQ ID NO: 43 is the nucleic acid sequence of clone JC-GMFL02220106H05A1, a soybean amino acid transporter gene.

SEQ ID NO: 44 is the predicted amino acid sequence of clone 700891976, a soybean amino acid transporter.

SEQ ID NO: 45 is the nucleic acid sequence of clone 700891976, a soybean amino acid transporter gene.

SEQ ID NO: 46 is the predicted amino acid sequence of clone LIB4281-017-R1-K1-E1, a soybean amino acid transporter.

SEQ ID NO: 47 is the nucleic acid sequence of clone LIB4281-017-R1-K1-E1, a soybean amino acid transporter gene.

SEQ ID NO: 48 is the predicted amino acid sequence of clone 701010016, a soybean amino acid transporter.

SEQ ID NO: 49 is the nucleic acid sequence of clone 701010016, a soybean amino acid transporter gene.

SEQ ID NO: 50 is the predicted amino acid sequence of clone LIB3040-014-B6_FLI_09-01, a soybean amino acid transporter.

SEQ ID NO: 51 is the nucleic acid sequence of clone LIB3040-014-B6_FLI_09-01, a soybean amino acid transporter gene.

SEQ ID NO: 52 is the predicted amino acid sequence of clone JC-GMFL02220103H07, a soybean amino acid transporter.

SEQ ID NO: 53 is the nucleic acid sequence of clone JC-GMFL02220103H07, a soybean amino acid transporter gene.

SEQ ID NO: 54 is the predicted amino acid sequence of clone LIB4167-002-A10, a soybean amino acid transporter.

SEQ ID NO: 55 is the nucleic acid sequence of clone LIB4167-002-A10, a soybean amino acid transporter gene.

SEQ ID NO: 56 is the nucleic acid sequence of clone UC-GMROMINSOY153C07B1, a partial soybean amino acid transporter gene.

SEQ ID NO: 57 is the nucleic acid sequence of clone 700943103H1, a partial soybean amino acid transporter gene.

SEQ ID NO: 58 is the nucleic acid sequence of clone 700993704H1, a partial soybean amino acid transporter gene.

SEQ ID NO: 59 is the nucleic acid sequence of clone JC-GMST02400026D05A1, a partial soybean amino acid transporter gene.

SEQ ID NO: 60 is the nucleic acid sequence of clone UC-GMFLMINSOY022H05B1, a partial soybean amino acid transporter gene.

SEQ ID NO: 61 is the nucleic acid sequence of clone 701100005H2, a partial soybean amino acid transporter gene.

SEQ ID NO: 62 is a PCR primer specific for the SP6 vector.

SEQ ID NO: 63 is a PCR primer specific for the T7 vector.

SEQ ID NO: 64 is the predicted amino acid sequence of *Arabidopsis* AAP6, contained in clone LIB3278-061-P1-K1-D12.

SEQ ID NO: 65 is the cDNA sequence of *Arabidopsis* AAP6, contained in clone LIB3278-061-P1-K1-D12.

SEQ ID NO: 66 is a DNA sequence coding for the *Arabidopsis* AAP-6 protein NCBI database, Accession Number X95736.

SEQ ID NO: 67 is a consensus amino acid sequence.

SEQ ID NO: 68 is the nucleic acid sequence of clone LIB3235-042-P1-K1-C11, a partial canola amino acid transporter gene.

SEQ ID NO: 69 is the nucleic acid sequence of clone LIB3235-017-P1-K1-C9, a partial canola amino acid transporter gene.

SEQ ID NO: 70 is the nucleic acid sequence of clone LIB3235-054-P1-K1-G6, a partial canola amino acid transporter gene.

SEQ ID NO: 71 is a DNA sequence coding for the *Arabidopsis* AAP-1 protein NCBI database, Accession Number L16240.

SEQ ID NO: 72 is a DNA sequence coding for the *Arabidopsis* AAP-2 protein NCBI database, Accession Number X71787.

SEQ ID NO: 73 is a DNA sequence coding for the *Arabidopsis* AAP-3 protein NCBI database, Accession Number X77499.

BRIEF DESCRIPTION OF THE FIGURES

FIG. 15 is an amino acid sequence alignment of eight maize amino acid transporters with an *Arabidopsis* AAP6 protein.

FIG. 16 is an amino acid sequence alignment of five rice amino acid transporters with an *Arabidopsis* AAP6 protein.

FIG. 17 is an amino acid sequence alignment of eleven soybean amino acid transporters with an *Arabidopsis* AAP6 protein.

DETAILED DESCRIPTION OF THE INVENTION

Figure 1:
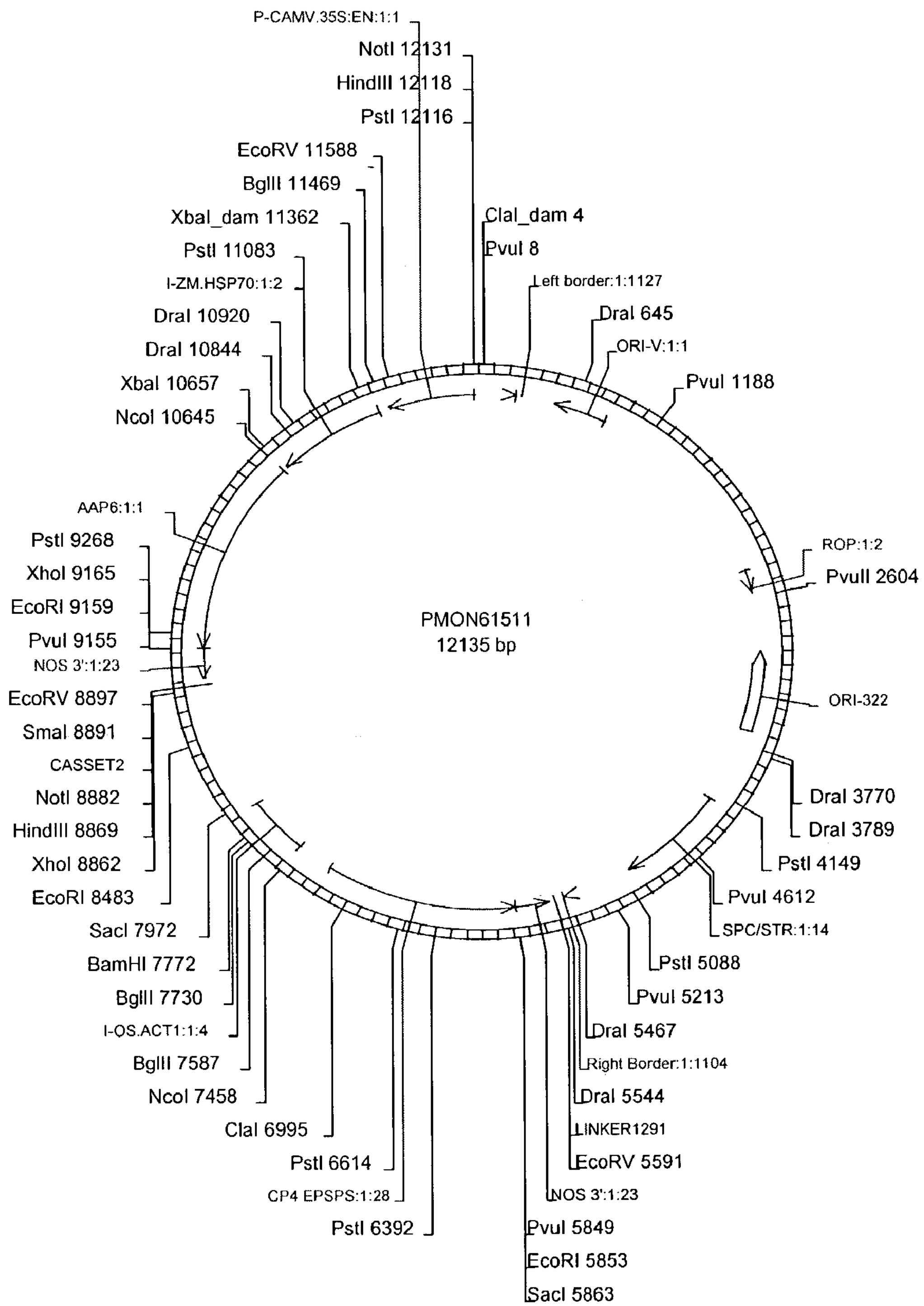
FIG. 1 is a plasmid map of pMON61511.

The present invention provides a number of agents, for example, nucleic acid molecules and polypeptides associated with the transport of amino acids, and provides uses of such agents.

Agents

The agents of the invention will preferably be biologically active with respect to either a structural attribute, such as the capacity of a nucleic acid to hybridize to another nucleic acid molecule, or the ability of a polypeptide to be bound by an antibody (or to compete with another molecule for such binding). Alternatively, such an attribute may be catalytic and thus involve the capacity of the agent to mediate a chemical reaction or response. Further, such an attribute may be related to the transport of molecules, such as the transport of amino acids across cell membranes. In this context, amino acid transport relates to movement of histidine, asparagine, glutamine, glutamate, arginine, aspartate, glycine, valine and serine, and, most preferably, the amino acid transport activity results in movement of all amino acids. The agents will preferably be substantially purified. The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native environmental conditions.

The agents of the invention may also be recombinant. As used herein, the term recombinant means any agent (e.g., DNA, peptide etc.), that is, or results, however indirectly, from human manipulation of a nucleic acid molecule.

It is understood that the agents of the invention may be labeled with reagents that facilitate detection of the agent (e.g., fluorescent labels, Prober et al., *Science* 238:336-340 (1987); Albarella et al., EP 144 914; chemical labels, Sheldon et al., U.S. Pat. No. 4,582,789; Albarella et al., U.S. Pat. No. 4,563,417; modified bases, Miyoshi et al., EP 119 448) including nucleotides with radioactive elements, e.g. $^{32}P$, $^{33}P$, $^{35}S$ or $^{125}I$, such as, for example, $^{32}P$ deoxycytidine-5'-triphosphate ($^{32}PdCTP$).

Nucleic Acid Molecules

Agents of the invention include nucleic acid molecules. In a preferred aspect of the present invention the nucleic acid molecule comprises a nucleic acid sequence, which encodes an amino acid transporter. As used herein, an amino acid transporter is any polypeptide that facilitates the translocation of an amino acid across cellular membranes. In a preferred embodiment of the present invention, amino acid transporters are plant amino acid transporters. In a further preferred embodiment, amino acid transporters of the present invention are selected from the group consisting of *Arabidopsis*, maize, soybean, rice, wheat, and canola amino acid transporters. In a further preferred embodiment, amino acid transporters of the present invention include maize amino acid transporters. An example of a more preferred amino acid transporter is a polypeptide with the amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, and 54. In a more preferred embodiment, an amino acid transporter of the present invention is encoded by a nucleic acid molecule having a sequence selected from the group consisting of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, and 70.

In another preferred aspect of the present invention, a nucleic acid molecule of the present invention comprises a nucleic acid sequence selected from the group consisting of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof. In another preferred aspect, a nucleic acid molecule of the present invention comprises a nucleic acid sequence selected from the group consisting of SEQ ID NOs: 3, 5, 7, 9, 11, 13, 15, 17, 19, 20, 21, 22, and 23. In another preferred aspect, a nucleic acid molecule of the present invention comprises a nucleic acid sequence selected from the group consisting of SEQ ID NOs: 25, 27, 29, 31, and 33. In another preferred aspect, a nucleic acid molecule of the present invention comprises a nucleic acid sequence selected from the group consisting of SEQ ID NOs: 35, 37, 39, 41, 43, 45, 47, 49, 51, 53, 55, 56, 57, 58, 59, 60, 61, 68, 69, and 70.

In a further aspect of the present invention the nucleic acid molecule comprises a nucleic acid sequence encoding an amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof. In a further aspect of the present invention the nucleic acid molecule comprises a nucleic acid sequence encoding an amino acid sequence selected from the group consisting of SEQ ID NOs: 2, 4, 6, 8, 10, 12, 14, and 16. In a further aspect of the present invention the nucleic acid molecule comprises a nucleic acid sequence encoding an amino acid sequence selected from the group consisting of SEQ ID NOs: 24, 26, 28, 30, and 32. In a further aspect of the present invention the nucleic acid molecule comprises a nucleic acid sequence encoding an amino acid sequence selected from the group consisting of SEQ ID NOs: 34, 36, 38, 40, 42, 44, 46, 48, 50, 52, and 54.

In another aspect, the present invention provides nucleic acid molecules comprising a sequence encoding a polypeptide comprising a conserved fragment of an amino acid consensus sequence as shown in FIGS. 15, 16, and 17. The present invention includes the use of the consensus sequence and fragments thereof in transgenic plants, other organisms, and for other uses, particularly those described herein. In a preferred embodiment, a nucleic acid of the present invention encodes a polypeptide comprising SEQ ID NO: 67. In a further preferred embodiment, a polypeptide of the present invention comprises SEQ ID NO: 67.

In a further aspect of the present invention, a nucleic acid molecule comprises a nucleic acid sequence encoding fragments of at least about 30 amino acids in length of an amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

In further preferred embodiments, a nucleic acid molecule of the present invention comprises a nucleic acid sequence encoding fragments of at least about 35, 40, 45, 50, 75, 100, 150, or 200 amino acids in length of an amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

In a further embodiment of the present invention, a nucleic acid molecule of the present invention comprises or consists of a nucleic acid sequence encoding fragments of about 30 to about 200, about 30 to about 150, about 30 to about 100, about 35 to about 75, or about 40 to about 50 amino acids in length of an amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

It is understood that in a further aspect of nucleic acid sequences of the present invention, the nucleic acids can encode a protein that differs from any of the proteins in that one or more amino acids have been deleted, substituted, or added without altering the function. For example, it is understood that codons capable of coding for such conservative amino acid substitutions are known in the art.

In one aspect of the present invention the nucleic acids of the present invention are said to be introduced nucleic acid molecules. A nucleic acid molecule is said to be "introduced" if it is inserted into a cell or organism as a result of human manipulation, no matter how indirect. Examples of introduced nucleic acid molecules include, without limitation, nucleic acids that have been introduced into cells via transformation, transfection, injection, and projection, and those that have been introduced into an organism via conjugation, endocytosis, phagocytosis, etc.

One subset of the nucleic acid molecules of the invention is fragment nucleic acids molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques* 25:112-123 (1998)), for example, can be used to identify potential PCR primers.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof. Nucleic acid molecules of the present invention also include those that specifically hybridize to nucleic acid molecules encoding an amino acid sequence selected from SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, *2nd Ed., Cold Spring Harbor Press*, Cold Spring Harbor, N.Y. (1989), and by Haymes et al., *Nucleic Acid Hybridization, A Practical Approach,* IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0×sodium chloride/sodium citrate (SSC) at about 45° C., followed by a wash of 2.0×SSC at about 20-25° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of 2.0×SSC at about 50° C. to a high stringency of 0.2×SSC at about 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof under high stringency conditions such as 0.2×SSC and about 65° C.

In one aspect of the present invention, the nucleic acid molecules of the present invention have one or more of the nucleic acid sequences set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof.

In another aspect of the present invention, one or more of the nucleic acid molecules of the present invention share at least about 80% sequence identity with one or more of the nucleic acid sequences set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof and fragments of either.

In another aspect of the present invention, one or more of the nucleic acid molecules of the present invention share at least about 90% sequence identity with one or more of the nucleic acid sequences set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof and fragments of either.

In a further aspect of the present invention, one or more of the nucleic acid molecules of the present invention share at least about 95% sequence identity with one or more of the nucleic acid sequences set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof and fragments of either.

In a more preferred aspect of the present invention, one or more of the nucleic acid molecules of the present invention share at least about 98% sequence identity with one or more of the nucleic acid sequences set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof and fragments of either.

In an even more preferred aspect of the present invention, one or more of the nucleic acid molecules of the present invention share at least about 99% sequence identity with one or more of the sequences set forth in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof and fragments of either.

In a preferred embodiment the percent identity calculations are performed using BLASTN or BLASTP (default, parameters, version 2.0.8, Altschul et al., *Nucleic Acids Res.* 25:3389-3402 (1997)).

A nucleic acid molecule of the invention can also encode a homolog polypeptide. As used herein, a homolog polypeptide molecule or fragment thereof is a counterpart protein molecule or fragment thereof in a second species (e.g., maize rubisco small subunit is a homolog of *Arabidopsis* rubisco small subunit). A homolog can also be generated by molecular evolution or DNA shuffling techniques, so that the molecule retains at least one functional or structure characteristic of the original polypeptide (see for example, U.S. Pat. No. 5,811,238).

In another embodiment, the homolog is selected from the group consisting of alfalfa, *Arabidopsis*, barley, *Brassica campestris*, oilseed rape, broccoli, cabbage, canola, citrus, cotton, garlic, oat, Allium, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, *Phaseolus*, crambe, mustard, castor bean, sesame, cottonseed, linseed, safflower, and oil palm. More particularly, preferred homologs are selected from canola, maize, *Brassica campestris*, oilseed rape, soybean, crambe, mustard, castor bean, peanut, sesame, cottonseed, linseed, rapeseed, safflower, oil palm, flax, and sunflower. In an even more preferred embodiment, the homolog is selected from the group consisting of canola, rapeseed, maize, *Brassica campestris*, oilseed rape, soybean, sunflower, safflower, oil palms, and peanut. In a particularly preferred embodiment, the homolog is soybean. In a particularly preferred embodiment, the homolog is canola. In a particularly preferred embodiment, the homolog is oilseed rape.

In a preferred embodiment, nucleic acid molecules having SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof can be utilized to obtain such homologs.

In another further aspect of the present invention, nucleic acid molecules of the present invention can comprise sequences that differ from those encoding a polypeptide or fragment thereof in SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 68, 69, and 70, due to the fact that a polypeptide can have one or more conservative amino acid changes, and nucleic acid sequences coding for the polypeptide can therefore have sequence differences. It is understood that codons capable of coding for such conservative amino acid substitutions are known in the art.

It is well known in the art that one or more amino acids in a native sequence can be substituted with other amino acid(s), the charge and polarity of which are similar to that of the native amino acid, i.e., a conservative amino acid substitution. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid substitution within the native polypeptide sequence can be made by replacing one amino acid from within one of these groups with another amino acid from within the same group. In a preferred aspect, biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the polypeptides of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle *J. Mol. Biol*. 157:105-132 (1982)). It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle *J. Mol. Biol*. 157:105-132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those that are within ±1 are particularly preferred, and those within ±0.5 are even more particularly preferred.

In a further aspect of the present invention, one or more of the nucleic acid molecules of the present invention differ in nucleic acid sequence from those for which a specific sequence is provided herein because one or more codons has been replaced with a codon that encodes a conservative substitution of the amino acid originally encoded.

In a preferred embodiment, any of the nucleic acid molecules of the present invention can be operably linked to a promoter region that functions in a plant cell to cause the production of a mRNA molecule, where the nucleic acid molecule that is linked to the promoter is heterologous with respect to that promoter. As used herein, "heterologous" means not naturally occurring together.

Protein and Peptide Molecules

A class of agents includes one or more of the polypeptide molecules encoded by a nucleic acid agent of the invention. A particular preferred class of polypeptides is that having an amino acid sequence selected from the group consisting of SEQ ID NOs: 2, 4, 6, 8, 10, 12, 14, 16, 24, 26, 28, 30, 32, 34, 36, 38, 40, 42, 44, 46, 48, 50, 52, 54, and complements thereof.

In a further aspect of the present invention, the polypeptide molecule comprises an amino acid sequence selected from the group consisting of SEQ ID NOs: 2, 4, 6, 8, 10, 12, 14, 16, and fragments thereof.

In a further aspect of the present invention the polypeptide molecule comprises an amino acid sequence selected from the group consisting of SEQ ID NOs: 24, 26, 28, 30, 32, and fragments thereof.

In a further aspect of the present invention the polypeptide molecule comprises an amino acid sequence selected from the group consisting of SEQ ID NOs: 34, 36, 38, 40, 42, 44, 46, 48, 50, 52, 54, and fragments thereof.

In a preferred aspect a polypeptide of the present invention is targeted to a plastid using either a native transit peptide sequence or a heterologous transit peptide sequence. In the case of nucleic acid sequences corresponding to nucleic acid sequences of non-higher plant organisms such as cyanobacteria, such nucleic acid sequences can be modified to attach the coding sequence of the polypeptide to a nucleic acid sequence of a plastid targeting peptide. In this embodiment, a preferred plastid targeting sequence is a CTP1 sequence (see for example, WO 00/61771).

As used herein, the terms "protein," "peptide molecule," or "polypeptide" includes any molecule that comprises five or more amino acids. It is well known in the art that protein, peptide, or polypeptide molecules may undergo modification, including post-translational modifications, such as, but not limited to, disulfide bond formation, glycosylation, phosphorylation, or oligomerization. Thus, as used herein, the terms "protein," "peptide molecule," or "polypeptide" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragments thereof, peptide molecules, or polypeptide molecules may be produced via chemical synthesis, or more preferably, by expression in a suitable bacterial or eukaryotic host. Suitable methods for expression are described by Sambrook et al., in *Molecular Cloning, A Laboratory Manual*, 2*nd Edition, Cold Spring Harbor Press*, Cold Spring Harbor, N.Y. (1989) or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the invention are preferably produced via recombinant means.

Another class of agents comprise protein, peptide molecules, or polypeptide molecules, or fragments, or fusions thereof comprising SEQ ID NOs: 2, 4, 6, 8, 10, 12, 14, 16, 24, 26, 28, 30, 32, 34, 36, 38, 40, 42, 44, 46, 48, 50, 52, 54, and complements thereof, in which conservative, non-essential or non-relevant amino acid residues have been added, replaced, or deleted. Computerized means for designing modifications in protein structure are known in the art (Dahiyat and Mayo *Science* 278:82-87 (1997)).

A protein, peptide, or polypeptide of the invention can also be a homolog protein, peptide or polypeptide. As used herein, a homolog protein, peptide, or polypeptide, or fragment thereof is a counterpart protein, peptide, or polypeptide, or fragment thereof in a second species. A homolog can also be generated by molecular evolution or DNA shuffling techniques, so that the molecule retains at least one functional or structure characteristic of the original (see for example, U.S. Pat. No. 5,811,238).

In another embodiment, the homolog is selected from the group consisting of alfalfa, *Arabidopsis*, barley, broccoli, cabbage, canola, citurs, cotton, garlic, oat, Allium, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, and *Phaseolus*. More particularly, preferred homologs are selected from canola, rapeseed, *Brassica campestris*, oilseed rape, soybean, crambe, mustard, castor bean, peanut, sesame, cottonseed, linseed, safflower, oil palm, flax, wheat, rice, maize, and sunflower. In an even more preferred embodiment, the homolog is selected from the group consisting of canola, rice, maize, wheat, and soybean. In a preferred embodiment, the homolog is soybean. In a preferred embodiment, the homolog is canola. In a preferred embodiment, the homolog is rice. In a preferred embodiment, the homolog is maize. In a preferred embodiment, the homolog is wheat.

In a preferred embodiment, the nucleic acid molecules of the present invention or complements and fragments of either can be utilized to obtain such homologs.

Agents of the invention include proteins and fragments thereof, comprising at least about a contiguous 30 amino acid region preferably comprising at least about a contiguous 35, 40, 45, 50, 75, 100, 150, or 200 amino acid region of a protein of the present invention. In another preferred embodiment, the proteins of the present invention include between about 30 and about 50 contiguous amino acid region, and even more preferably between about 40 and about 80 contiguous amino acid region.

Plant Constructs and Plant Transformants

One or more of the nucleic acid molecules of the invention may be used in plant transformation or transfection. Exogenous genetic material may be transferred into a plant cell and the plant cell regenerated into a whole, fertile, or sterile plant. Exogenous genetic material is any genetic material, whether naturally occurring or otherwise, from any source that is capable of being inserted into any organism.

In a preferred aspect of the present invention the exogenous genetic material comprises a nucleic acid sequence that encodes an amino acid transporter. In another preferred aspect of the present invention the exogenous genetic material of the invention comprises a nucleic acid sequence selected from the group consisting of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 65, 66, 68, 69, 70, and complements thereof and fragments of either.

In a further aspect of the present invention the exogenous genetic material comprises a nucleic acid sequence encoding an amino acid sequence selected from the group consisting of SEQ ID NOs: 1, 2, 4, 6, 8, 10, 12, 14, 16, 24, 26, 28, 30, 32, 34, 36, 38, 40, 42, 44, 46, 48, 50, 52, 54, and complements thereof.

In a further aspect of the present invention the nucleic acid molecule comprises a nucleic acid sequence encoding an amino acid sequence selected from the group consisting of SEQ ID NOs: 2, 4, 6, 8, 10, 12, 14, and fragments thereof.

In a further aspect of the present invention the nucleic acid molecule comprises a nucleic acid sequence encoding an amino acid sequence selected from the group consisting of SEQ ID NOs: 21, 23, 25, and fragments thereof.

In a further aspect of the present invention the nucleic acid molecule comprises a nucleic acid sequence encoding an amino acid sequence selected from the group consisting of SEQ ID NOs: 27, 29, 31, 33, 35, and fragments thereof.

In a further aspect of the present invention the nucleic acid molecule comprises a nucleic acid sequence encoding an amino acid sequence having SEQ ID NO: 1 or fragments thereof.

In a further aspect of the present invention, the nucleic acid sequences of the invention also encode peptides involved in intracellular localization, export, or post-translational modification.

In an embodiment of the present invention, exogenous genetic material comprising an amino acid transporter polypeptide or fragment thereof, is introduced into a plant with one or more additional genes. In a preferred embodiment, the additional genes comprise one or more nucleic acids of the present invention. In a further preferred embodiment, at least 1, 2, 3, 4, or 5 additional genes comprising one or more nucleic acids of the present invention are introduced into a plant.

Another particularly preferred combination that can be introduced is a nucleic acid molecule encoding an amino acid transporter and a nucleic acid molecule that results in the down regulation of an amino acid transporter. In such an aspect, it is preferred that the plant accumulates oil in its seed.

Such genetic material may be transferred into either monocotyledons or dicotyledons including, but not limited to canola, maize, soybean, *Arabidopsis Phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris*, oilseed rape, turfgrass, sugarbeet, coffee and dioscorea (Christou, in *Particle Bombardment for Genetic Engineering of Plants*, Biotechnology Intelligence Unit, Academic Press, San Diego, Calif. (1996)), with canola, maize, *Brassica campestris*, oilseed rape, rapeseed, soybean, crambe, mustard, castor bean, peanut, sesame, cottonseed, linseed, safflower, oil palm, flax, wheat, rice, and sunflower preferred, and canola, rapeseed, maize, *Brassica campestris*, oilseed rape, soybean, sunflower, safflower, oil palms, and peanut preferred. In a more preferred embodiment, the genetic material is transferred into canola. In another more preferred embodiment, the genetic material is transferred into maize. In another particularly preferred embodiment, the genetic material is transferred into soybean. In another particularly preferred embodiment, the genetic material is transferred into wheat.

Transfer of a nucleic acid molecule that encodes a protein can result in expression or overexpression of that polypeptide in a transformed cell or transgenic plant. One or more of the proteins or fragments thereof, encoded by nucleic acid molecules of the invention may be overexpressed in a transformed cell or transformed plant. Such expression or overexpression may be the result of transient or stable transfer of the exogenous genetic material.

In a preferred embodiment, expression or overexpression of a polypeptide of the present invention in a plant provides in that plant, relative to an untransformed plant with a similar genetic background, an increased level of amino acids in a tissue of the plant. In a preferred embodiment, the total amino acid content of a tissue of a plant of the present invention is increased by at least about 5% relative to an untransformed plant having a similar genetic background. In further preferred embodiments of the present invention, the total amino acid content of a tissue of a plant of the present invention is increased by at least about 10, 15, 20, 25, 50, or 100% relative to an untransformed plant having a similar genetic background. In a preferred embodiment the tissue is seed tissue. In a preferred embodiment the tissue is leaf tissue.

In a preferred embodiment of the present invention, expression or overexpression of a polypeptide of the present invention in a plant provides in that plant, relative to an untransformed plant with a similar genetic background, an increased level of one or more of the amino acids selected from the group consisting of alanine, asparagine, aspartate, glutamine, and serine. In a preferred embodiment, the amino acid content of a tissue of a plant of the present invention of one or more of the amino acids selected from the group consisting of alanine, asparagine, aspartate, glutamine, and serine is increased by at least about 5% relative to an untransformed plant having a similar genetic background. In further preferred embodiments of the present invention, the amino acid content of one or more of the amino acids selected from the group consisting of alanine, asparagine, aspartate, glutamine, and serine of a tissue of a plant of the present invention is increased by at least about 10, 15, 20, 25, 50, or 100% relative to an untransformed plant having a similar genetic background. In a preferred embodiment the tissue is seed tissue. In a preferred embodiment the tissue is leaf tissue. In a preferred embodiment, the amino acid is alanine. In a preferred embodiment, the amino acid is asparagine. In a preferred embodiment, the amino acid is aspartate. In a preferred embodiment, the amino acid is glutamine. In a preferred embodiment, the amino acid is serine.

In a preferred embodiment of the present invention, expression or overexpression of a polypeptide of the present invention in a plant results in accumulation of amino acids in one or more tissues of the plant. In a preferred embodiment, the tissue is leaf. In another preferred embodiment, the preferred tissue is seed. As used herein, "accumulation of amino acids" in a tissue of a plant refers to the buildup of the concentration of individual or groups of amino acids in a plant to a level that is greater than that which occurs in an untransformed plant with a similar genetic background. The accumulated amino acid content can be greater than an untransformed plant with a similar genetic background as described above.

In another embodiment of the present invention, expression or overexpression of a polypeptide of the present invention results in leaf free amino acid ("FAA") content of at least about 12,000 ppm. In further embodiments, expression or overexpression of a polypeptide of the present invention results in leaf FAA content of at least about 13,000 ppm, 15,000 ppm, 20,000 ppm, 25,000 ppm, or 50,000 ppm.

In another embodiment of the present invention, expression or overexpression of a polypeptide of the present invention results in seed protein content of at least about 5%, and more preferably at least about 10, 15, 20, 25, 50, 75, or 100% relative to an untransformed plant having a similar genetic background.

In another embodiment, expression or overexpression of a polypeptide of the present invention in a plant provides in that plant, or a tissue of that plant, relative to an untransformed plant or plant tissue, with a similar genetic background, an increased level of an amino acid transporter polypeptide or fragment thereof.

In some embodiments, the levels of one or more amino acids or in total amino acids in one or more tissues of the plant are increased by greater than 5%, or more preferably greater than 10, 25, 35, 50, 75, 80, 90, 100, 150, 200, 1,000, 2,000, or 2,500%. The levels of products may be increased throughout an organism such as a plant or localized in one or more specific organs or tissues of the organism. For example, the levels of products may be increased in one or more of the tissues and organs of a plant including without limitation: roots, tubers, stems, leaves, stalks, fruit, berries, nuts, bark, pods, seeds and flowers. A preferred organ is a seed. A preferred tissue is leaf.

In a preferred aspect, a similar genetic background is a background where the organisms being compared share 50% or greater of their nuclear genetic material. In a more preferred aspect a similar genetic background is a background where the organisms being compared share 75% or greater, even more preferably 90% or greater of their nuclear genetic material. In another even more preferable aspect, a similar genetic background is a background where the organisms being compared are plants, and the plants are isogenic except for any genetic material originally introduced using plant transformation techniques.

Exogenous genetic material may be transferred into a host cell by the use of a DNA vector or construct designed for such a purpose. Design of such a vector is generally within the skill of the art (see, *Plant Molecular Biology: A Laboratory Manual*, Clark (ed.), Springer, N.Y. (1997)).

A construct or vector may include a plant promoter to express the polypeptide of choice. In a preferred embodiment, any nucleic acid molecule described herein, can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter. In another preferred embodiment, the promoter is a vascular specific promoter. In another preferred embodiment, the promoter is a seed specific promoter. In another preferred embodiment, the promoter is a maize endosperm specific promoter. In another preferred embodiment, the promoter is selected from the group of promoters consisting of E35S-HSP70, Z27-HSP70, RTBV-HSP70, SuSy2, and BETL1-HSP70. In one embodiment, the promoter is E35S-HSP70. In another embodiment, the promoter is Z27-HSP70. In another embodiment, the promoter is RTBV-HSP70. In another embodiment, the promoter is SuSy2. In another embodiment, the promoter is BETL1-HSP70.

A number of promoters that are active in plant cells have been described in the literature. These include the nopaline synthase (NOS) promoter (Ebert et al., *Proc. Natl. Acad. Sci.* (*U.S.A*) 84:5745-5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol*. 9:315-324 (1987)) and the CaMV 35S promoter (Odell et al., *Nature* 313:810-812 (1985)), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci*. (*U.S.A.*) 84:6624-6628 (1987)), the sucrose synthase promoter (Yang et al., *Proc. Natl. Acad. Sci*. (*U.S.A.*) 87:4144-4148 (1990)), the R gene complex promoter (Chandler et al., *The Plant Cell* 1:1175-1183 (1989)) and the chlorophyll a/b binding protein gene promoter, etc. These promoters have been used to create DNA constructs that have been expressed in plants; see, e.g., WO 84/02913. The CaMV 35S promoters are preferred for use in plants. Promoters known or found to cause transcription of DNA in plant cells can be used in the invention.

For the purpose of expression in source tissues of the plant, such as the leaf, root, or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or enhanced expression. Examples of such promoters reported in the literature include the chloroplast glutamine synthetase GS2 promoter from pea (Edwards et al., *Proc. Natl. Acad. Sci.* (*U.S.A.*) 87:3459-3463 (1990)), the chloroplast fructose-1,6-biphosphatase (FBPase) promoter from wheat (Lloyd et al., *Mol. Gen. Genet*. 225:209-216 (1991)), the nuclear photosynthetic ST-LS1 promoter from potato (Stockhaus et al., *EMBO J.* 8:2445-2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol*. 35:773-778 (1994)), the promoter for the Cab-1 gene from wheat (Fejes et al., *Plant Mol. Biol*. 15:921-932 (1990)), the promoter for the CAB-1 gene from spinach (Lubberstedt et al., *Plant Physiol*. 104:997-1006 (1994)), the promoter for the cab1R gene from rice (Luan et al., *Plant Cell*. 4:971-981 (1992)), the pyruvate, orthophosphate dikinase (PPDK) promoter from maize (Matsuoka et al., *Proc. Natl. Acad. Sci*. (*U.S.A.*) 90:9586-9590 (1993)), the promoter for the tobacco Lhcb1*2 gene (Cerdan et al., *Plant Mol. Biol.* 33:245-255 (1997)), the *Arabidopsis thaliana* SUC2 sucrose-H+ symporter promoter (Truernit et al., *Planta*. 196:564-570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (*Sinapis alba*; Kretsch et al., *Plant Mol. Biol*. 28:219-229 (1995)).

For the purpose of expression in sink tissues of the plant, such as the tuber of the potato plant, the fruit of tomato, or the seed of maize, wheat, rice and barley, it is preferred that the promoters utilized in the invention have relatively high expression in these specific tissues. A number of promoters for genes with tuber-specific or tuber-enhanced expression are known, including the class I patatin promoter (Bevan et al., *EMBO J.* 8:1899-1906 (1986); Jefferson et al., *Plant Mol. Biol*. 14:995-1006 (1990)), the promoter for the potato tuber ADPGPP genes, both the large and small subunits, the sucrose synthase promoter (Salanoubat and Belliard *Gene* 60:47-56 (1987), Salanoubat and Belliard *Gene* 84:181-185 (1989)), the promoter for the major tuber proteins including the 22 kd protein complexes and protease inhibitors (Hannapel *Plant Physiol*. 101:703-704 (1993)), the promoter for the granule-bound starch synthase gene (GBSS) (Visser et al., *Plant Mol. Biol*. 17:691-699 (1991)) and other class I and II patatins promoters (Koster-Topfer et al., *Mol. Gen. Genet*. 219:390-396 (1989); Mignery et al., *Gene*. 62:27-44 (1988)).

Other promoters can also be used to express a polypeptide in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res*. 1:209:219 (1991)), phaseolin (Bustos et al., *Plant Cell* 1(9):839-853 (1989)), soybean trypsin inhibitor (Riggs et al., *Plant Cell* 1(6):609-621 (1989)), ACP (Baerson et al., *Plant Mol. Biol.* 22(2):255-267 (1993)), stearoyl-ACP desaturase (Slocombe et al., *Plant Physiol.* 104(4):167-176 (1994)), soybean a' subunit of β-conglycinin (soy 7s, (Chen et al., *Proc. Natl. Acad. Sci.* 83:8560-8564 (1986))), and oleosin (see for example, Hong et al., *Plant Mol. Biol.* 34(3):549-555 (1997)). Further examples include the promoter for β-conglycinin (Chen et al., *Dev. Genet.* 10:112-122 (1989)). Also included are the zeins, which are a group of storage proteins found in maize endosperm. Genomic clones for zein genes have been isolated (Pedersen et al., *Cell* 29:1015-1026 (1982), and Russell et al., *Transgenic Res.* 6(2):157-168) and the promoters from these clones, including the 15 kD, 16 kD, 19 kD, 22 kD, 27 kD and genes, could also be used. Other promoters known to function, for example, in maize include the promoters for the following genes: waxy, Brittle, Shrunken 2, branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol. Cell Biol.* 13:5829-5842 (1993)). Examples of promoters suitable for expression in wheat include those promoters for the ADP glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins, and the aleurone specific proteins.

Root specific promoters may also be used. An example of such a promoter is the promoter for the acid chitinase gene (Samac et al., *Plant Mol. Biol.* 25:587-596 (1994)). Expression in root tissue could also be accomplished by utilizing the root specific subdomains of the CaMV35S promoter that have been identified (Lam et al., *Proc. Natl. Acad. Sci.* (*U.S.A.*) 86:7890-7894 (1989)). Other root cell specific promoters include those reported by Conkling et al., (*Plant Physiol.* 93:1203-1211 (1990)).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell* 1:977-984 (1989)).

Other useful promoters include the tomato E8, patatin, ubiquitin, mannopine synthase (mas), soybean seed protein glycinin (Gly), soybean vegetative storage protein (vsp) promoters, and the *Arabidopsis* banyuls promoter (BANYULS gene (GenBank AF092912, Devic et.al., *The Plant Journal* 19(4): 387-398 (1999)). The promoter used may be a seed coat specific promoter.

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671-680 (1989); Bevan et al., *Nucleic Acids Res.* 11:369-385 (1983)). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements. Examples of such include the Adh intron 1 (Callis et al., *Genes and Develop.* 1:1183-1200 (1987)), the sucrose synthase intron (Vasil et al., *Plant Physiol.* 91:1575-1579 (1989)) and the TMV omega element (Gallie et al., *The Plant Cell* 1:301-311 (1989)). These and other regulatory elements maybe included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183-188 (1985)), which codes for kanamycin resistance and can be selected for using kanamycin, RptII, G418, hpt etc.; a bar gene which codes for bialaphos resistance; a mutant EPSP synthase gene (Hinchee et al., *Bio/Technology* 6:915-922 (1988); Reynaerts et al., Selectable and Screenable Markers, in Gelvin and Schilperoort (eds.), Plant Molecular Biology Manual, Kluwer, Dordrecht (1988)), which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (EP 154 204 (Sep. 11, 1985)), ALS (D'Halluin et al., *Bio/Technology* 10:309-314 (1992)), and a methotrexate resistant DHFR gene (Thillet et al., *J. Biol. Chem.* 263:12500-12508 (1988)).

A vector or construct may also include a transit peptide. Incorporation of a suitable chloroplast transit peptide may also be employed (EP 0 218 571). Translational enhancers may also be incorporated as part of the vector DNA. DNA constructs could contain one or more 5' non-translated leader sequences, which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996). A preferred transit peptide is CTP1.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson *Plant Mol. Biol, Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., *Stadler Symposium* 11:263-282 (1988)); a β-lactamase gene (Sutcliffe et al., *Proc. Natl. Acad. Sci.* (*U.S.A.*) 75:3737-3741 (1978)), a gene which encodes an enzyme for which various chromogenic substrates are known (e.g., PADAC, a chromogenic cephalosporin); a luciferase gene (Ow et al., Science 234:856-859 (1986)); a xylE gene (Zukowsky et al., *Proc. Natl. Acad. Sci.* (*U.S.A.*) 80:1101-1105 (1983)) which encodes a catechol dioxygenase that can convert chromogenic catechols; an α-amylase gene (Ikatu et al., *Bio/Technol*. 8:241-242 (1990)); a tyrosinase gene (Katz et al., *J. Gen. Microbiol*. 129:2703-2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, and the like (Potrykus *Ann. Rev. Plant Physiol. Plant Mol. Biol*. 42:205-225 (1991); Vasil *Plant Mol. Biol*. 25:925-937 (1994)). For example, electroporation has been used to transform maize protoplasts (Fromm et al., *Nature* 312:791-793 (1986)).

Other vector systems suitable for introducing transforming DNA into a host plant cell include but are not limited to binary artificial chromosome (BIBAC) vectors (Hamilton et al., *Gene* 200:107-116 (1997)); and transfection with RNA viral vectors (Della-Cioppa et al., *Ann. N.Y. Acad. Sci*. 792:57-61(1996)). Additional vector systems also include plant selectable YAC vectors such as those described in Mullen et al., *Molecular Breeding* 4:449-457 (1988).

Technology for introduction of DNA into cells is well known to those of skill in the art. Four general methods for delivering a gene into cells have been described: (1) chemical methods (Graham and van der Eb *Virology* 54:536-539 (1973)); (2) physical methods such as microinjection (Capecchi *Cell* 22:479-488 (1980)), electroporation (Wong and Neumann *Biochem. Biophys. Res. Commun*. 107:584-587 (1982); Fromm et al., *Proc. Natl. Acad. Sci*. (*U.S.A.*) 82:5824-5828 (1985); U.S. Pat. No. 5,384,253); the gene gun (Johnston and Tang *Methods Cell Biol*. 43:353-365 (1994)); and vacuum infiltration (Bechtold et al., *C.R. Acad. Sci. Paris, Life Sci*. 316:1194-1199 (1993)); (3) viral vectors (Clapp *Clin. Perinatol*. 20:155-168 (1993); Lu et al., *J. Exp. Med*. 178:2089-2096 (1993); Eglitis and Anderson *Biotechniques* 6:608-614 (1988)); and (4) receptor-mediated mechanisms (Curiel et al., *Hum. Gen. Ther*. 3:147-154 (1992), Wagner et al., *Proc. Natl. Acad. Sci*. (*U.S.A.*) 89:6099-6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994). Non-biological particles (microprojectiles) may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol*. 87:671-674 (1988)) nor the susceptibility to *Agrobacterium* infection is required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with maize cells cultured in suspension. Gordon-Kamm et al., describes the basic procedure for coating tungsten particles with DNA (Gordon-Kamm et al., *Plant Cell* 2:603-618 (1990)). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, Calif.) (Sanford et al., *Technique* 3:3-16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein, one may obtain 1000 or more loci of cells transiently expressing a marker gene. The number of cells in a focus that express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci*. (*U.S.A.*) 87:8526-8530 (1990); Svab and Maliga *Proc. Natl. Acad. Sci*. (*U.S.A.*) 90:913-917 (1993); Staub and Maliga *EMBO J*. 12:601-606 (1993); U.S. Pat. Nos. 5,451,513 and 5,545,818).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may, therefore, influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629-635 (1985) and Rogers et al., *Methods Enzymol*. 153:253-277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet*. 205:34 (1986)).

Modern *Agrobacterium* transformation vectors are capable of replication in *E. coli* as well as *Agrobacterium*, allowing for convenient manipulations as described (Klee et al., in *Plant DNA Infectious Agents*, Hohn and Schell (eds.), Springer-Verlag, NY, pp. 179-203 (1985)). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol*. 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (see for example, Potrykus et al., *Mol. Gen. Genet*. 205:193-200 (1986); Lorz et al., *Mol. Gen. Genet*. 199:178 (1985); Fromm et al., *Nature* 319:791 (1986); Uchimiya et al., *Mol. Gen. Genet*. 204:204 (1986); Marcotte et al., *Nature* 335:454-457 (1988)).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor. Appl. Genet*. 205:34 (1986); Yamada et al., *Plant Cell Rep*. 4:85 (1986); Abdullah et al., *Biotechnology* 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil *Biotechnology* 6:397 (1988)). In addition, "particle gun" or high-velocity microprojectile technology can be utilized (Vasil et al., *Bio/Technology* 10:667 (1992)).

Using the latter technology, DNA is carried through the cell wall and into the cytoplasm on the surface of small metal particles as described (Klein et al., *Nature* 328:70 (1987); Klein et al., *Proc. Natl. Acad. Sci.* (*U.S.A.*) 85:8502-8505 (1988); McCabe et al., *Bio/Technology* 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol*. 107:367 (1987); Luo et al., *Plant Mol Biol. Reporter* 6:165 (1988)), by direct injection of DNA into reproductive organs of a plant (Pena et al., *Nature* 325:274 (1987)), or by direct injection of DNA into the cells of immature embryos followed by the rehydration of desiccated embryos (Neuhaus et al., *Theor. Appl. Genet*. 75:30 (1987)).

The regeneration, development and cultivation of plants from single plant protoplast transformants or from various transformed explants is well known in the art (Weissbach and Weissbach, in *Methods for Plant Molecular Biology*, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 5,569,834 and 5,416,011; McCabe et al., *Biotechnology* 6:923 (1988); Christou et al., *Plant Physiol*. 87:671-674 (1988)); *Brassica* (U.S. Pat. No. 5,463,174); peanut (Cheng et al., *Plant Cell Rep*. 15:653-657 (1996), McKently et al., *Plant Cell Rep*. 14:699-703 (1995)); papaya; pea (Grant et al., *Plant Cell Rep*. 15:254-258 (1995)); and *Arabidopsis thaliana* (Bechtold et al., *C.R. Acad. Sci. Paris, Life Sci*. 316:1194-1199 (1993)). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci*. (*U.S.A*.) 84:5354 (1987)); barley (Wan and Lemaux *Plant Physiol*. 104:37 (1994)); maize (Rhodes et al., *Science* 240:204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995)); oat (Somers et al., *Bio/Technology* 10:1589 (1992)); orchard grass (Horn et al., *Plant Cell Rep*. 7:469 (1988)); rice (Toriyama et al., *Theor Appl. Genet*. 205:34 (1986); Part et al., *Plant Mol. Biol*. 32:1135-1148 (1996); Abedinia et al., *Aust. J. Plant Physiol*. 24:133-141 (1997); Zhang and Wu *Theor. Appl. Genet*. 76:835 (1988); Zhang et al., *Plant Cell Rep*. 7:379 (1988); Battraw and Hall *Plant Sci*. 86:191-202 (1992); Christou et al., *Bio/Technology* 9:957 (1991)); rye (De la Pena et al., *Nature* 325:274 (1987)); sugarcane (Bower and Birch *Plant J*. 2:409 (1992)); tall fescue (Wang et al., *Bio/Technology* 10:691 (1992)); and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev*. 6:609-618 (1992); Goff et al., *EMBO J*. 9:2517-2522 (1990)). Transient expression systems may be used to functionally dissect gene constructs (see generally, Mailga et al., *Methods in Plant Molecular Biology*, Cold Spring Harbor Press (1995)).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for expression or overexpression of the protein or fragment thereof, encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990); van der Krol et al., *Plant Cell* 2:291-299 (1990)). Cosuppression may result from stable transformation with a single copy nucleic acid molecule that is homologous to a nucleic acid sequence found with the cell (Prolls and Meyer *Plant J*. 2:465-475 (1992)) or with multiple copies of a nucleic acid molecule that is homologous to a nucleic acid sequence found with the cell (Mittlesten et al., *Mol. Gen. Genet*. 244:325-330 (1994)). Genes, even though different, linked to homologous promoters may result in the cosuppression of the linked genes (Vaucheret *C.R. Acad. Sci. III* 316:1471-1483 (1993); Flavell *Proc. Natl. Acad. Sci*. (*U.S.A*.) 91:3490-3496 (1994); van Blokland et al., *Plant J*. 6:861-877 (1994); Jorgensen *Trends Biotechnol*. 8:340-344 (1990); Meins and Kunz, in *Gene Inactivation and Homologous Recombination in Plants*, Paszkowski (ed.), pp. 335-348, Kluwer Academic, Netherlands (1994)).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett*. 268:427-430 (1990)). The objective of the antisense approach is to use a sequence complementary to the target gene to block its expression and create a mutant cell line or organism in which the level of a single chosen protein is selectively reduced or abolished. Antisense techniques have several advantages over other reverse genetic approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., in *Genetic Engineering*, Setlow (ed.), Vol. 11, NY: Plenum 49-63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem*. 55:569-597 (1986)). Under one embodiment, the process involves the introduction and expression of an antisense gene sequence. Such a sequence is one in which part or all of the normal gene sequences are placed under a promoter in inverted orientation so that the wrong or complementary strand is transcribed into a noncoding antisense RNA that hybridizes with the target mRNA and interferes with its expression (Takayama and Inouye *Crit. Rev. Biochem. Mol. Biol*. 25:155-184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

Various regulatory sequences of DNA can be altered (promoters, polyadenylation signals, post-transcriptional processing sites) or used to alter the expression levels (enhancers and silencers) of a specific mRNA.

Another strategy for gene down-regulation or suppression contemplated by this invention is RNA interference (RNAi). RNA interference is a phenomenon comprising the introduction of double-stranded RNA to induce potent and specific gene silencing. In RNAi, inverted repeats, which presumably form strong secondary structure in vivo, cause genetic down-regulation (Baulcombe *Curr. Biol*. 9:R599-R601 (1999); Sharp *Genes and Dev*. 13:139-141 (1999);

Sharp et al., *Science* 287:2431-2433 (2000)). The mechanisms of how RNAi results in the loss of the targeted homologous mRNA are still not well understood. The RNAi strategy is effective for gene down regulation in plants, and is distinct from the method using expression of antisense transcripts because the base pairing in RNAi occurs intramolecularly. In antisense RNA constructs, the transcribed segment typically comprises a partial or complete cDNA copy of the target gene. The transcribed segment is linked to the promoter in the inverted orientation, such that the transcripts produced are complementary to the messenger RNA of the target gene. Unlike cosuppression constructs, antisense RNA constructs seldom, if ever, include introns in the transcribed segment. Because RNA polymerase II promoters are used to express antisense RNA and cosuppression constructs, RNA transcripts produced from such constructs can be expected to be processed like messenger RNA transcripts normally produced from such promoters.

Messenger RNA (mRNA) post-transcriptional processing involves capping at the 5'-end and a coupled endonucleolytic cleavage and polyadenylation reaction at the 3'-end of the primary transcript. In addition, where the gene contains introns, the intervening sequences of the introns are spliced out from the transcript during the mRNA maturation process. These processing steps, with the exception of the capping reaction, are regulated by specific signals on the primary RNA transcript.

Yet another strategy for gene down-regulation or suppression contemplated by this invention is the use of ribozymes. Ribozymes, or catalytic RNA molecules capable of cleaving target mRNA at specific sites, are well know in the art (see for example, Gibson and Shillitoe *Molecular Biotechnology* 7(2):125-137 (1997)).

Another method for abolishing the expression of a gene is by insertion mutagenesis using the T-DNA of *Agrobacterium tumefaciens*. After generating the insertion mutants, the mutants can be screened to identify those containing the insertion in an amino acid transporter protein gene. Plants containing a single transgene insertion event at the desired gene can be crossed to generate homozygous plants for the mutation (Koncz et al., *Methods in Arabidopsis Research*, World Scientific (1992)).

Alternatively, a plant phenotype can be altered by eliminating amino acid transporter protein genes, such as AAP1-6, e.g., by homologous recombination (Kempin et al., *Nature* 389:802 (1997)). A plant trait can also be modified by using the cre-lox system (U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

One of ordinary skill in the art will recognize that a number of methods can be used to inactivate, abolish or suppress gene expression or the activity of the amino acid transporter proteins of the present invention, as noted at least in part above. For example, it is understood that the activity of a protein in a plant cell may be reduced or depressed by growing a transformed plant cell containing a nucleic acid molecule whose non-transcribed strand encodes a protein or fragment thereof. A preferred protein whose activity can be reduced or depressed, by any method, is an amino acid transporter. In such an embodiment of the invention, it is preferred that the concentration of oil in the seed as a percent weight measurement is increased. In a preferred embodiment, total oil in the seed of a transformed plant with reduced or depressed activity of an amino acid transporter is increased by at least about 5% relative to seed of a plant having a similar genetic background but lacking a nucleic acid molecule of the present invention. In further preferred embodiments, total oil in the seed of a transformed plant with reduced or depressed activity of an amino acid transporter is increased by at least about 10, 15, 20, 40, 60, 80, or 100% relative to seed of a plant having a similar genetic background but lacking a nucleic acid molecule of the present invention.

In a preferred embodiment, a maize plant of the present invention comprising a nucleic acid of the present invention will have a kernel protein content, as determined in the examples given below, of at least about 5% relative to an untransformed plant having a similar genetic background. In further embodiments, kernel protein content is at least about 10, 20, 30, 40, 50, 60, 75, or 100% relative to an untransformed plant having a similar genetic background. In another preferred embodiment, leaf free amino acid in a plant of the present invention is at least 11,000 ppm, and more preferably 12,000 ppm, 14,000 ppm, 16,000 ppm, 18,000 ppm, 20,000 ppm, 22,000 ppm, 24,000 ppm, 26,000 ppm, 28,000 ppm, or 30,000 ppm. In a further preferred embodiment, kernel endosperm protein content is at least about 5, 10, 20, 30, 40, 50, 60, 75, or 100% of total endosperm content relative to an untransformed plant having a similar genetic background.

In further embodiments, individual leaf free amino acids in the leaves of a plant of the present invention are increased relative to an untransformed plant having a similar genetic background. In one embodiment, alanine FAA is at least 3,000 ppm, and more preferably at least 3,500 ppm, 4,000 ppm, 5,000 ppm, 6,000 ppm, or 8,000 ppm in plant leaves. In another embodiment, asparagine FAA is at least 1,700 ppm, and more preferably at least 2,000 ppm, 2,500 ppm, 3,500 ppm, 4,000 ppm, or 5,000 ppm. In another embodiment, glutamate FAA is at least 1,700 ppm, and more preferably at least 2,000 ppm, 2,500 ppm, 3,500 ppm, 4,000 ppm, or 5,000 ppm. In another embodiment, aspartate or serine or both FAA is at least 1,000 ppm, and more preferably at least 2,000 ppm, 2,500 ppm, 3,500 ppm, 4,000 ppm, or 5,000 ppm. In another embodiment, glutamine FAA is at least 500 ppm, and more preferably at least 1,000 ppm, 2,000 ppm, 2,500 ppm, 3,500 ppm, 4,000 ppm, or 5,000 ppm. In another embodiment, glycine or valine or both FAA is at least 300 ppm, and more preferably at least 500 ppm, 1,000 ppm, 2,000 ppm, 2,500 ppm, 3,500 ppm, 4,000 ppm, or 5,000 ppm. In another embodiment, phenylalanine FAA is at least 150 ppm, and more preferably at least 500 ppm, 1,000 ppm, 2,000 ppm, 2,500 ppm, 3,500 ppm, 4,000 ppm, or 5,000 ppm. In another embodiment, threonine FAA is at least 250 ppm, and more preferably at least 500 ppm, 1,000 ppm, 2,000 ppm, 2,500 ppm, 3,500 ppm, 4,000 ppm, or 5,000 ppm.

Posttranscriptional gene silencing (PTGS) can result in virus immunity or gene silencing in plants. PTGS is induced by dsRNA and is mediated by an RNA-dependent RNA polymerase, present in the cytoplasm, which requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNAse molecules hybridize to the endogene mRNA and cleave the single-stranded RNA adjacent to the hybrid. The cleaved single-stranded RNAs are further degraded by other host RNAses because one will lack a capped 5' end and the other will lack a poly(A) tail (Waterhouse et al., *Proc. Natl. Acad. Sci.* (*U.S.A.*) 95:13959-13964 (1998)).

It is understood that one or more of the nucleic acids of the present invention may be introduced into a plant cell and transcribed using an appropriate promoter with such transcription resulting in the postranscriptional gene silencing of an endogenous transcript.

Antibodies have been expressed in plants (Hiatt et al., *Nature* 342:76-78 (1989); Conrad and Fielder *Plant Mol. Biol.* 26:1023-1030 (1994)). Cytoplasmic expression of a scFv (single-chain Fv antibody) has been reported to delay infection by artichoke mottled crinkle virus. Transgenic plants that express antibodies directed against endogenous proteins may exhibit a physiological effect (Philips et al., *EMBO J.* 16:4489-4496 (1997); Marion-Poll *Trends in Plant Science* 2:447-448 (1997)). For example, expressed anti-abscisic antibodies have been reported to result in a general perturbation of seed development (Philips et al., *EMBO J.* 16:4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas *Nature Biotechnology* 15:1313-1315 (1997); Baca et al., *Ann. Rev. Biophys. Biomol. Struct.* 26:461-493 (1997)). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289; and 5,194,585.

It is understood that any of the antibodies of the invention may be expressed in plants and that such expression can result in a physiological effect. It is also understood that any of the expressed antibodies may be catalytic.

The present invention also provides for parts of the plants, particularly reproductive or storage parts, of the present invention. Plant parts, without limitation, include seed, endosperm, ovule and pollen. In a particularly preferred embodiment of the present invention, the plant part is a seed. In one embodiment the seed is a constituent of animal feed.

The present invention also provides a container of over 10,000, more preferably 20,000, and even more preferably 40,000 seeds where over 10%, more preferably 25%, more preferably 50%, and even more preferably 75 or 90% of the seeds are seeds derived from a plant of the present invention.

The present invention also provides a container of over 10 kg, more preferably 25 kg, and even more preferably 50 kg seeds where over 10%, more preferably 25%, more preferably 50%, and even more preferably 75 or 90% of the seeds are seeds derived from a plant of the present invention.

Any of the plants or parts thereof of the present invention may be processed to produce a feed, meal, protein, or oil preparation, including oil preparations high in specific or total amino acid content or oil. A particularly preferred plant part for this purpose is a seed.

In a preferred embodiment the feed, meal, protein or oil preparation is designed for livestock, animals or humans, or both. Methods to produce feed, meal, protein and oil preparations are known in the art. See, for example, U.S. Pat. Nos. 4,957,748; 5,100,679; 5,219,596; 5,936,069; 6,005,076; 6,146,669; and 6,156,227.

In a preferred embodiment, the protein preparation is a high protein preparation. Such a high protein preparation preferably has a protein content of greater than 5% w/v, more preferably 10% w/v, and even more preferably 15% w/v.

In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10, or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils.

In a preferred embodiment, the oil produced from plants of the present invention or generated by a method of the present invention constitutes greater than 0.5, 1, 5, 10, 25, 50, 75, or 90% by volume or weight of the oil component of any product. In another embodiment, the oil preparation may be blended and can constitute greater than 10, 25, 35, 50, or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g. Fehr *Principles of Cultivar Development* Vol. 1, pp. 2-3 (1987)).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy, or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art (see, U.S. Pat. No. 5,811,636).

In a further embodiment of the present invention, a nucleic acid construct comprising SEQ ID NO: 65 or 66 is introduced into a plant other than *Arabidopsis thaliana*. In a preferred embodiment, the construct comprising SEQ ID NO: 65 or 66 is introduced into a rice, maize, or soybean plant. Any of the vectors, promoters, or other construct components given above can be used in combination with SEQ ID NO: 65 or 66 in this embodiment. In a further embodiment, a nucleic acid construct comprising a nucleic acid construct having a nucleic acid sequence coding for a protein having the amino acid sequence of SEQ ID NO: 1 is introduced into a plant other than *Arabidopsis thaliana*. In a preferred embodiment, the construct comprising a nucleic acid molecule encoding a protein having an amino acid sequence of SEQ ID NO: 1 is introduced into a rice, maize, or soybean plant. Any of the vectors, promoters, or other construct components given above can be used in combination with SEQ ID NO: 65 or 66 in this embodiment.

Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Particularly preferred bacteria are *Agrobacteruim tumefaciens* and *E. coli.*

Methods to transform such cells or organisms are known in the art (EP 0 238 023; Yelton et al., *Proc. Natl. Acad. Sci.* (*U.S.A.*) 81:1470-1474 (1984); Malardier et al., *Gene* 78:147-156 (1989); Becker and Guarente, in *Guide to Yeast Genetics and Molecular Biology, Method Enzymol*., Abelson and Simon (eds.), Vol. 194, pp. 182-187, Academic Press, Inc., NY; Ito et al., *J. Bacteriology* 153:163 (1983); Hinnen et al., *Proc. Natl. Acad. Sci*. (*U.S.A*) 75:1920 (1978); Bennett and LaSure (eds.), *More Gene Manipualtionins in fungi*, Academic Press, CA (1991)). Methods to produce proteins of the present invention are also known (Kudla et al., *EMBO J*. 9:1355-1364 (1990); Jarai and Buxton *Current Genetics* 26:2238-2244 (1994); Verdier *Yeast* 6:271-297 (1990); MacKenzie et al., *Journal of Gen. Microbiol*. 139:2295-2307 (1993); Hartl et al., *TIBS* 19:20-25 (1994); Bergenron et al., *TIBS* 19:124-128 (1994); Demolder et al., *J. Biotechnology* 32:179-189 (1994); Craig *Science* 260:1902-1903 (1993); Gething and Sambrook *Nature* 355:33-45 (1992); Puig and Gilbert *J. Biol. Chem*. 269:7764-7771 (1994); Wang and Tsou *FASEB Journal* 7:1515-1517 (1993); Robinson et al., *Bio/Technology* 1:381-384 (1994); Enderlin and Ogrydziak *Yeast* 10:67-79 (1994); Fuller et al., *Proc. Natl. Acad. Sci*. (*U.S.A.*) 86:1434-1438 (1989); Julius et al., *Cell* 37:1075-1089 (1984); Julius et al., *Cell* 32:839-852 (1983)).

In a preferred embodiment, expression or overexpression of a polypeptide of the present invention in a cell or organism provides in that cell or organism, relative to an untransformed cell or organism with a similar genetic background, an increased level of amino acids in a tissue of the plant. In a preferred embodiment, the total amino acid content of a cell or organism of the present invention is increased by at least about 5% relative to an untransformed cell or organism having a similar genetic background. In further preferred embodiments of the present invention, the total amino acid content of a cell or organism of the present invention is increased by at least about 10, 15, 20, 25, 50, or 100% relative to an untransformed cell or organism having a similar genetic background.

In a preferred embodiment of the present invention, expression or overexpression of a polypeptide of the present invention in a cell or organism provides in that cell or organism, relative to an untransformed cell or organism with a similar genetic background, an increased level of one or more of the amino acids selected from the group consisting of alanine, asparagine, aspartate, glutamine, and serine. In a preferred embodiment, the amino acid content of a cell or organism of the present invention of one or more of the amino acids selected from the group consisting of alanine, asparagine, aspartate, glutamine, and serine is increased by at least about 5% relative to an untransformed cell or organism having a similar genetic background. In further preferred embodiments of the present invention, the amino acid content of one or more of the amino acids selected from the group consisting of alanine, asparagine, aspartate, glutamine, and serine of a cell or organism of the present invention is increased by at least about 10, 15, 20, 25, 50, or 100% relative to an untransformed cell or organism having a similar genetic background. In a preferred embodiment, the amino acid is alanine. In a preferred embodiment, the amino acid is asparagine. In a preferred embodiment, the amino acid is aspartate. In a preferred embodiment, the amino acid is glutamine. In a preferred embodiment, the amino acid is serine.

Antibodies

One aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NOs: 2, 4, 6, 8, 10, 12, 14, 16, 24, 26, 28, 30, 32, 34, 36, 38, 40, 42, 44, 46, 48, 50, 52, 54, and complements thereof. In another embodiment, the antibody specifically binds to a fusion protein comprising an amino acid sequence selected from the amino acid sequence set forth in SEQ ID NOs: 2, 4, 6, 8, 10, 12, 14, 16, 24, 26, 28, 30, 32, 34, 36, 38, 40, 42, 44, 46, 48, 50, 52, 54, and complements thereof. Antibodies of the invention may be used to quantitatively or qualitatively detect the protein or peptide molecules of the invention, or to detect post translational modifications of the proteins. As used herein, an antibody or peptide is said to specifically bind to a protein or peptide molecule of the invention if such binding is not competitively inhibited by the presence of non-related molecules.

Nucleic acid molecules that encode all or part of the protein of the invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a fusion molecule (i.e., a part of a larger nucleic acid molecule) such that, upon expression, a fusion protein is produced. It is understood that any of the nucleic acid molecules of the invention may be expressed, via recombinant means, to yield proteins or peptides encoded by these nucleic acid molecules.

The antibodies that specifically bind proteins and protein fragments of the invention may be polyclonal or monoclonal and may comprise intact immunoglobulins, or antigen binding portions of immunoglobulins fragments (such as F(ab'), $F(ab')_2$), or single-chain immunoglobulins producible, for example, via recombinant means. It is understood that practitioners are familiar with the standard resource materials that describe specific conditions and procedures for the construction, manipulation and isolation of antibodies (see for example, Harlow and Lane, In: *Antibodies: A Laboratory Manual*, Cold Spring Harbor Press, Cold Spring Harbor, N.Y. (1988)).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the invention permits the identification of mimetic compounds derived from those molecules. These mimetic compounds may contain a fragment of the protein or peptide or merely a structurally similar region and nonetheless exhibits an ability to specifically bind to antibodies directed against that compound.

Exemplary Uses

Nucleic acid molecules and fragments thereof of the invention may be employed to obtain other nucleic acid molecules from the same species (nucleic acid molecules from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the invention may also be employed to obtain nucleic acid homologs. Such homologs include the nucleic acid molecules of plants and other organisms, including bacteria and fungi, including the nucleic acid molecules that encode, in whole or in part, protein homologues of other plant species or other organisms, sequences of genetic elements, such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those found in one or more of SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof, because complete complementarity is not needed for stable hybridization. The nucleic acid molecules of the invention, therefore, also include molecules that, although capable of specifically hybridizing with the nucleic acid molecules, may lack complete complementarity.

Any of a variety of methods may be used to obtain one or more of the above-described nucleic acid molecules (Zamechik et al., *Proc. Natl. Acad. Sci.* (*U.S.A.*) 83:4143-4146 (1986); Goodchild et al., *Proc. Natl. Acad. Sci.* (*U.S.A.*) 85:5507-5511 (1988); Wickstrom et al., *Proc. Natl. Acad. Sci.* (*U.S.A.*) 85:1028-1032 (1988); Holt et al., *Molec. Cell. Biol.* 8:963-973 (1988); Gerwirtz et al., *Science* 242:1303-1306 (1988); Anfossi et al., *Proc. Natl. Acad. Sci.* (*U.S.A.*) 86:3379-3383 (1989); Becker et al., *EMBO J.* 8:3685-3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263-273 (1986); Erlich et al., EP 050 424; 084 796; 258 017; and 237 362; Mullis, EP 201 184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of chromosome walking, or inverse PCR may be used to obtain such sequences (Frohman et al., *Proc. Natl. Acad. Sci.* (*U.S.A.*) 85:8998-9002 (1988); Ohara et al., *Proc. Natl. Acad. Sci.* (*U.S.A.*) 86:5673-5677 (1989); Pang et al., *Biotechniques* 22:1046-1048 (1977); Huang et al., *Methods Mol. Biol.* 69:89-96 (1997); Huang et al., *Method Mol. Biol.* 67:287-294 (1997); Benkel et al., *Genet. Anal.* 13:123-127 (1996); Hartl et al., *Methods Mol. Biol.* 58:293-301 (1996)). The term “chromosome walking” means a process of extending a genetic map by successive hybridization steps.

The nucleic acid molecules of the invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (see for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the invention includes nucleic acid molecules that are markers. The markers can be used in a number of conventional ways in the field of molecular genetics. Such markers include nucleic acid molecules SEQ ID NOs: 3, 5, 7, 9, 11, 13, 15, 17, 18, 19, 20, 21, 22, 23, 25, 27, 29, 31, 33, 35, 37, 39, 41, 43, 45, 47, 49, 51, 53, 55, 56, 57, 58, 59, 60, 61, 68, 69, 70, and complements thereof, and fragments of either that can act as markers and other nucleic acid molecules of the present invention that can act as markers.

Genetic markers of the invention include “dominant” or “codominant” markers. Codominant markers reveal the presence of two or more alleles (two per diploid individual) at a locus. Dominant markers reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that some other undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution (Gusella *Ann. Rev. Biochem.* 55:831-854 (1986)). A polymorphism is a variation or difference in the sequence of the gene or its flanking regions that arises in some of the members of a species. The variant sequence and the original sequence co-exist in the species' population. In some instances, such co-existence is in stable or quasi-stable equilibrium.

A polymorphism is thus said to be allelic, in that, due to the existence of the polymorphism, some members of a population may have the original sequence (i.e., the original allele) whereas other members may have the variant sequence (i.e., the variant allele). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as variable number tandem repeat (VNTR) polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39:144-147 (1987); Horn et al., WO 91/14003; Jeffreys, EP 370 719; Jeffreys, U.S. Pat. No. 5,175,082; Jeffreys et al., *Amer. J. Hum. Genet.* 39:11-24 (1986); Jeffreys et al., *Nature* 316: 76-79 (1985); Gray et al., *Proc. R. Acad. Soc. Lond.* 243: 241-253 (1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 124: 783-789 (1990)).

The detection of polymorphic sites in a sample of DNA may be facilitated through the use of nucleic acid amplification methods. Such methods specifically increase the concentration of nucleic acid molecules that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic, acid molecules comprising a nucleotide sequence of a nucleic acid molecule located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" (RFLPs) (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al., (WO 90/13668; Uhlen, WO 90/11369).

Polymorphisms can also be identified by Single Strand Conformation Polymorphism (SSCP) analysis (Elles Methods in *Molecular Medicine: Molecular Diagnosis of Genetic Diseases*, Humana Press (1996); Orita et al., *Genomics* 5:874-879 (1989)). A number of protocols have been described for SSCP including, but not limited to, Lee et al., *Anal. Biochem.* 205:289-293 (1992); Suzuki et al., *Anal. Biochem.* 192:82-84 (1991); Lo et al., *Nucleic Acids Research* 20:1005-1009 (1992); Sarkar et al., *Genomics* 13:441-443 (1992). It is understood that one or more of the nucleic acids of the invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407-4414 (1995)). This method allows for the specific co-amplification of high numbers of restriction fragments, which can be visualized by PCR without knowledge of the nucleic acid sequence. It is understood that one or more of the nucleic acids of the invention may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531-6535 (1990)) and cleaveable amplified polymorphic sequences (CAPS) (Lyamichev et al., *Science* 260: 778-783 (1993)). It is understood that one or more of the nucleic acid molecules of the invention, may be utilized as markers or probes to detect polymorphisms by RAPD or CAPS analysis.

Single Nucleotide Polymorphisms (SNPs) generally occur at greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980); Konieczny and Ausubel *Plant J.* 4:403-410 (1993)), enzymatic and chemical mismatch assays (Myers et al., *Nature* 313:495-498 (1985)), allele-specific PCR (Newton et al., *Nucl. Acids Res.* 17:2503-2516 (1989); Wu et al., *Proc. Natl. Acad. Sci.* (*U.S.A.*) 86:2757-2760 (1989)), ligase chain reaction (Barany *Proc. Natl. Acad. Sci.* (*U.S.A.*) 88:189-193 (1991)), single-strand conformation polymorphism analysis (Labrune et al., *Am. J. Hum. Genet.* 48:1115-1120 (1991)), single base primer extension (Kuppuswamy et al., *Proc. Natl. Acad. Sci.* (*U.S.A.*) 88:1143-1147 (1991), Goelet U.S. Pat. Nos. 6,004,744 and 5,888,819), solid-phase ELISA-based oligonucleotide ligation assays (Nikiforov et al., *Nucl. Acids Res.* 22:4167-4175 (1994)), dideoxy fingerprinting (Sarkar et al., *Genomics* 13:441-443 (1992)), oligonucleotide fluorescence-quenching assays (Livak et al., *PCR Methods Appl.* 4:357-362 (1995)), 5'-nuclease allele-specific hybridization TaqMan™ assay (Livak et al., *Nature Genet.* 9:341-342 (1995)), template-directed dye-terminator incorporation (TDI) assay (Chen and Kwok *Nucl. Acids Res.* 25:347-353 (1997)), allele-specific molecular beacon assay (Tyagi et al., *Nature Biotech.* 16:49-53 (1998)), PinPoint assay (Haff and Smirnov *Genome Res.* 7:378-388 (1997)), dCAPS analysis (Neff et al., *Plant J.* 14:387-392 (1998)), pyrosequencing (Ronaghi et al., *Analytical Biochemistry* 267:65-71 (1999); Ronaghi et al,. WO 98/13523; Nyren et al., WO 98/28440; www.pyrosequencing.com), using mass spectrometry, e.g. the Masscode™ system (Howbert et al., WO 99/05319; Howbert et al., WO 97/27331; www.rapigene.com; Becker et al., WO 98/26095; Becker et al., WO 98/12355; Becker et al., WO 97/33000; Monforte et al., U.S. Pat. No. 5,965,363), invasive cleavage of oligonucleotide probes (Lyamichev et al., *Nature Biotechnology* 17:292-296;

www.twt.com), and using high density oligonucleotide arrays (Hacia et al., *Nature Genetics* 22:164-167; www.affymetrix.com).

Polymorphisms may also be detected using allele-specific oligonucleotides (ASO), which, can be for example, used in combination with hybridization based technology including Southern, Northern, dot blot hybridizations, reverse dot blot hybridizations, and hybridizations performed on microarray and related technology.

The stringency of hybridization for polymorphism detection is highly dependent upon a variety of factors, including length of the allele-specific oligonucleotide, sequence composition, degree of complementarity (i.e. presence or absence of base mismatches), concentration of salts and other factors such as formamide and temperature. These factors are important both during the hybridization itself and during subsequent washes performed to remove target nucleic acid molecule that is not specifically hybridized. In practice, the conditions of the final, most stringent wash are most critical. In addition, the amount of target nucleic acid molecule that is able to hybridize to the allele-specific oligonucleotide is also governed by such factors as the concentration of both the ASO and the target nucleic acid molecule, the presence and concentration of factors that act to tie up water molecules, so as to effectively concentrate the reagents (e.g., PEG, dextran, dextran sulfate, etc.), whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula: $T_m$=81.5+16.6×(log10[Na+])+0.41×(% G+C)−675/n; where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target nucleic acid molecule of the correct allele and a target nucleic acid molecule of the incorrect allele. Preferably, there will be at least a two-fold differential between the signal produced by the ASO hybridizing to a target nucleic acid molecule of the correct allele and the level of the signal produced by the ASO cross-hybridizing to a target nucleic acid molecule of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target nucleic acid molecule of the correct allele and the level of the signal produced by the ASO cross-hybridizing to a target nucleic acid molecule of the incorrect allele.

While certain methods for detecting polymorphisms are described herein, other detection methodologies may be utilized. For example, additional methodologies are known and set forth, in Birren et al., *Genome Analysis* 4:135-186; *A Laboratory Manual. Mapping Genomes*, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R. G. Landes Co., Georgetown, Tex., and Academic Press, San Diego, Calif. (1996); *The Corn Handbook*, Freeling and Walbot (eds.), Springer-Verlag, NY, N.Y. (1994); *Methods in Molecular Medicine: Molecular Diagnosis of Genetic Diseases*, Elles, (ed.), Humana Press, Totowa, N.J. (1996); and Clark, (ed.), *Plant Molecular Biology: A Laboratory Manual*, Clark, (ed.), Springer-Verlag, Berlin, Germany (1997).

Factors for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein *Genetics* 121:185-199 (1989) and the interval mapping, based on maximum likelihood methods described by Lander and Botstein *Genetics* 121:185-199 (1989) and implemented in the software package MAPMAKER/QTL (Lincoln and Lander *Mapping Genes Controlling Quantitative Traits Using MAPMAKER/QTL*, Whitehead Institute for Biomedical Research, MA (1990). Additional software includes Qgene, Version 2.23 (1996), Department of Plant Breeding and Biometry, 266 Emerson Hall, Cornell University, Ithaca, N.Y. Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein *Genetics* 121:185-199 (1989) and further described by Arús and Moreno-González *Plant Breeding*, Hayward et al. (eds.), Chapman & Hall, London, pp. 314-331 (1993).

In a preferred embodiment of the present invention the nucleic acid marker exhibits a LOD score of greater than 2.0, more preferably 2.5, even more preferably greater than 3.0 or 4.0 with the trait or phenotype of interest. In a preferred embodiment, the trait of interest is altered tocopherol levels or compositions or altered tocotrienol levels or compositions.

Additional models can be used. Many modifications and alternative approaches to interval mapping have been reported, including the use of non-parametric methods (Kruglyak and Lander *Genetics* 139:1421-1428 (1995)). Multiple regression methods or models can also be used, in which the trait is regressed on a large number of markers (Jansen *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke *Advances in Plant Breeding*, Blackwell, Berlin, 16 (1994)). Procedures combining interval mapping with regression analysis, whereby the phenotype is regressed onto a single putative QTL at a given marker interval and at the same time onto a number of markers that serve as cofactors, have been reported by Jansen and Stam *Genetics* 136:1447-1455 (1994), and Zeng *Genetics* 136:1457-1468 (1994). Generally, the use of cofactors reduces the bias and sampling error of the estimated QTL positions (Utz and Melchinger *Biometrics in Plant Breeding*, van Oijen and Jansen (eds.), Proceedings of the Ninth Meeting of the Eucarpia Section Biometrics in Plant Breeding, The Netherlands, pp.195-204 (1994)), thereby improving the precision and efficiency of QTL mapping (Zeng *Genetics* 136:1457-1468 (1994)). These models can be extended to multi-environment experiments to analyze genotype-environment interactions (Jansen et al., *Theo. Appl. Genet*. 91:33-37 (1995)).

It is understood that one or more of the nucleic acid molecules of the invention may be used as molecular markers. It is also understood that one or more of the protein molecules of the invention may be used as molecular markers.

In a preferred embodiment, the polymorphism is present and screened for in a mapping population, e.g. a collection of plants capable of being used with markers such as polymorphic markers to map genetic position of traits. The choice of appropriate mapping population often depends on the type of marker systems employed. Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large number of polymorphisms when compared to progeny in a narrow cross (adapted×adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather *Measurement of Linkage in Heredity*, Methuen and Co., (1938)). In the case of dominant markers, progeny tests (e.g., $F_3$, $BCF_2$) are required to identify the heterozygotes, in order to classify the population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and codominant markers evaluated in RIL populations provide more information per individual than either marker type in backcross populations (Reiter *Proc. Natl. Acad. Sci*. (*U.S.A.*) 89:1477-1481 (1992)). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci*. (*U.S.A.*) 89:1477-1481 (1992)). Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as a mapping population. In mapping with NILs, only a portion of the polymorphic loci is expected to map to a selected region.

Bulk segregant analysis (BSA) is a method developed for the rapid identification of linkage between markers and traits of interest (Michelmore et al., *Proc. Natl. Acad. Sci*. (*U.S.A.*) 88:9828-9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

In an aspect of the present invention, one or more of the nucleic molecules of the present invention are used to determine the level (i.e., the concentration of mRNA in a sample, etc.) in a plant (preferably canola, maize, *Brassica campestris*, oilseed rape, rapeseed, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecule of the present invention (collectively, the Expression Response of a cell or tissue).

As used herein, the Expression Response manifested by a cell or tissue is said to be altered if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement, yield, etc.). A change in genotype or phenotype may be transient or permanent. Also, as used herein, a tissue sample is any sample that comprises more than one cell. In a preferred aspect, a tissue sample comprises cells that share a common characteristic (e.g. derived from root, seed, flower, leaf, stem, pollen, etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as Northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.* 101:477-484 (1984); Angerer et al., *Dev. Biol.* 112:157-166 (1985); Dixon et al., *EMBO J.* 10:1317-1324 (1991)). In situ hybridization may be used to measure the steady-state level of RNA accumulation (Hardin et al., *J. Mol. Biol.* 202:417-431 (1989)). A number of protocols have been devised for in situ hybridization, each with tissue preparation, hybridization and washing conditions (Meyerowitz *Plant Mol. Biol. Rep.* 5:242-250 (1987); Cox and Goldberg, in: *Plant Molecular Biology: A Practical Approach*, Shaw (ed.), pp. 1-35, IRL Press, Oxford (1988); Raikhel et al., *In situ RNA Hybridization in Plant Tissues*, in: *Plant Molecular Biology Manual*, Vol. B9:1-32, Kluwer Academic Publisher, Dordrecht, Belgium (1989)).

In situ hybridization also allows for the localization of proteins within a tissue or cell (Wilkinson *In Situ Hybridization*, Oxford University Press, Oxford (1992); Langdale *In Situ Hybridization* in: *The Corn Handbook*, Freeling and Walbot (eds.), pp. 165-179, Springer-Verlag, NY (1994)). It is understood that one or more of the molecules of the invention, preferably one or more of the nucleic acid molecules or fragments thereof, of the invention or one or more of the antibodies of the invention may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species (Griffor et al., *Plant Mol. Biol.* 17:101-109 (1991); Gustafson et al., *Proc. Natl. Acad. Sci.* (*U.S.A.*) 87:1899-1902 (1990); Mukai and Gill *Genome* 34:448-452 (1991); Schwarzacher and Heslop-Harrison *Genome* 34:317-323 (1991); Wang et al., *Jpn. J. Genet.* 66:313-316 (1991); Parra and Windle *Nature Genetics* 5:17-21 (1993)). It is understood that the nucleic acid molecules of the invention may be used as probes or markers to localize sequences along a chromosome.

Another method to localize the expression of a molecule is tissue printing. Tissue printing provides a way to screen, at the same time on the same membrane many tissue sections from different plants or different developmental stages (Yomo and Taylor *Planta.* 112:35-43 (1973); Harris and Chrispeels *Plant Physiol.* 56:292-299 (1975); Cassab and Varner *J. Cell. Biol.* 105:2581-2588 (1987); Spruce et al., *Phytochemistry* 26:2901-2903 (1987); Barres et al., *Neuron* 5:527-544 (1990); Reid and Pont-Lezica *Tissue Printing: Tools for the Study of Anatomy, Histochemistry and Gene Expression*, Academic Press, NY (1992); Reid et al., *Plant Physiol.* 93:160-165 (1990); Ye et al., *Plant J.* 1:175-183 (1991)).

One skilled in the art can refer to general reference texts for detailed descriptions of known techniques discussed herein or equivalent techniques. These texts include *Current Protocols in Molecular Biology*, Ausubel et al. (eds.), John Wiley & Sons, NY (1989), and supplements through September (1998), *Molecular Cloning, A Laboratory Manual*, Sambrook et al., 2$^{nd}$ Ed., Cold Spring Harbor Press, Cold Spring Harbor, N.Y. (1989), *Genome Analysis: A Laboratory Manual* 1*: Analyzing DNA*, Birren et al., Cold Spring Harbor Press, Cold Spring Harbor, N.Y. (1997); *Genome Analysis: A Laboratory Manual* 2*: Detecting Genes*, Birren et al., Cold Spring Harbor Press, Cold Spring Harbor, N.Y. (1998); *Genome Analysis: A Laboratory Manual* 3*: Cloning Systems*, Birren et al., Cold Spring Harbor Press, Cold Spring Harbor, N.Y. (1999); *Genome Analysis: A Laboratory Manual* 4*: Mapping Genomes*, Birren et al., Cold Spring Harbor Press, Cold Spring Harbor, N.Y. (1999); *Plant Molecular Biology: A Laboratory Manual*, Clark, Springer-Verlag, Berlin, (1997), *Methods in Plant Molecular Biology*, Maliga et al., Cold Spring Harbor Press, Cold Spring Harbor, N.Y. (1995). These texts can, of course, also be referred to in making or using an aspect of the invention. It is understood that any of the agents of the invention can be substantially purified and/or be biologically active and/or recombinant.

Having now generally described the invention, the same will be more readily understood through reference to the following examples that are provided by way of illustration, and are not intended to be limiting of the present invention, unless specified.

A sequence of any of the molecules of this invention can be provided in a variety of media to facilitate use thereof. Such media can also provide a subset thereof, in a form that allows a skilled artisan to examine the sequences. In a preferred embodiment, one or more of the nucleic acid sequences and/or the cognate nucleic acid molecule sequences of the present invention can be recorded on computer readable media. As used herein,"computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising a computer readable medium having recorded thereon a nucleotide sequence of the present invention.

As used herein, the term "recorded" refers to a process for storing information on computer readable media. A skilled artisan can readily adopt any of the presently known methods for recording information on computer readable media to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable media. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g., text file or database) in order to obtain a computer readable medium having recorded thereon the nucleotide sequence information of the present invention.

By providing one or more nucleic acid molecule or polypeptide sequences of the present invention in a computer readable medium, a skilled artisan can routinely access the sequence information for a variety of purposes. Examples set forth herein below demonstrate how software that implements the BLAST (Altschul et al., *J. Mol. Biol.* 215:403-410 (1990)) and BLAZE (Brutlag et al., *Comp. Chem.* 17:203-207 (1993)) search algorithms on a Sybase system can be used to identify open reading frames (ORFs) within the genome that contain homology to ORFs or polypeptides from other organisms. Such ORFs are polypeptide encoding fragments within the sequences of the present invention and are useful in producing important polypeptides such as enzymes used in amino acid biosynthesis, metabolism, transcription, translation, RNA processing, nucleic acid and protein degradation, protein modification, and DNA replication, restriction, modification, recombination, and repair.

The present invention further provides systems, particularly computer-based systems, that contain the sequence information described herein. Such systems are designed to identify commercially important fragments of the nucleic acid molecule of the present invention. As used herein, the phrase "a computer-based system" refers to the hardware, software, and memory used to analyze the sequence information of the present invention. A skilled artisan can readily appreciate that any one of the currently available computer-based systems are suitable for use in the present invention.

As indicated above, the computer-based systems of the present invention comprise a database having stored therein a nucleotide sequence of the present invention and the necessary hardware and software for supporting and implementing a homology search. As used herein, the term "database" refers to a memory system that can store searchable nucleotide sequence information. As used herein the phrase "query sequence" is a nucleic acid sequence, or an amino acid sequence, or a nucleic acid sequence corresponding to an amino acid sequence, or an amino acid sequence corresponding to a nucleic acid sequence, that is used to query a collection of nucleic acid or amino acid sequences. As used herein, the phrase "homology search" refers to one or more programs that are implemented on the computer-based system to compare a query sequence, i.e., gene or peptide or a conserved region (motif), with the sequence information stored within the database. Homology searches are used to identify segments and/or regions of the sequence of the present invention that match a particular query sequence. A variety of known searching algorithms are incorporated into commercially available software for conducting homology searches of databases using computer readable media comprising sequences of molecules of the present invention.

Commonly preferred sequence length of a query sequence is from about 10 to about 100 or more amino acids or from about 20 to about 300 or more nucleotide residues. There are a variety of motifs known in the art. Protein motifs include, but are not limited to, enzymatic active sites and signal sequences. An amino acid query is converted to all of the nucleic acid sequences that encode that amino acid sequence by a software program, such as TBLASTN, which is then used to search the database. Nucleic acid query sequences that are motifs include, but are not limited to, promoter sequences, cis elements, hairpin structures and inducible expression elements (protein binding sequences).

A variety of comparing programs can be used to compare a query sequence with the database to identify sequence of the present invention. For example, implementing software that implement the BLAST and BLAZE algorithms (Altschul et al., *J. Mol. Biol.* 215:403-410 (1990)) can be used to identify open frames within the nucleic acid molecules of the present invention. A skilled artisan can readily recognize that any one of the publicly available homology search programs can be used for the computer-based systems of the present invention.

EXAMPLE 1

*Arabidopsis* generic amino acid transporter genes have been reported (Hsu et al., *Proc. Natl. Acad. Sci.* 90:7441-7445 (1993); Frommer et al., *Proc. Natl. Acad. Sci.* 90:5944-5948 (1993)), and by convention have been designated AAP-1 through AAP-6. The sequence of an *Arabidopsis* AAP-6 protein has been published in the NCBI database, Accession Number X95736, and identified herein as SEQ ID NO: 1. By standard sequence homology studies, the gene encoding the *Arabidopsis* AAP-6 protein is found to be contained within clone LIB3278-061-P1-K1-D12 from the Monsanto *Arabidopsis* DNA database. The insert DNA from the clone is sequenced using standard sequencing methodology and the predicted polypeptide based on that sequence is confirmed to be an AAP-6, i.e., identical to the aforementioned Accession Number X95736.

The sequence of the *Arabidopsis* AAP-6 is used to search against Monsanto maize databases. The search is accomplished using a BLASTALL program in accordance with the procedure set forth by Altschul et al., *J. Mol. Biol.* 215:403-410 (1993). In particular, the following parameters are used: tblastn search program (protein query against DNA databases with all 6 reading frames), standard genetic codes for both query and database DNA sequences and BLOSUN 62 matrix for making comparisons (Henikoff and Henikoff *Proc. Natl. Acad. Sci.* (*U.S.A.*) 89:10915-10919 (1992)). Seventeen maize sequences are identified in the Monsanto unigene database in this manner, each with an E value of more than $1^{e-30}$, and twenty-four cDNA clones are identified in Monsanto cDNA libraries that represent at least 14 maize sequences identified by *Arabidopsis* AAP-6 protein sequence. cDNA inserts of eight such clones are selected based on the BLASTALL homology search and disclosed herein as SEQ ID NOs: 3, 5, 7, 9, 11, 13, 15, and 17. Predicted protein sequences (SEQ ID NOs: 2, 4, 6, 8, 10, 12, 14, and 16, respectively) from these eight maize clones exhibit 65-85% homology to *Arabidopsis* amino acid transporter protein AAP-6 (FIG. 15), as well as other *Arabidopsis* AAP proteins such as AAP1-5. Table 1 sets forth the identification, cDNA length and predicted amino acid length of the protein sequence of eight of the predicted amino acid transporters from maize of the present invention:

TABLE 1

| Clone ID | cDNA (#nucleotides) | Predicted protein (#amino acids) |
|---|---|---|
| LIB3332-019-P1-K1-A6 | SEQ ID NO: 3 (1821) | SEQ ID NO: 2 (471) |
| UC-ZMF1B73151A04B1 | SEQ ID NO: 5 (1640) | SEQ ID NO: 4 (484) |
| 700202115H1 | SEQ ID NO: 7 (1535) | SEQ ID NO: 6 (462) |
| LIB3689-227-Q1-K6-A12 | SEQ ID NO: 9 (1700) | SEQ ID NO: 8 (473) |
| LIB3632-059-Q6-K6-D5 | SEQ ID NO: 11 (1906) | SEQ ID NO: 10 (548) |
| UC-ZMFLB73290D08B1 | SEQ ID NO: 13 (1558) | SEQ ID NO: 12 (447) |
| LIB3079-043-Q1-K2-B1 | SEQ ID NO: 15 (1617) | SEQ ID NO: 14 (462) |
| UC-ZMROB73055H08 | SEQ ID NO: 17 (1977) | SEQ ID NO: 16 (478) |

Rice DNA databases are searched using the same criteria as described above for maize. Five cDNA clones are identified and characterized as amino acid transporters based on high homology to the *Arabidopsis* AAP-6 protein. FIG. 16 shows the alignment of the predicted amino acid sequences for the five rice clones aligned against the *Arabidopsis* AAP-6 protein.

Table 2 shows the identification, cDNA length and predicted amino acid length of the protein sequence of the five predicted amino acid transporters from rice of the present invention:

TABLE 2

| Clone ID | cDNA (# of nucleotides) | Predicted protein (# of aa) |
|---|---|---|
| UC-osflm202054e03b1 | SEQ ID NO: 25 (1829) | SEQ ID NO: 24 (538) |
| ORYSA-14MAR01-CLUSTER4446_1 | SEQ ID NO: 27 (1993) | SEQ ID NO: 26 (495) |
| fC-osflM202028F09 | SEQ ID NO: 29 (1609) | SEQ ID NO: 28 (475) |
| LIB3475-006-A4_FLI | SEQ ID NO: 31 (1632) | SEQ ID NO: 30 (469) |
| UC-OSFLM2O273D08 | SEQ ID NO: 33 (1692) | SEQ ID NO: 32 (451) |

Similar to the rice and maize examples described above, eleven soybean amino acid transporter clones are identified based on homology to AAP-6. FIG. 17 shows the alignment of the predicted amino acid sequences for the eleven soybean clones aligned against the *Arabidopsis* AAP-6 protein. The identification, cDNA length and predicted amino acid length of the protein sequence of the eleven predicted amino acid transporters from soybean are shown in Table 3:

TABLE 3

| Clone ID | cDNA (# of nucleotides) | Predicted protein (# of aa) |
|---|---|---|
| 701045628H1 | SEQ ID NO: 35 (1905) | SEQ ID NO: 34 (470) |
| 701208649H1 | SEQ ID NO: 37 (1614) | SEQ ID NO: 36 (461) |
| LIB3107-061-Q1-K1-F5 | SEQ ID NO: 39 (1825) | SEQ ID NO: 38 (488) |
| JC-GMFL02220088D03A1 | SEQ ID NO: 41 (1924) | SEQ ID NO: 40 (462) |
| JC-GMFL02220106H05A1 | SEQ ID NO: 43 (1893) | SEQ ID NO: 42 (462) |

TABLE 3-continued

| Clone ID | cDNA (# of nucleotides) | Predicted protein (# of aa) |
|---|---|---|
| 700891976-B1-K1 | SEQ ID NO: 45 (1743) | SEQ ID NO: 44 (513) |
| LIB4281-017-E1 | SEQ ID NO: 47 (1862) | SEQ ID NO: 46 (513) |
| 701010016 | SEQ ID NO: 49 (2191) | SEQ ID NO: 48 (463) |
| LIB3040-014-B6_FLI_09-01 | SEQ ID NO: 51 (1988) | SEQ ID NO: 50 (478) |
| JC-GMFL02220103H07 | SEQ ID NO: 53 (1873) | SEQ ID NO: 52 (479) |
| LIB4167-002-A10 | SEQ ID NO: 55 (1572) | SEQ ID NO: 54 (463) |

Similar to the rice and maize examples described above, three partial canola amino acid transporter genes are identified based on homology to *Arabidopsis* AAP genes, AtAAP1, AtAAP2 and AtAAP3. The *Arabidopsis* gene, the clone ID and the SEQ ID NO of the nucleotide sequences of the three predicted partial amino acid transporters from canola (*Brassica napus*) are shown in Table 4:

TABLE 4

| *Arabidopsis* Gene | Canola Clone ID | DNA (# of nucleotides) |
|---|---|---|
| AtAAP1 (L16240) | LIB3235-042-P1-K1-C11 | SEQ ID NO: 68 (1069) |
| AtAAP2 (X71787) | LIB3235-017-P1-K1-C9 | SEQ ID NO: 69 (402) |
| AtAAP3 (X77499) | LIB3235-054-P1-K1-G6 | SEQ ID NO: 70 (422) |

EXAMPLE 2

The clones LIB3332-019-P1-K1-A6, UC-ZMF1B73151A04B1, 700202115H1, and LIB3689-227-Q1-K6-A12 are subcloned into commercially available pYES2 vectors in order to over-express the genes in the mutant yeast JT16 (MATa hip1-614 his4-401 ura3-52 inol can1)—a yeast mutant deficient in histidine amino acid transport activity. Complementation studies are performed essentially as described in Tanaka and Fink *Gene* 38:205-214 (1985) using yeast strain JT16.

DNA fragments encoding the predicted amino acid transporter proteins in clones UC-ZMF1B73151A04B1, 700202115H1 and LIB3689-227-Q1-K6-A12 are released by digestion with restriction enzymes Kpn I and BamH I. Those DNA fragments are further cloned into pYES2 yeast expression vector (Invitrogen, Carlsbad, Calif., catalog number 825-20) at the Kpn I and BamH I restriction sites. For the cloning of predicted amino acid transporter DNA fragment of LIB3332-019-P1-K1-A6 into a yeast expression vector, the DNA insert is amplified by PCR using the vector-specific primers,

SP6, 5'-ATTTAGGTGACACTATA-3' SEQ ID NO: 62 and T7, 5'-TAATACGACTCACTATAGGG-3' SEQ ID NO: 63 and high affinity Tag polymerase (Boehringer Mannheim, Indianapolis, Ind.) using an otherwise standard PCR procedure. Amplified DNA fragments are subcloned into yeast expression vector pYES2.1/V5-His-TOPO (Invitrogen, Carlsbad, Calif.) following the manufacturer's instructions. Vector pYES2.1/V5-His-TOPO is a derivative of pYES2 and is designed for PCR cloning of DNA into pYES2. The resultant plasmids are introduced into cells of yeast strain JT16 by a chemical-mediated transformation protocol as described below (Dr. Gerald Fink at whitehead Institute, Cambridge, Mass.). Expression of predicted maize amino acid transporter genes in yeast cells is driven by a pGAL1 promoter, which has been built in the pYES2 and pYES2.1/V5-His-TOPO vectors.

Yeast cells of JT16 are maintained on YDP medium (2% yeast extract, 1% peptone, 2% dextrose and 1.5% agar) supplemented with 650 μM histidine. For preparing JT16 cells for transformation, 2-ml of overnight-grown JT16 cells are harvested in a 1.5 ml Eppendorf centrifuge tube by centrifugation. Cells are resuspended in a buffer containing 100 μL 1 M DTT, 200 μL 1 M LiCl and 660 μL 50% polyethyleneglycol (PEG) (MW 3350). Five microliters of salmon sperm DNA (2 mg/mL) is further added into cell suspension. For transformation of cells, 10 μL of pYES2 DNA from a plasmid DNA mini-prep is mixed with the chemical-treated cells, followed by incubation at 45° C. for 30 minutes and chilling on ice for 2 minutes. Transformed cells are then placed on SC-URA medium consisting of 0.17% yeast nitrogen base, 2% glucose, 0.5% ammonium sulfate, 0.19% SC micronutrient minus urea (BIO101, Carlsbad, Calif., catalog number 441-622), 650 μM histidine and 1M sorbitol, and 1.5% agar, and incubated for 3 days at 30° C. for selection of $URA^+$ transformants.

Colonies of $URA^+$ transformants are picked up and subcultured on the same $URA^+$ selective medium without sorbitol. The existence of plasmid DNA along with genes of interest is confirmed by PCR reaction. For function assay of transporter activity, the JT16 cells containing putative amino acid transporter genes are placed on histidine-limiting medium (HLM) consisting of 4% galactose, 0.17% yeast nitrogen base (without amino acids or ammonia sulphate), 0.5% ammonia sulphate, 0.002% inosine, 0.1% arginine, and 130 μM histidine (Hsu et al., *Proc. Natl. Acad. Sci.* 90:7441-7445 (1993)). Only JT16 cells harboring functional amino acid transporter genes are able to grow on HLM medium by complementation of mutated gene his4401 in JT16 cells. Wild-type JT16 cells or cells containing pYES2 vector only are unable to grow on HLM medium. The four predicted maize amino acid transporter genes exhibit amino acid transporter activity, along with additional two maize, three rice and ten soybean orthologues as detailed in TABLE 5.

TABLE 5

Maize, rice and soybean AAP orthologues and their functional analysis by complementation of mutant yeast JT16 cells

| Species | Clone ID | Protein SEQ ID NO | cDNA length (nt) | Predicted protein (aa) | Functionality by yeast complementation assay |
|---|---|---|---|---|---|
| Maize | LIB3332-019-P1-K1-A6 | 2 | 1821 | 472 | Positive |
| Maize | UC-ZMF1B73151A04B1 | 4 | 1640 | 485 | Positive |
| Maize | 700202115H1 | 6 | 1535 | 463 | Positive |
| Maize | LIB3689-227-Q1-K6-A12 | 8 | 1700 | 474 | Positive |
| Maize | LIB3632-059-Q6-K6-D5 | 10 | 1943 | 548 | Positive |
| Maize | UC-ZMROB73055H08_FLI | 16 | 1977 | 479 | Positive |
| Rice | UC-0SFLM202054E0361 | 24 | 1839 | 539 | Positive |
| Rice | ORYSA-14MAR01-cluster 4446_1 | 26 | 1993 | 496 | Positive |
| Rice | fC-osflM202028F09 | 28 | 1069 | 476 | Positive |
| Soybean | 701045628H1 | 34 | 1917 | 471 | Positive |
| Soybean | 701208649H1 | 36 | 1616 | 462 | Positive |
| Soybean | LIB3107-061-Q1-K1-F5 | 38 | 1825 | 488 | Positive |
| Soybean | JC-GMFL02220088D03A1 | 40 | 1933 | 462 | Positive |
| Soybean | JC-GMFL02220106H05A1 | 42 | 1902 | 462 | Positive |
| Soybean | 700891976 | 44 | 1754 | 514 | Positive |
| Soybean | LIB4281-017-R1-K1-E1 | 46 | 1863 | 514 | Positive |
| Soybean | 701010016 | 48 | 2192 | 464 | Positive |
| Soybean | JC-GMFL02220103H07 | 52 | 1873 | 480 | Positive |
| Soybean | LIB3040-014-B6_FLI_09-01 | 50 | 1987 | 479 | Positive |

EXAMPLE 3

Figure 2:
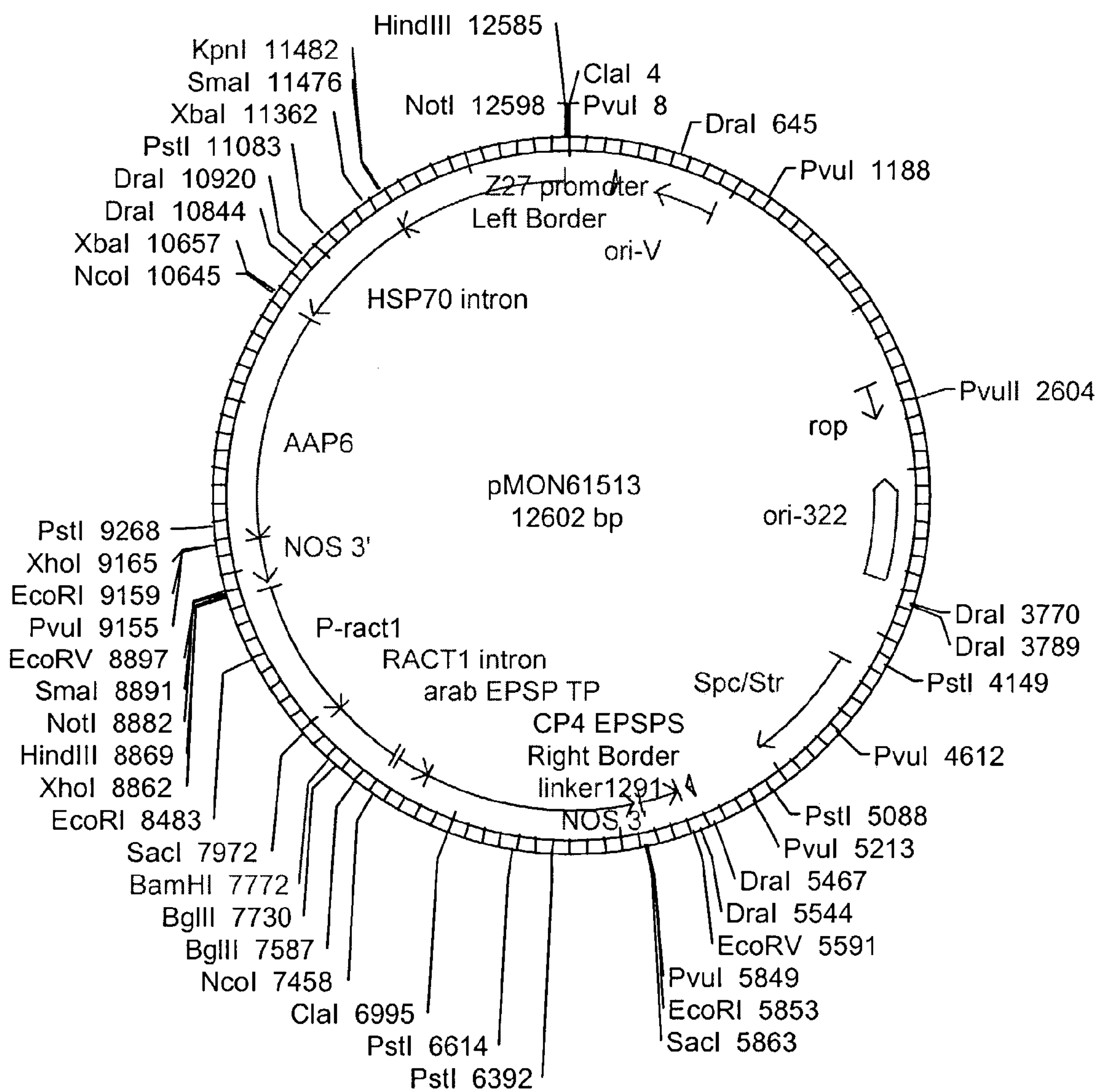
FIG. 2 is a plasmid map of pMON61513.
Figure 3:
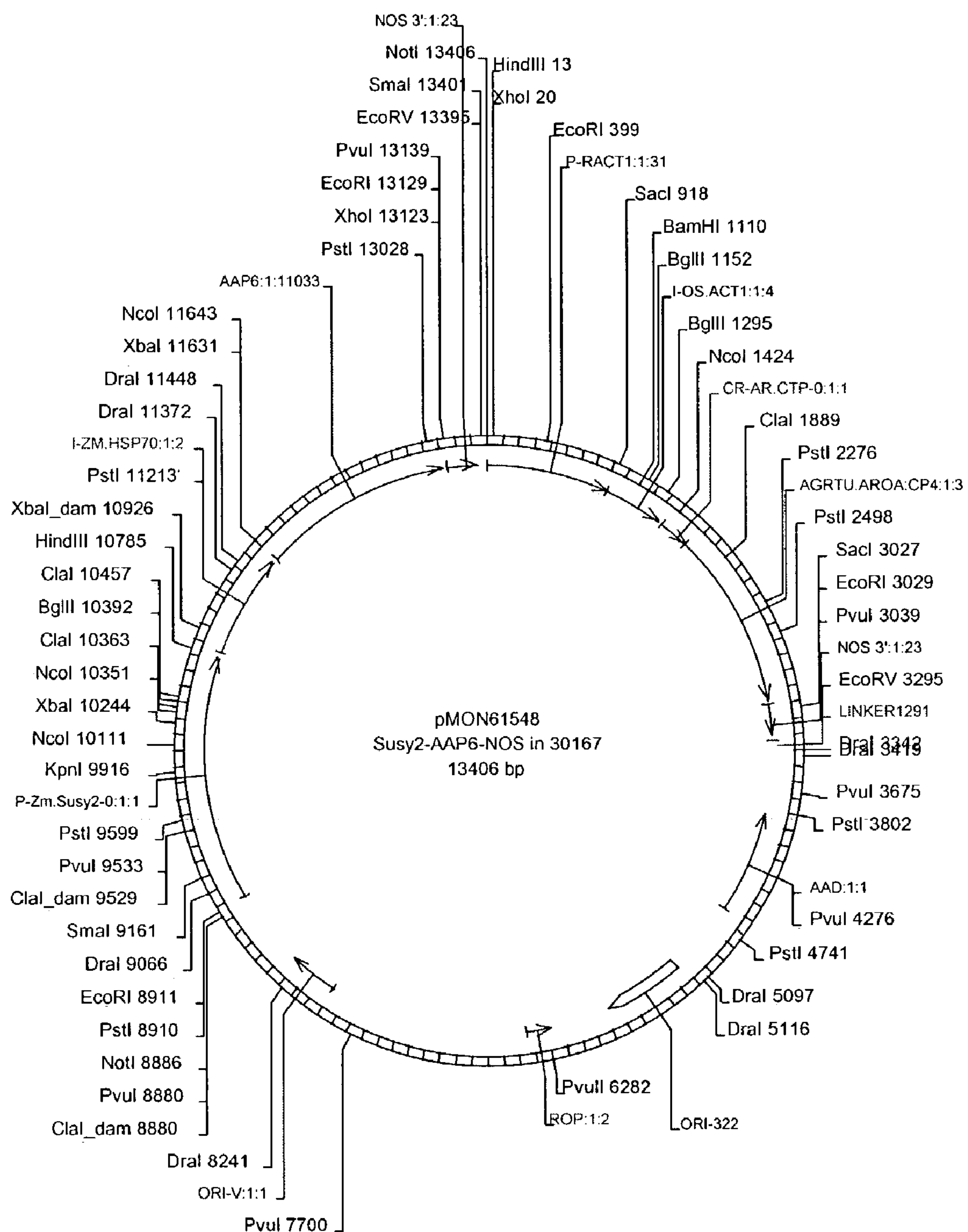
FIG. 3 is a plasmid map of pMON61548.
Figure 4:
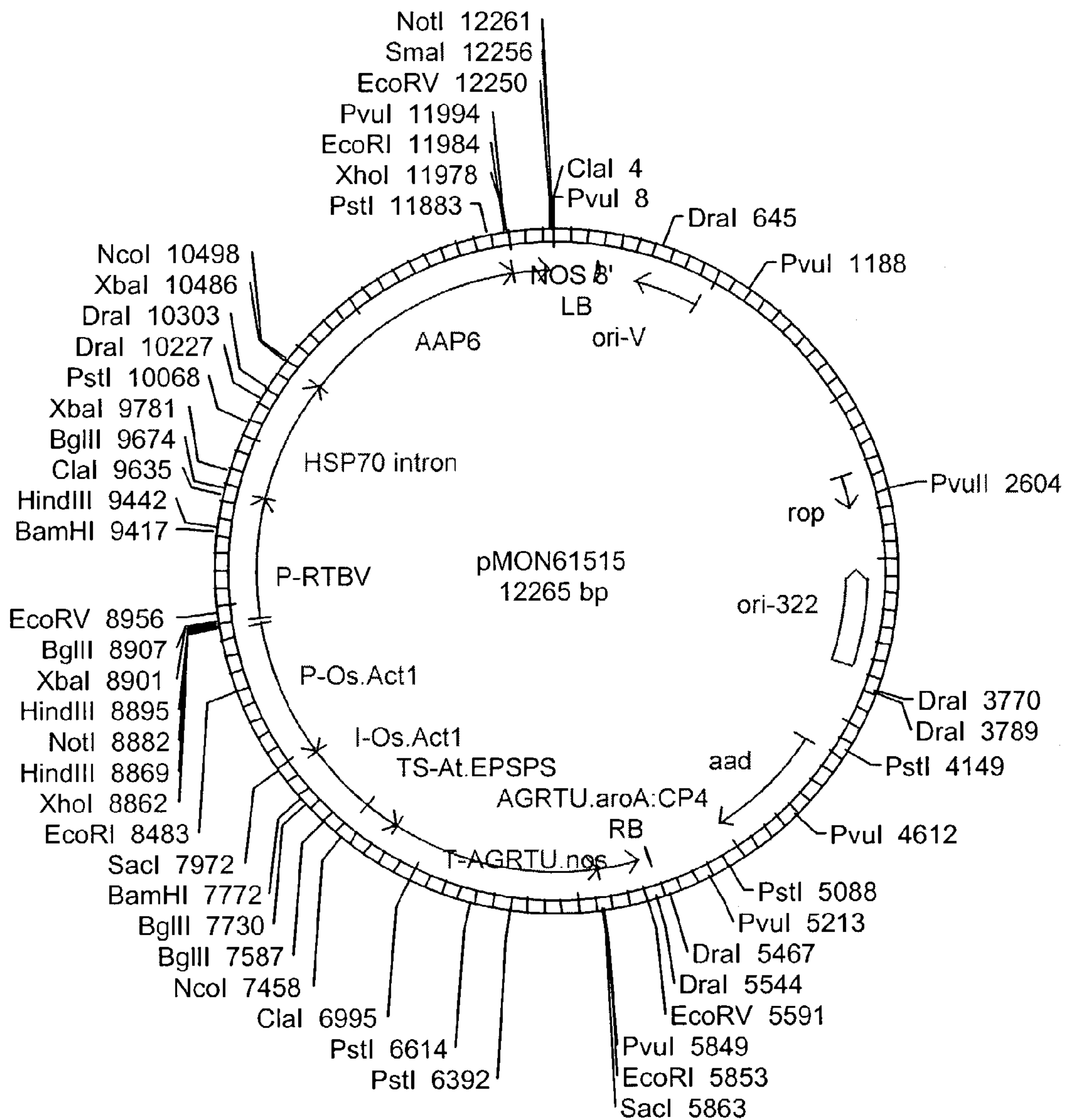
FIG. 4 is a plasmid map of pMON61515.
Figure 5:
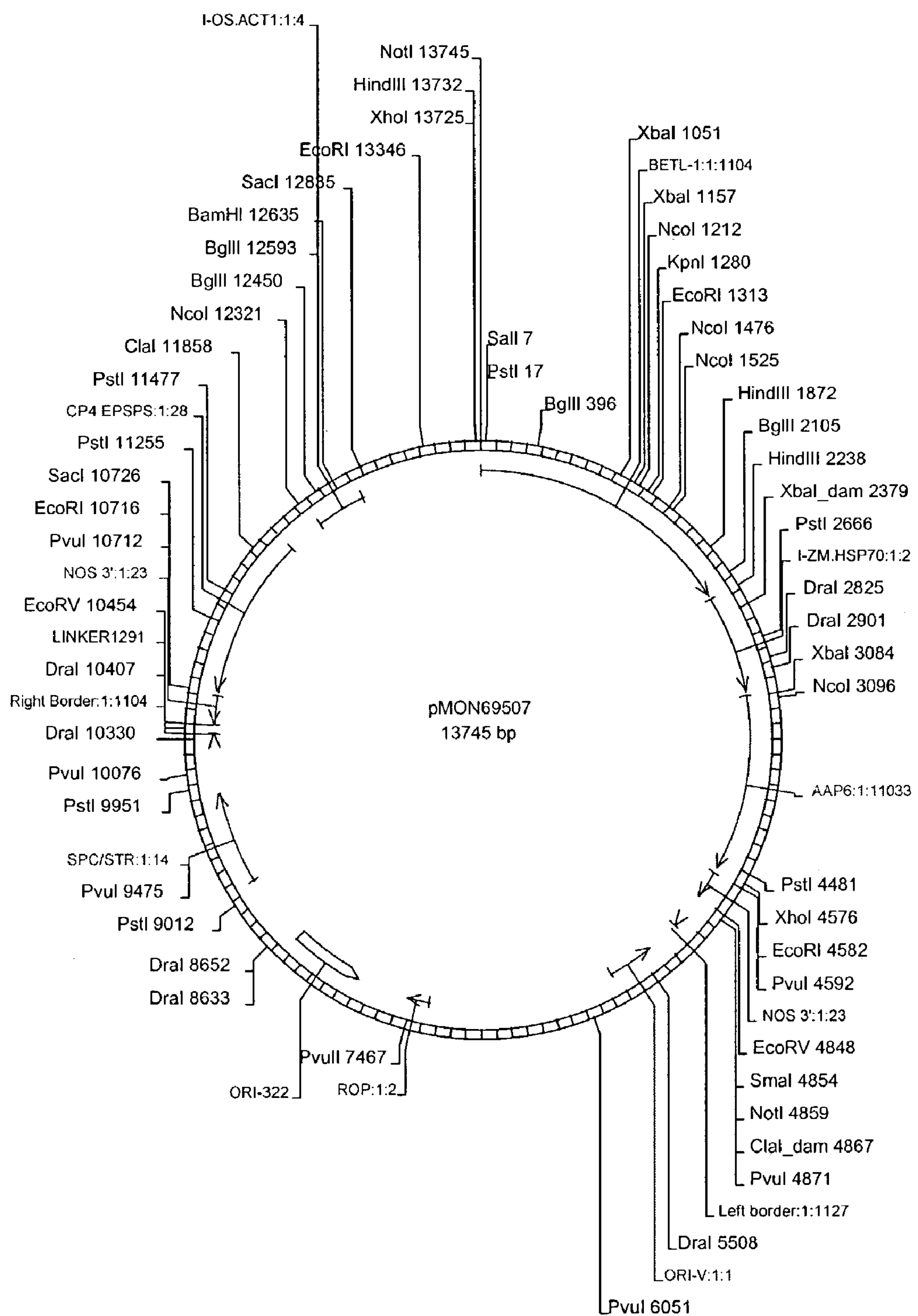
FIG. 5 is a plasmid map of pMON69507.
Figure 6:
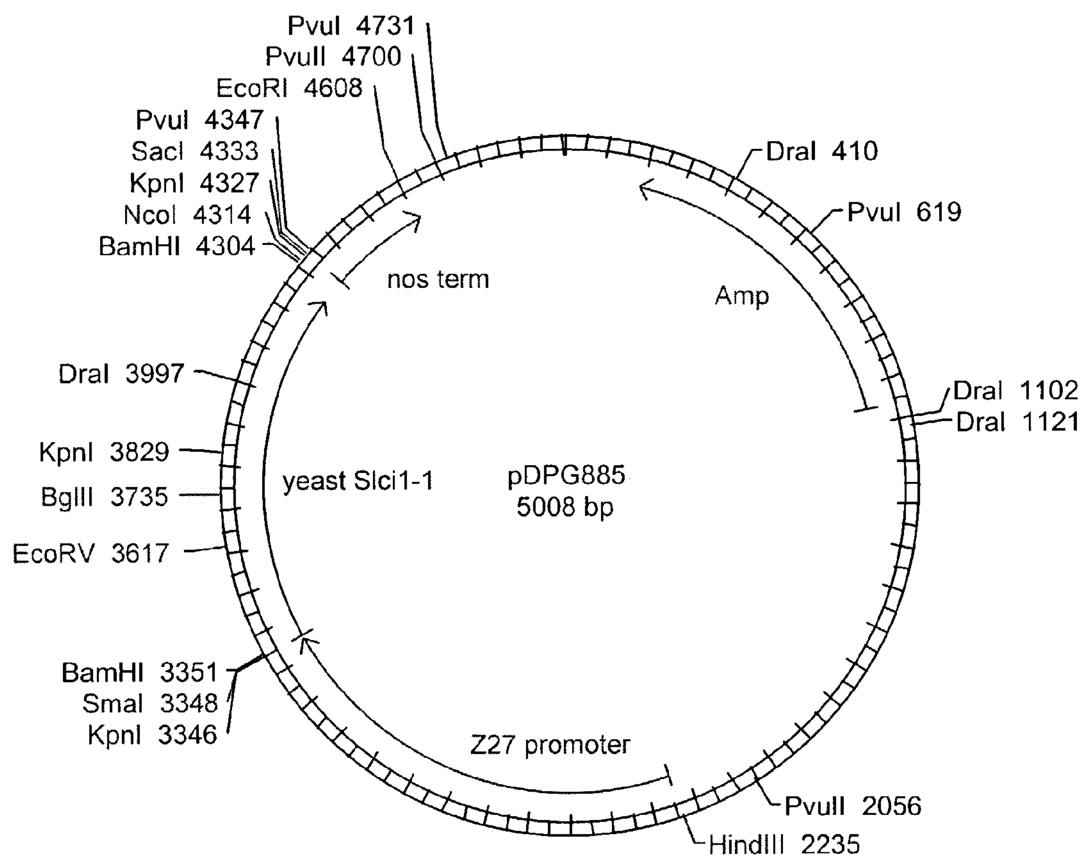
FIG. 6 is a plasmid map of pDPG885.
Figure 7:
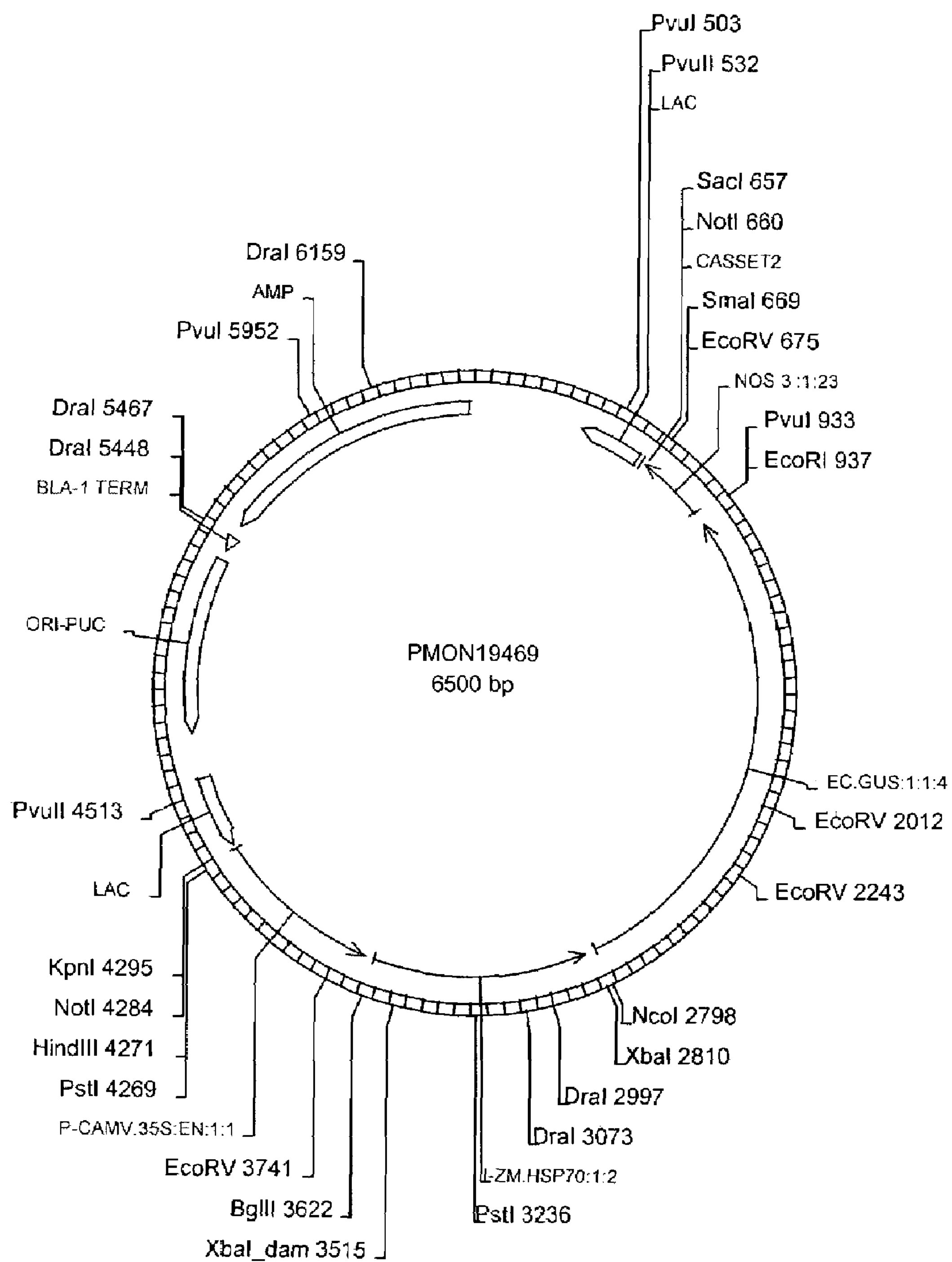
FIG. 7 is a plasmid map of pMON19469.
Figure 8:
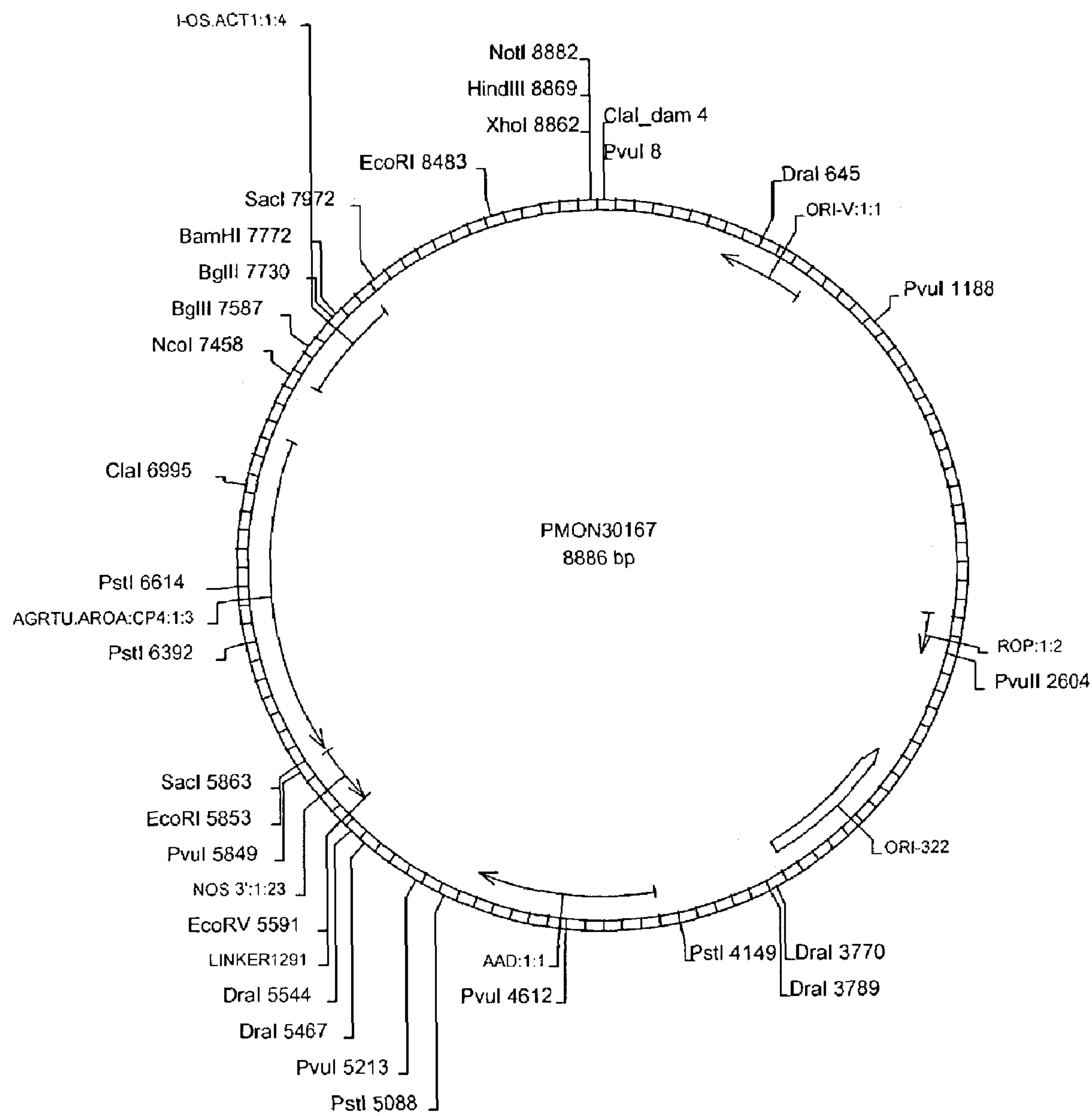
FIG. 8 is a plasmid map of pMON30167.
Figure 9:
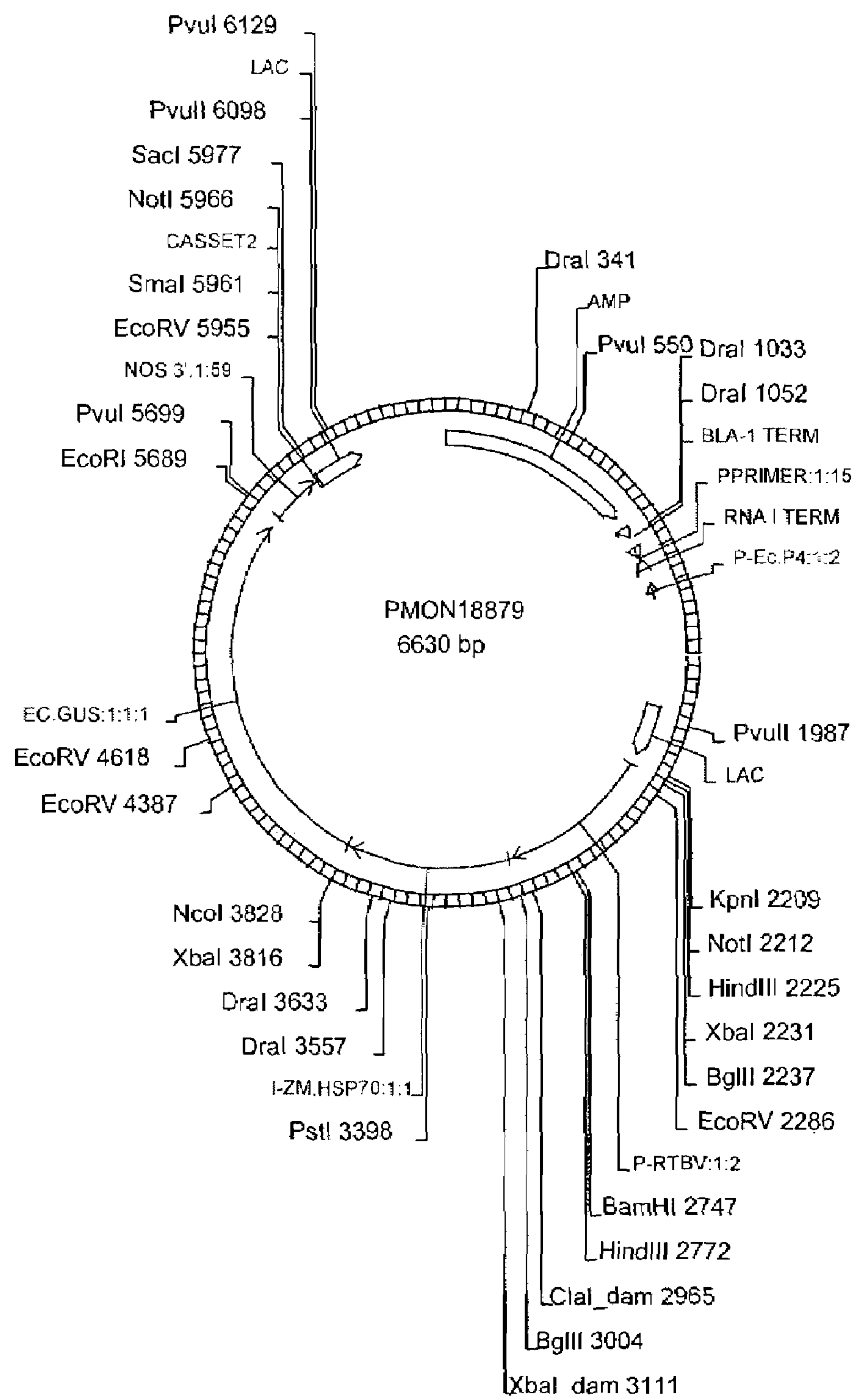
FIG. 9 is a plasmid map of pMON18879.
Figure 10:
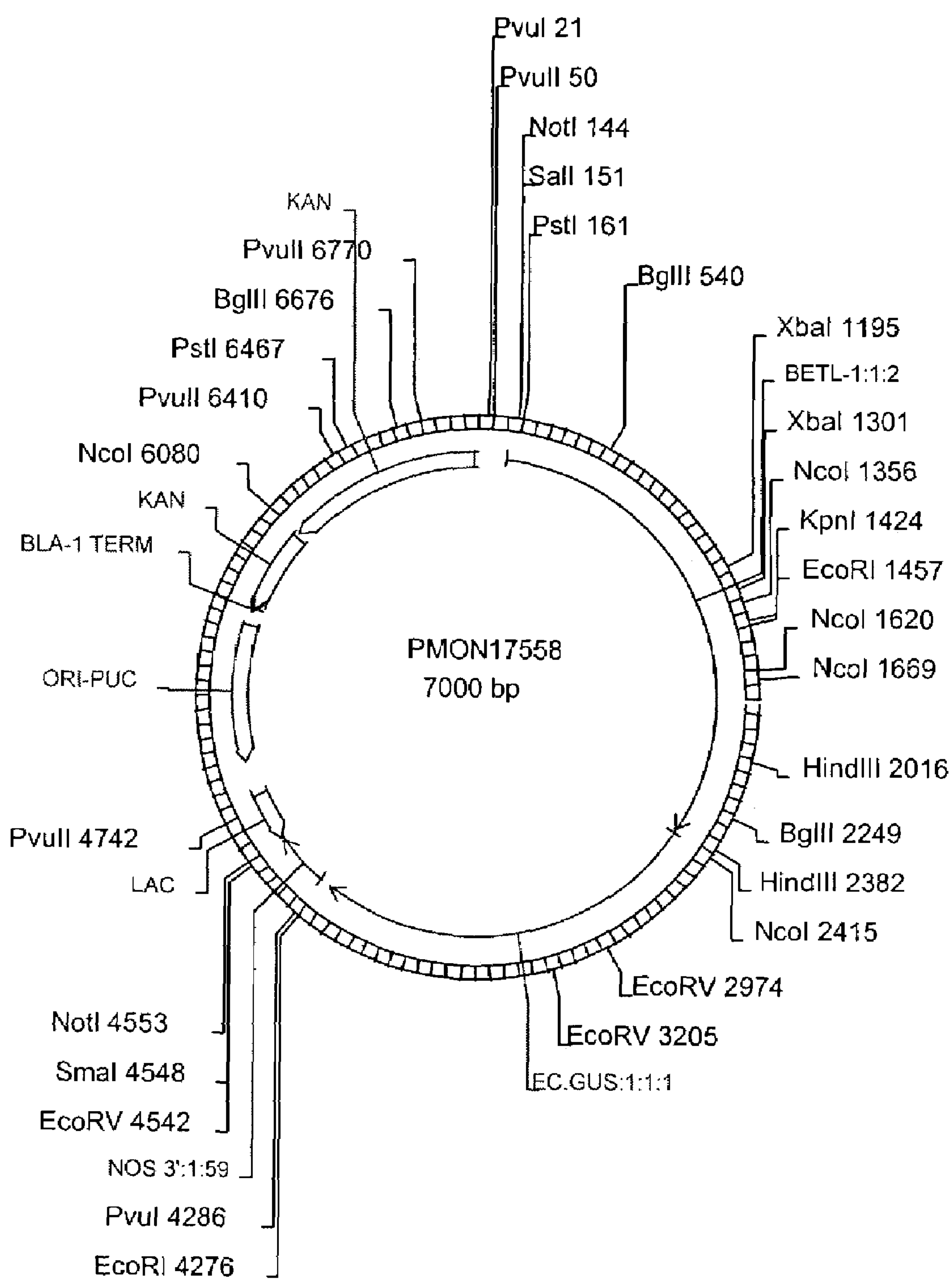
FIG. 10 is a plasmid map of pMON17558.
Figure 11:
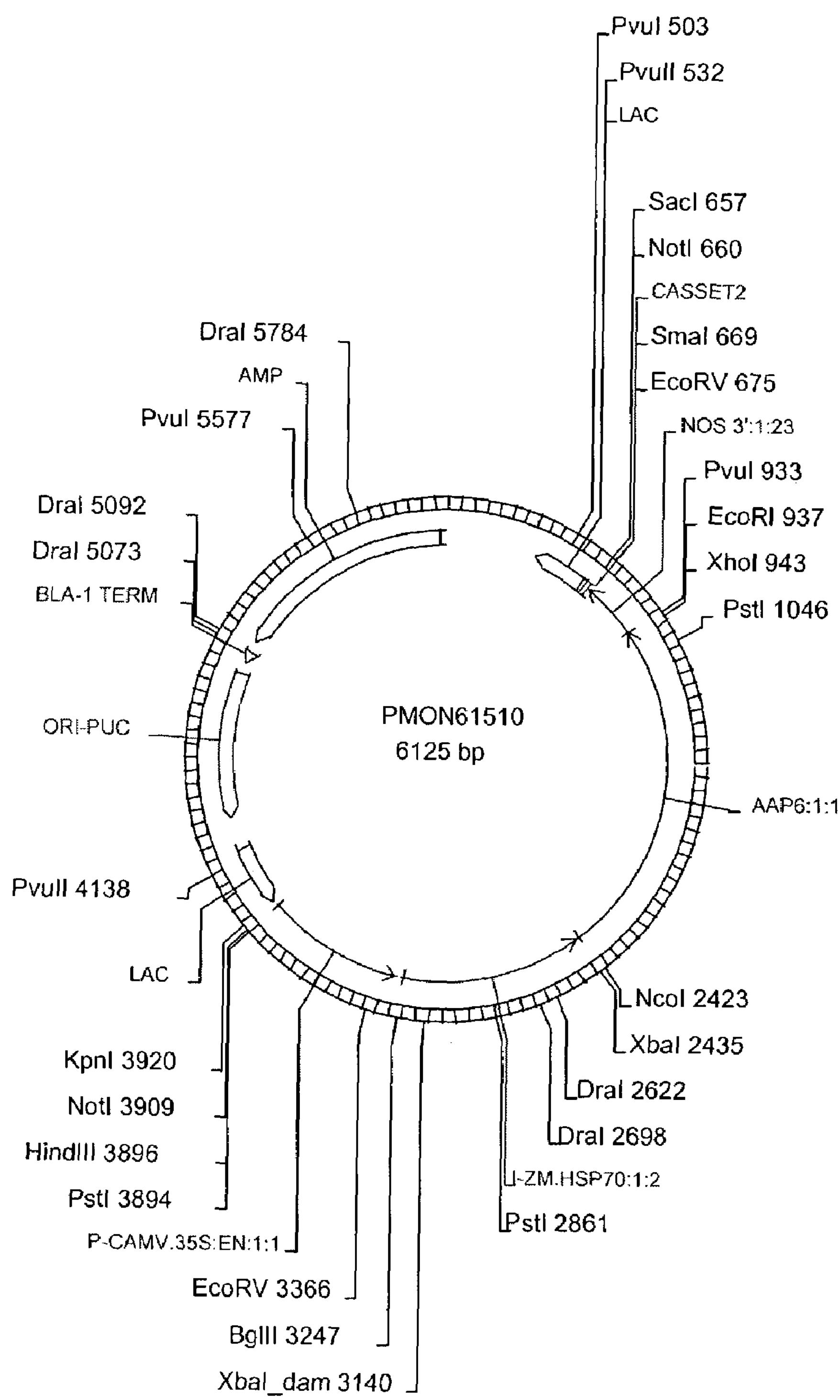
FIG. 11 is a plasmid map of pMON61510.
Figure 12:
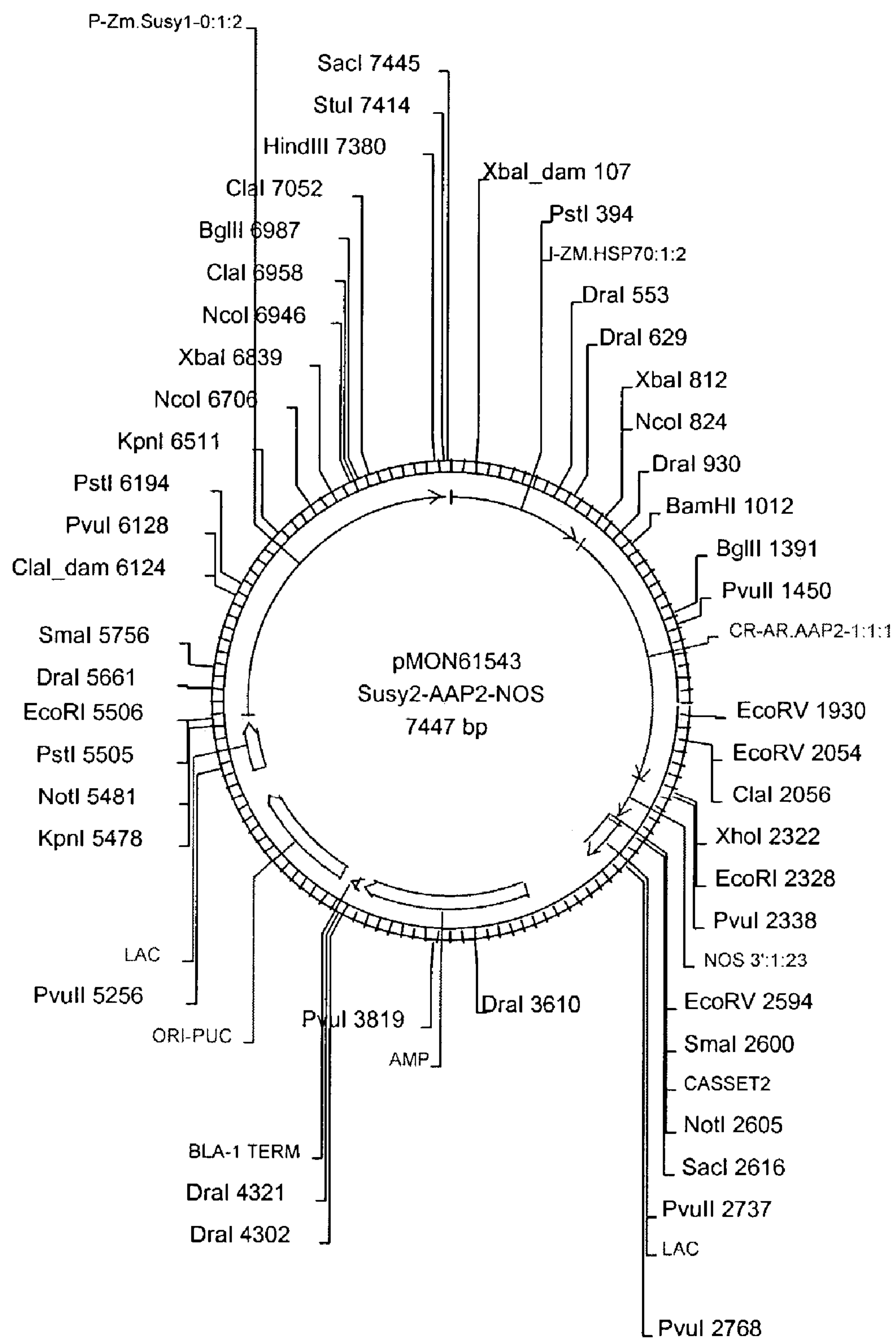
FIG. 12 is a plasmid map of pMON61543.
Figure 13:
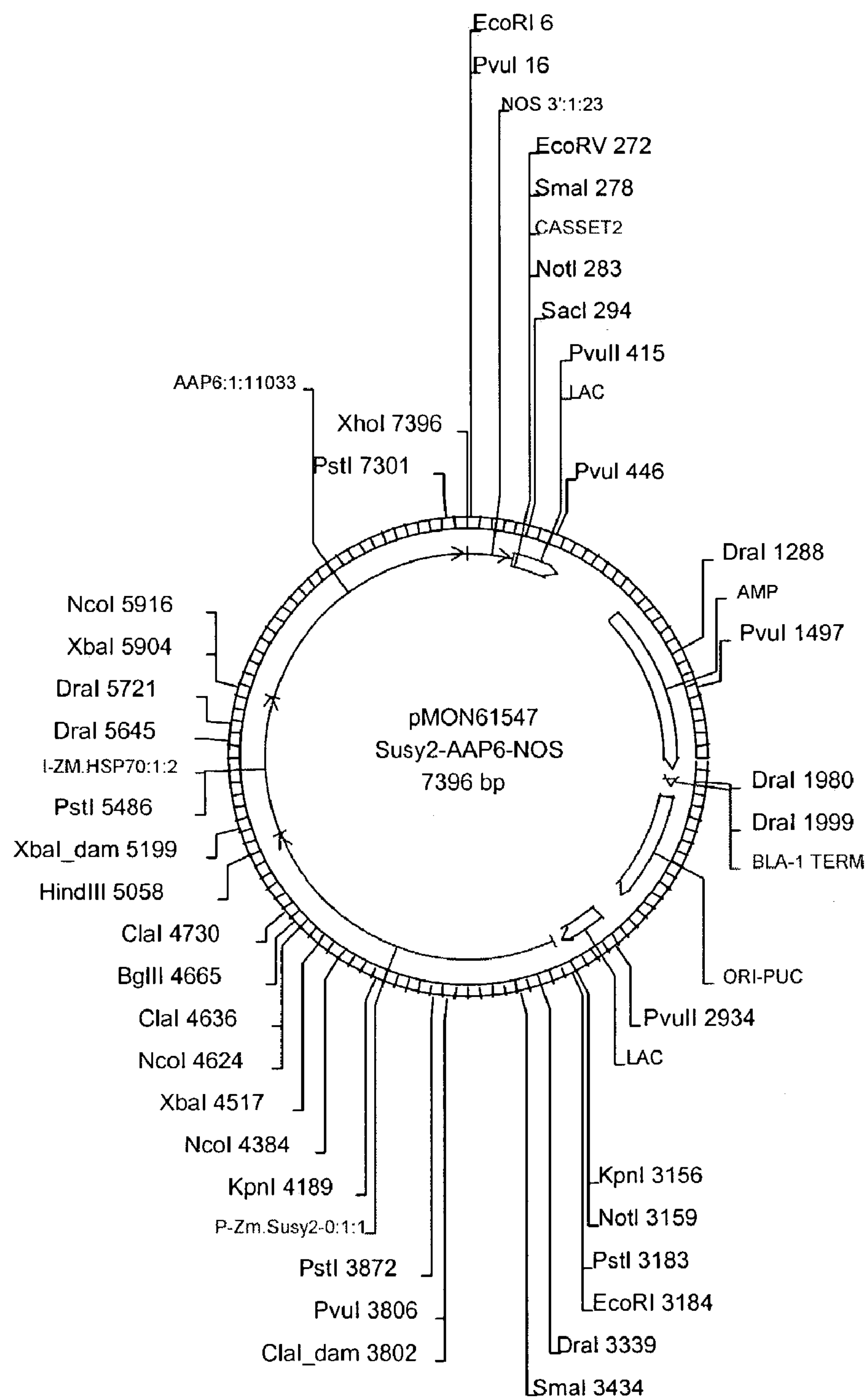
FIG. 13 is a plasmid map of pMON61547.
Figure 14:
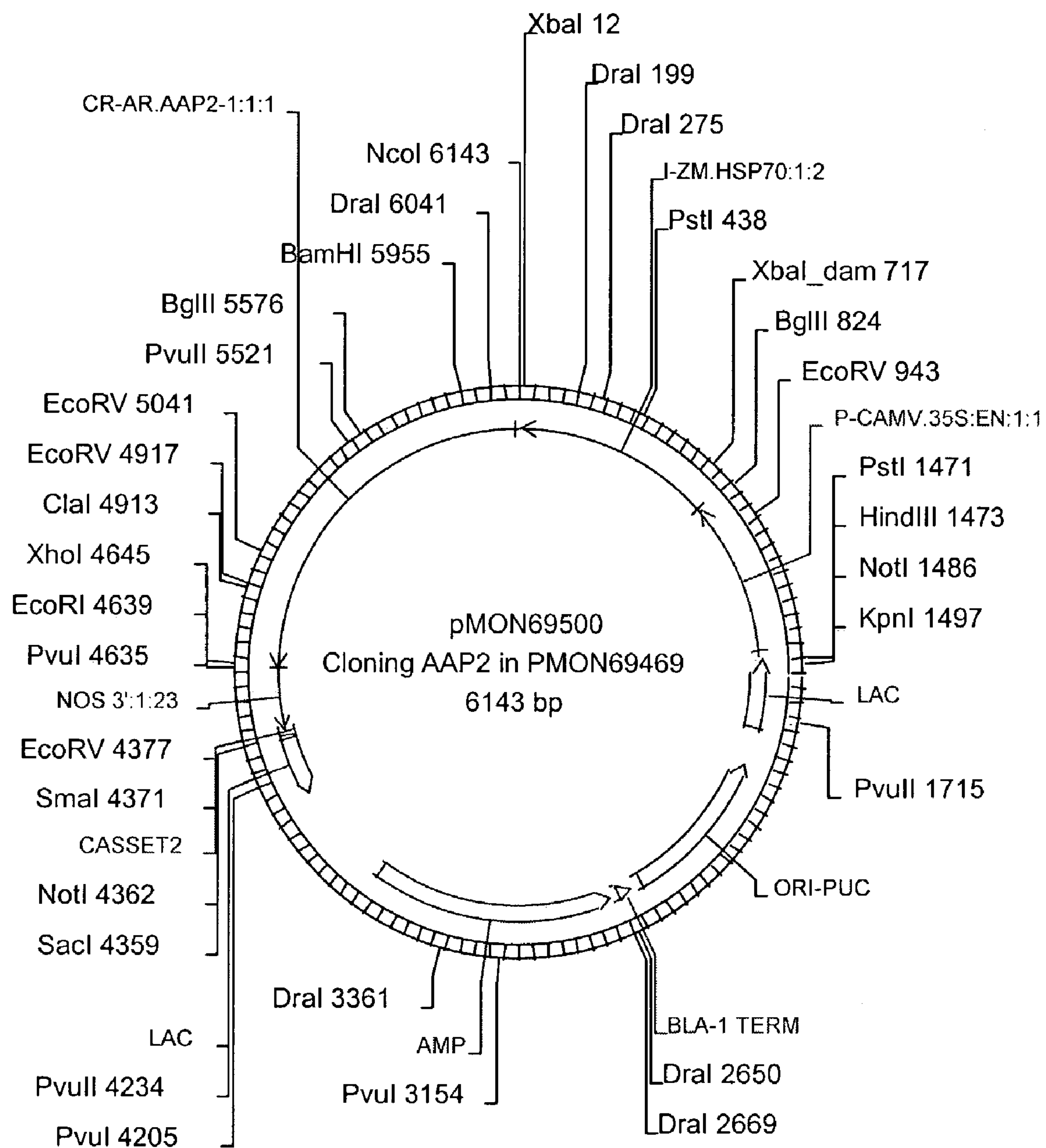
FIG. 14 is a plasmid map of pMON69500.

*Arabidopsis* AAP6 cDNA identified as clone LIB3278-061-P1-K1-D12 (SEQ ID NO: 64) is released by digestion using restriction enzymes Not I and EcoR I and subcloned into plasmid pRSET (Invitrogen, Carlsbad, Calif.) at the same cloning sites. The following plasmids are prepared for transformation into maize: (1) pMON61511 (FIG. 1) (contains a constitutive promoter); (2) pMON61513 (FIG. 2) (contains an endosperm-specific promoter); and (3) pMON61515 (FIG. 4) (contains a phloem-specific promoter); (4) pMON61548 (FIG. 3) (contains a maize sucrose synthase 2 promoter); (5) pMON69507 (FIG. 5) (contains a basal endosperm transfer layer abundance promoter). The construction of the plasmids is described below.

pMON61511. The pMON61511 plasmid includes the following insert: The constitutive promoter E35S-HSP70 ligated to the 5' end of the *Arabidopsis* AAP6 cDNA followed by the NOS terminator sequence. Enhanced 35S promoter is derived from cauliflower mosaic virus 35S protein. NOS stands for the 3' termination end of *E. coli* nopaline synthase gene. HSP70 is an intron from maize heat shock protein 70. *Arabidopsis* clone LIB3278-061-P1-K1-D12 AAP6 cDNA from plasmid pRSET is retrieved by restriction enzyme digest using Nco I and EcoR I restriction endonucleases. The resulting 1.6 kb fragment is ligated into vector pMON19469 (FIG. 7) at the Not I and EcoR I sites, forming pMON61510 (FIG. 11), also referred to as E35S-HSP70::AAP6::NOS. The cassette is then put into a binary vector pMON30167 (FIG. 8) at the Not I site to obtain pMON61511 (FIG. 1).

pMON61513. The pMON61513 plasmid includes the following insert: The endosperm-specific promoter Z27-HSP70 ligated to the 5' end of the *Arabidopsis* AAP6 cDNA followed by the NOS terminator sequence. The Z27 promoter, from the 5' regulatory region of a maize 27 kD zein protein gene, is isolated from vector DPG885 (pMON61252) (FIG. 6). by restriction enzyme digest with Hind III and BamH I. The resulting 1.1 Kb fragment corresponding to Z27 is used to replace the E35S promoter of pMON61510 at Hind III and Bgl II sites. The resulting Z27-HSP70::AAP6::NOS cassette is named pMON61512. This cassette is then shuttled to the binary vector pMON30167 at the Not I site to obtain pMON61513 (FIG. 2).

pMON61515. The pMON61515 plasmid includes the following insert: The phloem-specific promoter from the rice tungro bacilliform virus (RTBV-HSP70) ligated to the 5' end of the *Arabidopsis* AAP6 cDNA followed by the NOS terminator sequence. The AAP6 clone fragment is obtained from pMON61512 by restriction enzyme digest using Nco I and EcoR I. The resulting 1.5 Kb fragment corresponding to the AAP6 clone is ligated with a 4.7 Kb fragment from plasmid pMON18879 (FIG. 9) to construct a shuttle vector containing the RTBV promoter-HSP70::AAP6::NOS cassette. This cassette is then shuttled to a binary vector pMON30167 at the Not I site to obtain pMON61515 (FIG. 4).

pMON61548. Construct pMON61548 contains following insert: Maize SuSy2 promoter attached the 5' end of the *Arabidopsis* AAP6 cDNA followed by the NOS terminator sequence. Maize SuSy2 promoter is derived from the 5' regulatory region of maize sucrose synthase 2 (SuSy2) gene (Genbank Accession Number L33244). A promoter region of SuSy2 gene is amplified by PCR and inserted into a cloning vector pCR2.1 (InVitrogen, Carlsbad, Calif.), resulting in YYLIU016529. SuSy2 promoter DNA fragment is isolated from YYLIU016529 by restriction endonuclease digestion with EcoR V and BamH I and cloned into pMON69500 (FIG. 14) which is prepared by Hind III digestion with overhanging nucleotides treated with Klenow to fill in the nucleotides. This vector is then partially digested with Bgl II, forming transient vector pMON61543 (FIG. 12). AAP6 and HSP70 intron from pMON61510 (FIG. 11) is prepared by digesting the vector with Bgl II cut and end blunted, followed by Xho I digestion. The HSP70-AAP6 fragment is then cloned to vector pMON61543 (FIG. 12), and digested with Stu I and Xho I, to provide SuSy2::

HSP70::AAP6::NOS in pMON61547 (FIG. 13). This expression cassette is further shuttled to binary vector pMON30167 at Not I site, resulting in maize transformation vector pMON61548 (FIG. 3).

pMON69507. The pMON69507 plasmid includes the following insert: Maize basal endosperm transfer layer specific promoter (BETL1-HSP70) ligated the 5' end of the *Arabidopsis* AAP6 cDNA followed by the NOS terminator sequence. Tissue-specificity of maize BETL1 promoter in maize has been reported (Hueros et al., *Plant Physiology* 121:1143-1152, (1999)). A DNA fragment of BETL1-HSP70 element is released from plasmid pMON61547 (FIG. 13) by partial digestion with Hind III and Sma I and is inserted into plasmid pMON17558 (FIG. 10). The resultant plasmid contains an expression cassette of BETL1-HSP70-AAP6, from which the expression cassette is shuttled to a binary vector pMON30167 to obtain pMON69507 (FIG. 5).

EXAMPLE 4

Maize plants (inbred line LH198/Hi11) are grown in a greenhouse under standard practices. The ears of the plants are harvested when the embryos are 1.5 to 2.0 mm in length, usually 10-15 days after pollination. The ears are surface sterilized by spraying or soaking in 80% ethanol.

The immature embryos are isolated from individual kernels using methods known to those of skill in the art. Immature embryos are culture on medium 211 (N6 salts, 2% sucrose, 1 mg/L 2,4-dichlorophenyoxyacetic acid (2,4-D), 0.5 mg/L niacin, 1.0 mg/L thiamine-HCl, 0.91 g/L L-asparagine, 100 mg/L myo-inositol, 0.5 g/L MES, 100 mg/L casein hydrolysate, 1.6 g/L MgCl2, 0.69 g/L L-proline, 2 g/L GELGRO tm, pH 5.8) containing 16.9 mg/L AgNO3 (designated medium 2112V) for 3-6 days prior to transformation.

Methods of *Agrobacterium* mediated transformation of maize cells and other monocots are known (U.S. Pat. Nos. 5,591,616 and 5,981,840; and EP 0 672 752). The *Agrobacterium* strain ABI, and an *Agrobacterium tumefaciens* binary vector system are used for the transformations.

Prior to co-culture with the maize embryo cells, *Agrobacterium* cells are grown at 28° C. in LB (DIFCO) liquid medium containing approximately 50 μg/ml kanamycin and 100 μg/ml spectinomycin to select for maintenance of the modified Ti plasmid and binary vector. Prior to inoculation of maize cells the *Agrobacterium* cells are grown overnight at room temperature in AB medium (Chilton et al., 1974, *Proc. Natl. Acad. Sci.* (*U.S.A.*) 71:3672-3676) comprising appropriate antibiotics for plasmid maintenance and 200 μM acetosyringone. Immediately prior to inoculation the *Agrobacterium* cells are pelleted by centrifugation, washed in ½ MSVI medium (2.2 g/L GIBCO MS (Murashige and Skoog *Physiol. Plant* 15:473-497 (1962)) basal salts, 2 mg/L glycine, 0.5 g/L niacin, 0.5 g/L L-pyridoxin-HCl, 0.1 mg/L thiamine, 115 g/L L-proline, 10 g/L D-glucose, and 10 g/L sucrose, pH 5.4) containing 200 μM acetosyringone.

The immature maize embryos are excised, immersed in an *Agrobacterium* suspension in ½ MSPL medium and incubated at room temperature with *Agrobacterium* for approximately 5 minutes.

Following *Agrobacterium* infection and co-culture, the embryos are transferred to type II delay medium for 5 to 7 days and cultured at 27° C. in the dark. The delay medium consists of MS basal salts containing 2.0 mg/L 2,4-D (GIBCO), 100 mg/L-casamino acids, 12 mM proline, 500 mg/L carbenicillin and 20 μM silver thiosulfate. All media chemicals were tissue culture grade. Once signs of type II callus initiation from immature embryos are observed, as defined by Selman et al., in *The Maize Handbook*, Freeling and Walbot (eds.), Springer Verlag, p. 672 (1994), the coleoptiles are removed from the embryos. The embryos are then transferred to MS medium containing 2.0 mg/L 2,4-D, 12 mM proline, 20 μM silver thiosulfate, 500 mg/L carbenicillin and 0.5 mM glyphosate (Monsanto Company, St. Louis, Mo.) and incubated at 27° C. in the dark for 2 weeks.

Embryos forming callus are transferred to the MS medium described above, but additionally containing 1.0 mM glyphosate. The cultures are then incubated for 2 weeks in the dark at 27° C. The embryos still having callus are then transferred to MS medium containing 3.0 mM glyphosate for an additional 2 weeks.

Plant regeneration is achieved by transferring the callus to MS medium containing 0.1 mg/L 2,4-D and 0.1 μM abscisic acid (ABA) for 2 weeks and then to MS medium containing 6% sucrose and no 2,4-D for another 2 weeks. Both incubations are done in the dark at 27° C. to permit somatic embryo maturation and conversion in the regeneration process.

Somatic embryos that are ready to germinate are transferred to hormone-free MS medium, and incubated in the light until shoots with attached roots are produced. After approximately 2 to 3 weeks, plantlets are produced.

Plantlets are then transferred to the greenhouse and grown under standard greenhouse conditions.

Following *Agrobacterium* infection and co-culture, the embryos are transferred to type II delay medium for 5 to 7 days and cultured at 27° C. in the dark. The delay medium consists of MS basal salts, 2.0 mg/L 2,4-D, 100 mg/L-casamino acids, 12 mM proline, 500 mg/L carbenicillin and 20 μM silver thiosulfate. Once signs of type II callus initiation from immature embryos are observed, as defined by Selman et al. in *The Maize Handbook*, Freeling and Walbot (eds.), Springer Verlag, p. 672 (1994), the coleoptiles are removed from the embryos. The embryos are then transferred to MS medium containing 2.0 mg/L 2,4-D, 12 mM proline, 20 μM silver thiosulfate, 500 mg/L carbenicillin and 0.5 mM glyphosate and incubated at 27° C. in the dark for 2 weeks.

Embryos forming callus are transferred to the MS medium described above, but additionally containing 1.0 mM glyphosate. The cultures are then incubated for 2 weeks in the dark at 27° C. The embryos still having callus are then transferred to MS medium containing 3.0 mM glyphosate for an additional 2 weeks.

Plant regeneration is achieved by transferring the callus to MS medium containing 0.1 mg/L 2,4-D and 0.1 μM ABA for 2 weeks and then to MS medium containing 6% sucrose and no 2,4-D for another 2 weeks. Both incubations are done in the dark at 27° C. to permit somatic embryo maturation and conversion in the regeneration process.

Somatic embryos that are ready to germinate are transferred to hormone-free MS medium, and incubated in the light until shoots with attached roots are produced. After approximately 2 to 3 weeks, plantlets are produced.

Plantlets are then transferred to the greenhouse and grown under standard greenhouse conditions.

EXAMPLE 5

The existence and expression of transgenes in transgenic maize plants is determined by a standard PCR and RT-PCR protocols, respectively, with transgene-specific primers. The following protocols are used for extraction of plant DNA and total RNA, and for PCR amplification.

A young leaf from a transgenic plant is cut up and a small amount is placed in a 0.5 ml PCR tube. The leaf is covered with 40 μl of 0.25N NaOH and heated in a PCR thermocycler (MJ Research, Watertown, Mass.) at 98° F. for 30-60 seconds. An aliquot of 40 μl of 0.25 N HCl is added and mixed. Then an aliquot of 20 μl of 0.5 M Tris-HCl, pH 8.0 plus 0.25% NP40 is added and mixed. The mixture is heated at 98° F. for 2 minutes before spinning down for 1 minute. For a 50 μl PCR reaction, 3 μl of the genomic DNA extract is used. PCR mixture (total 50 μl ): 31.5 μl sterile water, 3 μl genomic DNA extract, 4 μl DNTP (2 mM each), 2 μl Primer 1 (10 μM stock) (Transgene specific), 2 μl Primer 2 (10 μM stock) (Transgene specific), 1.5 μl 50 mM MgCl2 (GBL), 5 μl 10×buffer (GBL), 1 μl Taq DNA polymerase (GBL). PCR Program (CZYANG-PLT50): 95° C. 2 minutes, 95° C. 30 seconds, 50° C. 15 seconds, 72° C. 2 minutes, 35 cycles, 72° C. 8 minutes. The PCR products are viewed under UV light following separation by agarose gel electrophoresis. The existence of DNA bands corresponding to the *Arabidopsis* AAP6 gene is the positive indication of transgenic plants.

Total RNA is extracted from V8 maize leave samples using Qiagen's RNeasy® S Plant Mini Kit (Valencia, Calif., Cat. #74904). Thermoscript™ RT-PCR System (Cat. #11146-24) from Life Technologies (Rockville, Md.) is employed for RT-PCR. Ten ng total RNA is used for initial cDNA synthesis with oligo (dT)20. One tenth of the synthesized cDNA is then used as template for PCR with one primer from the transgene AAP6, the other from the 3' UTR region. PCR conditions are the same as described above.

EXAMPLE 6

This example describes the analysis of free amino acids in leaf extracts and the analysis of total kernel protein of transformed maize plants.

Leaves from transformed plants are taken at various times during the growing period. The leaves are dried in an oven with forced air or alternatively lyophilized using standard laboratory equipment. The dry plant material is ground to a fine powder by standard laboratory practices such as mortar and pestle or Wiley mill. A 30-60 mg aliquot of the dry powder is placed into 2.0 ml screw top plastic tube. One milliliter of 5% trifluoroacetic acid (TFA) is added and left overnight at room temperature. The samples are then centrifuged and the supernatant removed. The samples are frozen at −80° C. prior to analysis by high performance liquid chromatography (HPLC).

The determination of free amino acids is done by HPLC using a pre-column derivatization with OPA reagent (Agilent Technologies, Palo Alto, Calif.), separated at pH 7.8 on a C18 column and using fluorescence detection.

For kernel protein analysis, small bulk samples consisting of 50-100 kernels for each treatment are measured using near infrared reflectance spectroscopy (InfraTec Model 1221, Teccator, Hogannas, Sweden). This procedure is based upon the observation that a linear relation exists between the absorption of near infrared radiation and the quantity of chemical constituents comprised in a typical grain sample. Prior to analyzing unknown samples, spectral data is collected with calibration samples that are subsequently analyzed using a primary analysis technique. The primary technique used is nitrogen combustion (Murray, I., and P. C. Williams (1987), *Chemical Priciples of Near-infrared Technology*, in *Near-Infrared Technology in the Agricultural and Food Industries*, P. Williams and K. Norris (eds.)). A multivariate model is developed using the spectral data from the spectrometer and the primary data. In the present case a PLS-1 (Partial Least Squares Regression Type I) multivariate model is constructed using 152 calibration samples. Each unknown sample is scanned on the spectrometer at least 5 times and its protein content predicted with each scan. Each time the sample is scanned it is added back to the sample cuvette to minimize multiplicative scattering effects, which are not correlated to chemical property of interest. The predicted protein is averaged for the multiple scans and then reported for each sample.

Increased leaf Free Amino Acid (FAA) and kernel protein contents are observed in $R_0$ transgenic maize plants as shown in the table below. The average kernel protein and leaf FAA contents of 3 non-transgenic plants that are grown under the same conditions as those transgenic plants are approximately 14.0% and 9704 ppm, respectively. By comparison, the average kernel protein contents of $F_1$ kernels harvested from $R_0$ transgenic maize plants ranged from 16.4 to 18.4% and leaf FAA ranged from 12026 to 24248 ppm. Increased leaf FAA appears positively to be correlated with kernel protein content as seen in TABLE 6 below.

TABLE 6

Increased leaf FAA and kernel protein contents in $R_0$ transgenic maize plants transformed with *Arabidopsis* generic amino acid transporter AAP6 gene driven by the e35S promoter.

| Plant ID | Plant type | Kernel protein content (%) | Leaf FAA Sum (ppm) |
|---|---|---|---|
| TP-A29 | Transgenic | 18.4 | 12433 |
| TP-A25 | Transgenic | 17.8 | 12026 |
| TP-A20 | Transgenic | 17.4 | 12777 |
| TP-A28 | Transgenic | 17.1 | 24248 |
| TP-A24 | Transgenic | 17.1 | 14021 |
| TP-A14 | Transgenic | 16.7 | 19375 |
| TP-A4 | Transgenic | 16.4 | 13332 |
| TP-A16 | Transgenic | 16.4 | 13295 |
| NTP-A27 | Non-Transgenic | 14.6 | 10435 |
| NTP-A7 | Non-Transgenic | 14.5 | 10088 |
| NTP-A26 | Non-Transgenic | 13.0 | 8588 |

The elevation in leaf FAA content in the $R_0$ transgenic maize plants resulted from increased levels of most of the individual amino acids. TABLE 7 below shows the major amino acid contents in transgenic and non-transgenic $R_0$ maize plants. The data indicate that alanine, asparagines, aspartate, glutamine, and serine are particularly increased in transgenic as compared to non-transgenic plants.

TABLE 7

| Plant ID | Plant type | Leaf FAA (ppm) | Ala | Asn | Asp | Gln | Glu | Gly | Phe | Ser | Thr | Val |
|---|---|---|---|---|---|---|---|---|---|---|---|---|
| TP-B2 | T | 19679.9 | 6545.4 | 2541.3 | 1990.8 | 1148.3 | 3684.7 | 672.7 | 78.4 | 1368.3 | 531.9 | 189.1 |
| TP-B3 | T | 18588.0 | 5628.5 | 4026.8 | 1561.5 | 500.7 | 3508.6 | 370.3 | 272.3 | 1241.2 | 623.7 | 242.3 |
| TP-B4 | T | 18030.5 | 6109.2 | 2585.5 | 2267.2 | 817.5 | 3277.0 | 649.8 | 357.8 | 1280.3 | 393.8 | 208.6 |

TABLE 7-continued

| Plant ID | Plant type | Leaf FAA (ppm) | Ala | Asn | Asp | Gln | Glu | Gly | Phe | Ser | Thr | Val |
|---|---|---|---|---|---|---|---|---|---|---|---|---|
| TP-B5 | T | 17913.6 | 4159.8 | 3839.3 | 1954.7 | 921.2 | 3393.1 | 509.0 | 254.7 | 1627.3 | 614.8 | 199.0 |
| TP-B6 | T | 17090.5 | 4964.7 | 4198.8 | 1612.1 | 671.2 | 2454.7 | 637.5 | 184.4 | 1540.4 | 450.1 | 181.3 |
| TP-B7 | T | 16403.1 | 4894.8 | 3055.9 | 1571.0 | 769.7 | 2438.8 | 488.0 | 88.6 | 1129.9 | 771.3 | 210.4 |
| TP-B8 | T | 15967.9 | 4788.1 | 2393.6 | 1319.7 | 434.8 | 4025.2 | 283.8 | 62.2 | 917.7 | 615.7 | 255.6 |
| TP-B9 | T | 15398.3 | 5909.5 | 1431.9 | 1634.6 | 993.7 | 2411.3 | 680.8 | 366.6 | 1382.7 | 363.2 | 161.9 |
| TP-B10 | T | 14310.8 | 5174.0 | 1321.8 | 1151.4 | 491.2 | 2966.4 | 231.7 | 116.4 | 940.4 | 510.1 | 231.2 |
| TP-B11 | T | 14280.0 | 4845.9 | 2336.2 | 1332.7 | 489.6 | 2846.4 | 217.2 | 161.6 | 947.3 | 511.6 | 170.6 |
| TP-B12 | T | 14233.8 | 4379.4 | 1927.5 | 1465.4 | 373.1 | 3178.2 | 265.5 | 67.3 | 858.7 | 577.4 | 216.7 |
| NTP-B31 | N | 9845.6 | 2794.9 | 1564.5 | 659.7 | 427.8 | 1531.1 | 282.9 | 96.3 | 753.2 | 523.0 | 230.9 |
| NTP-B37 | N | 9114.9 | 2630.0 | 1069.2 | 931.0 | 371.0 | 1459.2 | 249.1 | 109.1 | 642.2 | 535.1 | 224.5 |
| NTP-B42 | N | 8291.7 | 2308.7 | 1135.6 | 670.1 | 285.8 | 1646.8 | 112.9 | 95.6 | 437.3 | 513.9 | 196.2 |

EXAMPLE 7

This example describes the analysis of free amino acids in leaf extracts from $F_2$ transgenic maize plants transformed with the AtAAP6 gene driven by the RTBV promoter.

$R_0$ transgenic plants were crossed with pollen from LH198 and the resulting BC1 ($F_1$) seeds were grown in the field nursery. A CP4-gene check was conducted with all individual plants in the field. Western and Northern blot analysis further confirmed AtAAP6 expression in CP4-positive transgenic plants. $F_1$ transgenic plants and their CP4-negative isolines were self-crossed in the field to produce $F_2$ seeds. Transgenic plants and their negative isolines were advanced in parallel into the $F_2$ generation in the field.

The zygosity of transgenic plants was analyzed by Invader Technology (Lyamichev et al., *Nature Biotechnology* 17:292-296 (1999)). Ear leaves of homozygous plants and their negative isolines were collected about 1 week before pollination from 2:00 AM to 4:00 AM during which time period the leaf free amino acid content is least affected by the diurnal cycle. Samples were processed and analyzed as described in Example 6.

Analytical data indicated that leaf free amino acid content significantly increased in transgenic plants compared to their non-transgenic isolines (TABLE 8). The content of most individual amino acids increased in the transgenic plants and asparagine, glutamine, glutamate and serine content showed significant increase in most of the transgenic events (TABLE 9).

TABLE 8

Total free amino acid content in ear leaves of transgenic plants and their negative isolines transformed with *Arabidopsis* AAP6 gene driven by the phloem-enhancing RTBV promoter.

| Transgenic event | Leaf FAA in homo plants (ppm) | Leaf FAA in neg plants (ppm) | Difference (homo-neg) (ppm) | T-Test |
|---|---|---|---|---|
| ZM_S44865 | 8850 | 6356 | 2494 | 0.0013 |
| ZM_S44890 | 6390 | 5695 | 694 | 0.0329 |
| ZM_S44913 | 7365 | 5513 | 1852 | 0.0002 |
| ZM_S44917 | 7264 | 3881 | 3383 | 0.0001 |
| ZM_S44923 | 6326 | 4182 | 2144 | 0.0012 |

TABLE 9

Comparison of major amino acid content (ppm) in the leaves of $F_2$ transgenic corn plants containing *Arabidopsis* AAP6 genes driven by the RTBV promoter compared with those in negative isolines.

| Event | Description | Ala | Asn | Asp | Gln | Glu | Gly | Phe | Ser | Thr | Val |
|---|---|---|---|---|---|---|---|---|---|---|---|
| ZM_S 44865 | Positive average | 1001 | 794 | 2583 | 208 | 2621 | 228 | 127 | 401 | 261 | 100 |
| | Negative average | 811 | 268 | 2051 | 148 | 1692 | 101 | 121 | 276 | 240 | 92 |
| | Difference (pos-neg) | 190 | 526 | 533 | 59 | 929 | 127 | 5 | 125 | 21 | 8 |
| | TTEST | 0.2323 | 0.0034 | 0.0004 | 0.0276 | 0.0000 | 0.0012 | 0.7953 | 0.0023 | 0.6443 | 0.4591 |
| ZM_S 44890 | Positive average | 1002 | 135 | 1829 | 151 | 1915 | 91 | 95 | 302 | 332 | 84 |
| | Negative average | 939 | 106 | 1520 | 167 | 1564 | 70 | 133 | 269 | 221 | 93 |
| | Difference (pos-neg) | 63 | 29 | 309 | −16 | 351 | 21 | −38 | 33 | 111 | −10 |
| | TTEST | 0.0163 | 0.0039 | 0.0700 | 0.0055 | 0.0783 | 0.9590 | 0.0947 | 0.0375 | 0.3829 | 0.1821 |
| ZM_S 44913 | Positive average | 920 | 222 | 2169 | 194 | 2396 | 84 | 95 | 355 | 297 | 90 |
| | Negative average | 837 | 106 | 1677 | 197 | 1533 | 57 | 113 | 283 | 286 | 67 |

TABLE 9-continued

Comparison of major amino acid content (ppm) in the leaves of $F_2$ transgenic corn plants containing *Arabidopsis* AAP6 genes driven by the RTBV promoter compared with those in negative isolines.

| Event | Description | Ala | Asn | Asp | Gln | Glu | Gly | Phe | Ser | Thr | Val |
|---|---|---|---|---|---|---|---|---|---|---|---|
| | Difference (pos-neg) | 84 | 116 | 492 | −3 | 863 | 27 | −17 | 72 | 12 | 24 |
| | TTEST | 0.3016 | 0.0344 | 0.0004 | 0.9051 | 0.0000 | 0.2600 | 0.2452 | 0.0558 | 0.7188 | 0.0023 |
| ZM_S 44917 | Positive average | 1627 | 281 | 1117 | 88 | 1592 | 654 | 159 | 565 | 317 | 169 |
| | Negagtive average | 648 | 51 | 1137 | 105 | 1057 | 20 | 112 | 194 | 173 | 50 |
| | Difference (pos-neg) | 979 | 230 | −20 | −17 | 535 | 635 | 48 | 371 | 144 | 119 |
| | TTEST | 0.0003 | 0.0008 | 0.8511 | 0.1580 | 0.0000 | 0.0000 | 0.0251 | 0.0003 | 0.0001 | 0.0000 |
| ZM_S 44923 | Positive average | 1011 | 429 | 1798 | 148 | 1867 | 211 | 93 | 345 | 237 | 92 |
| | Negative average | 529 | 35 | 1477 | 79 | 1232 | 19 | 92 | 177 | 166 | 47 |
| | Difference (pos-neg) | 482 | 393 | 321 | 69 | 635 | 192 | 0 | 169 | 71 | 45 |
| | TTEST | 0.0003 | 0.0004 | 0.0129 | 0.0018 | 0.0000 | 0.0000 | 0.9806 | 0.0005 | 0.0017 | 0.0002 |

A TTEST of less than or equal to 0.05 implies a significant result.

EXAMPLE 8

This example describes Northern blot analysis of AtAAP6 gene expression and Western blot analysis of AtAAP6 protein accumulation in transgenic maize plants.

Total RNA was extracted from corn tissues (leaves or developing kernels, dependent on the expected AtAAP6 gene expression) with Qiagen RNeasy Plant Mini kit (Valencia, Calif., Cat. #74904). Total RNA was separated in 1.2% agarose gel and Northern blots were performed according to Dong and Dunstan (*Plant Cell Reports* 15:516-521 (1996)). $^{32}$P-labeled AtAAP6 DNA was used as the probe to detect accumulation of AtAAP6 transcripts in transgenic plants. AtAAP6 transcripts in transgenic corn plants regulated by cauliflower mosaic virus e35S, RTBV, Z27 or BETL1 promoter, respectively, were observed with various accumulation levels and were not detectable in non-transgenic plants. TABLE 9 lists transgenic events derived from the constructs with the relative expression levels of AtAA6 gene in the tissues examined.

A 17-amino acid oligopeptide located at position 11-27 of the AtAAP6 protein was identified according to the AtAAP6 antigenic index. The oligopeptide were synthesized and antibodies against it were produced in rabbits according to the standard procedure. Preliminary experiments demonstrated that the antibodies were able to successfully recognize AtAAP6 proteins in transgenic corn and *Arabidopsis* plants.

To perform Western blots, an aliquot of 50-100 mg leaf or immature kernel tissue previously ground by Meg shaker was transferred into a 1.5-ml Eppendorf tube. Protein extraction buffer (600 µl) consisting of 50 mM Tris-HCl (pH 7.4)/0.4 M NaCl and freshly prepared protease inhibitor was added. After incubation at 4° C. for 10 minutes, the mixture was spun at 10,000 rpm for 8 min at 4° C. to remove the supernatant. The pellet was re-extracted with an additional 600 µl of protein extraction buffer. The supernatant was removed and 300 µl of 2×SDS sample buffer was added to the pellet. Unsolved cell debris was removed by spinning and the supernatant was used for Western blot analysis. Proteins were segregated in 10-20% Tris-Glycine gel. After the proteins were transferred to the membrane, the Western blot was conducted according to standard procedures. The NBT/BCIP detection system (Sigma, Cat. #B-5655) was used for visualizing AtAAP6 proteins on the membrane. The AtAAP6 proteins were observed only in corn tissues transformed with AtAAP6 (TABLE 10) and not in the tissues from non-transformed corn plants. The accumulation level of AtAAP6 proteins was dependent on the promoters used and varied among transgenic events as well (TABLE 10).

TABLE 10

*Arabidopsis* AAP6 gene expression in transgenic corn plants determined by Northern and Western blot analysis.

| Construct | Promoter | Tissues examined | Transgenic event | Northern | Western |
|---|---|---|---|---|---|
| pMON61511 | e35S | Leaves | ZM_S40125 | +++ | +++ |
| pMON61511 | e35S | Leaves | ZM_S40162 | ++ | ++ |
| pMON61511 | e35S | Leaves | ZM_S41495 | ++ | ++ |
| pMON61511 | e35S | Leaves | ZM_S41496 | ++ | +++ |
| pMON61511 | e35S | Leaves | ZM_S41519 | ++ | +++ |
| pMON61511 | e35S | Leaves | ZM_S41491 | ++ | +++ |
| pMON61511 | e35S | Leaves | ZM_S41500 | N.D. | + |
| pMON61511 | e35S | Leaves | ZM_S41506 | ++ | ++ |
| pMON61511 | e35S | Leaves | ZM_S41485 | N.D. | + |
| pMON61511 | e35S | Leaves | ZM_S41493 | +++ | +++ |

TABLE 10-continued

*Arabidopsis* AAP6 gene expression in transgenic corn plants determined by Northern and Western blot analysis.

| Construct | Promoter | Tissues examined | Transgenic event | Northern | Western |
|---|---|---|---|---|---|
| pMON61513 | Z27 | Immature kernels | ZM_S44313 | + | + |
| pMON61513 | Z27 | Immature kernels | ZM_S44673 | ++ | ++ |
| pMON61513 | Z27 | Immature kernels | ZM_S44697 | +++ | +++ |
| pMON61513 | Z27 | Immature kernels | ZM_S44811 | ++ | + |
| pMON61513 | Z27 | Immature kernels | ZM_S44822 | ++ | + |
| pMON61513 | Z27 | Immature kernels | ZM_S44312 | + | + |
| pMON61513 | Z27 | Immature kernels | ZM_S44317 | ++ | ++ |
| pMON61513 | Z27 | Immature kernels | ZM_S44678 | + | + |
| pMON61513 | Z27 | Immature kernels | ZM_S44814 | ++ | +++ |
| pMON69507 | BETL1 | Lower part of immature kernels | ZM_S49206 | + | N.D. |
| pMON69507 | BETL1 | Lower part of immature kernels | ZM_S49258 | + | N.D. |
| pMON69507 | BETL1 | Lower part of immature kernels | ZM_S49279 | + | N.D. |
| pMON69507 | BETL1 | Lower part of immature kernels | ZM_S49288 | + | N.D. |
| pMON69507 | BETL1 | Lower part of immature kernels | ZM_S49214 | +++ | N.D. |
| pMON69507 | BETL1 | Lower part of immature kernels | ZM_S49226 | ++ | N.D. |
| pMON69507 | BETL1 | Lower part of immature kernels | ZM_S49232 | +++ | N.D. |
| pMON69507 | BETL1 | Lower part of immature kernels | ZM_S49263 | +++ | N.D. |
| pMON69507 | BETL1 | Lower part of immature kernels | ZM_S49269 | +++ | N.D. |
| pMON69507 | BETL1 | Lower part of immature kernels | ZM_S49276 | +++ | N.D. |
| pMON61515 | RTBV | Leaves | ZM_S44865 | ++ | ++ |
| pMON61515 | RTBV | Leaves | ZM_S44890 | +++ | +++ |
| pMON61515 | RTBV | Leaves | ZM_S44913 | N.D. | +++ |
| pMON61515 | RTBV | Leaves | ZM_S44917 | N.D. | ++ |
| pMON61515 | RTBV | Leaves | ZM_S44923 | N.D. | +++ |
| pMON61515 | RTBV | Leaves | ZM_S44864 | +++ | +++ |
| pMON61515 | RTBV | Leaves | ZM_S44903 | ++ | +++ |
| pMON61515 | RTBV | Leaves | ZM_S44908 | N.D. | ++ |
| pMON61515 | RTBV | Leaves | ZM_S44869 | +++ | +++ |

N.D. = not determined.
" + " = Relatively low AtAAP6 expression among the transgenic events derived from same construct.
" ++ " = Relatively median AtAAP6 expression among the transgenic events derived from same construct.
" +++ " = Relatively high AtAAP6 expression among the transgenic events derived from same construct.

EXAMPLE 9

This example describes functional analysis of the AtAAP6 transgene in transgenic maize plants.

A protocol for in vitro measurement of amino acid uptake with leaf discs was developed according to Eksittikul et al., *Plant Science* 160:733-737 (2001) with some modifications. $F_2$ transgenic seeds, containing the AtAAP6 gene driven by the e35S promoter, and non-transgenic (negative isolines) seeds were planted in soil and grown in a growth chamber under normal growth conditions. The gene expression of individual plants was determined by Western blot analysis prior to amino acid uptake assay. Leaf discs approximately 0.5 cm diameter in size were punctuated at V4 stage for in vitro amino acid uptake assay. The leaf discs were incubated at room temperature in an assay buffer containing 0.6 M mannitol, 2 mM MES, 10 mM $CaCl_2$, 200 μM glucose, 0.05% Tween 20 (pH 5.6), 200 μM assayed amino acid and 0.2 μCi $^{14}C$-labeled assayed amino acid. For each treatment, 6 leaf discs were taken at each time point of 0, 30, 60, 90, and 210 min after incubation. Three replicates were designed for each treatment. After washing and drying the leaf discs, the radioactivity accumulated in the leaf discs was measured by a scintillation counter.

According to the specificity of AtAAP6 for various amino acids previously measured with yeast mutant JT16 cells complemented with AtAAP6 gene (Rentsch et al., *Plant Cell* 8:1437-1446 (1996) and EXAMPLE 2), 2 amino acids, glutamine and histidine, were chosen for functional analysis of AtAAP6 proteins in transgenic corn plants. AtAAP6 proteins showed high affinity to glutamine and low affinity to histidine with yeast cells.

Figure 18:
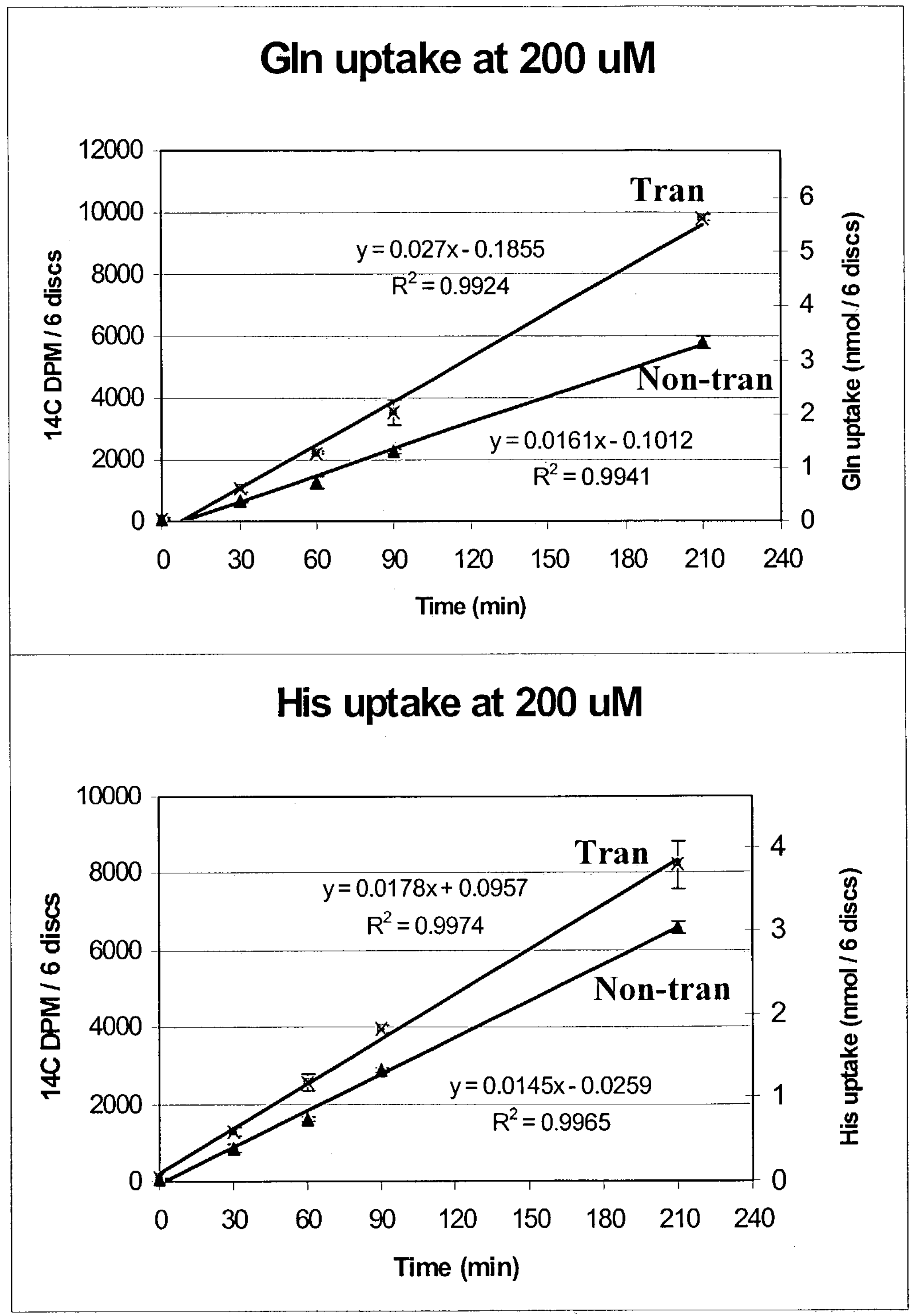
FIG. 18 is a graph of glutamine and histidine uptake in leaf discs from maize plants transformed with an *Arabidopsis* AAP6 gene.

Results from 3 independent experiments demonstrated that both of glutamine and histidine was accumulated at a significant higher level in the leaf discs from AtAAP6 protein-containing transgenic plants (from transgenic events ZM_S41491 and ZM_S41519) than those from their negative isolines (FIG. 18). Glutamine accumulation in transgenic leaves showed about a 68% increase after a 3.5-hour incubation compared to non-transgenic leaves and histidine showed about a 23% increase for the same time period. This observation is consistent with the affinity determined with complemented yeast cells. The results clearly demonstrate that the AtAAP6 gene encodes a functional protein in transgenic corn plants that leads to an increase in amino acid uptake in leaf tissues in vitro.

EXAMPLE 10

This example describes the determination of the specificity of amino acid transporters using complemented yeast cells.

Measurement of amino acid uptake with the complemented yeast cells in vitro (Hsu et al., *Proc. Natl. Acad. Sci.* (*U.S.A.*) 90:7441-7445 (1993); Fischer et al., *J. Biol. Chem.* 270:16315-16320 (1995); Boorer and Fischer *J. Biol. Chem.* 272:13040-13046 (1997); Boorer et al., *J. Biol. Chem.* 271:2213-2220 (1996); Kwart et al., *Plant J.* 4:993-1002

Figure 19:
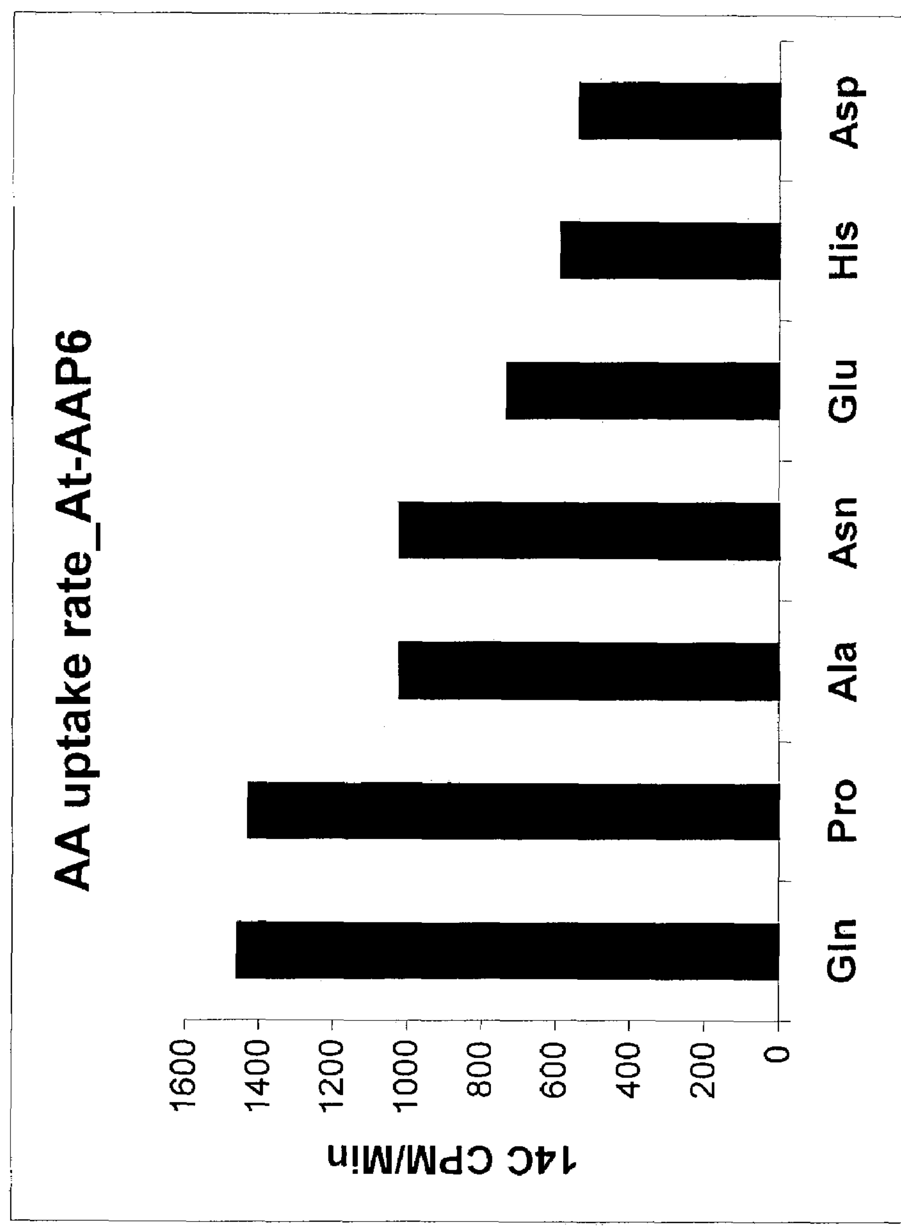
FIG. 19 is a chart of the substrate specificity of an *Arabidopsis* AAP6 protein to seven amino acids determined by measuring amino acid uptake with complemented yeast cells.
Figure 20:
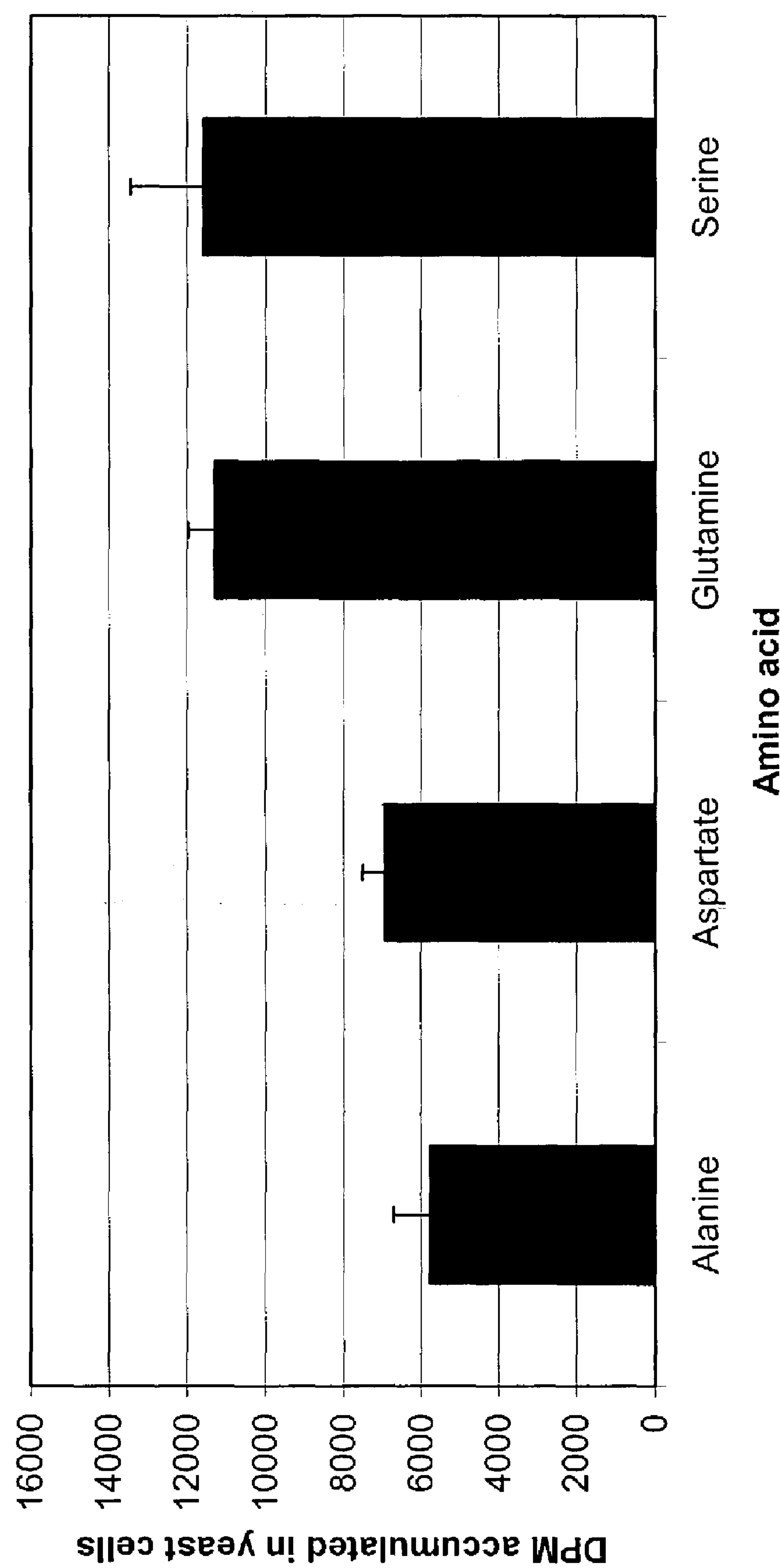
FIG. 20 is a chart of the substrate specificity of a maize AAP orthologue to four amino acids determined by measuring amino acid uptake with complemented yeast cells.

(1993)) has demonstrated that 5 members of the *Arabidopsis* AAP family possess different substrate specificity to individual amino acids. A limited study of substrate specificity of AtAAP6 is available in the literature (Rentsch et al., *Plant Cell* 8:1437-1446 (1996)). The substrate specificity of AtAAP6 and novel AAP orthologues identified in maize, rice and soybean can be determined by the method described by Hsu et al., *Proc. Natl, Acad. Sci.* (*U.S.A.*) 90:7441-7445 (1993) with minor modifications. FIG. 19 shows the specificity of AtAAP6 to 7 major amino acids in plants. AtAAP6 has relative high uptake specificity to glutamine and proline and low uptake specificity to histidine and aspartate. The specificity of the maize AAP orthologue LIB3689-227-Q1-K6-A12 to 4 amino acids was analyzed with a similar protocol with its complemented yeast cells. This maize AAP shows high affinity to glutamine and serine (FIG. 20).

What is claimed is:

1. A method for increasing amino acid content in a plant tissue comprising: (A) preparing a nucleic acid molecule encoding a plant amino acid transporter, wherein the nucleic acid molecule is operably linked to a promoter that is active in the plant tissue, and wherein the nucleic acid molecule comprises a nucleic acid sequence selected from the group consisting of (1) a nucleic acid sequence with at least 90% sequence identity to SEQ ID NO: 5 and which encodes a protein having amino acid transporter activity, (2) a nucleic acid sequence encoding the polypeptide of SEQ ID NO:4, and (3) a nucleic acid sequence that hybridizes to the nucleic acid sequence of SEQ ID NO:5 under high stringency conditions of 0.2×SSC and 65° C. and which encodes a protein having amino acid transporter activity; (B) transforming a plant with said nucleic acid molecule; and (C) growing said plant, wherein expression of said nucleic acid molecule increases amino acid content in said plant relative to an untransformed plant having a similar genetic background.

2. The method of claim 1, wherein said plant tissue is seed tissue.

3. The method of claim 2, wherein said plant tissue is selected from the group consisting of canola, maize, soybean, *Arabidopsis*, phaseolus, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliaces, cotton, eucalyptus, sunflower, *Brassica campestris*, oilseed rape, turfgrass, sugarbeet, coffee and dioscorea.

4. The method of claim 2, wherein said plant is selected from the group consisting of canola, maize, soybean, wheat, and rice.

5. The method of claim 2, wherein the seed tissue has an amino acid content that is increased at least 5% relative to an untransformed seed tissue having a similar genetic background.

6. The method of claim 2, wherein said nucleic acid molecule comprises the sequence of SEQ ID NO:5, or the full-length complement thereof.

7. The method of claim 2, wherein said plant amino acid transporter is a maize amino acid transporter.

8. The method of claim 2, wherein said plant amino acid transporter comprises the amino acid sequence of SEQ ID NO:4.

9. A transformed plant comprising an introduced nucleic acid molecule encoding an amino acid transporter, wherein the nucleic acid molecule comprises a nucleic acid sequence selected from the group consisting of (1) a nucleic acid sequence with at least 90% sequence identity to SEQ ID NO:5 and which encodes a protein having amino acid transporter activity, (2) a nucleic acid sequence encoding the polypeptide of SEQ ID NO:4, and (3) a nucleic acid sequence that hybridizes to the nucleic acid sequence of SEQ ID NO:5 under high stringency conditions of 0.2×SSC and 65° C. and which encodes a protein having amino acid transporter activity.

10. The transformed plant of claim 9, wherein said nucleic acid molecule comprises the sequence of SEQ ID NO:5, or the full-length complement thereof.

11. The transformed plant of claim 9, wherein said nucleic acid molecule encodes a polypeptide having the amino acid sequence of SEQ ID NO:4.

12. The transformed plant of claim 9, wherein a seed of said plant comprising said nucleic acid molecule has increased amino acid content relative to an untransformed seed having a similar genetic background.

13. The transformed plant of claim 12, wherein said seed has an increased amino acid content of one or more of the amino acids selected from the group consisting of alanine, asparagine, aspartate, glutamine, and serine, wherein the increase is at least 5% relative to an untransformed seed having a similar genetic background.

14. The transformed plant of claim 12, further comprising a promoter operably linked to said nucleic acid molecule.

15. A transformed plant comprising a nucleic acid molecule comprising a promoter region that functions in plant cells to cause the production of an mRNA molecule, wherein said promoter region is operably linked to a nucleic acid sequence selected from the group consisting of (1) a nucleic acid sequence with at least 90% sequence identity to SEQ ID NO:5 and which encodes a protein having amino acid transporter activity, (2) a nucleic acid sequence encoding the polypeptide of SEQ ID NO:4, and (3) a nucleic acid that hybridizes to the nucleic acid sequence of SEQ ID NO:5 under high stringency conditions of 0.2×SSC and 65° C. and which encodes a protein having amino acid transporter activity, and wherein said nucleic acid molecule is further operably linked to a 3' non-translated sequence that functions in the plant cells to cause termination of transcription.

16. A purified nucleic acid molecule, comprising a sequence selected from the group consisting of (1) a nucleic acid sequence with at least 90% sequence identity to SEQ ID NO:5 and which encodes a protein having amino acid transporter activity, (2) a nucleic acid sequence encoding the polypeptide of SEQ ID NO:4, and (3) a nucleic acid sequence that hybridizes to the nucleic acid sequence of SEQ ID NO:5 under high stringency conditions of 0.2×SSC and 65° C. and which encodes a protein having amino acid transporter activity, or the full-length complement of (1), (2) or (3).

17. A purified nucleic acid molecule that encodes a protein having an amino acid sequence of SEQ ID NO:4 or the full-length complement thereof.

* * * * *

UNITED STATES PATENT AND TRADEMARK OFFICE

CERTIFICATE OF CORRECTION

PATENT NO. : 7,288,408 B2
APPLICATION NO. : 10/355430
DATED : October 30, 2007
INVENTOR(S) : Jinzhuo Dong It is certified that error appears in the above-identified patent and that said Letters Patent is hereby corrected as shown below:

In claim 3, column 194, line 54, delete "liliaces" and insert --liliacea--.

Signed and Sealed this

Twenty-ninth Day of April, 2008

JON W. DUDAS
*Director of the United States Patent and Trademark Office*